(12) United States Patent
Brandl et al.

(10) Patent No.: US 9,290,485 B2
(45) Date of Patent: Mar. 22, 2016

(54) N-((6-AMINO-PYRIDIN-3-YL)METHYL)-HETEROARYL-CARBOXAMIDES

(75) Inventors: Trixi Brandl, Basel (CH); Stefanie Flohr, Basel (CH); Sebastian Kopec, Basel (CH); Julie Lachal, Basel (CH); Christian Markert, Basel (CH); Kenji Namoto, Basel (CH); Perle Nganga, Basel (CH); Bernard Pirard, Basel (CH); Martin Renatus, Basel (CH); Richard Sedrani, Basel (CH); Thomas Zoller, Basel (CH)

(73) Assignee: NOVARTIS AG, Basel (CH)

( * ) Notice: Subject to any disclaimer, the term of this patent is extended or adjusted under 35 U.S.C. 154(b) by 72 days.

(21) Appl. No.: 13/194,009

(22) Filed: Jul. 29, 2011

(65) Prior Publication Data

US 2012/0035168 A1    Feb. 9, 2012

Related U.S. Application Data

(60) Provisional application No. 61/370,612, filed on Aug. 4, 2010.

(51) Int. Cl.
| | |
|---|---|
| C07D 401/14 | (2006.01) |
| C07D 409/14 | (2006.01) |
| C07D 403/12 | (2006.01) |
| C07D 403/14 | (2006.01) |
| C07D 405/14 | (2006.01) |
| C07D 413/12 | (2006.01) |
| C07D 417/14 | (2006.01) |

(52) U.S. Cl.
CPC ............ C07D 409/14 (2013.01); C07D 403/12 (2013.01); C07D 403/14 (2013.01); C07D 405/14 (2013.01); C07D 413/12 (2013.01); C07D 417/14 (2013.01)

(58) Field of Classification Search
CPC .................................................... C07D 401/14
USPC ......................................... 546/175; 514/314
See application file for complete search history.

(56) References Cited

U.S. PATENT DOCUMENTS 7,429,604 B2    9/2008    Corte et al.

FOREIGN PATENT DOCUMENTS

| WO | WO0179261 | 10/2001 |
|---|---|---|
| WO | 0187854 | 11/2001 |
| WO | 02/00651 A2 | 1/2002 |
| WO | 03007690 | 1/2003 |
| WO | 03/076458 A2 | 9/2003 |
| WO | 2004/071440 A2 | 8/2004 |
| WO | 2005/039506 A2 | 5/2005 |
| WO | 2005/123680 A1 | 12/2005 |
| WO | 2006/008194 A1 | 1/2006 |
| WO | 2006/055184 A2 | 5/2006 |
| WO | 2007/000582 A1 | 1/2007 |
| WO | 2007/070818 A1 | 6/2007 |
| WO | 2008/016883 A2 | 2/2008 |
| WO | 2009/133348 A1 | 11/2009 |
| WO | 2010/078408 A1 | 7/2010 |
| WO | 2010/108187 A2 | 9/2010 |
| WO | 2010/111059 | 9/2010 |
| WO | 2010/137351 | 12/2010 |
| WO | 2011/017142 | 2/2011 |
| WO | 2011/051671 A1 | 5/2011 |
| WO | 2011/051672 A1 | 5/2011 |
| WO | 2011/051673 A1 | 5/2011 |
| WO | 2011/075684 A1 | 6/2011 |

OTHER PUBLICATIONS

Kirschfeld, "Treatment of serous, etc.," Pub Med ID: 25278347 (2014).*
Phipps et al., "The kallikrein, etc.," Kidney International (2008) 73, 1114-1119.*
Webb, "The Kallidrein/Kinin, etc.," Journal of Ocular Pharmacology and Therapeutics 27(6), 2011, 539-543.*
Pruneau et al., "Targeting the, etc.," Current Opinion in Investigational Drugs 2010 11(5):507-514.*
Liu et al., "Plasma kallikein, etc.," Biol. Chem. 2013; 394(3): 319-328.*

* cited by examiner

Primary Examiner — Patricia L Morris
(74) Attorney, Agent, or Firm — Joshua Roth

(57) ABSTRACT

The invention relates to compound of the formula I

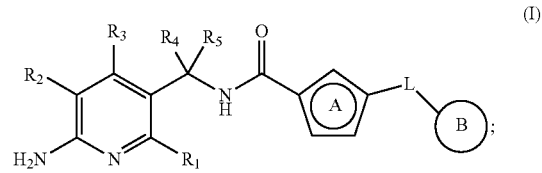

in which the substituents are as defined in the specification; in free form or in salt form; to its preparation, to its use as medicament and to medicaments comprising it.

5 Claims, 1 Drawing Sheet

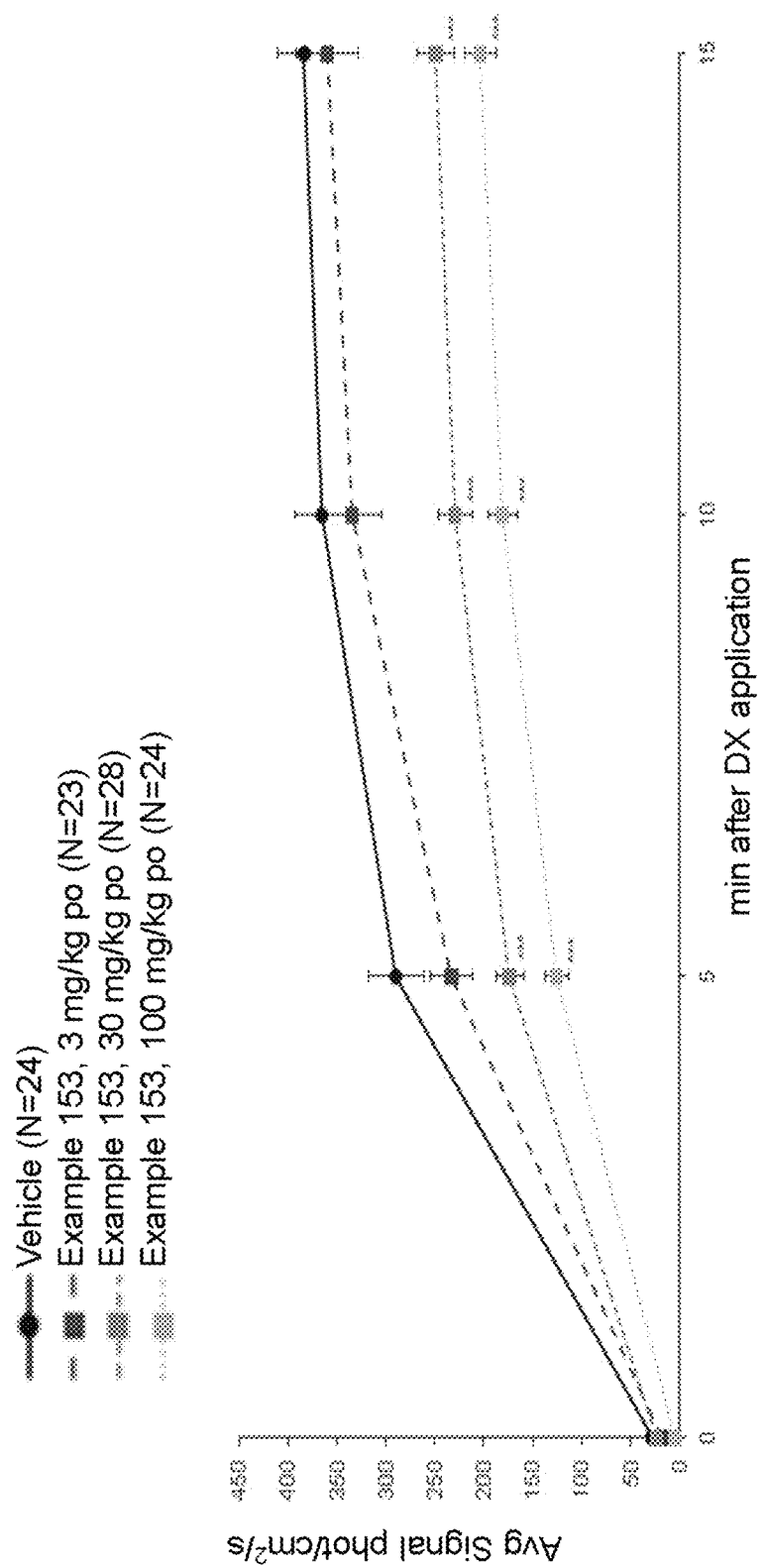

N-((6-AMINO-PYRIDIN-3-YL)METHYL)-HETEROARYL-CARBOXAMIDES

The invention relates to N-((6-amino-pyridin-3-yl)methyl)-heteroaryl-carboxamides, to their preparation, to their use as medicaments and to medicaments comprising them.

Plasmakallikrein (PK) is the activated form of the trypsin-like serine protease plasma-prokallikrein and is mainly expressed by hepatocytes in the liver. Activation of plasma-prokallikrein is believed to be mainly mediated through coagulation factor XIIa (fXIIa). Binding of the zymogen factor XII (fXII) to negatively charged surfaces is thought to induce a major conformational change in the protein, resulting in the expression of endogeneous (auto)activity sufficient to activate a small number of plasma-prokallikrein molecules. In a positive feedback mechanism, active plasmakallikrein efficiently activates surface-bound fXII to fXIIa and vice versa. This reciprocal activation of fXII and plasmakallikrein is critical for the formation of sufficient plasmakallikrein activity to trigger downstream proteolytic cascades. FXIIa is the first component of the intrinsic pathway of coagulation activating factor XI to factor XIa. Moreover, plasmakallikrein activated by fXIIa cleaves high molecular weight kininogen to bradykinin (BK). The nonapeptide BK is a potent mediator of inflammation, vasodilation, pain and increased vascular permeability. The functional C1 esterase inhibitor (C1Inh) regulates the activation of several proteolytic systems in plasma and is the major endogeneous inhibitor of PK.

Low molecular weight plasmakallikrein inhibitors are described e.g. in WO2008016883.

Plasma kallikrein may have numerous implications in disorders such as hereditary angioedema (HAE) (J A Bernstein et al, Expert Rev. Clin. Immunol., 6, 29-39, 2010; U C Nzeako et al., Arch Intern Med., 161, 2417-2429, 2001), retinopathy or diabetic retinopathy (A C Clermont et al, Abstract 5035-D883, ARVO 2010, Fort Lauderdale, Fla.), proliferative and non-proliferative retinopathy, diabetic macular edema (DME), clinically significant macular edema (CSME), cystoid macular edema (CME), CME following cataract extraction, CME induced by cryotherapy, CME induced by uveitis, CME following vascular occlusion (e.g. central retina vein occlusion, branch retinal vein occlusion, or hemiretinal vein occlusion), retinal edema, complications related to cataract surgery in diabetic retinopathy, hypertensive retinopathy (J A Phipps et al, Hypertension, 53, 175-181, 2009), retinal trauma, dry and wet aged-related macular degeneration (AMD), ischemic reperfusion injuries (C Storoni et al, JPET, 318, 849-954, 2006), e.g. in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke, myocardial infarction, acquired angioedema drug-related (ACE-inhibitors), edema, high altitude cerebral edema, cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, hemorrhagic transformation of ischemic stroke, cerebral trauma associate with injury or surgery, brain aneurysm, arterio-venous malformation, reduction of blood losses during surgical procedures (e.g. cardiothoracic surgery, such as cardiopulmonary bypass or coronary artery bypass grafting), blood coagulation disorders such as thrombosis, itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, chronic kidney disease, heart failure, microalbuminuria, albuminuria, proteinuria, disorders associated with increased vascular permeability (e.g. increased retinal vascular permeability, increased leg, feet, ankle vascular permeability), cerebral hemorrhage, microalbuminuria, albuminuria and proteinuria, deep vein thrombosis, coagulation from post fibrinolytic treatments, angina, angioedema, sepsis, arthritis (e.g. rheumatoid arthritis, osteoarthritis, infection arthritis), lupus, gout, psoriasis, blood loss during cardiopulmonary bypass, inflammatory bowel, diabetes, diabetic complications, infectious diseases, astrocyte-activation related diseases (e.g. Alzheimer's disease or multiple sclerosis), Parkinson's disease, amyotrophic lateral sclerosis, Creutzfeld-Jacob disease, stroke, epilepsy and trauma (e.g. brain trauma).

Plasma kallikrein inhibitors are considered to be useful in the treatment of a wide range of disorders, in particular retinopathy or edema-associated diseases, such as hereditary angioedema, macular edema and brain edema.

Plasma kallikrein inhibitors are considered to be especially useful in the treatment of retinopathy, e.g. retinopathy associated with diabetes and/or hypertension.

Plasma kallikrein inhibitors are considered to be especially useful in the treatment of hereditary angioedema.

Plasma kallikrein inhibitors are considered to be especially useful in the treatment of edema formation in diseases, e.g. edema formation related to ischemic reperfusion injuries.

Plasma kallikrein inhibitors are considered to be especially useful in the treatment of macular edema, e.g. macular edema associated with diabetes and/or hypertension.

There is a need to provide new plasmakallikrein inhibitors that are good drug candidates. In particular, preferred compounds should bind potently to plasmakallikrein whilst showing little affinity for other proteases. They should be well absorbed from the gastrointestinal tract, be sufficiently metabolically stable and possess favorable pharmacokinetic properties. They should be non-toxic and demonstrate few side-effects. Furthermore, the ideal drug candidate will be able to exist in a physical form that is stable, non-hygroscopic and easily formulated.

The compounds of the invention are plasmakallikrein inhibitors and are therefore potentially useful in the treatment of a wide range of disorders, particularly retinopathy or edema-associated diseases.

FIG. 1 shows the leakage vs min after dextran sulfate (DX) injection for a compound of the invention at doses of 3, 30 and 100 mg/kg po.

In a first aspect, the invention relates to a compound of the formula I

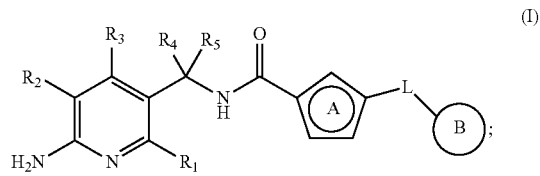

wherein
$R_1$ is hydrogen; halogen; cyano; nitro; hydroxy; amino; —C(O)H; —C(O)OH; —C(O)NH$_2$;
$C_{1-6}$alkyl; $C_{1-6}$halogenalkyl; $C_{1-6}$hydroxyalkyl; $C_{1-4}$alkoxy—$C_{1-6}$alkyl; $C_{1-6}$aminoalkyl;
$C_{2-6}$alkenyl; $C_{2-6}$halogenalkenyl; $C_{2-6}$alkinyl; $C_{2-6}$halogenalkinyl;

$C_{1-6}$alkoxy; $C_{1-6}$halogenalkoxy; $C_{1-4}$alkoxy-$C_{1-6}$alkoxy; $C_{1-6}$alkylamino; di($C_{1-6}$alkyl)amino;

or $C_{3-7}$cycloalkyl, wherein one carbon atom may be replaced by an oxygen atom, wherein the $C_{3-7}$cycloalkyl may be attached directly to the pyridine ring or via a $C_{1-2}$alkylene or an oxygen, and wherein the $C_{3-7}$cycloalkyl may be substituted once or more than once by halogen, $C_{1-4}$alkyl or $C_{1-4}$alkoxy;

$R_2$ is hydrogen or fluoro;

$R_3$ is hydrogen; halogen; cyano; nitro; hydroxy; amino; —C(O)H; —C(O)OH; —C(O)NH$_2$; or —X$_1$—R$_6$;

$X_1$ is selected from bond; carbonyl; oxygen; sulfur; —S(O)—; —S(O)$_2$—; amino, which may be substituted by $C_{1-4}$alkyl; —NH—C(O)—; —C(O)—NH—; —NH—S(O)$_2$—; and —S(O)$_2$—NH—;

$R_6$ is $C_{1-6}$alkyl; $C_{1-6}$halogenalkyl; $C_{1-6}$cyanoalkyl; $C_{1-6}$-carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; $C_{2-6}$halogenalkinyl;

or $R_6$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may be attached directly to group $X_1$ or via a $C_{1-2}$alkylene, wherein the ring system may in turn be substituted once or more than once by $R_7$, and wherein a substituent on a nitrogen in a heterocyclic ring system may not be halogen;

each $R_7$ independently is halogen, cyano, $C_{1-4}$alkyl, $C_{1-4}$halogenalkyl, $C_{1-4}$alkoxy, or $C_{1-4}$halogenalkoxy; or two $R_7$ at the same ring atom together are oxo;

$R_4$ and $R_5$ are each independently hydrogen; cyano; $C_{1-6}$alkyl; $C_{1-6}$halogenalkyl; $C_{1-6}$hydroxyalkyl; $C_{1-4}$alkoxy-$C_{1-6}$alkyl; $C_{2-6}$alkenyl; $C_{2-6}$halogenalkenyl; $C_{2-6}$alkinyl; $C_{2-6}$halogenalkinyl;

$C_{1-6}$alkylamino; di($C_{1-6}$alkyl)amino;

or $C_{3-7}$cycloalkyl, wherein one carbon atom may be replaced by an oxygen atom, wherein the $C_{3-7}$cycloalkyl may be attached directly to the methylene or via a $C_{1-2}$alkylene, and wherein the $C_{3-7}$cycloalkyl may be substituted once or more than once by halogen, $C_{1-4}$alkyl or $C_{1-4}$alkoxy;

or $R_4$ and $R_5$ together with the carbon atom to which they are bound form a $C_{3-7}$cycloalkyl;

or $R_4$ and $R_5$ together are oxo;

or $R_4$ and $R_5$ together are imino, which may be substituted by $C_{1-4}$alkyl;

A is a five-membered monocyclic aromatic ring system which contains from 1 to 4 hetero atoms selected from nitrogen, oxygen and sulfur, wherein the ring system may contain not more than 1 hetero atom selected from oxygen and sulfur, and wherein the group L is attached to a ring atom being separated by one further ring atom from the ring atom to which the carboxamide group is attached, wherein the ring system may be substituted once, twice or three times by $R_8$, and wherein a substituent on a ring nitrogen atom may not be halogen;

each $R_8$ independently is halogen; cyano; nitro; hydroxy; amino; —C(O)H; —C(O)OH; —C(O)NH$_2$;

$C_{1-6}$alkyl; $C_{1-6}$halogenalkyl; $C_{1-6}$hydroxyalkyl; $C_{1-4}$alkoxy-$C_{1-6}$alkyl; $C_{1-6}$-aminoalkyl;

$C_{2-6}$alkenyl; $C_{2-6}$halogenalkenyl; $C_{2-6}$alkinyl; $C_{2-6}$halogenalkinyl;

$C_{1-6}$alkoxy; $C_{1-6}$halogenalkoxy; $C_{1-4}$alkoxy-$C_{1-6}$alkoxy; $C_{1-6}$alkylamino; di($C_{1-6}$alkyl)amino;

or $C_{3-7}$cycloalkyl, wherein one carbon atom may be replaced by an oxygen atom, wherein the $C_{3-7}$cycloalkyl may be attached directly to group A or via a $C_{1-2}$alkylene or an oxygen, and wherein the $C_{3-7}$cycloalkyl may be substituted once or more than once by halogen, $C_{1-4}$alkyl or $C_{1-4}$alkoxy;

or two $R_8$ at adjacent ring atoms atoms form together with said ring atoms a fused five- to seven-membered monocyclic aromatic or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_9$, and wherein a substituent on a nitrogen in a heterocyclic ring system may not be halogen; and wherein each $R_9$ independently is halogen, $C_{1-4}$alkyl or $C_{1-4}$alkoxy, or two $R_9$ at the same ring atom together are oxo;

L is —C($R_{10}$)$_2$—; —O—; —S—; —N($R_{11}$)—; —S(O)—; or —S(O)$_2$—;

each $R_{10}$ independently is hydrogen;

halogen; cyano; hydroxy; nitro; amino;

$C_{1-6}$alkyl; $C_{1-6}$halogenalkyl; $C_{1-6}$hydroxyalkyl; $C_{1-4}$alkoxy-$C_{1-6}$alkyl; amino-$C_{1-6}$alkyl; $C_{1-4}$alkylamino-$C_{1-6}$alkyl; di($C_{1-4}$alkyl)amino-$C_{1-6}$alkyl;

$C_{2-6}$alkenyl; $C_{2-6}$halogenalkenyl; $C_{2-6}$alkinyl; $C_{2-6}$halogenalkinyl;

$C_{1-6}$alkoxy; $C_{1-6}$halogenalkoxy; $C_{1-4}$alkoxy-$C_{1-6}$alkoxy; $C_{1-6}$alkylamino; di($C_{1-6}$alkyl)amino; or $C_{3-7}$cycloalkyl, wherein one carbon atom may be replaced by an oxygen atom, wherein the $C_{3-7}$cycloalkyl may be attached directly to the methylene or via a $C_{1-2}$alkylene or an oxygen, and wherein the $C_{3-7}$cycloalkyl may be substituted once or more than once by halogen, $C_{1-4}$alkyl or $C_{1-4}$alkoxy;

or two $R_{10}$ together with the carbon atom to which they are bound form a $C_{3-7}$cycloalkyl;

or two $R_{10}$ together are oxo;

or two $R_{10}$ together are imino, which may be substituted by $C_{1-4}$alkyl;

$R_{11}$ is hydrogen;

$C_{1-6}$alkyl;

or $C_{3-7}$cycloalkyl, wherein one carbon atom may be replaced by an oxygen atom, wherein the $C_{3-7}$cycloalkyl may be attached directly to the nitrogen atom or via a $C_{1-2}$alkylene;

B is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_{12}$, and wherein a substituent on a nitrogen in a heterocyclic ring system may not be halogen;

each $R_{12}$ independently is halogen; cyano; nitro; hydroxy; amino; —C(O)H; —C(O)OH; —C(O)NH$_2$; —X$_2$—R$_{13}$; or —X$_3$—B$_1$;

$X_2$ is selected from bond; carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$R_{13}$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; $C_{2-6}$halogenalkinyl;

$X_3$ is bond or $C_{1-3}$alkylene, wherein one carbon atom of the $C_{1-3}$alkylene may be replaced by a group selected from carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$B_1$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may in turn be substituted once or more than once by $R_{14}$, and wherein a substituent on a nitrogen in a heterocyclic ring system may not be halogen;

each $R_{14}$ independently is halogen, cyano, $C_{1-4}$alkyl, $C_{1-4}$halogenalkyl, $C_{1-4}$alkoxy, or $C_{1-4}$halogenalkoxy; or two $R_{14}$ at the same ring atom together are oxo;

or two $R_{12}$ at adjacent ring atoms atoms form together with said ring atoms a fused five- to seven-membered monocyclic unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{15}$, and wherein a substituent on a nitrogen in a heterocyclic ring system may not be halogen; and wherein each $R_{15}$ independently is halogen, $C_{1-4}$alkyl, $C_{1-4}$alkoxy, or $C_{1-4}$alkoxy$C_{1-4}$alkyl, or two $R_{15}$ at the same ring atom together are oxo;

or B is a three- to ten-membered monocyclic or fused polycyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_{16}$, and wherein a substituent on a nitrogen in a heterocyclic ring system may not be halogen;

each $R_{16}$ independently is halogen; cyano; nitro; hydroxy; amino; —C(O)H; —C(O)OH; —C(O)NH$_2$; —X$_4$—R$_{17}$; or —X$_5$—B$_2$;

$X_4$ is selected from bond; carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$R_{17}$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; $C_{2-6}$halogenalkinyl;

$X_5$ is bond or $C_{1-3}$alkylene, wherein one carbon atom of the $C_{1-3}$alkylene may be replaced by a group selected from carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may in turn be substituted once or more than once by $R_{18}$, and wherein a substituent on a nitrogen in a heterocyclic ring system may not be halogen;

each $R_{18}$ independently is halogen, cyano, $C_{1-4}$alkyl, $C_{1-4}$halogenalkyl, $C_{1-4}$alkoxy, or $C_{1-4}$halogenalkoxy; or two $R_{18}$ at the same ring atom together are oxo;

or two $R_{16}$ at adjacent ring atoms atoms form together with said ring atoms a fused five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{19}$, and wherein a substituent on a nitrogen in a heterocyclic ring system may not be halogen; and wherein each $R_{19}$ independently is halogen, $C_{1-4}$alkyl or $C_{1-4}$alkoxy;

or two $R_{16}$ at the same ring atom together are oxo;
or two $R_{16}$ at the same ring atom together with the ring atom to which they are bound form a $C_{3-7}$cycloalkyl;
or two $R_{16}$ at the same ring atom together are imino, which may be substituted by $C_{1-4}$alkyl;

in free form or in salt form or in pharmaceutically acceptable salt form.

In a second aspect, the invention relates to a compound of the formula I

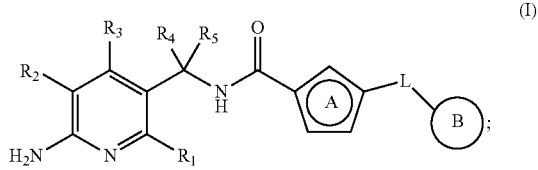

wherein
$R_1$ is hydrogen; halogen; cyano; nitro; hydroxy; amino; —C(O)H; —C(O)OH; —C(O)NH$_2$; $C_{1-6}$alkyl; $C_{1-6}$halogenalkyl; $C_{1-6}$hydroxyalkyl; $C_{1-4}$alkoxy-$C_{1-6}$alkyl; $C_{1-6}$aminoalkyl; $C_{1-6}$alkenyl; $C_{1-6}$halogenalkenyl; $C_{1-4}$alkinyl; $C_{2-6}$halogenalkinyl;

$C_{1-6}$alkoxy; $C_{1-6}$halogenalkoxy; $C_{1-4}$alkoxy-$C_{1-6}$alkoxy; $C_{1-6}$alkylamino; di($C_{1-6}$alkyl)amino;

or $C_{3-7}$cycloalkyl, wherein one carbon atom may be replaced by an oxygen atom, wherein the $C_{3-7}$cycloalkyl may be attached directly to the pyridine ring or via a $C_{1-2}$alkylene or an oxygen, and wherein the $C_{3-7}$cycloalkyl may be substituted once or more than once by halogen, $C_{1-4}$alkyl or $C_{1-4}$alkoxy;

$R_2$ is hydrogen or fluoro;

$R_3$ is hydrogen; halogen; cyano; nitro; hydroxy; amino; —C(O)H; —C(O)OH; —C(O)NH$_2$; or —X$_1$—R$_6$;

$X_1$ is selected from bond; carbonyl; oxygen; sulfur; —S(O)—; —S(O)$_2$—; amino, which may be substituted by $C_{1-4}$alkyl; —NH—C(O)—; —C(O)—NH—; —NH—S(O)$_2$—; and —S(O)$_2$—NH—;

$R_6$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl; $C_{2-6}$alkenyl; $C_{2-6}$halogenalkenyl; $C_{2-6}$alkinyl; $C_{2-6}$halogenalkinyl;

or $R_6$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may be attached directly to group $X_1$ or via a $C_{1-2}$alkylene, wherein the ring system may in turn be substituted once or more than once by $R_7$, and wherein a substituent on a nitrogen in a heterocyclic ring system may not be halogen;

each $R_7$ independently is halogen, cyano, $C_{1-4}$alkyl, $C_{1-4}$halogenalkyl, $C_{1-4}$alkoxy, or $C_{1-4}$halogenalkoxy; or two $R_7$ at the same ring atom together are oxo;

$R_4$ and $R_5$ are each independently hydrogen; cyano; $C_{1-6}$alkyl; $C_{1-6}$halogenalkyl; $C_{1-6}$hydroxyalkyl; $C_{1-4}$alkoxy-$C_{1-6}$alkyl; $C_{2-6}$alkenyl; $C_{2-6}$halogenalkenyl; $C_{2-6}$alkinyl; $C_{2-6}$halogenalkinyl;

$C_{1-6}$alkylamino; di($C_{1-6}$alkyl)amino;

or $C_{3-7}$cycloalkyl, wherein one carbon atom may be replaced by an oxygen atom, wherein the $C_{3-7}$cycloalkyl may be attached directly to the methylene or via a $C_{1-2}$alkylene, and wherein the $C_{3-7}$cycloalkyl may be substituted once or more than once by halogen, $C_{1-4}$alkyl or $C_{1-4}$alkoxy;

or $R_4$ and $R_5$ together with the carbon atom to which they are bound form a $C_{3-7}$cycloalkyl;

or $R_4$ and $R_5$ together are oxo;

or $R_4$ and $R_5$ together are imino, which may be substituted by $C_{1-4}$alkyl;

A is a five-membered monocyclic aromatic ring system which contains from 1 to 4 hetero atoms selected from nitrogen, oxygen and sulfur, wherein the ring system may contain not more than 1 hetero atom selected from oxygen and sulfur, and wherein the group L is attached to a ring atom being separated by one further ring atom from the ring atom to which the carboxamide group is attached, wherein the ring system may be substituted once, twice or three times by $R_8$, and wherein a substituent on a ring nitrogen atom may not be halogen;

each $R_8$ independently is halogen; cyano; nitro; hydroxy; amino; —C(O)H; —C(O)OH; —C(O)NH$_2$;

$C_{1-6}$alkyl; $C_{1-6}$halogenalkyl; $C_{1-6}$hydroxyalkyl; $C_{1-4}$alkoxy-$C_{1-6}$alkyl; $C_{1-6}$aminoalkyl;

$C_{2-6}$alkenyl; $C_{2-6}$halogenalkenyl; $C_{2-6}$alkinyl; $C_{2-6}$halogenalkinyl;

$C_{1-6}$alkoxy; $C_{1-6}$halogenalkoxy; $C_{1-4}$alkoxy-$C_{1-6}$alkoxy; $C_{1-6}$alkylamino; di($C_{1-6}$alkyl)amino; or $C_{3-7}$cycloalkyl, wherein one carbon atom may be replaced by an oxygen atom, wherein the $C_{3-7}$cycloalkyl may be attached directly to group A or via a $C_{1-2}$alkylene or an oxygen, and wherein the $C_{3-7}$cycloalkyl may be substituted once or more than once by halogen, $C_{1-4}$alkyl or $C_{1-4}$alkoxy;

or two $R_8$ at adjacent ring atoms atoms form together with said ring atoms a fused five- to seven-membered monocyclic aromatic or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_9$, and wherein a substituent on a nitrogen in a heterocyclic ring system may not be halogen; and wherein each $R_9$ independently is halogen, $C_{1-4}$alkyl or $C_{1-4}$alkoxy, or two $R_9$ at the same ring atom together are oxo;

L is —C(R$_{10}$)$_2$—; —O—; —S—; —N(R$_{11}$)—; —S(O)—; or —S(O)$_2$—;

each $R_{10}$ independently is hydrogen; halogen; cyano; hydroxy; nitro; amino; $C_{1-6}$alkyl; $C_{1-6}$halogenalkyl; $C_{1-6}$hydroxyalkyl; $C_{1-4}$alkoxy-$C_{1-6}$alkyl; amino-$C_{1-6}$alkyl; $C_{1-4}$alkylamino-$C_{1-6}$alkyl; di($C_{1-4}$alkyl)amino-$C_{1-6}$alkyl;

$C_{2-6}$alkenyl; $C_{2-6}$halogenalkenyl; $C_{2-6}$alkinyl; $C_{2-6}$halogenalkinyl;

$C_{1-6}$alkoxy; $C_{1-6}$halogenalkoxy; $C_{1-4}$alkoxy-$C_{1-6}$alkoxy; $C_{1-4}$alkylamino; di($C_{1-4}$alkyl)amino;

or $C_{3-7}$cycloalkyl, wherein one carbon atom may be replaced by an oxygen atom, wherein the $C_{3-7}$cycloalkyl may be attached directly to the methylene or via a $C_{1-2}$alkylene or an oxygen, and wherein the $C_{3-7}$cycloalkyl may be substituted once or more than once by halogen, $C_{1-4}$alkyl or $C_{1-4}$alkoxy;

or two $R_{10}$ together with the carbon atom to which they are bound form a $C_{3-7}$cycloalkyl;

or two $R_{10}$ together are oxo;

or two $R_{10}$ together are imino, which may be substituted by $C_{1-4}$alkyl;

$R_{11}$ is hydrogen;

$C_{1-6}$alkyl;

or $C_{3-7}$cycloalkyl, wherein one carbon atom may be replaced by an oxygen atom, wherein the $C_{3-7}$cycloalkyl may be attached directly to the nitrogen atom or via a $C_{1-2}$alkylene;

B is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_{12}$, and wherein a substituent on a nitrogen in a heterocyclic ring system may not be halogen;

each $R_{12}$ independently is halogen; cyano; nitro; hydroxy; amino; —C(O)H; —C(O)OH; —C(O)NH$_2$; —X$_2$—R$_{13}$; or —X$_3$—B$_1$;

$X_2$ is selected from bond; carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$R_{13}$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$ alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; $C_{2-6}$halogenalkinyl;

$X_3$ is bond or $C_{1-3}$alkylene, wherein one carbon atom of the $C_{1-3}$alkylene may be replaced by a group selected from carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$B_1$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may in turn be substituted once or more than once by $R_{14}$, and wherein a substituent on a nitrogen in a heterocyclic ring system may not be halogen;

each $R_{14}$ independently is halogen, cyano, $C_{1-4}$alkyl, $C_{1-4}$halogenalkyl, $C_{1-4}$alkoxy, or $C_{1-4}$halogenalkoxy; or two $R_{14}$ at the same ring atom together are oxo;

or two $R_{12}$ at adjacent ring atoms atoms form together with said ring atoms a fused five- to seven-membered monocyclic unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{15}$, and wherein a substituent on a nitrogen in a heterocyclic ring system may not be halogen; and wherein each $R_{15}$ independently is halogen, $C_{1-4}$alkyl or $C_{1-4}$alkoxy, or two $R_{15}$ at the same ring atom together are oxo;

or B is a three- to ten-membered monocyclic or fused polycyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_{16}$, and wherein a substituent on a nitrogen in a heterocyclic ring system may not be halogen;

each $R_{16}$ independently is halogen; cyano; nitro; hydroxy; amino; —C(O)H; —C(O)OH; —C(O)NH$_2$; —$X_4$—$R_{17}$; or —$X_5$—$B_2$;

$X_4$ is selected from bond; carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$R_{17}$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl; $C_{2-6}$alkenyl; $C_{2-6}$halogenalkenyl; $C_{2-6}$alkinyl; $C_{2-6}$halogenalkinyl;

$X_5$ is bond or $C_{1-3}$alkylene, wherein one carbon atom of the $C_{1-3}$alkylene may be replaced by a group selected from carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may in turn be substituted once or more than once by $R_{15}$, and wherein a substituent on a nitrogen in a heterocyclic ring system may not be halogen;

each $R_{18}$ independently is halogen, cyano, $C_{1-4}$alkyl, $C_{1-4}$halogenalkyl, $C_{1-4}$alkoxy, or $C_{1-4}$halogenalkoxy; or two $R_{18}$ at the same ring atom together are oxo;

or two $R_{16}$ at adjacent ring atoms atoms form together with said ring atoms a fused five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{19}$, and wherein a substituent on a nitrogen in a heterocyclic ring system may not be halogen; and wherein each $R_{19}$ independently is halogen, $C_{1-4}$alkyl or $C_{1-4}$alkoxy;

or two $R_{16}$ at the same ring atom together are oxo;

or two $R_{16}$ at the same ring atom together with the ring atom to which they are bound form a $C_{3-7}$cycloalkyl;

or two $R_{16}$ at the same ring atom together are imino, which may be substituted by $C_{1-4}$alkyl;

in free form or in salt form.

Unless specified otherwise, the term "compounds of the present invention" refers to compounds of Formula (I) and (IA), prodrugs thereof, salts of the compound and/or prodrugs, hydrates or solvates of the compounds, salts and/or prodrugs, as well as all stereoisomers (including diastereoisomers and enantiomers), tautomers and isotopically labeled compounds (including deuterium substitutions), as well as inherently formed moieties (e.g., polymorphs, solvates and/or hydrates).

Unless indicated otherwise, the expressions used in this invention have the following meaning:

"Alkyl" represents a straight-chain or branched-chain alkyl group, for example, methyl, ethyl, n- or iso-propyl, n-, iso-, sec- or tert-butyl, n-pentyl, n-hexyl; $C_{1-6}$alkyl preferably represents a straight-chain or branched-chain $C_{1-4}$alkyl with particular preference given to methyl, ethyl, n-propyl, iso-propyl and tert-butyl.

Each alkyl part of "alkoxy", "halogenalkyl" and so on shall have the same meaning as described in the above-mentioned definition of "alkyl", especially regarding linearity and preferential size.

"$C_{3-7}$cycloalkyl" represents a saturated alicyclic moiety having from three to seven carbon atoms. This term refers to groups such as cyclopropyl, cyclobutyl, cyclopentyl and cyclohexyl.

A substituent being substituted "once or more than once", for example as defined for $R_1$, is preferably substituted by one to three substituents.

Halogen is generally fluorine, chlorine, bromine or iodine; preferably fluorine, chlorine or bromine. Halogenalkyl groups preferably have a chain length of 1 to 4 carbon atoms and are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,2-trichloroethyl, 1,1,2,2-tetrafluoroethyl, 2,2,3,3-tetrafluoropropyl, 2,2,3, 3,3-pentafluoropropyl or 2,2,3,4,4,4-hexafluorobutyl; preferably —$CF_3$, —$CHF_2$, —$CH_2F$, —CHF—$CH_3$, —$CF_2CH_3$, or —$CH_2CF_3$.

In the context of the invention, the definition of $X_3$ and/or $X_4$ as a "$C_{1-3}$alkylene, wherein one carbon atom of the $C_{1-3}$alkylene may be replaced by a group selected from carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH-" encompasses e.g. —$CH_2$—; —O—; —$CH_2$—O—; —O—$CH_2$—; —C($CH_3$)H—O—; and —$CH_2$—NHC(O)NH—.

In the context of the invention, the definition of $R_6$, $B_1$ and/or $B_2$ as a "three- to seven-membered monocyclic ring system which may be aromatic, saturated or unsaturated non-aromatic and which may contain from 1 to 4 hetero atoms" encompasses three- to seven-membered monocyclic aromatic or non-aromatic hydrocarbon groups and aromatic or non-aromatic heterocyclic ring systems of the same sizes.

In the context of the invention, the definition of A as a "five-membered monocyclic aromatic ring system which contains from 1 to 4 hetero atoms" encompasses five-membered monocyclic aromatic heterocyclic ring systems.

In the context of the invention, the definition of two $R_8$ as a "fused five- to seven-membered monocyclic aromatic or unsaturated non-aromatic ring system which may contain from 1 to 4 hetero atoms" encompasses a $C_6$-aromatic hydrocarbon group, a five- to seven-membered monocyclic unsaturated non-aromatic hydrocarbon group or a five- to seven-membered monocyclic heterocyclic aromatic or unsaturated non-aromatic ring system. All said groups/ring systems comprise at least one double-bond, which is shared with the aromatic ring system A they are fused to.

In the context of the invention, the definition of B as a "five- to ten-membered monocyclic or fused polycyclic aromatic ring system which may contain from 1 to 4 heteroatoms" encompasses a $C_6$- or $C_{10}$-aromatic hydrocarbon group or a five- to ten-membered heterocyclic aromatic ring system.

In the context of the invention, the definition of two $R_{12}$ as a "fused five- to seven-membered monocyclic unsaturated non-aromatic ring system which may contain from 1 to 4 hetero atoms" encompasses five- to seven-membered non-aromatic hydrocarbon and heterocyclic groups which comprise at least one double-bond, which is shared with the aromatic ring system B they are fused to.

In the context of the invention, the definition of B as a "three- to ten-membered monocyclic or fused polycyclic saturated or unsaturated non-aromatic ring system which may contain from 1 to 4 heteroatoms" encompasses three- to ten-membered non-aromatic hydrocarbon groups and non-aromatic heterocyclic ring systems of the same sizes.

In the context of the invention, the definition of two $R_{16}$ as a "fused five- to six-membered monocyclic aromatic ring system which may contain from 1 to 4 hetero atoms" encompasses a $C_6$-aromatic hydrocarbon group or a five- to six-membered monocyclic heterocyclic aromatic ring system. In all said groups/ring systems one double-bond is shared with the ring system B they are fused to.

"Polycyclic" means preferably bicyclic.

The term "fused polycyclic aromatic ring system" refers to an aromatic substituent which consists of multiple, e.g. two, aromatic rings that are fused together.

A $C_6$- or $C_{10}$-aromatic hydrocarbon group is typically phenyl or naphthyl respectively. A $C_6$-aromatic hydrocarbon group is especially phenyl.

Preferably, but also depending on substituent definition, "five- to six-membered heterocyclic aromatic ring systems" consist of 5 to 6 ring atoms of which 1-3 ring atoms are hetero atoms.

Examples of heterocyclic ring systems are: imidazo[2,1-b]thiazole, pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, oxadiazole, dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, isothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pteridine, and the corresponding benz-annelated heterocycles, e.g. indole, isoindole, coumarin, isoquinoline, quinoline and the like. Preferred heterocycles are: pyrrole, imidazole, pyrazole, oxazole, isoxazole, triazole or oxadiazole.

The compounds of formula I may exist in optically active form or in form of mixtures of optical isomers, e.g. in form of racemic mixtures or diastereomeric mixtures. In particular, further asymmetrical carbon atom(s) may be present in the compounds of formula I and their salts. All optical isomers and their mixtures, including the racemic mixtures, are embraced by the invention.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. The compounds described herein may contain one or more asymmetric centers and may thus give rise to enantiomers, diastereomers, and other stereoisomeric forms that may be defined, in terms of absolute stereochemistry, as (R)- or (S)-. The invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any asymmetric atom (e.g. carbon or the like) of the compound(s) of the invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Depending on substituent definition, compounds of formula I may occur in various tautomeric forms. All tautomeric forms of the compounds of formula I are embraced by the invention.

Compounds of formula I may exist in free form or as a salt. In this specification, unless otherwise indicated, language such as "compound of formula I" is to be understood as embracing the compounds in any form, for example free or acid addition salt form. Salts, which are unsuitable for pharmaceutical uses, but which can be employed, for example, for the isolation or purification of free compounds of formula I, such as picrates or perchlorates, are also included. For therapeutic use, only pharmaceutically acceptable salts or free compounds are employed (where applicable in the form of pharmaceutical preparations), and are therefore preferred. Salts are preferably physiologically acceptable salts, formed by the addition of an acid.

As used herein, the term "pharmaceutically acceptable salts" refers to salts that retain the biological effectiveness and properties of the compounds of this invention and, which typically are not biologically or otherwise undesirable. The compounds of the invention may be capable of forming acid salts by virtue of the presence of suitable groups, such as amino groups.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

The pharmaceutically acceptable salts of the invention can be synthesized from a parent compound by conventional chemical methods. Generally, such salts can be prepared by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts Properties, Selection, and Use" by Stahl and Wermuth (Wiley-VCH, Weinheim, Germany, 2002).

The invention includes all pharmaceutically acceptable isotopically-labeled compounds of the invention, i.e. compounds of formula (I), wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio.

Examples of isotopes suitable for inclusion in the compounds of the invention comprises isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Tomography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula I with the co-crystal former under crystallization conditions and isolating co-crystals thereby formed. Suitable co-crystal formers include those described in WO 2004/078163. Hence the invention further provides co-crystals comprising a compound of formula (I).

Compounds of the invention are either obtained in the free form, as a salt thereof, or as prodrug derivatives thereof.

The invention also provides pro-drugs of the compounds of the invention that converts in vivo to the compounds of the invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxy groups with lipophilic carboxylic acids (e.g., a carboxylic acid having at least one lipophilic moiety).

Exemplary prodrugs are, e.g., O-acyl derivatives of alcohols. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the -(amino, mono- or di-lower alkylamino, carboxy, lower alkoxycarbonyl)-lower alkyl esters, the -(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the invention, including their salts, can also be obtained in the form of their hydrates, or include other solvents used for their crystallization.

Preferred substituents, preferred ranges of numerical values or preferred ranges of the radicals present in compounds of the formula I and the corresponding intermediate compounds are defined below. The definition of the substituents applies to the end-products as well as to the corresponding intermediates. The definitions of the substituents may be combined at will, e.g. preferred substituents $R_1$ and particularly preferred substituents $R_2$.

In especially preferred embodiments, the invention relates to one or more than one of the compounds of the formula I mentioned in the Examples hereinafter, in free form or in salt form, or in pharmaceutically acceptable salt form.

One class of compounds of the invention, are compounds of formula I, wherein $R_1$ is halogen; cyano; nitro; hydroxy; amino; —C(O)H; —C(O)OH; —C(O)$NH_2$;

$C_{1-6}$alkyl; $C_{1-6}$halogenalkyl; $C_{1-6}$hydroxyalkyl; $C_{1-4}$alkoxy-$C_{1-6}$alkyl; $C_{1-6}$aminoalkyl;

$C_{2-6}$alkenyl; $C_{2-6}$halogenalkenyl; $C_{2-6}$alkinyl; $C_{2-6}$halogenalkinyl;

$C_{1-6}$alkoxy; $C_{1-6}$halogenalkoxy; $C_{1-4}$alkoxy-$C_{1-6}$alkoxy; $C_{1-6}$alkylamino; di($C_{1-6}$alkyl)amino; or $C_{3-7}$cycloalkyl, wherein one carbon atom may be replaced by an oxygen atom, wherein the $C_{3-7}$cycloalkyl may be attached directly to the pyridine ring or via a $C_{1-2}$alkylene or an oxygen, and wherein the $C_{3-7}$cycloalkyl may be substituted once or more than once by halogen, $C_{1-4}$alkyl or $C_{1-4}$alkoxy.

One class of compounds of the invention, are compounds of formula I, wherein $R_1$ is $C_{1-6}$alkyl, $C_{1-6}$halogenalkyl; or $C_{3-7}$cycloalkyl, wherein the $C_{3-7}$cycloalkyl may be attached directly to the pyridine ring or via a $C_{1-2}$alkylene and wherein the $C_{3-7}$cycloalkyl may be substituted once or more than once by $C_{1-4}$alkyl.

One class of compounds of the invention, are compounds of formula I, wherein $R_1$ is $C_{1-4}$alkyl or $C_{1-4}$halogenalkyl.

One class of compounds of the invention, are compounds of formula I, wherein $R_1$ is methyl, —$CFH_2$, —$CF_2H$, or —$CF_3$.

One class of compounds of the invention, are compounds of formula I, wherein $R_1$ is methyl.

One class of compounds of the invention, are compounds of formula I, wherein $R_2$ is hydrogen.

One class of compounds of the invention, are compounds of formula I, wherein $R_3$ is halogen; cyano; nitro; hydroxy; amino; —C(O)H; —C(O)OH; —C(O)NH$_2$; or —X$_1$—R$_6$;

$X_1$ is selected from bond; carbonyl; oxygen; sulfur; —S(O)—; —S(O)$_2$—; amino, which may be substituted by $C_{1-4}$alkyl; —NH—C(O)—; —C(O)—NH—; —NH—S(O)$_2$—; and —S(O)$_2$—NH—;

$R_6$ is $C_{1-6}$alkyl, $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; $C_{2-6}$halogenalkinyl;

or $R_6$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may be attached directly to group $X_1$ or via a $C_{1-2}$alkylene, wherein the ring system may in turn be substituted once or more than once by $R_7$, and wherein a substituent on a nitrogen in a heterocyclic ring system may not be halogen;

each $R_7$ independently is halogen, cyano, $C_{1-4}$alkyl, $C_{1-4}$halogenalkyl, $C_{1-4}$alkoxy, or $C_{1-4}$halogenalkoxy; or two $R_7$ at the same ring atom together are oxo.

One class of compounds of the invention, are compounds of formula I, wherein $R_3$ is —X$_1$—R$_6$;

$X_1$ is bond; and $R_6$ is $C_{1-6}$alkyl; $C_{1-6}$halogenalkyl; or $C_{3-7}$cycloalkyl, wherein the $C_{3-7}$cycloalkyl may be attached directly to group $X_1$ or via a $C_{1-2}$alkylene and wherein the $C_{3-7}$cycloalkyl may be substituted once or more than once by $C_{1-4}$alkyl.

One class of compounds of the invention, are compounds of formula I, wherein $R_3$ is —X$_1$—R$_6$;

$X_1$ is bond; and $R_6$ is $C_{1-4}$alkyl or $C_{1-4}$halogenalkyl.

One class of compounds of the invention, are compounds of formula I, wherein $R_3$ is —X$_1$—R$_6$;

$X_1$ is bond; and $R_6$ is methyl, —CFH$_2$, —CF$_2$H, or —CF$_3$.

One class of compounds of the invention, are compounds of formula I, wherein $R_3$ is —X$_1$—R$_6$;

$X_1$ is bond; and $R_6$ is methyl.

One class of compounds of the invention, are compounds of formula I, wherein $R_3$ is —X$_1$—R$_6$;

$X_1$ is selected from carbonyl; oxygen; sulfur; —S(O)—; —S(O)$_2$—; and amino, which may be substituted by $C_{1-4}$alkyl; and $R_6$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; $C_{2-6}$halogenalkinyl;

or $R_6$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may be attached directly to group $X_1$ or via a $C_{1-2}$alkylene, wherein the ring system may in turn be substituted once or more than once by $R_7$, and wherein a substituent on a nitrogen in a heterocyclic ring system may not be halogen;

each $R_7$ independently is halogen, cyano, $C_{1-4}$alkyl, $C_{1-4}$halogenalkyl, $C_{1-4}$alkoxy, or $C_{1-4}$halogenalkoxy; or two $R_7$ at the same ring atom together are oxo.

One class of compounds of the invention, are compounds of formula I, wherein $R_3$ is —X$_1$—R$_6$;

$X_1$ is oxygen; and $R_6$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkoxy; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; $C_{2-6}$halogenalkinyl;

or $R_6$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may be attached directly to group $X_1$ or via a $C_{1-2}$alkylene, wherein the ring system may in turn be substituted once or more than once by $R_7$, and wherein a substituent on a nitrogen in a heterocyclic ring system may not be halogen;

each $R_7$ independently is halogen, cyano, $C_{1-4}$alkyl, $C_{1-4}$halogenalkyl, $C_{1-4}$alkoxy, or $C_{1-4}$halogenalkoxy; or two $R_7$ at the same ring atom together are oxo.

One class of compounds of the invention, are compounds of formula I, wherein $R_3$ is —X$_1$—R$_6$;

$X_1$ is oxygen; and $R_6$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; or $C_{2-6}$halogenalkinyl.

One class of compounds of the invention, are compounds of formula I, wherein $R_3$ is —X$_1$—R$_6$;

$X_1$ is oxygen; and $R_6$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may be attached directly to group $X_1$ or via a $C_{1-2}$alkylene, wherein the ring system may in turn be substituted once or more than once by $R_7$, and wherein a substituent on a nitrogen in a heterocyclic ring system may not be halogen;

each $R_7$ independently is halogen, cyano, $C_{1-4}$alkyl, $C_{1-4}$halogenalkyl, $C_{1-4}$alkoxy, or $C_{1-4}$halogenalkoxy; or two $R_7$ at the same ring atom together are oxo.

One class of compounds of the invention, are compounds of formula I, wherein $R_3$ is $—X_1—R_6$;

$X_1$ is oxygen; and $R_6$ is a five- to six-membered monocyclic aromatic ring system which contains from 1 to 4 hetero atoms selected from nitrogen, oxygen and sulfur, wherein the ring system may contain not more than 2 oxygen atoms and not more than 2 sulfur atoms, wherein the ring system may be attached directly to group $X_1$ or via a $C_{1-2}$alkylene, wherein the ring system may in turn be substituted once or more than once by $R_7$, and wherein a substituent on a nitrogen in a heterocyclic ring system may not be halogen;

each $R_7$ independently is halogen, $C_{1-4}$alkyl, $C_{1-4}$halogenalkyl, $C_{1-4}$alkoxy, or $C_{1-4}$halogenalkoxy.

One class of compounds of the invention, are compounds of formula I, wherein $R_4$ and $R_5$ are each hydrogen.

One class of compounds of the invention, are compounds of formula I, wherein A is a five-membered monocyclic aromatic ring system which contains from 1 to 4 hetero atoms selected from nitrogen, oxygen and sulfur, wherein the ring system may contain not more than 1 hetero atom selected from oxygen and sulfur, and wherein the group L is attached to a ring atom being separated by one further ring atom from the ring atom to which the carboxamide group is attached, wherein the ring system may be substituted once, twice or three times by $R_8$, and wherein a substituent on a ring nitrogen atom may not be halogen; and each $R_8$ independently is halogen; $C_{1-6}$alkyl; $C_{1-6}$halogenalkyl; $C_{1-6}$alkoxy; or $C_{1-6}$halogenalkoxy; or two $R_8$ at adjacent ring atoms atoms form together with said ring atoms a fused five- to seven-membered monocyclic aromatic or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_9$, and wherein a substituent on a nitrogen in a heterocyclic ring system may not be halogen; and wherein each $R_9$ independently is halogen, $C_{1-4}$alkyl or $C_{1-4}$alkoxy, or two $R_9$ at the same ring atom together are oxo.

One class of compounds of the invention, are compounds of formula I, wherein A is a five-membered monocyclic aromatic ring system which contains from 1 to 4 hetero atoms selected from nitrogen, oxygen and sulfur, wherein the ring system may contain not more than 1 hetero atom selected from oxygen and sulfur, and wherein the group L is attached to a ring atom being separated by one further ring atom from the ring atom to which the carboxamide group is attached, wherein the ring system may be substituted once, twice or three times by $R_8$, and wherein a substituent on a ring nitrogen atom may not be halogen; and each $R_8$ independently is halogen; $C_{1-6}$alkyl; $C_{1-6}$halogenalkyl; $C_{1-6}$alkoxy; or $C_{1-6}$halogenalkoxy.

One class of compounds of the invention, are compounds of formula I, wherein A is a ring system selected from pyrrole, imidazole, pyrazole, oxazole, isoxazole, triazole and oxadiazole and wherein the group L is attached to a ring atom being separated by one further ring atom from the ring atom to which the carboxamide group is attached, wherein the ring system may be substituted once, twice or three times by $R_8$, and wherein a substituent on a ring nitrogen atom may not be halogen; and each $R_8$ independently is halogen; $C_{1-6}$alkyl; $C_{1-6}$halogenalkyl; $C_{1-6}$alkoxy; or $C_{1-6}$halogenalkoxy.

One class of compounds of the invention, are compounds of formula I, wherein A is a ring system selected from

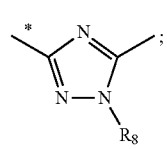
$A_1$

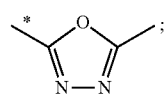
$A_2$

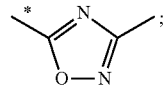
$A_3$

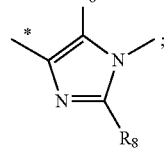
$A_4$

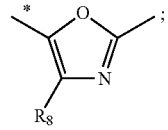
$A_5$

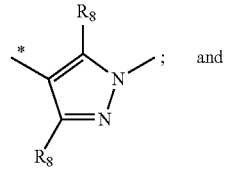
$A_6$
and

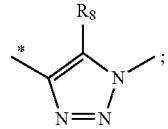
$A_7$ wherein the bond marked with the asterisk is attached to the carboxamide group and wherein each $R_8$ independently is hydrogen; halogen; $C_{1-4}$alkyl; $C_{1-4}$halogenalkyl; $C_{1-4}$alkoxy; or $C_{1-4}$halogenalkoxy.

One class of compounds of the invention, are compounds of formula I, wherein A is $A_1$.

One class of compounds of the invention, are compounds of formula I, wherein A is $A_2$.

One class of compounds of the invention, are compounds of formula I, wherein A is $A_3$.

One class of compounds of the invention, are compounds of formula I, wherein A is $A_4$.

One class of compounds of the invention, are compounds of formula I, wherein A is $A_5$.

One class of compounds of the invention, are compounds of formula I, wherein A is $A_6$.

One class of compounds of the invention, are compounds of formula I, wherein A is $A_7$.

One class of compounds of the invention, are compounds of formula I, wherein L is $-C(R_{10})_2-$; and each $R_{10}$ independently is hydrogen; halogen; cyano; hydroxy; nitro; amino; $C_{1-6}$alkyl; $C_{1-6}$halogenalkyl; $C_{1-6}$hydroxyalkyl; $C_{1-4}$alkoxy-$C_{1-6}$alkyl; amino-$C_{1-6}$alkyl; $C_{1-4}$alkylamino-$C_{1-6}$alkyl; di($C_{1-4}$alkyl)amino-$C_{1-6}$alkyl; $C_{2-6}$alkenyl; $C_{2-6}$halogenalkenyl; $C_{2-6}$alkinyl; $C_{2-6}$halogenalkinyl; $C_{1-6}$alkoxy; $C_{1-6}$halogenalkoxy; $C_{1-4}$alkoxy-$C_{1-6}$alkoxy; $C_{1-6}$alkylamino; di($C_{1-6}$alkyl)amino; or $C_{3-7}$cycloalkyl, wherein one carbon atom may be replaced by an oxygen atom, wherein the $C_{3-7}$cycloalkyl may be attached directly to the methylene or via a $C_{1-2}$alkylene or an oxygen, and wherein the $C_{3-7}$cycloalkyl may be substituted once or more than once by halogen, $C_{1-4}$alkyl or $C_{1-4}$alkoxy; or two $R_{10}$ together with the carbon atom to which they are bound form a $C_{3-7}$cycloalkyl; or two $R_{10}$ together are oxo; or two $R_{10}$ together are imino, which may be substituted by $C_{1-4}$alkyl.

One class of compounds of the invention, are compounds of formula I, wherein L is $-C(R_{10})_2-$; and each $R_{10}$ is hydrogen.

One class of compounds of the invention, are compounds of formula I, wherein L is $-O-$.

One class of compounds of the invention, are compounds of formula I, wherein L is $-N(R_{11})-$; and $R_{11}$ is hydrogen; $C_{1-6}$alkyl; or $C_{3-7}$cycloalkyl, wherein one carbon atom may be replaced by an oxygen atom, wherein the $C_{3-7}$cycloalkyl may be attached directly to the nitrogen atom or via a $C_{1-2}$alkylene.

One class of compounds of the invention, are compounds of formula I, wherein L is $-N(R_{11})-$; and $R_{11}$ is hydrogen.

One class of compounds of the invention, are compounds of formula I, wherein L is $-S(O)_2-$.

One class of compounds of the invention, are compounds of formula I, wherein B is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_{12}$; and wherein a substituent on a nitrogen in a heterocyclic ring system may not be halogen.

One class of compounds of the invention, are compounds of formula I, wherein B is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted once by $-X_3-B_1$; and wherein the ring system may be further substituted once or more than once by halogen; cyano; nitro; hydroxy; amino; $-C(O)H$; $-C(O)OH$; $-C(O)NH_2$; or $-X_2-R_{13}$; and wherein a substituent on a nitrogen in a heterocyclic ring system may not be halogen.

One class of compounds of the invention, are compounds of formula I, wherein B is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted once by $-X_3-B_1$; and wherein the ring system may be further substituted once or more than once by halogen; cyano; hydroxy; amino; or $-X_2-R_{13}$; and wherein a substituent on a nitrogen in a heterocyclic ring system may not be halogen;

$X_2$ is selected from bond; oxygen; amino, which may be substituted by $C_{1-4}$alkyl;

$R_{13}$ is $C_{1-6}$alkyl; $C_{1-6}$halogenalkyl; $C_{1-6}$hydroxyalkyl; $C_{1-4}$alkoxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl;

$X_3$ is bond or $C_{1-3}$alkylene, wherein one carbon atom of the $C_{1-3}$alkylene may be replaced by a group selected from oxygen; sulfur; amino, which may be substituted by $C_{1-4}$alkyl; $B_1$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may in turn be substituted once or more than once by $R_{14}$, and wherein a substituent on a nitrogen in a heterocyclic ring system may not be halogen;

each $R_{14}$ independently is halogen, cyano, $C_{1-4}$alkyl, $C_{1-4}$halogenalkyl, $C_{1-4}$alkoxy, or $C_{1-4}$halogenalkoxy; or two $R_{14}$ at the same ring atom together are oxo.

One class of compounds of the invention, are compounds of formula I, wherein B is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted once by $-X_3-B_1$; and wherein the ring system may be further substituted once or more than once by halogen; cyano; hydroxy; amino; or $-X_2-R_{13}$; and wherein a substituent on a nitrogen in a heterocyclic ring system may not be halogen;

$X_2$ is selected from bond; oxygen;

$R_{13}$ is $C_{1-6}$alkyl; $C_{1-6}$halogenalkyl;

$X_3$ is bond or $C_{1-3}$alkylene, wherein one carbon atom of the $C_{1-3}$alkylene may be replaced by a group selected from oxygen; sulfur; amino, which may be substituted by $C_{1-4}$alkyl;

$B_1$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may in turn be substituted once or more than once by $R_{14}$, and wherein a substituent on a nitrogen in a heterocyclic ring system may not be halogen;

each $R_{14}$ independently is halogen, cyano, $C_{1-4}$alkyl, $C_{1-4}$halogenalkyl, $C_{1-4}$alkoxy, or $C_{1-4}$halogenalkoxy; or two $R_{14}$ at the same ring atom together are oxo.

One class of compounds of the invention, are compounds of formula I, wherein B is phenyl, wherein the phenyl is substituted once by $-X_3-B_1$ in the para-position to the group L and wherein the phenyl may be further substituted once or more than once by halogen; cyano; hydroxy; amino; or $-X_2-R_{13}$; and wherein a substituent on a nitrogen in a heterocyclic ring system may not be halogen;

$X_2$ is selected from bond; oxygen;

$R_{13}$ is $C_{1-6}$alkyl; $C_{1-6}$halogenalkyl;

$X_3$ is bond or $C_{1-3}$alkylene, wherein one carbon atom of the $C_{1-3}$alkylene may be replaced by a group selected from oxygen; sulfur; amino, which may be substituted by $C_{1-4}$alkyl; $B_1$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may in turn be substituted once or more than once by R$_{14}$, and wherein a substituent on a nitrogen in a heterocyclic ring system may not be halogen;

each R$_{14}$ independently is halogen, cyano, C$_{1-4}$alkyl, C$_{1-4}$halogenalkyl, C$_{1-4}$alkoxy, or C$_{1-4}$halogenalkoxy; or two R$_{14}$ at the same ring atom together are oxo.

One class of compounds of the invention, are compounds of formula I, wherein B is a five- to six-membered monocyclic aromatic ring system which contains from 1 to 4 hetero atoms selected from nitrogen, oxygen and sulfur, wherein the ring system may contain not more than 2 oxygen atoms and not more than 2 sulfur atoms, and wherein the ring system is substituted once by —X$_3$—B$_1$; and wherein the ring system may be further substituted once or more than once by halogen; cyano; hydroxy; amino; or —X$_2$—R$_{13}$; and wherein a substituent on a nitrogen in a heterocyclic ring system may not be halogen;

X$_2$ is selected from bond; oxygen;

R$_{13}$ is C$_{1-6}$alkyl; C$_{1-6}$halogenalkyl;

X$_3$ is bond or C$_{1-3}$alkylene, wherein one carbon atom of the C$_{1-3}$alkylene may be replaced by a group selected from oxygen; sulfur; amino, which may be substituted by C$_{1-4}$alkyl; B$_1$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may in turn be substituted once or more than once by R$_{14}$, and wherein a substituent on a nitrogen in a heterocyclic ring system may not be halogen;

each R$_{14}$ independently is halogen, cyano, C$_{1-4}$alkyl, C$_{1-4}$halogenalkyl, C$_{1-4}$alkoxy, or C$_{1-4}$halogenalkoxy; or two R$_{14}$ at the same ring atom together are oxo.

One class of compounds of the invention, are compounds of formula I, wherein B is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by R$_{12}$; and wherein a substituent on a nitrogen in a heterocyclic ring system may not be halogen;

each R$_{12}$ independently is halogen; cyano; nitro; hydroxy; amino; —C(O)H; —C(O)OH; —C(O)NH$_2$; —X$_2$—R$_{13}$.

One class of compounds of the invention, are compounds of formula I, wherein B is a nine- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by R$_{12}$; and wherein a substituent on a nitrogen in a heterocyclic ring system may not be halogen;

each R$_{12}$ independently is halogen; cyano; hydroxy; amino; —X$_2$—R$_{13}$;

X$_2$ is selected from bond; oxygen; and amino, which may be substituted by C$_{1-4}$alkyl; R$_{13}$ is C$_{1-6}$alkyl; C$_{1-6}$halogenalkyl.

One class of compounds of the invention, are compounds of formula I, wherein B is a three- to ten-membered monocyclic or fused polycyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by R$_{16}$, and wherein a substituent on a nitrogen in a heterocyclic ring system may not be halogen.

One class of compounds of the invention, are compounds of formula IA,

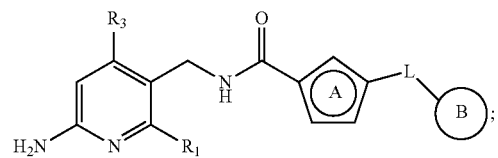

(IA)

wherein

R$_1$ and R$_3$ are each independently C$_{1-4}$alkyl or C$_{1-4}$halogenalkyl;

A is a ring system selected from

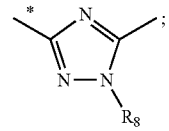

A$_1$

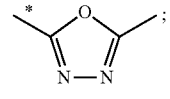

A$_2$

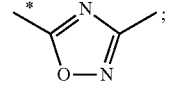

A$_3$

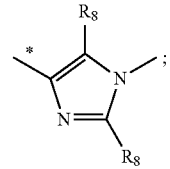

A$_4$

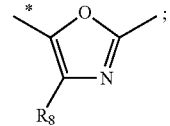

A$_5$

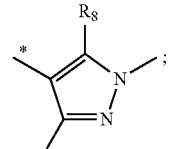

A$_6$ and

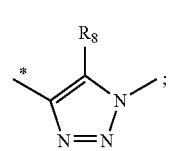

A$_7$ wherein the bond marked with the asterisk is attached to the carboxamide group and wherein each $R_8$ independently is hydrogen; halogen; $C_{1-4}$alkyl; $C_{1-4}$halogenalkyl; $C_{1-4}$alkoxy; or $C_{1-4}$halogenalkoxy;

L is —C($R_{10}$)$_2$—; and each $R_{10}$ is hydrogen;

B is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted once by —$X_3$—$B_1$; and wherein the ring system may be further substituted once or more than once by halogen; cyano; hydroxy; amino; or —$X_2$—$R_{13}$; and wherein a substituent on a nitrogen in a heterocyclic ring system may not be halogen;

$X_2$ is selected from bond; oxygen;

$R_{13}$ is $C_{1-6}$alkyl; $C_{1-6}$halogenalkyl;

$X_3$ is bond or $C_{1-3}$alkylene, wherein one carbon atom of the $C_{1-3}$alkylene may be replaced by a group selected from oxygen; sulfur; amino, which may be substituted by $C_{1-4}$alkyl; $B_1$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may in turn be substituted once or more than once by $R_{14}$, and wherein a substituent on a nitrogen in a heterocyclic ring system may not be halogen; and each $R_{14}$ independently is halogen, cyano, $C_{1-4}$alkyl, $C_{1-4}$halogenalkyl, $C_{1-4}$alkoxy, or $C_{1-4}$halogenalkoxy; or two $R_{14}$ at the same ring atom together are oxo.

One class of compounds of the invention, are compounds of formula IA,

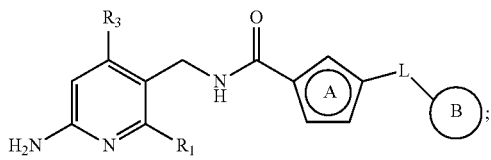
(IA)

wherein $R_1$ and $R_3$ are each independently $C_{1-4}$alkyl or $C_{1-4}$halogenalkyl;

A is a ring system selected from

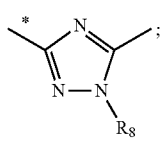
$A_1$

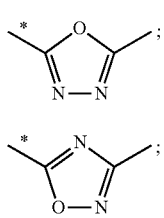
$A_2$ $A_3$

-continued

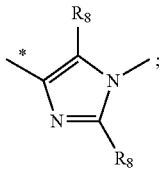
$A_4$

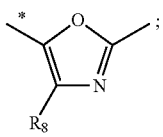
$A_5$

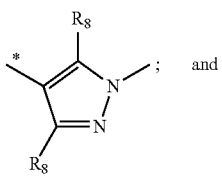
$A_6$ and

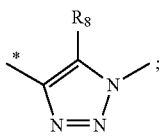
$A_7$ wherein the bond marked with the asterisk is attached to the carboxamide group and wherein each $R_8$ independently is hydrogen; halogen; $C_{1-4}$alkyl; $C_{1-4}$halogenalkyl; $C_{1-4}$alkoxy; or $C_{1-4}$halogenalkoxy;

L is —C($R_{10}$)$_2$—; and each $R_{10}$ is hydrogen;

B is a nine- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_{12}$; and wherein a substituent on a nitrogen in a heterocyclic ring system may not be halogen; each $R_{12}$ independently is halogen; cyano; hydroxy; amino; —$X_2$—$R_{13}$;

$X_2$ is selected from bond; oxygen; and amino, which may be substituted by $C_{1-4}$alkyl; and $R_{13}$ is $C_{1-6}$alkyl; $C_{1-6}$halogenalkyl.

One class of compounds of the invention, are compounds of formula IA,

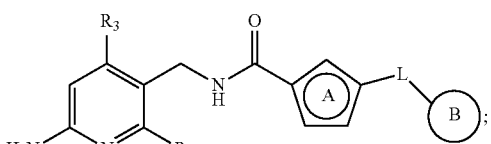
(IA)

wherein $R_1$ is $C_{1-4}$alkyl or $C_{1-4}$halogenalkyl;

$R_3$ is —$X_1$—$R_6$; $X_1$ is oxygen; and $R_6$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy- $C_{1-6}$ alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; $C_{2-6}$halogenalkinyl;

or $R_6$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may be attached directly to group $X_1$ or via a $C_{1-2}$alkylene, wherein the ring system may in turn be substituted once or more than once by $R_7$, and wherein a substituent on a nitrogen in a heterocyclic ring system may not be halogen;

each $R_7$ independently is halogen, cyano, $C_{1-4}$alkyl, $C_{1-4}$halogenalkyl, $C_{1-4}$alkoxy, or $C_{1-4}$halogenalkoxy; or two $R_7$ at the same ring atom together are oxo;

A is a ring system selected from

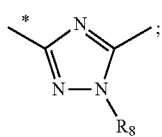 $A_1$

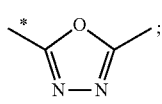 $A_2$

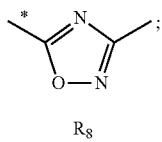 $A_3$

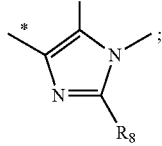 $A_4$

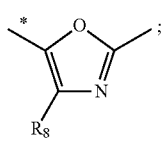 $A_5$

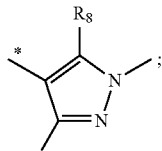 $A_6$

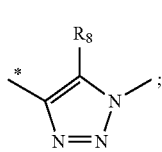 ; and $A_7$ wherein the bond marked with the asterisk is attached to the carboxamide group and wherein each $R_8$ independently is hydrogen; halogen; $C_{1-4}$alkyl; $C_{1-4}$halogenalkyl; $C_{1-4}$alkoxy; or $C_{1-4}$halogenalkoxy;

L is $-C(R_{10})_2-$; and each $R_{10}$ is hydrogen;

B is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted once by $-X_3-B_1$; and wherein the ring system may be further substituted once or more than once by halogen; cyano; hydroxy; amino; or $-X_2-R_{13}$; and wherein a substituent on a nitrogen in a heterocyclic ring system may not be halogen;

$X_2$ is selected from bond; oxygen;

$R_{13}$ is $C_{1-6}$alkyl; $C_{1-6}$halogenalkyl;

$X_3$ is bond or $C_{1-3}$alkylene, wherein one carbon atom of the $C_{1-3}$alkylene may be replaced by a group selected from oxygen; sulfur; amino, which may be substituted by $C_{1-4}$alkyl; $B_1$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may in turn be substituted once or more than once by $R_{14}$, and wherein a substituent on a nitrogen in a heterocyclic ring system may not be halogen; and each $R_{14}$ independently is halogen, cyano, $C_{1-4}$alkyl, $C_{1-4}$halogenalkyl, $C_{1-4}$alkoxy, or $C_{1-4}$halogenalkoxy; or two $R_{14}$ at the same ring atom together are oxo.

One class of compounds of the invention, are compounds of formula IA,

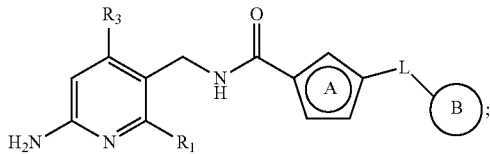

(IA)

wherein $R_1$ is $C_{1-4}$alkyl or $C_{1-4}$halogenalkyl;

$R_3$ is $-X_1-R_6$; is oxygen; and $R_6$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$ alkyl; $C_{1-4}$alkylcarbonylamino-$C_{1-6}$ alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; $C_{2-6}$halogenalkinyl;

or $R_6$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may be attached directly to group $X_1$ or via a $C_{1-2}$alkylene, wherein the ring system may in turn be substituted once or more than once by $R_7$, and wherein a substituent on a nitrogen in a heterocyclic ring system may not be halogen;

each $R_7$ independently is halogen, cyano, $C_{1-4}$alkyl, $C_{1-4}$halogenalkyl, $C_{1-4}$alkoxy, or $C_{1-4}$halogenalkoxy; or two $R_7$ at the same ring atom together are oxo;

A is a ring system selected from

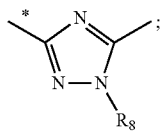
$A_1$

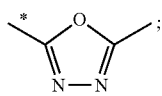
$A_2$

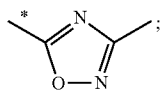
$A_3$

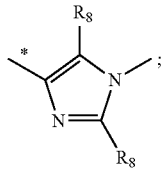
$A_4$

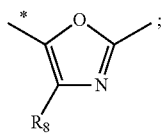
$A_5$

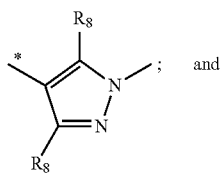
$A_6$
and

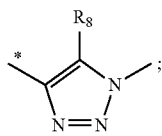
$A_7$ wherein the bond marked with the asterisk is attached to the carboxamide group and wherein each $R_8$ independently is hydrogen; halogen; $C_{1-4}$alkyl; $C_{1-4}$halogenalkyl; $C_{1-4}$alkoxy; or $C_{1-4}$halogenalkoxy;

L is —C($R_{10}$)$_2$—; and each $R_{10}$ is hydrogen;

B is a nine- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_{12}$; and wherein a substituent on a nitrogen in a heterocyclic ring system may not be halogen; each $R_{12}$ independently is halogen; cyano; hydroxy; amino; —X$_2$—R$_{13}$;

$X_2$ is selected from bond; oxygen; and amino, which may be substituted by $C_{1-4}$alkyl; and $R_{13}$ is $C_{1-6}$alkyl; $C_{1-6}$halogenalkyl.

One class of compounds of the invention, are compounds of formula IA,

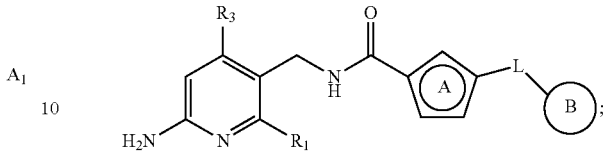
(IA)

wherein $R_1$ and $R_3$ are $C_{1-4}$alkyl;

A is a ring system selected from

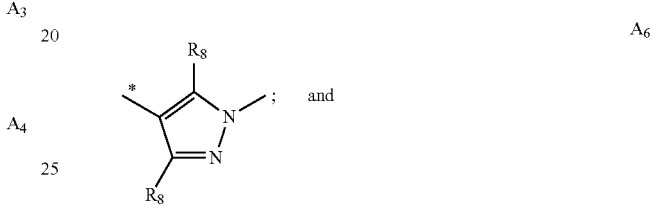
$A_6$
and

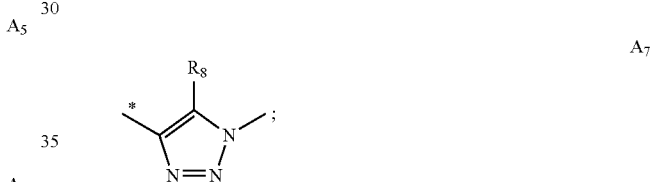
$A_7$ wherein the bond marked with the asterisk is attached to the carboxamide group and wherein each $R_8$ is hydrogen;

L is —C($R_{10}$)$_2$—; and each $R_{10}$ is hydrogen;

B is a nine- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_{12}$; and wherein a substituent on a nitrogen in a heterocyclic ring system may not be halogen; each $R_{12}$ independently is halogen; —X$_2$—R$_{13}$;

$X_2$ is selected from bond; and $R_{13}$ is $C_{1-6}$alkyl; $C_{1-6}$halogenalkyl.

One class of compounds of the invention, are compounds of formula IA,

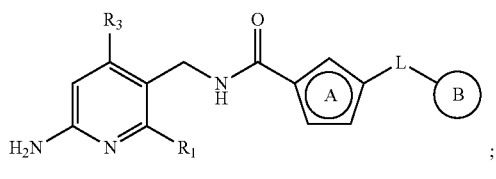
(IA)

wherein
$R_1$ and $R_3$ are $C_{1-4}$alkyl;
A is a ring system selected from

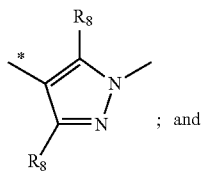
A6

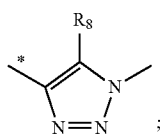
A7 wherein the bond marked with the asterisk is attached to the carboxamide group and wherein each $R_8$ is hydrogen;
L is —C($R_{10}$)$_2$—; and each $R_{10}$ is hydrogen;
B is a quinolinyl or an indolyl, wherein the quinolinyl or indolyl may be substituted once or more than once by $R_{12}$; and wherein a substituent on a nitrogen in a heterocyclic ring system may not be halogen;
each $R_{12}$ independently is halogen; —$X_2$—$R_{13}$;
$X_2$ is selected from bond; and
$R_{13}$ is $C_{1-6}$alkyl; $C_{1-6}$halogenalkyl.

One class of compounds of the invention, are compounds of formula IA,

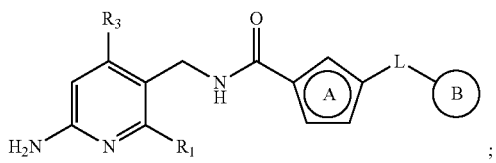
(IA)

wherein
$R_1$ and $R_3$ are $C_{1-4}$alkyl;
A is a ring system selected from

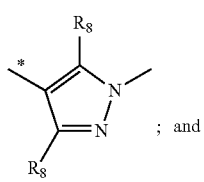
A6

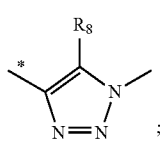
A7 wherein the bond marked with the asterisk is attached to the carboxamide group and wherein each $R_8$ is hydrogen;
L is —C($R_{10}$)$_2$—; and each $R_{10}$ is hydrogen;
B is a quinolin-2-yl, quinol-3-yl, quinol-6-yl, or an indol-3-yl, wherein the quinolinyl or indolyl may be substituted once or more than once by $R_{12}$; and wherein a substituent on a nitrogen in a heterocyclic ring system may not be halogen;
each $R_{12}$ independently is halogen; —$X_2$—$R_{13}$;
$X_2$ is selected from bond; and
$R_{13}$ is $C_{1-6}$alkyl; $C_{1-6}$halogenalkyl.

In one embodiment, the invention provides a compound selected from
N-((6-amino-2,4-dimethylpyridin-3-yl)methyl)-5-benzyl-1-methyl-1H-1,2,4-triazole-3-carboxamide;
N-((6-amino-2,4-dimethylpyridin-3-yl)methyl)-3-benzyl isoxazole-5-carboxamide;
N-((6-amino-2,4-dimethylpyridin-3-yl)methyl)-5-benzyl-1,3,4-oxadiazole-2-carboxamide;
N-((6-amino-2,4-dimethylpyridin-3-yl)methyl)-3-benzyl-1,2,4-oxadiazole-5-carboxamide;
1-(4-((1H-pyrazol-1-yl)methyl)benzyl)-N-((6-amino-2,4-dimethylpyridin-3-yl)methyl)-1H-imidazole-4-carboxamide;
N-((6-amino-2,4-dimethylpyridin-3-yl)methyl)-5-benzyloxazole-2-carboxamide;
N-((6-amino-2,4-dimethylpyridin-3-yl)methyl)-2-(4-methoxybenzyl)oxazole-4-carboxamide 1-(4-((1H-pyrazol-1-yl)methyl)-3-methoxybenzyl)-N-((6-amino-2,4-dimethylpyridin-3-yl)methyl)-1H-pyrazole-4-carboxamide;
N-((6-amino-2,4-dimethylpyridin-3-yl)methyl)-1-(biphenyl-4-ylmethyl)-1H-1,2,3-triazole-4-carboxamide;
N-((6-amino-2,4-dimethylpyridin-3-yl)methyl)-1-(2-hydroxy-1-phenylethyl)-1H-pyrazole-4-carboxamide;
N-((6-amino-2,4-dimethylpyridin-3-yl)methyl)-1-(phenylsulfonyl)-1H-pyrrole-3-carboxamide;
N-((6-amino-2,4-dimethylpyridin-3-yl)methyl)-1-(4-methoxybenzyl)-1H-pyrazole-4-carboxamide;
N-((6-amino-4-methoxy-2-methylpyridin-3-yl)methyl)-1-benzyl-1H-pyrazole-4-carboxamide;
N-((6-amino-4-(cyclohexyloxy)-2-methylpyridin-3-yl)methyl)-1-benzyl-1H-pyrazole-4-carboxamide;
N-((6-amino-2,4-dimethylpyridin-3-yl)methyl)-1-(4-(hydroxymethyl)benzyl)-1H-pyrazole-4-carboxamide;
N-((6-amino-2,4-dimethylpyridin-3-yl)methyl)-1-(4-((2,5-dioxopyrrolidin-1-yl)methyl)benzyl)-1H-pyrazole-4-carboxamide;
N-((6-amino-2,4-dimethylpyridin-3-yl)methyl)-1-(pyridin-4-ylmethyl)-1H-pyrazole-4-carboxamide;
N-((6-amino-2,4-dimethylpyridin-3-yl)methyl)-1-benzyl-1H-1,2,3-triazole-4-carboxamide;
N-((6-amino-2,4-dimethylpyridin-3-yl)methyl)-1-benzyl-1H-imidazole-4-carboxamide;
N-((6-amino-2,4-dimethylpyridin-3-yl)methyl)-1-(4-phenoxybenzyl)-1H-imidazole-4-carboxamide;
1-(4-(1H-pyrazol-1-yl)benzyl)-N-((6-amino-2,4-dimethylpyridin-3-yl)methyl)-1H-imidazole-4-carboxamide;
N-((6-amino-2,4-dimethylpyridin-3-yl)methyl)-1-((2-(phenylamino)thiazol-4-yl)methyl)-1H-pyrazole-4-carboxamide;
N-((6-amino-2,4-dimethylpyridin-3-yl)methyl)-1-((4-methyl-2-phenylthiazol-5-yl)methyl)-1H-pyrazole-4-carboxamide;
N-((6-amino-2,4-dimethylpyridin-3-yl)methyl)-1-((2-benzylthiazol-4-yl)methyl)-1H-pyrazole-4-carboxamide;
N-((6-amino-2,4-dimethylpyridin-3-yl)methyl)-1-((2-tert-butylthiazol-4-yl)methyl)-1H-pyrazole-4-carboxamide;
N-((6-amino-2,4-dimethylpyridin-3-yl)methyl)-1-((2-(2-(dimethylamino)-2-oxoethyl)thiazol-4-yl)methyl)-1H-pyrazole-4-carboxamide;
N-((6-amino-2,4-dimethylpyridin-3-yl)methyl)-1-(imidazo[1,2-a]pyridin-2-ylmethyl)-1H-pyrazole-4-carboxamide;

N-((6-amino-2,4-dimethylpyridin-3-yl)methyl)-1-(benzofuran-2-ylmethyl)-1H-pyrazole-4-carboxamide;
N-((6-amino-2,4-dimethylpyridin-3-yl)methyl)-1-((2-phenyloxazol-4-yl)methyl)-1H-pyrazole-4-carboxamide;
1-((1H-benzo[d]imidazol-5-yl)methyl)-N-((6-amino-2,4-dimethylpyridin-3-yl)methyl)-1H-pyrazole-4-carboxamide;
N-((6-amino-2,4-dimethylpyridin-3-yl)methyl)-1-((1-methyl-1H-indol-6-yl)methyl)-1H-pyrazole-4-carboxamide;
N-((6-amino-2,4-dimethylpyridin-3-yl)methyl)-1-((5-phenyloxazol-4-yl)methyl)-1H-pyrazole-4-carboxamide;
N-((6-amino-2,4-dimethylpyridin-3-yl)methyl)-1-(4-((3,5-dimethyl-1H-pyrazol-1-yl)methyl)benzyl)-1H-pyrazole-4-carboxamide;
N-((6-amino-2,4-dimethylpyridin-3-yl)methyl)-1-(3-cyanophenylsulfonyl)-1H-pyrazole-4-carboxamide;
N-((6-amino-2,4-dimethylpyridin-3-yl)methyl)-1-(4-phenoxybenzyl)-1H-1,2,3-triazole-4-carboxamide;
N-((6-amino-2,4-dimethylpyridin-3-yl)methyl)-1-(naphthalen-1-ylmethyl)-1H-1,2,3-triazole-4-carboxamide;
N-((6-amino-2,4-dimethylpyridin-3-yl)methyl)-1-(naphthalen-2-ylmethyl)-1H-1,2,3-triazole-4-carboxamide;
1-(4-(1H-pyrazol-1-yl)benzyl)-N-((6-amino-2,4-dimethylpyridin-3-yl)methyl)-1H-1,2,3-triazole-4-carboxamide;
1-(3-(1H-pyrazol-1-yl)benzyl)-N-((6-amino-2,4-dimethylpyridin-3-yl)methyl)-1H-1,2,3-triazole-4-carboxamide;
N-((6-amino-2,4-dimethylpyridin-3-yl)methyl)-1-(3-(pyrrolidin-1-yl)benzyl)-1H-1,2,3-triazole-4-carboxamide;
N-((6-amino-2,4-dimethylpyridin-3-yl)methyl)-2-(benzofuran-2-ylmethyl)-2H-1,2,3-triazole-4-carboxamide;
1-(4-((1H-imidazol-1-yl)methyl)benzyl)-N-((6-amino-2,4-dimethylpyridin-3-yl)methyl)-1H-1,2,3-triazole-4-carboxamide;
1-(3-((1H-imidazol-1-yl)methyl)benzyl)-N-((6-amino-2,4-dimethylpyridin-3-yl)methyl)-1H-1,2,3-triazole-4-carboxamide;
N-((6-amino-2,4-dimethylpyridin-3-yl)methyl)-2-benzylthiazole-4-carboxamide;
N-((6-amino-2,4-dimethylpyridin-3-yl)methyl)-5-phenoxyfuran-2-carboxamide;
N-((6-amino-2,4-dimethylpyridin-3-yl)methyl)-1-benzyl-3-methyl-1H-pyrazole-4-carboxamide;
N-((6-amino-2,4-dimethylpyridin-3-yl)methyl)-1-(furan-2-ylmethyl)-2,5-dimethyl-1H-pyrrole-3-carboxamide;
N-((6-amino-2,4-dimethylpyridin-3-yl)methyl)-2,5-dimethyl-1-(1-phenylethyl)-1H-pyrrole-3-carboxamide;
N-((6-amino-2,4-dimethylpyridin-3-yl)methyl)-4-(morpholinosulfonyl)-1H-pyrrole-2-carboxamide;
N-((6-amino-2,4-dimethylpyridin-3-yl)methyl)-1-(2,6-difluorobenzyl)-1H-1,2,3-triazole-4-carboxamide;
N-((6-amino-2,4-dimethylpyridin-3-yl)methyl)-1-(3-cyanobenzyl)-1H-1,2,3-triazole-4-carboxamide;
N-((6-amino-2,4-dimethylpyridin-3-yl)methyl)-2-benzyl-4-methylthiazole-5-carboxamide;
N-((6-amino-2,4-dimethylpyridin-3-yl)methyl)-1-benzyl-1H-1,2,4-triazole-3-carboxamide;
N-((6-amino-2,4-dimethylpyridin-3-yl)methyl)-1-(4-(6-methylpyrazin-2-yloxy)benzyl)-1H-pyrazole-4-carboxamide;
N-((6-amino-2,4-dimethylpyridin-3-yl)methyl)-2-benzyloxazole-4-carboxamide;
1-(4-((1H-1,2,4-triazol-1-yl)methyl)benzyl)-N-((6-amino-2,4-dimethylpyridin-3-yl)methyl)-1H-1,2,4-triazole-3-carboxamide;
N-((6-amino-4-(2-methoxyethoxy)-2-methylpyridin-3-yl)methyl)-1-benzyl-1H-pyrazole-4-carboxamide;
N-((6-amino-2,4-dimethylpyridin-3-yl)methyl)-1-(biphenyl-4-ylmethyl)-1H-1,2,4-triazole-3-carboxamide;
N-((6-amino-2,4-dimethylpyridin-3-yl)methyl)-1-(naphthalen-1-ylmethyl)-1H-1,2,4-triazole-3-carboxamide;
N-((6-amino-2,4-dimethylpyridin-3-yl)methyl)-1-(4-phenoxybenzyl)-1H-1,2,4-triazole-3-carboxamide;
N-((6-amino-2,4-dimethylpyridin-3-yl)methyl)-1-(naphthalen-2-ylmethyl)-1H-1,2,4-triazole-3-carboxamide;
N-((6-amino-2,4-dimethylpyridin-3-yl)methyl)-1-(4-(2-oxopyrrolidin-1-yl)benzyl)-1H-pyrazole-4-carboxamide;
1-(4-(1H-pyrazol-1-yl)benzyl)-N-((6-amino-2,4-dimethylpyridin-3-yl)methyl)-1H-1,2,4-triazole-3-carboxamide;
1-(3-(1H-pyrazol-1-yl)benzyl)-N-((6-amino-2,4-dimethylpyridin-3-yl)methyl)-1H-1,2,4-triazole-3-carboxamide;
N-((6-amino-2,4-dimethylpyridin-3-yl)methyl)-1-(3-(pyrrolidin-1-yl)benzyl)-1H-1,2,4-triazole-3-carboxamide;
N-((6-amino-2,4-dimethylpyridin-3-yl)methyl)-1-((2-morpholinopyridin-4-yl)methyl)-1H-pyrazole-4-carboxamide;
N-((6-amino-2,4-dimethylpyridin-3-yl)methyl)-1-benzyl-1H-pyrrole-3-carboxamide;
N-((6-amino-2,4-dimethylpyridin-3-yl)methyl)-1-(3-(2-methoxyethyl)benzyl)-1H-pyrazole-4-carboxamide;
N-((6-amino-2,4-dimethylpyridin-3-yl)methyl)-2,5-dimethyl-1-(phenylsulfonyl)-1H-pyrrole-3-carboxamide;
N-((6-amino-2,4-dimethylpyridin-3-yl)methyl)-1-(3,5-dimethoxybenzyl)-1H-pyrazole-4-carboxamide;
N-((6-amino-2,4-dimethylpyridin-3-yl)methyl)-4-methyl-1-(phenylsulfonyl)-1H-pyrrole-3-carboxamide;
N-((6-amino-2,4-dimethylpyridin-3-yl)methyl)-1-((2,3-dimethyl-1H-indol-5-yl)methyl)-1H-pyrazole-4-carboxamide;
N-((6-amino-2,4-dimethylpyridin-3-yl)methyl)-1-benzyl-4-methyl-1H-pyrrole-3-carboxamide;
N-((6-amino-2,4-dimethylpyridin-3-yl)methyl)-2-methyl-5-((1-oxoisoquinolin-2(1H)-yl)methyl)furan-3-carboxamide;
N-((6-amino-2,4-dimethylpyridin-3-yl)methyl)-1-(4-(trifluoromethoxy)benzyl)-1H-pyrazole-4-carboxamide;
N-((6-amino-2,4-dimethylpyridin-3-yl)methyl)-1-(3-cyanobenzyl)-1H-pyrazole-4-carboxamide;
N-((6-amino-2,4-dimethylpyridin-3-yl)methyl)-1-(4-cyanobenzyl)-1H-pyrazole-4-carboxamide;
N-((6-amino-2,4-dimethylpyridin-3-yl)methyl)-1-(naphthalen-2-ylmethyl)-1H-pyrazole-4-carboxamide;
N-((6-amino-2,4-dimethylpyridin-3-yl)methyl)-1-(3-fluorobenzyl)-1H-pyrazole-4-carboxamide;
N-((6-amino-2-methylpyridin-3-yl)methyl)-1-benzyl-1H-pyrazole-4-carboxamide;
N-((6-amino-2,4-dimethylpyridin-3-yl)methyl)-1-((6-methylpyridin-2-yl)methyl)-1H-pyrazole-4-carboxamide;
N-((6-amino-2,4-dimethylpyridin-3-yl)methyl)-1-(2-chlorobenzyl)-1H-pyrazole-4-carboxamide;
N-((6-amino-2,4-dimethylpyridin-3-yl)methyl)-1-(cyclohexylmethyl)-1H-pyrazole-4-carboxamide;
N-((6-amino-2,4-dimethylpyridin-3-yl)methyl)-1-(4-(phenoxymethyl)benzyl)-1H-pyrazole-4-carboxamide;
N-((6-amino-2,4-dimethylpyridin-3-yl)methyl)-1-(3,4-difluorobenzyl)-1H-pyrazole-4-carboxamide;
N-((6-amino-2,4-dimethylpyridin-3-yl)methyl)-1-(4-(3-methyl-1,2,4-oxadiazol-5-yl)benzyl)-1H-pyrazole-4-carboxamide;
N-((6-amino-2,4-dimethylpyridin-3-yl)methyl)-1-(3-chlorobenzyl)-1H-pyrazole-4-carboxamide;
N-((6-amino-2,4-dimethylpyridin-3-yl)methyl)-1-(2,4-difluorobenzyl)-1H-pyrazole-4-carboxamide;

N-((6-amino-2,4-dimethylpyridin-3-ylmethyl)-1-(4-(benzyloxy)benzyl)-1H-pyrazole-4-carboxamide;
N-((6-amino-2,4-dimethylpyridin-3-yl)methyl)-1-((3,4-dihydro-2H-benzo[b][1,4]dioxepin-6-yl)methyl)-1H-pyrazole-4-carboxamide;
N-((6-amino-2,4-dimethylpyridin-3-yl)methyl)-1-(4-chlorobenzyl)-1H-pyrazole-4-carboxamide;
N-((6-amino-2,4-dimethylpyridin-3-yl)methyl)-1-((2-methylthiazol-4-yl)methyl)-1H-pyrazole-4-carboxamide;
N-((6-amino-2,4-dimethylpyridin-3-yl)methyl)-1-(pyridin-3-ylmethyl)-1H-pyrazole-4-carboxamide;
N-((6-amino-2,4-dimethylpyridin-3-yl)methyl)-1-((6-(hydroxymethyl)pyridin-2-yl)methyl)-1H-pyrazole-4-carboxamide;
N-((6-amino-2,4-dimethylpyridin-3-yl)methyl)-1-(1-phenylethyl)-1H-pyrazole-4-carboxamide;
N-((6-amino-2,4-dimethylpyridin-3-yl)methyl)-1-((1-methyl-1H-benzo[d][1,2,3]triazol-5-yl)methyl)-1H-pyrazole-4-carboxamide;
N-((6-amino-2,4-dimethylpyridin-3-yl)methyl)-1-(3-carbamoylbenzyl)-1H-pyrazole-4-carboxamide;
N-((6-amino-2,4-dimethylpyridin-3-yl)methyl)-1-(benzo[d][1,3]dioxol-5-ylmethyl)-1H-pyrazole-4-carboxamide;
N-((6-amino-2,4-dimethylpyridin-3-yl)methyl)-1-((3-methylquinoxalin-2-yl)methyl)-1H-pyrazole-4-carboxamide;
N-((6-amino-2,4-dimethylpyridin-3-yl)methyl)-1-(benzo[d]thiazol-2-ylmethyl)-1H-pyrazole-4-carboxamide;
N-((6-amino-2,4-dimethylpyridin-3-yl)methyl)-1-(benzo[d]isoxazol-3-ylmethyl)-1H-pyrazole-4-carboxamide;
N-((6-amino-2,4-dimethylpyridin-3-yl)methyl)-1-(2-cyanobenzyl)-1H-indole-3-carboxamide;
N-((6-amino-2,4-dimethylpyridin-3-yl)methyl)-1-benzyl-1H-indole-3-carboxamide;
N-((6-amino-2,4-dimethylpyridin-3-yl)methyl)-1-benzyl-2,5-dimethyl-1H-pyrrole-3-carboxamide;
N-((6-amino-2,4-dimethylpyridin-3-yl)methyl)-1-(4-(morpholinomethyl)benzyl)-1H-pyrazole-4-carboxamide;
N-((6-amino-2,4-dimethylpyridin-3-yl)methyl)-1-(4-(3-cyclopropylureido)benzyl)-1H-pyrazole-4-carboxamide;
N-((6-amino-2,4-dimethylpyridin-3-yl)methyl)-5-benzyl-1H-1,2,4-triazole-3-carboxamide;
N-((6-amino-2,4-dimethylpyridin-3-yl)methyl)-1-(4-(pyridin-4-yl)benzyl)-1H-pyrazole-4-carboxamide;
N-((6-amino-2,4-dimethylpyridin-3-yl)methyl)-1-(biphenyl-3-ylmethyl)-1H-pyrazole-4-carboxamide;
N-((6-amino-2,4-dimethylpyridin-3-yl)methyl)-1-(3-(morpholinosulfonyl)benzyl)-1H-pyrazole-4-carboxamide;
N-((6-amino-2,4-dimethylpyridin-3-yl)methyl)-1-(3-(phenylcarbamoyl)benzyl)-1H-pyrazole-4-carboxamide;
N-((6-amino-2,4-dimethylpyridin-3-yl)methyl)-1-(4-(pyrrolidin-1-ylmethyl)benzyl)-1H-pyrazole-4-carboxamide;
N-((6-amino-2,4-dimethylpyridin-3-yl)methyl)-1-(3-(piperidine-1-carbonyl)benzyl)-1H-pyrazole-4-carboxamide;
N-((6-amino-2,4-dimethylpyridin-3-yl)methyl)-1-(4-(isopropylcarbamoyl)benzyl)-1H-pyrazole-4-carboxamide;
N-((6-amino-2,4-dimethylpyridin-3-yl)methyl)-1-(4-(morpholine-4-carbonyl)benzyl)-1H-pyrazole-4-carboxamide;
N-((6-amino-2,4-dimethylpyridin-3-yl)methyl)-1-(4-(1-methyl-1H-pyrazol-3-ylcarbamoyl)benzyl)-1H-pyrazole-4-carboxamide;
5-(amino(phenyl)methyl)-N-((6-amino-2,4-dimethylpyridin-3-yl)methyl)-1H-1,2,4-triazole-3-carboxamide;
N-((6-amino-2,4-dimethylpyridin-3-yl)methyl)-3-(biphenyl-4-ylmethyl)-1H-1,2,4-triazole-5-carboxamide;
N-((6-amino-2,4-dimethylpyridin-3-yl)methyl)-3-(4-phenoxybenzyl)-1H-1,2,4-triazole-5-carboxamide;
N-((6-amino-2,4-dimethylpyridin-3-yl)methyl)-1-(4-(N,N-dimethylsulfamoyl)benzyl)-1H-pyrazole-4-carboxamide;
N-((6-amino-2,4-dimethylpyridin-3-yl)methyl)-1-(biphenyl-4-ylsulfonyl)-1H-pyrrole-3-carboxamide;
N-((6-amino-2,4-dimethylpyridin-3-yl)methyl)-1-(5-chlorothiophen-2-ylsulfonyl)-1H-pyrrole-3-carboxamide;
N-((6-amino-2,4-dimethylpyridin-3-yl)methyl)-1-(3-methoxyphenylsulfonyl)-1H-pyrrole-3-carboxamide;
N-((6-amino-2,4-dimethylpyridin-3-yl)methyl)-1-(4-methyl-3,4-dihydro-2H-benzo[b][1,4]oxazin-6-ylsulfonyl)-1H-pyrrole-3-carboxamide;
N-((6-amino-2,4-dimethylpyridin-3-yl)methyl)-1-(1-methyl-1H-indol-5-ylsulfonyl)-1H-pyrrole-3-carboxamide;
N-((6-amino-2,4-dimethylpyridin-3-yl)methyl)-1-(3-(pyrimidin-2-yl)phenylsulfonyl)-1H-pyrrole-3-carboxamide;
N-((6-amino-2,4-dimethylpyridin-3-yl)methyl)-1-(4-(3,5-dimethyl-1H-pyrazol-1-yl)phenylsulfonyl)-1H-pyrrole-3-carboxamide;
2-(4-((4-((6-amino-2,4-dimethylpyridin-3-yl)methylcarbamoyl)-1H-pyrazol-1-yl)methyl)phenoxy)acetic acid;
N-((6-amino-2,4-dimethylpyridin-3-yl)methyl)-1-(4-(cyanomethoxy)benzyl)-1H-pyrazole-4-carboxamide;
N-((6-amino-2-methyl-4-(oxazol-2-ylmethoxy)pyridin-3-yl)methyl)-1-benzyl-1H-1,2,3-triazole-4-carboxamide;
N-((6-amino-2-methyl-4-(oxazol-2-ylmethoxy)pyridin-3-yl)methyl)-1-benzyl-1H-1,2,3-triazole-4-carboxamide;
N-((6-amino-4-methylpyridin-3-yl)methyl)-1-benzyl-1H-pyrazole-4-carboxamide;
N-((6-amino-2,4-dimethylpyridin-3-yl)methyl)-1-(4-((3-oxo-2,3-dihydro-1H-pyrazol-1-yl)methyl)benzyl)-1H-pyrazole-4-carboxamide;
1-(4-((1H-1,2,3-triazol-1-yl)methyl)benzyl)-N-((6-amino-2,4-dimethylpyridin-3-yl)methyl)-1H-pyrazole-4-carboxamide;
N-((6-amino-2,4-dimethylpyridin-3-yl)methyl)-1-(4-((2,5-dimethyl-3-oxo-2,3-dihydro-1H-pyrazol-1-yl)methyl)benzyl)-1H-pyrazole-4-carboxamide;
N-((6-amino-2,4-dimethylpyridin-3-yl)methyl)-1-(4-((2-oxopyridin-1(2H)-yl)methyl)benzyl)-1H-pyrazole-4-carboxamide;
N-((6-amino-2,4-dimethylpyridin-3-yl)methyl)-1-(4-((2-oxopyrrolidin-1-yl)methyl)benzyl)-1H-pyrazole-4-carboxamide;
N-((6-amino-4-chloro-2-methylpyridin-3-yl)methyl)-1-benzyl-1H-pyrazole-4-carboxamide;
1-(4-((1H-pyrazol-1-yl)methyl)benzyl)-N-((6-amino-2,4-dimethylpyridin-3-yl)methyl)-1H-pyrazole-4-carboxamide;
N-((6-amino-2,4-dimethylpyridin-3-yl)methyl)-1-(4-((4-methyl-1H-pyrazol-1-yl)methyl)benzyl)-1H-pyrazole-4-carboxamide;
N-((6-amino-2,4-dimethylpyridin-3-yl)methyl)-1-(4-((5-methyl-1H-pyrazol-1-yl)methyl)benzyl)-1H-1,2,3-triazole-4-carboxamide;
N-((6-amino-2,4-dimethylpyridin-3-yl)methyl)-1-(4-((3,5-dimethyl-1H-pyrazol-1-yl)methyl)benzyl)-1H-1,2,3-triazole-4-carboxamide;
N-((6-amino-4-(3,3-dimethyl-2-oxobutoxy)-2-methylpyridin-3-yl)methyl)-1-(naphthalen-2-ylmethyl)-1H-pyrazole-4-carboxamide;
N-((6-Amino-2,4-dimethylpyridin-3-yl)methyl)-1-((1-(2-methoxyethyl)-1,2,3,4-tetrahydroquinolin-7-yl)methyl)-1H-pyrazole-4-carboxamide;
N-((6-Amino-2,4-dimethylpyridin-3-yl)methyl)-1-((4-methyl-3-oxo-3,4-dihydro-2H-benzo[b][1,4]oxazin-6-yl)methyl)-1H-pyrazole-4-carboxamide;

N-((6-Amino-2,4-dimethylpyridin-3-yl)methyl)-1-((1-methyl-1,2,3,4-tetrahydroquinolin-7-yl)methyl)-1H-pyrazole-4-carboxamide;

N-((6-amino-2,4-dimethylpyridin-3-yl)methyl)-1-((2-methylquinolin-6-yl)methyl)-1H-1,2,3-triazole-4-carboxamide;

N-((6-amino-2,4-dimethylpyridin-3-yl)methyl)-1-((2-methylquinolin-6-yl)methyl)-1H-pyrazole-4-carboxamide;

N-((6-amino-2,4-dimethylpyridin-3-yl)methyl)-1-(quinolin-3-ylmethyl)-1H-pyrazole-4-carboxamide;

N-((6-amino-2,4-dimethylpyridin-3-yl)methyl)-1-((7-methylquinolin-3-yl)methyl)-1H-1,2,3-triazole-4-carboxamide;

N-((6-amino-2,4-dimethylpyridin-3-yl)methyl)-1-((7-chloroquinolin-2-yl)methyl)-1H-pyrazole-4-carboxamide;

N-((6-amino-2,4-dimethylpyridin-3-yl)methyl)-1-((7-chloroquinolin-2-yl)methyl)-1H-1,2,3-triazole-4-carboxamide;

N-((6-amino-2-methylpyridin-3-yl)methyl)-1-((2-methylquinolin-6-yl)methyl)-1H-pyrazole-4-carboxamide;

N-((6-amino-2-methylpyridin-3-yl)methyl)-1-((6-fluoro-4-(trifluoromethyl)quinolin-2-yl)methyl)-1H-pyrazole-4-carboxamide;

N-((6-amino-2-methylpyridin-3-yl)methyl)-1-((2,5,7-trimethylquinolin-3-yl)methyl)-1H-pyrazole-4-carboxamide;

N-((6-amino-2,4-dimethylpyridin-3-yl)methyl)-1-((6-fluoro-4-(trifluoromethyl)quinolin-2-yl)methyl)-1H-pyrazole-4-carboxamide;

N-((6-amino-2,4-dimethylpyridin-3-yl)methyl)-1-((6-methoxynaphthalen-2-yl)methyl)-1H-pyrazole-4-carboxamide;

N-((6-Amino-2,4-dimethylpyridin-3-yl)cyclopropyl)-1-((2-methylquinolin-6-yl)methyl)-1H-1,2,3-triazole-4-carboxamide;

N-((6-Amino-2,4-dimethylpyridin-3-yl)methyl)-1-((1,2-dimethyl-1H-benzo[d]imidazol-5-yl)methyl)-1H-pyrazole-4-carboxamide;

N-((6-amino-2,4-dimethylpyridin-3-yl)methyl)-1-((1,2,3-trimethyl-1H-indol-5-yl)methyl)-1H-1,2,3-triazole-4-carboxamide;

N-((6-Amino-4-chloro-2-methylpyridin-3-yl)methyl)-1-(4-((2-oxopyridin-1-((2H)-yl)methyl)benzyl)-1H-pyrazole-4-carboxamide;

N-((6-Amino-2,4-dimethylpyridin-3-yl)methyl)-1-((1,2-dimethyl-1H-indol-5-yl)methyl)-1H-pyrazole-4-carboxamide;

N-((6-amino-2,4-dimethylpyridin-3-yl)methyl)-1-((2-methylimidazo[1,2-a]pyridin-6-yl)methyl)-1H-pyrazole-4-carboxamide;

N-((6-amino-2,4-dimethylpyridin-3-yl)methyl)-2-((2-methylquinolin-6-yl)methyl)oxazole-4-carboxamide;

N-((6-Amino-2,4-dimethylpyridin-3-yl)methyl)-1-((7-aminothieno[2,3-c]pyridin-5-yl)methyl)-1H-pyrazole-4-carboxamide;

N-((6-Amino-4-chloro-2-methylpyridin-3-yl)methyl)-1-(naphthalen-2-ylmethyl)-1H-pyrazole-4-carboxamide;

N-((6-Amino-2,4-dimethylpyridin-3-yl)methyl)-1-((3-chloroquinolin-6-yl)methyl)-1H-pyrazole-4-carboxamide;

N-((6-amino-2,4-dimethylpyridin-3-yl)methyl)-1-((1,1-dioxido-2,3-dihydrobenzo[b]thiophen-5-yl)methyl)-1H-pyrazole-4-carboxamide and N-((6-Amino-4-chloro-2-methylpyridin-3-yl)methyl)-1-((2-methylquinolin-6-yl)methyl)-1H-1,2,3-triazole-4-carboxamide.

In one embodiment, the invention provides a compound which is (S)-5-(amino(phenyl)methyl)-N-((6-amino-2,4-dimethylpyridin-3-yl)methyl)-1H-1,2,4-triazole-3-carboxamide.

In a further aspect, the invention also provides a process for the production of compounds of the formula I. Compounds of the formula I are obtainable according to the following process as described in scheme 1:

Scheme 1:

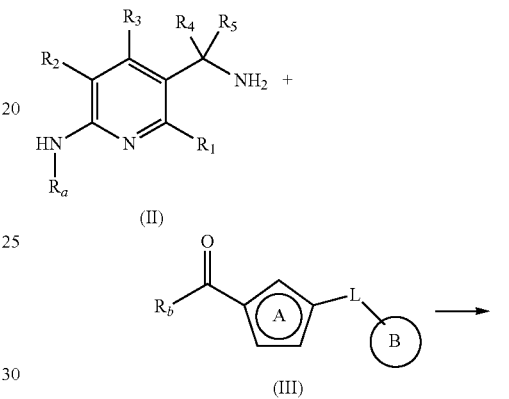

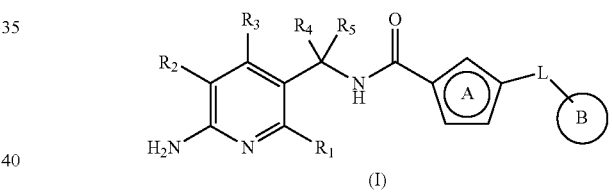

A compound of formula I may be obtained by reacting a compound of formula II, in which $R_1$, $R_2$, $R_3$, $R_4$ and $R_5$ are as defined under formula I, and $R_a$ is hydrogen or an amine protecting group, for example $C_{1-6}$alkoxycarbonyl, e.g. tertiary butyloxycarbonyl, allyloxycarbonyl, benzyloxycarbonyl or fluorenylmethoxycarbonyl, with a compound of formula III, in which A, L and B are as defined under formula I, and $R_b$ is hydroxy, halogen or $C_{1-6}$alkoxy, in the presence of a suitable base, e.g. collidine, N,N-diisopropylethylamine (DIPEA), triethylamine or 4-DMAP (4-dimethylaminopyridine), in the presence of a suitable solvent, e.g. dimethylformamide (DMF), DMSO (dimethylsulfoxide), tetrahydrofurane (THF) or DCM, and, if $R_b$ is hydroxy, in the presence of a suitable coupling reagent, e.g. O-(7-azabenzotriazol-1-yl)-N,N,N',N'-tetramethyluronium hexafluorophosphate (HATU), propyl phosphonic anhydride, O-(benzotriazol-1-yl)-N,N,N',N'-tetramethyluronium hexafluorophosphate (HBTU) or 2-tert-butylimino-2-diethylamino-1,3-dimethylperhydro-1,3,2-diazaphosphorine (BEMP); and, if $R_a$ is an amine protecting group, followed by deprotecting the amine-functionality.

Compounds of the formula IIa are obtainable according to the following process as described in scheme 2:

Scheme 2:

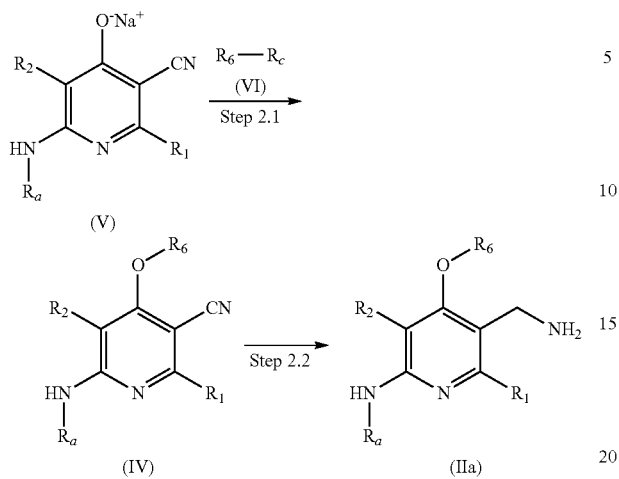

Step 2.1: A nitrile of formula IV, in which $R_1$, $R_2$ and $R_6$ are as defined under formula I, and $R_a$ is hydrogen or an amine protecting group, for example $C_{1-6}$alkoxycarbonyl, e.g. tertiary butyloxycarbonyl, allyloxycarbonyl, benzyloxycarbonyl or fluorenylmethoxycarbonyl, may be obtained by reacting a nitrile of formula V, in which $R_1$ and $R_2$ are as defined under formula I, and $R_a$ is hydrogen or an amine protecting group, for example $C_{1-6}$alkoxycarbonyl, e.g. tertiary butyloxycarbonyl, allyloxycarbonyl, benzyloxycarbonyl or fluorenylmethoxycarbonyl, with a compound of formula VI, in which $R_6$ is as defined under formula I and $R_c$ is a leaving group, for example mesylate, tosylate, triflate or halogen, in the presence of a suitable base, e.g. potassium carbonate or cesium carbonate, and in the presence of a suitable solvent, e.g. DMF or DMSO.

Step 2.2: A compound of formula IIa, in which $R_1$, $R_2$ and $R_6$ are as defined under formula I, and $R_a$ is hydrogen or an amine protecting group, for example $C_{1-6}$alkoxycarbonyl, e.g. tertiary butyloxycarbonyl, allyloxycarbonyl, benzyloxycarbonyl or fluorenylmethoxycarbonyl, may be obtained by reacting the nitrile of formula IV with a suitable hydrogenation agent, e.g. diisobutyl aluminium hydride, borane or hydrogen in the presence of palladium/charcoal, raney-nickel or platinum oxide, optionally in the presence of a suitable acid or base, e.g. HCl or ammonia, when using hydrogen in the presence of palladium/charcoal, raney-nickel or platinum oxide, and in the presence of a suitable solvent, e.g. THF for diisobutyl aluminium hydride or borane or a solvent selected from methanol, ethanol and chloroform for hydrogen in the presence of palladium/charcoal, raney-nickel or platinum oxide.

Further compounds of formula I may be obtainable from compounds of formula I—prepared as described according to scheme 1—by reduction, oxidation and/or other functionalization of resulting compounds and/or by cleavage of any protecting group(s) optionally present, and of recovering the so obtainable compound of the formula I.

The reactions can be effected according to conventional methods, for example as described in the Examples.

The work-up of the reaction mixtures and the purification of the compounds thus obtainable may be carried out in accordance with known procedures.

Acid addition salts may be produced from the free bases in known manner, and vice-versa.

Compounds of the formula I can also be prepared by further conventional processes, e.g. as described in the Examples, which processes are further aspects of the invention.

The starting materials, e.g. compounds of the formulae III, V and VI, are known or may be prepared according to conventional procedures starting from known compounds, for example as described in the Examples.

In a further aspect, the invention also provides a compound of formula IIa

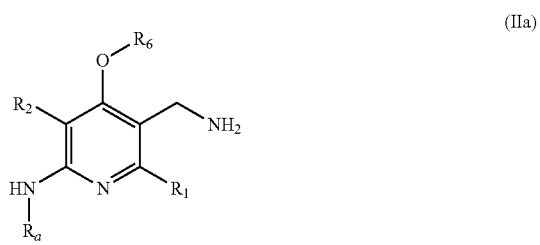

in which $R_1$, $R_2$ and $R_6$ are as defined under formula I, and $R_a$ is hydrogen or an amine protecting group, for example $C_{1-6}$alkoxycarbonyl, e.g. tertiary butyloxycarbonyl. Preferably, $R_a$ is hydrogen.

In another aspect, the invention provides a pharmaceutical composition comprising a compound of the invention and a pharmaceutically acceptable carrier. The pharmaceutical composition can be formulated for particular routes of administration such as oral administration, parenteral administration, and rectal administration, etc. In addition, the pharmaceutical compositions of the invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and/or
  e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention further provides anhydrous pharmaceutical compositions and dosage forms comprising the compounds of the invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (a g., vials), blister packs, and strip packs.

The invention further provides pharmaceutical compositions and dosage forms that comprise one or more agents that reduce the rate by which the compound of the invention as an active ingredient will decompose. Such agents, which are referred to herein as "stabilizers," include, but are not limited to, antioxidants such as ascorbic acid, pH buffers, or salt buffers, etc.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The compounds of formula I in free form or in pharmaceutically acceptable salt form, exhibit valuable pharmacological properties, e.g. plasmakallikrein inhibiting properties, e.g. as indicated in in-vitro and in-vivo tests as provided in the next sections and are therefore indicated for therapy.

Compounds of the invention may be useful in the treatment of indications, such as: hereditary angioedema (HAE), retinopathy or diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, CME following vascular occlusion (e.g. central retina vein occlusion, branch retinal vein occlusion, or hemiretinal vein occlusion), retinal edema, complications related to cataract surgery in diabetic retinopathy, hypertensive retinopathy, retinal trauma, dry and wet aged-related macular degeneration (AMD), ischemic reperfusion injuries, e.g. in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke, myocardial infarction, acquired angioedema drug-related (ACE-inhibitors), edema, high altitude cerebral edema, cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, hemorrhagic transformation of ischemic stroke, cerebral trauma associate with injury or surgery, brain aneurysm, arterio-venous malformation, reduction of blood losses during surgical procedures (e.g. cardiothoracic surgery, such as cardiopulmonary bypass or coronary artery bypass grafting), blood coagulation disorders such as thrombosis, itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, chronic kidney disease, heart failure, microalbuminuria, albuminuria, proteinuria, disorders associated with increased vascular permeability (e.g. increased retinal vascular permeability, increased leg, feet, ankle vascular permeability), cerebral hemorrhage, microalbuminuria, albuminuria and proteinuria, deep vein thrombosis, coagulation from post fibrinolytic treatments, angina, angioedema, sepsis, arthritis (e.g. rheumatoid arthritis, osteoarthritis, infection arthritis), lupus, gout, psoriasis, blood loss during cardiopulmonary bypass, inflammatory bowel, diabetes, diabetic complications, infectious diseases, astrocyte-activation related diseases (e.g. Alzheimer's disease or multiple sclerosis), Parkinson's disease, amyotrophic lateral sclerosis, Creutzfeld-Jacob disease, stroke, epilepsy and trauma (e.g. brain trauma)

Compounds of the invention may be especially useful in the treatment of an indication selected from: retinopathy and edema-associated diseases.

Thus, as a further embodiment, the invention provides the use of a compound of formula (I) in free form or in pharmaceutically acceptable salt form as a medicament.

As a further embodiment, the invention provides the use of a compound of formula (I) in free form or in pharmaceutically acceptable salt form in therapy.

In a further embodiment, the therapy is selected from a disease which is ameliorated by inhibition of plasmakallikrein. In another embodiment, the disease is selected from the afore-mentioned list, e.g. retinopathy and edema-associated diseases.

In another embodiment, the invention provides a method of treating a disease which is ameliorated by inhibition of plasmakallikrein comprising administration of a therapeutically acceptable amount of a compound of formula (I) in free form or in pharmaceutically acceptable salt form. In a further embodiment, the disease is selected from the afore-mentioned list, suitably retinopathy and edema-associated diseases.

In one embodiment, the invention provides a method of inhibiting plasmakallikrein in a subject, wherein the method comprises administering to the subject a therapeutically effective amount of a compound of formula I.

In a further embodiment, the invention provides a method of treating a disorder or a disease in a subject mediated by plasmakallikrein, wherein the method comprises administering to the subject a therapeutically effective amount of a compound of formula I. Preferably said disorder or said disease is selected from retinopathy and edema-associated diseases.

In yet a further embodiment, the invention provides the use of a compound of formula I, for the treatment of a disorder or disease in a subject mediated by plasmakallikrein.

In yet a further embodiment, the invention provides the use of a compound of formula I, for the treatment of a disorder or disease in a subject characterized by an abnormal activity of plasmakallikrein. Preferably said disorder or said disease is selected from retinopathy and edema-associated diseases.

The term "a therapeutically effective amount" of a compound of the invention refers to an amount of the compound of the invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the invention that, when administered to a subject, is effective to (1) at least partially alleviating, inhibiting, preventing and/or ameliorating a condition, or a disorder or a disease (i) mediated by plasmakallikrein, or (ii) associated with plasmakallikrein activity, or (iii) characterized by abnormal activity of plasmakallikrein; or (2) reducing or inhibiting the activity of plasmakallikrein; or (3) reducing or inhibiting the expression of plasmakallikrein. In another non-limiting embodiment, the term "a therapeutically effective amount" refers to the amount of the compound of the invention that, when administered to a cell, or a tissue, or a non-cellular biological material, or a medium, is effective to at least partially reducing or inhibiting the activity of plasmakallikrein; or at least partially reducing or inhibiting the expression of plasmakallikrein.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

The pharmaceutical composition or combination of the invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the invention can be assessed by in vitro & in vivo methods described herein.

The compound of the invention may be administered either simultaneously with, or before or after, at least one other therapeutic agent. The compound of the invention may be administered separately, by the same or different route of administration, or together in the same pharmaceutical composition.

The following Examples illustrate the invention, but do not limit it. In all structural formulas shown in the Examples methyl groups are represented as an open chemical bond. For elucidation, Example 134 is shown as

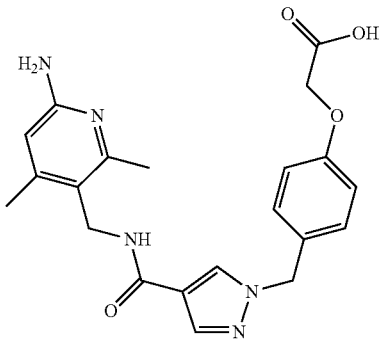 [SMILES: Cc1cc(N)nc(C)c1CNC(=O)c1cnn(Cc2ccc(OCC(=O)O)cc2)c1]

An alternative image would be:

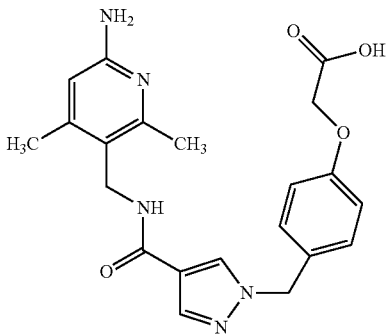 [SMILES: Cc1cc(N)nc(C)c1CNC(=O)c1cnn(Cc2ccc(OCC(=O)O)cc2)c1]

ABBREVIATIONS

ACN Acetonitrile
AcOH acetic acid
BEMP 2-tert-butylimino-2-diethylamino-1,3-dimethylperhydro-1,3,2-diazaphosphorine
br broad signal (NMR)
DCM dichloromethane
DIBAL-H diisobutylaluminum hydride
DIPEA N,N-diisopropylethylamine
4-DMAP 4-dimethylaminopyridine
DMF dimethylformamide
DMSO dimethylsulfoxide
DPPA diphenyl phosphoryl azide
EA ethyl acetate
EtOH ethanol
h hour(s)
HBTU O-(benzotriazol-1-yl)-N,N,N',N'-tetramethyluronium hexafluorophosphate
HATU O-(7-azabenzotriazol-1-yl)-N,N,N',N'-tetramethyluronium hexafluorophosphate
HOAt 1-hydroxy-7-azabenzotriazole
HOBt 1-hydroxybenzotriazole
HPLC high pressure liquid chromatography
LHMDS lithium bis(trimethylsilyl)amide
LiOH Lithium hydroxide
MeOH methanol
min minute(s)
MS mass spectrometry
NMR nuclear magnetic resonance spectroscopy
PTFA polytetrafluoroethylene
quant. quantitative
rt room temperature
Rt retention time
TBME tert-butyl methyl ether
TFA trifluoroacetic acid
THF tetrahydrofurane
UPLC ultra performance liquid chromatography

EXPERIMENTAL

1H NMR spectra were recorded using a Bruker AM 300 Spectrometer. HPLC was performed using an Agilent 1100 or 1200 series instrument. Mass spectra and LC/MS were determined using an Agilent 1100 series instrument, a HPLC-MS Waters Alliance 2690 instrument, or a HPLC-MS Waters Acquity SQD system.

Method A: LC-MS (method A) Instrument: Agilent 1100 series; column: Waters Sunfire 2.5 um C18, 3×30 mm, flow 1.4 mL/min, 40° C.; solvent: CH$_3$CN (0.1% CHOOH)=A; H$_2$O (0.1% CHOOH)=B; gradient: 0-2.5 min: NB=10/90 to 98/2, 0.5 min: 98% A, 0.1 min: A/B=98/2 to 10/90.

Method B: UPLC-MS Waters Alliance 2690; column: Acquity HSS T3, 1.8 um, 2.1×50 mm, flow 1.2 ml/min., 60° C., Solvent: CH$_3$CN (0.05% HCOOH)=A, H$_2$O (0.05% HCOOH)=B, gradient: 0-1.5 min: A/B=10/90 to 95/5.

Method C: HPLC Instrument: Agilent 1100 series; column: Agilent Eclipse 1.8 um, XBD-C18, 4.6×50 mm, flow 1.0 mL/min, 30° C.; solvent: CH$_3$CN (0.1% CF$_3$CO$_2$H)=A; H$_2$O (0.1% CF$_3$CO$_2$H)=B; gradient: 0-3 min: A/B=5/95 to 100/0, 1.5 min: 100% A, 0.5 min: A/B 100/0 to 5/95.

Method D: MS Instrument: Agilent 1100 series; detection: API-ES, positive/negative Method E: HPLC Instrument: Agilent 1100 series; column: Agilent Eclipse 1.8 um, XBD-C18, 2.1×30 mm, flow 0.6 mL/min, 30° C.; solvent: CH$_3$CN (0.1% CF$_3$CO$_2$H)=A; H$_2$O (0.1% CF$_3$CO$_2$H)=B; gradient: 0-6 min: A/B=5/95 to 100/0, 1.5 min: 100% A, 0.5 min: A/B 100/0 to 5/95.

Method F: UPLC-MS Waters Acquity; UPLC; column Acquity UPLC HSS T3 1.8 μm 2.1 mm×50 mm; flow 1.2 ml/min; 60° C.; solvent: A water+0.1% HCOOH/B acetonitrile+0.1% HCOOH; 0-0.5 min 90A:10B; 0.5-2.0 min 90A:10B-5A:95B; 2.0-3.0 min 5A:95B Method G: HPLC Instrument Agilent 1100 series; column: Waters SunFire, 2.5 um, 3×30 mm, flow 1.4 ml/min, 40° C.; solvent: H$_2$O (0.1% CF$_3$CO$_2$H); CH$_3$CN (0.1% CF$_3$CO$_2$H); gradient: FAST 10-98% CH$_3$CN in 2.5 min).

Method H: HPLC Instrument Agilent 1200 series; column: Agilent eclipse XDB-C18, 1.8 microm., 2.1×30 mm, flow 0.6 mL/min, 30° C.; solvent: CH$_3$CN (0.1% CF$_3$CO$_2$H)=A, H$_2$O (0.1% CF$_3$CO$_2$H)=B; gradient: 0-3 min: A/B=5/95 to 100/0, 3-3.75 min: 100% A, 3.75-4 min: NB=100/0 to 5/95.

Method I: Agilent 1100 series, LC-ZMD; column XBridge C18; 2.5 μm; 3×30 mm; gradient: A water+5% acetonitrile/B acetonitrile+0.5-1.0% HCOOH; 0-1.7 min 90A:10B-5A:95B, 1.6 ml/min flow; 1.7-2.4 min 5A:95B, 2.4 ml/min flow; column temperature 50° C.

Method J: HPLC Instrument Agilent 1100 series; column: Waters Symmetry C18, 3.5 um, 2.1×50 mm, flow 0.6 ml/min, 40° C.; Solvent: CH$_3$CN (0.1% CF$_3$CO$_2$H)=A, H$_2$O (0.1% CF$_3$CO$_2$H)=B gradient: 0-3.5 min: A/B=5/95 to 95/5.

Method K: (Rt$_K$=retention time K) Agilent 1100 series, LC-MSD; column X-Bridge C18 2.5 μm; 3×30 mm; gradient:

A water+0.05% formic acid+3.75 mM ammonium acetate/B acetonitrile+0.04% formic acid; 0-1.70 min 90A:10B-5A:95B, flow 1.2-1.4 ml/min; 1.70-2.40 min 5A:95B, flow 1.4-2.4 ml/min; 2.40-2.45 min 10A:90B-90A:10B, flow 2.4 ml/min; 2.45-2.50 min 90A:10B, flow 2.4-1.2 ml/min; column temperature 50° C.

Method L: ($Rt_L$=retention time L) Agilent 1100 series, LC-MSD; column X-Bridge C18 2.5 µm; 3×30 mm; gradient: A water+0.05% formic acid+3.75 mM ammonium acetate/B acetonitrile+0.04% formic acid; 0-3.70 min 95A:5B-5A:95B, flow 1.2-1.4 ml/min; 3.70-4.40 min 5A:95B, flow 1.4-2.4 ml/min; 4.40-4.45 min 5A:95B-95A:5B, flow 2.4 ml/min; 4.45-4.50 min 95A:5B, flow 2.4-1.2 ml/min; column temperature 50° C.

Method M: ($Rt_M$=retention time M): Agilent 1100 series, LC-MSD; column X-Bridge C18 2.5 µm; 3×30 mm; gradient: A water+0.05% formic acid+3.75 mM ammonium acetate/B acetonitrile+0.04% formic acid; 0-0.50 min 99A:1B, flow 1.2 ml/min; 0.50-2.20 min 99A:1B-5A:95B, flow 1.2-1.4 ml/min; 2.20-2.90 min 5A:95B, flow 1.4-2.4 ml/min; 2.90-2.95 min 5A:95B-99A:1B, flow 2.4-1.2 ml/min; column temperature 50° C.

Method N: ($Rt_N$=retention time N): Agilent 1100 series, LC-MSD; column X-Bridge C18 2.5 µm; 3×30 mm; gradient: A water+0.05% TFA/B acetonitrile+0.04% TFA; 0-0.50 min 99A:1B, flow 1.2 ml/min; 0.50-2.20 min 99A:1B-5A:95B, flow 1.2-1.4 ml/min; 2.20-2.90 min 5A:95B, flow 1.4-2.4 ml/min; 2.90-2.95 min 5A:95B-99A:1B, flow 2.4-1.2 ml/min; column temperature 50° C.

Method O: ($Rt_O$=retention time O): Agilent 1100 series, LC-MSD; column X-Bridge C18 2.5 µm; 3×30 mm; gradient: A water+0.05% TFA/B acetonitrile+0.04% TFA; 0-1.70 min 90A:10B-5A:95B, flow 1.2-1.4 ml/min; 1.70-2.40 min 5A:95B, flow 1.4-2.4 ml/min; 2.40-2.45 min 10A:90B-90A:10B, flow 2.4 ml/min; 2.45-2.50 min 90A:10B, flow 2.4-1.2 ml/min; column temperature 50° C.

Method P: ($Rt_P$=retention time P): Waters 2795 Alliance HT, LC-MSD; column X-Terra C18 3.5 µm; 4.6×20 mm; gradient: A water+0.1% TFA/B acetonitrile+0.1% TFA; 0-8 min 95A:5B-0A: 100B, flow 2 ml/min; 8-9.80 min 0A: 100B, flow 2 ml/min; 9.80-9.81 min 0A: 100B-95A:5B, flow 2-0.1 ml/min; column temperature 45° C.

Method Q: ($Rt_Q$=retention time Q): Waters 2795 Alliance HT, LC-MSD; column Sunfire C18 5 µm; 4.6×50 mm; gradient: A water+0.1% TFA/B acetonitrile+0.1% TFA; 0-8 min 97A:3B-17A:83B, flow 2 ml/min; 8-9.80 min 17A:83B-0A: 100B, flow 2 ml/min; 9.80-9.81 min 0A: 100B-95A:5B, flow 2-0.1 ml/min; column temperature 45° C.

Method R: Agilent 1100 series, LC-ZMD; column XBridge C18; 2.5 µm; 3×30 mm; gradient: A water+5% acetonitrile/B acetonitrile+0.05% TFA; 0-1.7 min 90A:10B-5A:95B, 1.6 ml/min flow; 1.7-2.4 min 5A:95B, 2.4 ml/min flow; column temperature 50° C.

Method S: Agilent 1100 series, LC-ZMD; column XBridge C18; 2.5 µm; 3×30 mm; gradient: A water+5% acetonitrile/B acetonitrile+0.05% TFA; 0-0.5 min 99A:1B, 1.4 ml/min flow; 0.5-2.2 min 99A:1B-5A:95B, 1.6 ml/min flow; 2.2-2.9 min 5A:95B, 2.4 ml/min flow; column temperature 50° C.

Method T: Agilent 1100 series, LC-ZMD; column Ascentis Express FusedCore C18 2.7 µm; 2.1×30 mm; gradient: A water+0.05% TFA/B acetonitrile+0.04% TFA; 0-1.40 min 98A:2B-2A:98B; 1.40-2.15 min 2A:98B; flow 1.2 ml/min; column temperature 50° C.

Method U: LC-MS (method V) Instrument: Agilent 1100 series; column: Waters Sunfire 2.5 um C18, 3×30 mm, flow 1.4 mL/min, 40° C.; solvent: CH3CN (0.1% TFA)=A; H₂O (0.1% TFA)=B; gradient: 0-2.5 min: A/B=10/90 to 98/2, 0.5 min: 98% A, 0.1 min: AB =98/2 to 10/90.

Method V: UPLC-MS Waters Acquity; UPLC; column Acquity UPLC HSS T3 1.8 µm 2.1 mm×50 mm; flow 1.2 ml/min; 60° C.; solvent: A water+0.05% HCOOH+ammonium acetate (3.75 mM)/B acetonitrile+0.04% HCOOH; 0-0.5 min 90A:10B; 0.5-2.0 min 90A:10B-5A:95B; 2.0-3.0 min 5A:95B.

Example 1

N-((6-amino-2,4-dimethylpyridin-3-yl)methyl)-2-methyl-5-((1-oxoisoquinolin-2(1H)-yl)methyl)furan-3-carboxamide

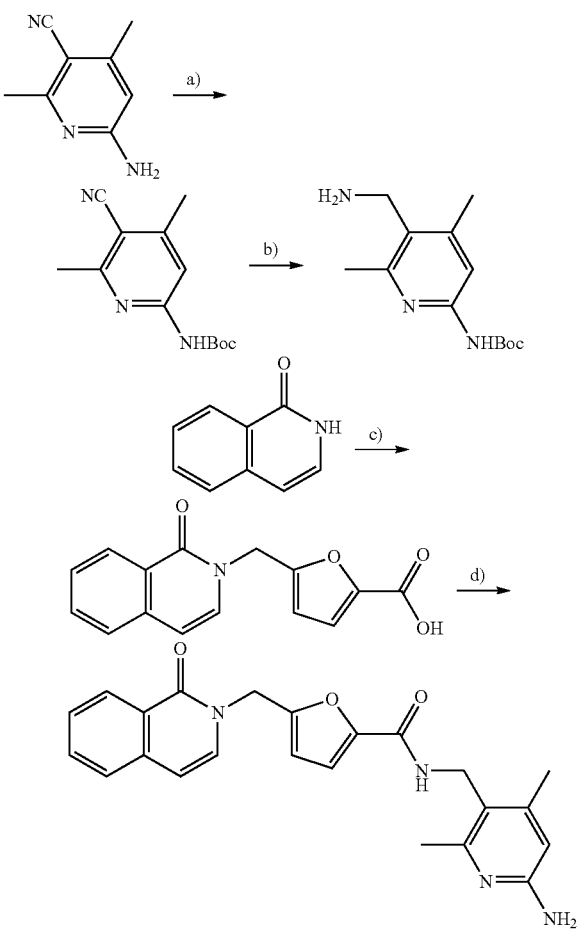

a) tent-Butyl 5-cyano-4,6-dimethylpyridin-2-ylcarbamate

To a mixture of 6-amino-2,4-dimethylnicotinonitrile (10 g, 67.9 mmol, prepared according to K. Sato, M. Shashi, T. Amakasu, K. Takeda, *Bulletin of the Chemical Society of Japan* 1969, 42, 2319) and DMAP (0.830 g, 6.79 mmol) in THF (200 ml) was added Boc₂O (27.5 g, 126 mmol) at rt. The reaction mixture was stirred for 14 h, before it was concentrated. Purification by column chromatography (CombiFlash Companion, 120 g SiO₂, heptane to heptane:EA 3:1) afforded a mixture of the mono- and bis-protected starting material.

This mixture was dissolved in MeOH (270 ml) and DCM (80 ml) and cooled to 0° C. NaOH (1N, 102 ml, 102 mmol) and H₂O₂ (35%, 8.92 ml, 102 mmol) were added and the reaction mixture was stirred at 0° C. for 75 min after which LCMS indicated complete conversion. The reaction mixture was transferred to an aqueous solution of Na₂SO₃ (2N, 300 ml, 600 mmol), concentrated in vacuo to ca. 300 ml (bath temperature<50° C.), and extracted with DCM (6×150 ml). The combined extracts were dried over Na₂SO₄, filtered and concentrated to dryness affording the desired product. LCMS $Rt_M$=1.97 min, [M+H]⁺=248.2.

b) tent-Butyl 5-(aminomethyl)-4,6-dimethylpyridin-2-ylcarbamate

To a mixture of tert-butyl 5-cyano-4,6-dimethylpyridin-2-ylcarbamate (10.8 g, 43.7 mmol) in THF (100 ml) were added about 15 cm³ of a Raney-Ni suspension in MeOH under Ar. The flask was sealed, and the suspension was vigorously stirred at it for 6 d under an atmosphere of hydrogen. The reaction mixture was filtered over a plug of cellite and eluted with DCM (200 ml), DCM-MeOH (9:1, 200 ml) and NH₃ in MeOH (7N, 100 ml). Removal of all volatiles in vacuo afforded the crude product which was recrystallized from MeOH-DCM to afford the title compound. LCMS $Rt_M$=1.13 min, [M+H]⁺=252.2.

c) 5-((1-oxoisoquinolin-2(1H-yl)methyl)furan-2-carboxylic acid

A solution of 1-hydroxychinolin (100 mg, 0.689 mmol) in dry THF (12 ml) was treated with LHMDS (1N in hexane, 1.45 ml, 1.45 mmol) and kept at 11 for 90 min. The reaction mixture was cooled to −10° C., before methyl 5-(chloromethyl)furan-2-carboxylate (120 mg, 0.689 mmol) and NaI (103 mg, 0.689 mmol) were added, and stirring was continued for 18 h while warming to rt. All volatiles were removed in vacuo. The crude product was partitioned between EA (10 ml) and water (20 ml), washed with brine (20 ml), dried over Na₂SO₄, filtered and concentrated. Purification by column chromatography (CombiFlash Companion, 12 g SiO₂, heptane to EA) afforded the substituted ester which was dissolved in EtOH (2 ml) and LiOH (2N, 0.420 ml, 0.840 mmol). After stirring at it for 18 h, the reaction mixture was acidified with 1N HCl, and all volatiles were removed in vacuo. The remaining residue was suspended in MeOH (2 ml) and filtered. Concentration of the filtrate afforded the title compound. LCMS $Rt_M$=1.71 min, [M+H]⁺=284.1.

d) N-((6-amino-2,4-dimethylpyridin-3-yl)methyl)-5-((1-oxoisoquinolin-2(1H)-yl)methyl)furan-2-carboxamide To a solution of tert-butyl 5-(aminomethyl)-4,6-dimethylpyridin-2-ylcarbamate (41.1 mg, 0.163 mmol) in THF (5 ml) were added collidine (0.022 ml, 0.163 mmol), 5-((1-oxoisoquinolin-2(1H)-yl)methyl)furan-2-carboxylic acid (44.0 mg, 0.163 mmol) and HATU (81.0 mg, 0.212 mmol). After stirring for 18 h at rt, all volatiles were removed in vacuo. The crude intermediate was purified by column chromatography (CombiFlash Companion, 12 g SiO₂, heptane to EA), dissolved in DCM (1 ml) and TFA (1 ml), kept for 1 h at rt, and concentrated. Purification by preparative HPLC (Waters Sunfire Prep C18 OBD 5 um, 100×19 mm, A: H₂O+0.1% TFA, B: MeCN+0.1% TFA, 6-36% B in 10 min, 30 ml/min, rt) afforded the title compound. ¹H-NMR (DMSO-d6, 400 MHz): 2.37 (s, 3H), 4.28 (d, 2H), 5.23 (s, 2H), 6.45 (d, 1H), 6.62 (s, 1H), 6.68 (d, 1H), 7.06 (d, 1H), 7.49-7.59 (m, 4H), 7.65-7.76 (m, 2H), 8.21 (d, 1H), 8.52 (t, 1H), 13.33 (s, 1H). LCMS $Rt_M$=1.50 min, [M+H]⁺=403.3.

Example 2

5-Benzyl-1-methyl-1H-[1,2,4]triazole-3-carboxylic acid (6-amino-2,4-dimethyl-pyridin-3-ylmethyl)-amide

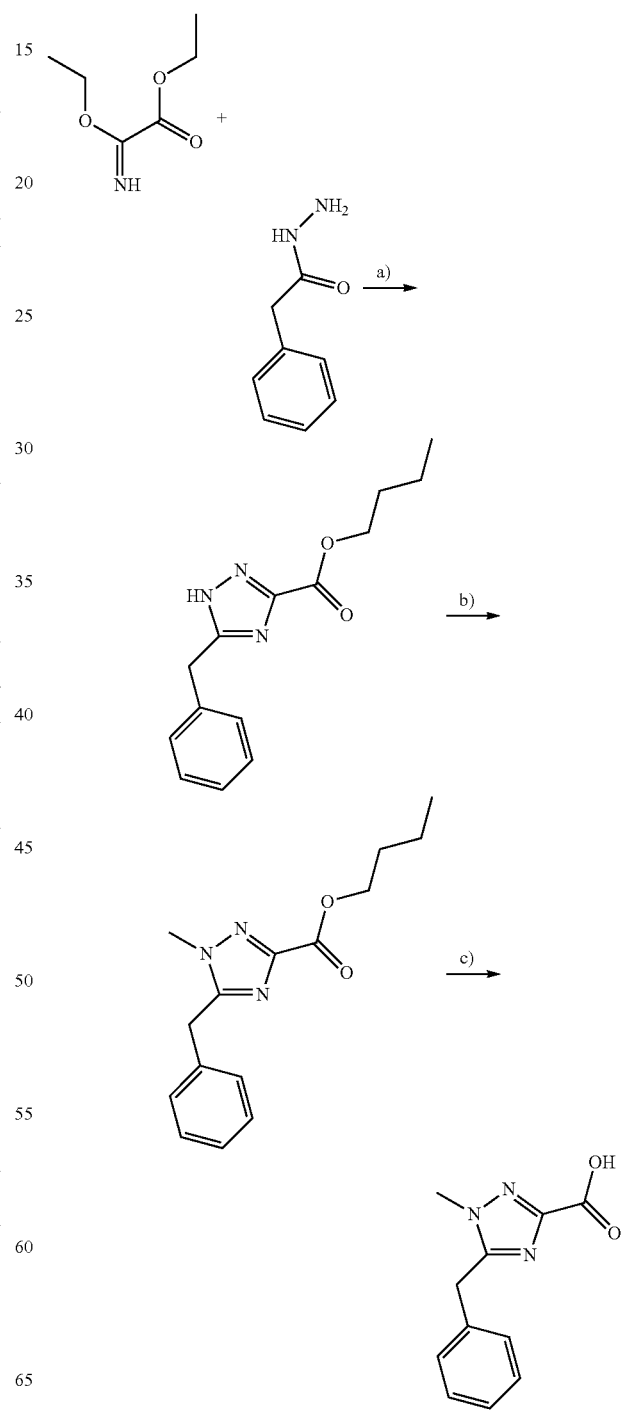

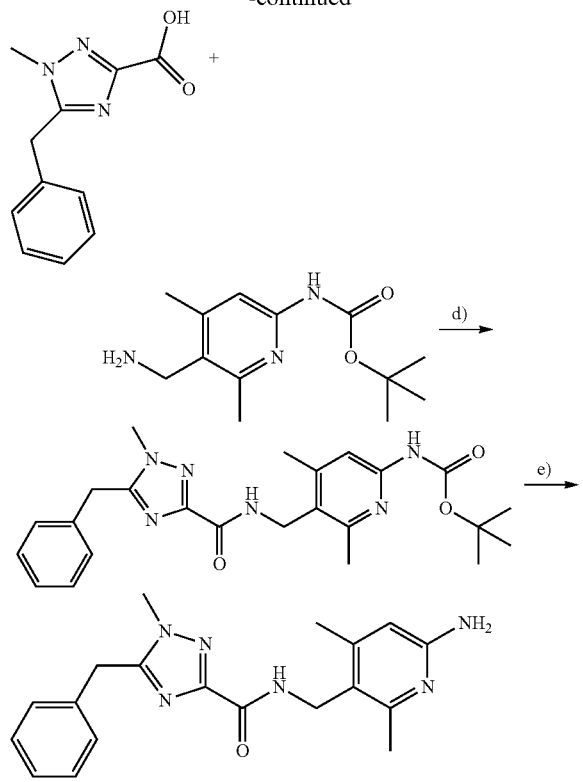

Ethyl-2-ethoxy-2-iminoacetate was prepared from ethyl cyano formate and ethanol according to N. Bozhkova, H. Heimgartner, *Helvetica Chimica Acta*, 1989, 72, 825-837.

a) 5-Benzyl-1H-[1,2,4]triazole-3-carboxylic acid butyl ester

Ethyl-2-ethoxy-2-iminoacetate (1.318 g, 9.08 mmol) and phenyl acetic acid hydrazide (1.364 g, 9.08 mmol) were mixed together in ethanol (20 ml) and stirred at 80° C. for 1 h. Ethanol was evaporated. The residue was dissolved in n-butanol (20 ml). The reaction mixture was stirred at 150° C. for 20 h, then solvents were evaporated.

The residue was suspended in acetonitrile and the precipitate was filtered off. The filtrate was purified by prep. HPLC (column: Interchrom C18 ODB, 10 um, 250×28 mm, 23° C.; A: water+0.1% HCOOH, B: ORG+0.1% HCOOH [ORG=methanol/acetonitrile 4:1]; gradient 20% B 2.5 min, 20-100% B in 35 min, 100% B for 2.5 min) to give the title compound. UPLC-MS (method F) Rt=0.85 min, [M+H]+=260.3; HPLC (method G) Rt=1.861 min.

b) 5-Benzyl-1-methyl-1H-[1,2,4]triazole-3-carboxylic acid butyl ester

5-Benzyl-1H-[1,2,4]triazole-3-carboxylic acid butyl ester (100 mg, 0.386 mmol) was dissolved in acetone (3 ml), to which were added potassium carbonate (80 mg, 0.578 mmol) and iodomethane (27 µl, 0.432 mmol) as a solution in acetone (2 ml) at 23° C. The reaction mixture was stirred at 23° C. for 72 h, then filtered and concentrated. The residue was purified by silica gel chromatography (cyclohexane/ethyl acetate; 25 g column; flow 40 ml/min; 0% ethyl acetate to 100% ethyl acetate in 20 min) to give the title compound. UPLC-MS (method F) Rt=0.96 min, [M+H]+=274.3.

c) 5-Benzyl-1-methyl-1H-[1,2,4]triazole-3-carboxylic acid

5-Benzyl-1-methyl-1H-[1,2,4]triazole-3-carboxylic acid butyl ester (45 mg, 0.165 mmol) was dissolved in ethanol (2 ml), followed by addition of 6M sodium hydroxide aqueous solution (55 µl, 0.330 mmol). The reaction mixture was stirred at 80° C. for 18 h, then cooled to 23° C. and neutralized with 1M hydrochloric acid. Solvents were removed in vacuo. The crude mixture of title compound and NaCl was used without further purification for the next step. HPLC (method G) Rt=1.241 min.

d) (5-{[(5-Benzyl-1-methyl-1H-1,2,4]triazole-3-carbonyl)-amino]-methyl}-4,6-dimethyl-pyridin-2-yl)-carbamic acid tert-butyl ester To a mixture of 5-benzyl-1-methyl-1H-[1,2,4]triazole-3-carboxylic acid (55 mg, 0.165 mmol, contains about 35% NaCl) in DMF (1 ml) were added (5-aminomethyl-4,6-dimethyl-pyridin-2-yl)-carbamic acid tert-butyl ester (54 mg, 0.215 mmol) and HBTU (65 mg, 0.171 mmol) followed by BEMP (50 µl, 0.173 mmol) as last. The reaction mixture was stirred at 23° C. for 20 h. The reaction mixture was diluted with water and methanol, then purified by prep. HPLC (WATERS C18 ODB, 5 µm, 50×19 mm; A: water+0.1% HCOOH, B: ORG+0.1% HCOOH [ORG=methanol/acetonitrile 4:1] gradient 10% ORG 2.5 min, 10-100% ORG in 15 min, 100% ORG 2.5 min) to give the title compound. UPLC-MS (method F) Rt=0.82 min, [M+H]+=451.5; HPLC (method G) Rt=1.624 min.

e) 5-Benzyl-1-methyl-1H-[1,2,4]triazole-3-carboxylic acid (6-amino-2,4-dimethyl-pyridin-3-ylmethyl)-amide (5-{[(5-Benzyl-1-methyl-1H-[1,2,4]triazole-3-carbonyl)-amino]-methyl}-4,6-dimethyl-pyridin-2-yl)-carbamic acid tert-butyl ester (29 mg, 0.064 mmol) was dissolved in a mixture of dichloromethane (4 ml) and TFA (1 ml). The reaction mixture was shaken at 23° C. for 18 h. Solvents were removed in vacuo. The residue was dissolved in dichloromethane/methanol 1:1 (1 ml) and purified over VARIAN SCX-SPE cartridge (strong cation exchange), washing with methanol and releasing the compound with 2M ammonia in methanol. The basic fraction was evaporated in vacuo to give the title compound. 1H-NMR (DMSO, 400 MHz) 8.5 (s, 1H), 7.2-7.3 (m, 5H), 7.0 (br s, 2H) 6.5 (s, 1H), 4.3 (d, 2H), 4.2 (s, 2H), 3.8 (s, 3H), 2.4 (s, 3H), 2.3 (s, 3H). UPLC-MS (method F) Rt=0.92 min, [M+H]+=351.4. HPLC (method G) Rt=1.281 min.

Example 3

N-((6-amino-2,4-dimethylpyridin-3-yl)methyl)-3-benzylisoxazole-5-carboxamide

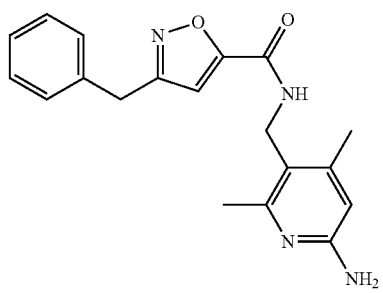 [SMILES: Cc1cc(N)nc(C)c1CNC(=O)c1cc(Cc2ccccc2)no1]

The title compound was prepared in analogy to example 13, Step b) starting from 3-Benzyl-isoxazole-5-carboxylic acid (WO2006123061). 1H-NMR (d3-MeOD, 400 MHz): 7.34-7.27 (m, 5H), 6.77 (s, 1H), 6.71 (s, 1H), 4.49 (s, 2H), 4.08 (s, 2H), 2.59 (s, 3H), 2.47 (s, 3H). HPLC (Method J) Rt=3.16 min; MS [M+H]$^+$=337.1.

Example 4

N-((6-amino-2,4-dimethylpyridin-3-yl)methyl)-5-benzyl-1,3,4-oxadiazole-2-carboxamide

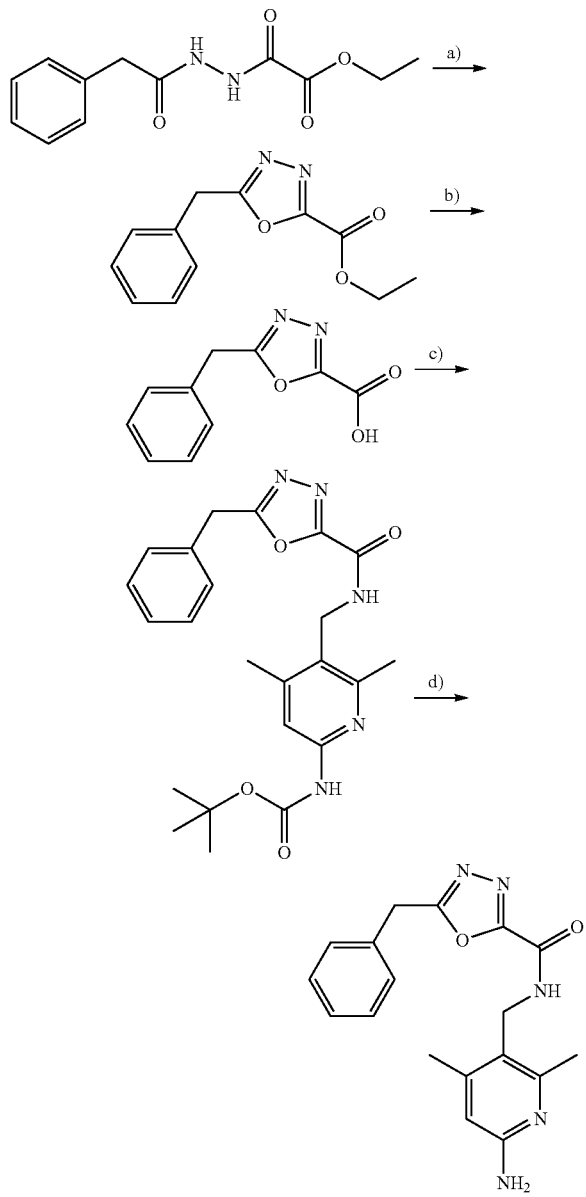

a) 5-Benzyl-[1,3,4]oxadiazole-2-carboxylic acid ethyl ester

5-Benzyl-[1,3,4]oxadiazole-2-carboxylic acid ethyl ester can be prepared as described by J. Dost, M. Heschel, J. Stein J. Prakt. Chem. 1985, 327, 109-116. LCMS (method A) Rt$_A$=1.670 min; [M+H]$^+$=233.1 b) 5-Benzyl-[1,3,4]oxadiazole-2-carboxylic acid

A mixture of 5-Benzyl-[1,3,4]oxadiazole-2-carboxylic acid ethyl ester (2.6 g, 11 mmol) and lithiumhydroxide-hydrate (0.4 g, 11 mmol) in 60 mL MeOH and 30 mL water was stirred at room temperature for 1 h. The mixture was evaporated in vacuo to yield the crude product as lithium salt which was used in the next step without further purification. LCMS (method A) Rt$_A$=1.018 min; [M+H]$^+$=205.0.

c) (5-{[(5-Benzyl-[1,3,4]oxadiazole-2-carbonyl)-amino]-methyl}-4,6-dimethyl-pyridin-2-yl)-carbamic acid tert-butyl ester A mixture of Benzyl-[1,3,4]oxadiazole-2-carboxylic acid (2.4 g, 11 mmol), (5-Aminomethyl-4,6-dimethyl-pyridin-2-yl)-carbamic acid tert-butyl ester (2.8 g, 11 mmol), HATU (5.5 g, 15 mmol) and DIPEA (7.8 mL, 45 mmol) in 20 mL DMF was stirred at room temperature for 16 h. The mixture was evaporated and the residue was partitioned between ethyl acetate and 1 N aq. HCl. The organic layer was dried over MgSO$_4$ and evaporated in vacuo. The crude product was purified by preparative HPLC (Waters Sunfire Prep C18 PBD 5 um, 30×100 mm, 5 to 100% ACN and 0.1% TFA, flow 40 ml/min). HPLC (method C) Rt$_A$=3.114.

d) N-((6-amino-2,4-dimethylpyridin-3-yl)methyl)-5-benzyl-1,3,4-oxadiazole-2-carboxamide A mixture of (5-{[(5-Benzyl-[1,3,4]oxadiazole-2-carbonyl)-amino]-methyl}-4,6-dimethyl-pyridin-2-yl)-carbamic acid tert-butyl ester (412 mg, 0.94 mmol), 4 mL TFA and 8 mL DCM was stirred of room temperature for 2 h. The mixture was evaporated in vacuo and the residue was purified by preparative HPLC (Macherey-Nagel Nucleosil 250×40 mm, 5 to 100% ACN and 0.1% TFA, flow 40ml/min). The product containing fractions were lyophilised, then dissolved in 1 mL MeOH and the resulting mixture was filtered over a MeOH flushed PL-HCO$_3$ MP-resin column. The column was washed with MeOH, the solvent was removed and the crude product was dissolved in water/ACN and lyophilised to yield the title compound. 1H-NMR (DMSO-d6, 400 MHz) 9.33 (t, 1H), 7.29-7.39 (m, 5H), 6.11 (s, 1H), 5.71 (bs, 2H), 4.34-4.36 (m, 4H), 2.30 (s, 3 H), 2.17 (s, 3H); LCMS (method A) Rt$_A$=0.814 min; [M+H]$^+$=338.0.

Example 5

N-((6-amino-2,4-dimethylpyridin-3-yl)methyl)-3-benzyl-1,2,4-oxadiazole-5-carboxamide

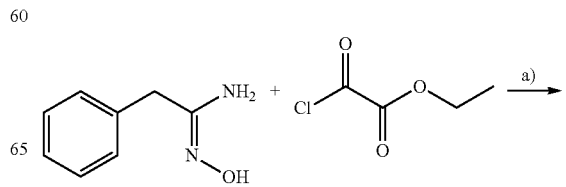

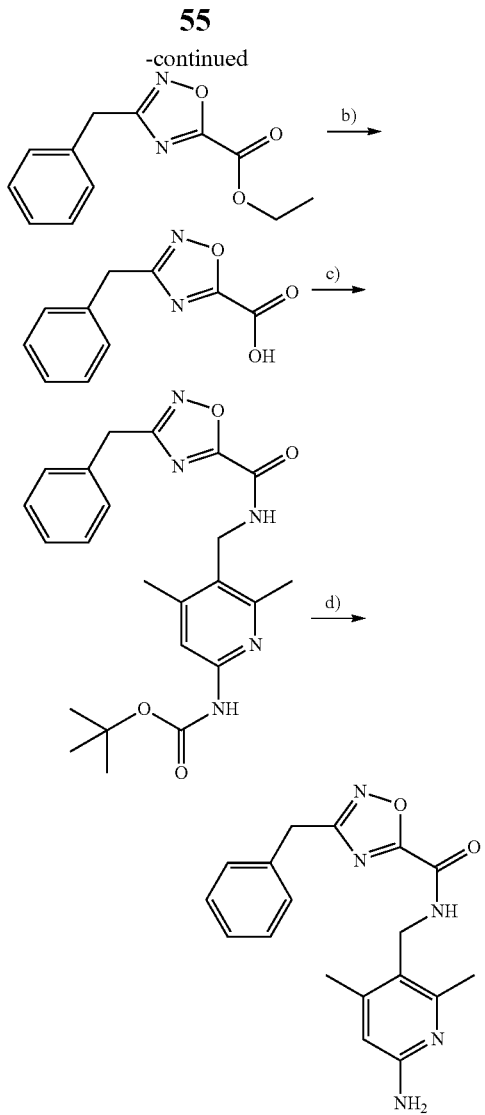

a) 3-Benzyl-[1,2,4]oxadiazole-5-carboxylic acid ethyl ester

To a mixture of N-Hydroxy-2-phenyl-acetamidine (1 g, 6.7 mmol) in 7 mL ethyl acetate was added a solution of Chloro-oxo-acetic acid ethyl ester (1.5 g, 10.7 mmol) in 7 mL ethyl acetate at 0° C. The mixture was stirred for 1.5 h at room temperature and then heated to 80° C. for 2.5 h. The reaction mixture was treated with aq. NaHCO$_3$-solution and extracted with ethyl acetate. The organic layers were dried over MgSO$_4$ and evaporated in vacuo. The crude product was purified by preparative HPLC (Waters Sunfire Prep C18 PBD 5 um, 30×100 mm, 5 to 100% ACN and 0.1% TFA, flow 40ml/min) to yield the title compound. LCMS (method A) Rt$_A$=1.938 min; [M+H]$^+$=233.1.

b) 3-Benzyl-[1,2,4]oxadiazole-5-carboxylic acid

A mixture of 3-Benzyl-[1,2,4]oxadiazole-5-carboxylic acid ethyl ester (360 mg, 1.6 mmol) and lithiumhydroxide-hydrate (65 mg, 1.6 mmol) in 10 mL MeOH and 5 mL water was stirred at room temperature for 1 h. The mixture was evaporated in vacuo to yield the crude product which was used in the next step without further purification.

c) (5-{[(3-Benzyl-[1,2,4]oxadiazole-5-carbonyl)-amino]-methyl}-4,6-dimethyl-pyridin-2-yl)-carbamic acid tert-butyl ester A mixture of 3-Benzyl-[1,2,4]oxadiazole-5-carboxylic acid (330 mg, 1.5 mmol), (5-Aminomethyl-4,6-dimethyl-pyridin-2-yl)-carbamic acid tert-butyl ester (389 mg, 1.5 mmol), HATU (1.1 g, 3.1 mmol) and DIPEA (0.8 mL, 4.7 mmol) in 10 mL DMF was stirred at room temperature for 16 h. The mixture was evaporated and the residue was partitioned between ethyl acetate and 1 N aq. HCl. The organic layer was dried over MgSO$_4$ and evaporated in vacuo. The crude product was purified by preparative HPLC (Waters Sunfire Prep C18 PBD 5 um, 30×100 mm, 5 to 100% ACN and 0.1% TFA, flow 40 ml/min). LCMS (method A) Rt$_A$=1.834 min; [M+H]$^+$= 438.1.

d) N-((6-amino-2,4-dimethylpyridin-3-yl)methyl)-3-benzyl-1,2,4-oxadiazole-5-carboxamide A mixture of (5-{[(3-Benzyl-[1,2,4]oxadiazole-5-carbonyl)-amino]-methyl}-4,6-dimethyl-pyridin-2-yl)-carbamic acid tert-butyl ester (65 mg, 0.09 mmol), 2 mL TFA and 4 mL DCM was stirred of room temperature for 1 h. The mixture was evaporated in vacuo and the residue was purified by prep HPLC (Macherey-Nagel Nucleosil 250×40 mm, 5 to 100% ACN and 0.1% TFA, flow 40ml/min). Aq. NaHCO$_3$-solution was added to the product containing fractions and after evaporation the aq. layer was extracted with ethyl acetate. The organic layer was dried over MgSO$_4$ and concentrated to give the title compound. 1H-NMR (DMSO-d6, 400 MHz) 9.43 (t, 1H), 7.25-7.36 (m, 5H), 6.10 (s, 1H), 5.70 (s, 2H), 4.35 (d, 2H), 4.18 (s, 2H), 2.29 (s, 3H), 2.16 (s, 3H); LCMS (method A) Rt$_A$=1.024 min; [M+H]$^+$=338.0.

Example 6

1-(4-((1H-pyrazol-1-yl)methyl)benzyl)-N-((6-amino-2,4-dimethylpyridin-3-yl)methyl)-1H-imidazole-4-carboxamide

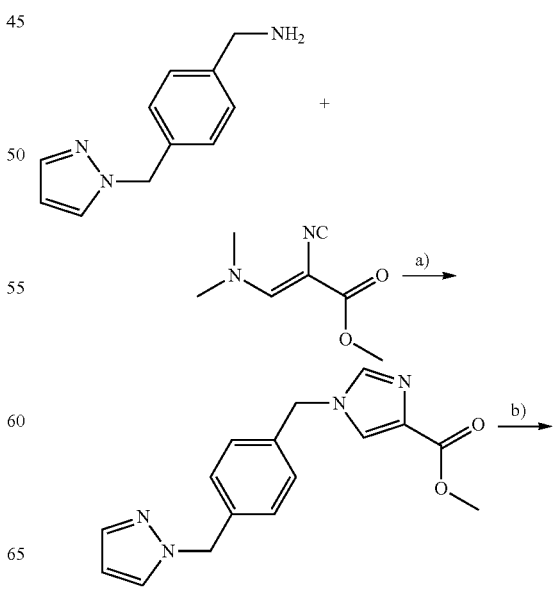

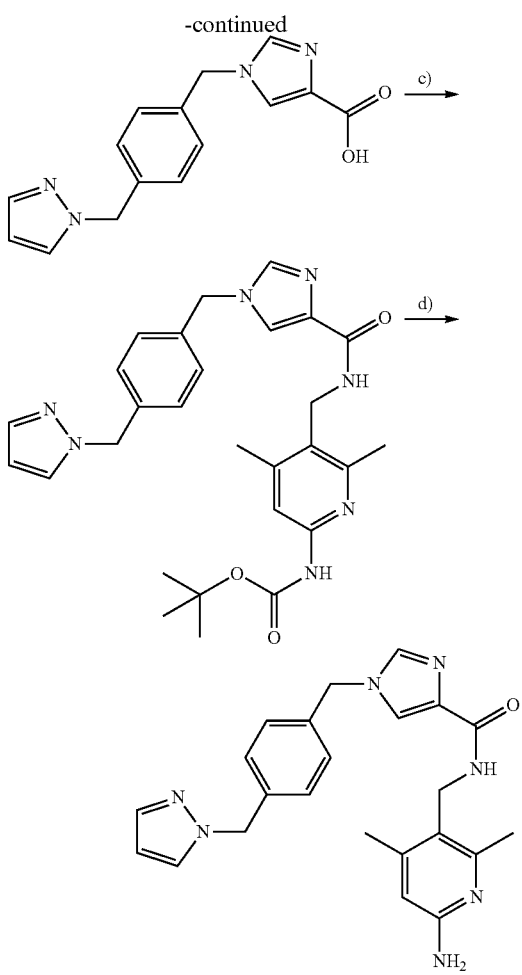

a) 1-(4-Pyrazol-1-ylmethyl-benzyl)-1H-imidazole-4-carboxylic acid methyl ester

A mixture of 4-Pyrazol-1-ylmethyl-benzylamine (550 mg, 2.5 mmol), (Z)-methyl-3-(dimethylamino)-2-isocyanoacrylate (380 mg, 2.5 mmol) and DIPEA (1.3 mL, 7.4 mmol) in 20 mL nBuOH was heated to 120° C. for 16 h. The mixture was concentrated in vacuo and the crude product was used in the next step without further purification. LCMS (method A) $Rt_A$=1.210 min; $[M+H]^+$=297.0.

b) 1-(4-Pyrazol-1-ylmethyl-benzyl)-1H-imidazole-4-carboxylic acid

A mixture of 1-(4-Pyrazol-1-ylmethyl-benzyl)-1H-imidazole-4-carboxylic acid methyl ester (730 mg, 2.5 mmol) and lithiumhydroxyde-hydrate (210 mg, 4.9 mmol) in 10 mL MeOH and 5 mL water was stirred at room temperature for 3 h. The mixture was evaporated in vacuo, the residue was acidified with 1 N aq. HCl and lyophilised to yield the crude product which was used in the next step without further purification. LCMS (method A) $Rt_A$=0.412 min; $[M+H]^+$=283.0.

c) [4,6-Dimethyl-5-({[1-(4-pyrazol-1-ylmethyl-benzyl)-1H-imidazole-4-carbonyl]-amino}-methyl)-pyridin-2-yl]-carbamic acid tert-butyl ester A mixture of 1-(4-Pyrazol-1-ylmethyl-benzyl)-1H-imidazole-4-carboxylic acid (0.67 g, 2.4 mmol), (5-Aminomethyl-4,6-dimethyl-pyridin-2-yl)-carbamic acid tert-butyl ester (0.61 g, 2.4 mmol), HATU (1.8 g, 4.8 mmol) and DIPEA (1.3 mL, 7.2 mmol) in 10 mL DMF was stirred at room temperature for 16 h. The mixture was evaporated and the residue was partitioned between ethyl acetate and 1 N aq. HCl. The organic layer was dried over MgSO₄ and evaporated in vacuo. The crude product was purified by preparative HPLC (Waters Sunfire Prep C18 PBD 5 um, 30×100 mm, 5 to 100% ACN and 0.1% TFA, flow 40 ml/min). LCMS (method A) $Rt_A$=1.418 min; $[M+H]^+$=516.1.

d) 1-(4-((1H-pyrazol-1-yl)methyl)benzyl)-N-((6-amino-2,4-dimethylpyridin-3-yl)methyl)-1H-imidazole-4-carboxamide A mixture of [4,6-Dimethyl-5-({[1-(4-pyrazol-1-ylmethyl-benzyl)-1H-imidazole-4-carbonyl]-amino}-methyl)-pyridin-2-yl]-carbamic acid tert-butyl ester (260 mg, 0.37 mmol), 5 mL TFA and 10 mL DCM was stirred of room temperature for 1 h. The mixture was evaporated in vacuo and the residue was purified by preparative HPLC (Macherey-Nagel Nucleosil 250×40 mm, 5 to 100% ACN and 0.1% TFA, flow 40ml/min). Aq. NaHCO₃-solution was added to the product containing fractions and after evaporation the aq. layer was extracted with ethyl acetate. The organic layer was dried over MgSO₄ and concentrated to give the title compound. 1H-NMR (DMSO-d6, 400 MHz) 7.80 (s, 2H), 7.66-7.69 (m, 2H), 7.45 (s, 1H), 7.28 (d, 2H), 7.20 (d, 2H), 6.26 (s, 1H), 6.21 (s, 1H), 6.04 (s, 2H), 5.31 (s, 2H), 5.19 (s, 2H), 4.30 (d, 2H), 2.34 (s, 3H), 2.21 (s, 3H); LCMS (method A) $Rt_A$=0.832 min; $[M+H]^+$=416.0

Example 7

N-((6-amino-2,4-dimethylpyridin-3-yl)methyl)-5-benzyloxazole-2-carboxamide

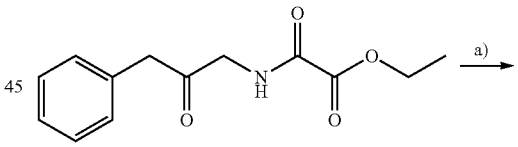

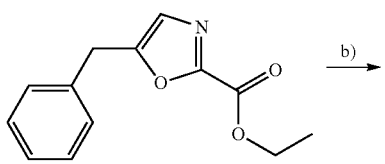

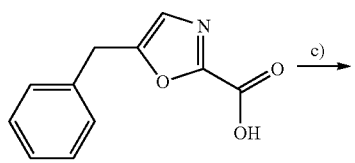

-continued

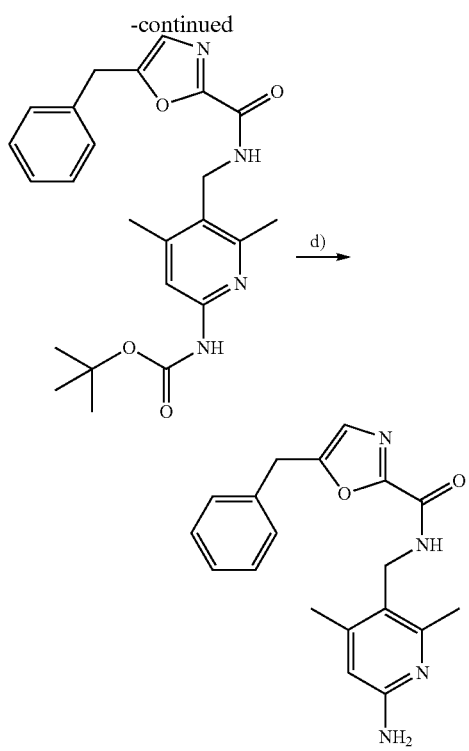

a) 5-Benzyl-oxazole-2-carboxylic acid ethyl ester

5-Benzyl-oxazole-2-carboxylic acid ethyl ester can be prepared as described by R. H. Good, G. Jones, *J. Chem. Soc.* (C) 1970, 1938-1945. LCMS (method A) Rt$_A$=1.847 min; [M+H]$^+$=232.0 b) 5-Benzyl-oxazole-2-carboxylic acid

A mixture of 5-Benzyl-oxazole-2-carboxylic acid ethyl ester (0.95 g, 3.5 mmol) and lithiumhydroxide-hydrate (0.73 g, 17.5 mmol) in 20 mL MeOH and 10 mL water was stirred at room temperature for 2 h. The mixture was evaporated in vacuo, extracted with hexane and the aq. layer was acidified with 1 N aq. HCl. After extraction with ethyl acetate, the organic layer was dried over MgSO$_4$, and evaporated to yield the crude product which was used in the next step without further purification. LCMS (method A) Rt$_A$=1.350 min; [M+H]$^+$=203.9.

c) (5-{[(5-Benzyl-oxazole-2-carbonyl)-amino]-methyl}-4,6-dimethyl-pyridin-2-yl)-carbamic acid tert-butyl ester A mixture of 5-Benzyl-oxazole-2-carboxylic acid (0.86 g, 2.8 mmol), (5-Aminomethyl-4,6-dimethyl-pyridin-2-yl)-carbamic acid tert-butyl ester (0.70 g, 2.8 mmol), HATU (1.4 g, 3.6 mmol) and DIPEA (2.0 mL, 11.7 mmol) in 10 mL DMF was stirred at room temperature for 16 h. The mixture was evaporated and the residue was partitioned between ethyl acetate and 1 N aq. HCl. The organic layer was dried over MgSO$_4$ and evaporated in vacuo. The crude product was purified by preparative HPLC (Waters Sunfire Prep C18 PBD 5 um, 30×100 mm, 5 to 100% ACN and 0.1% TFA, flow 40 ml/min). LCMS (method A) Rt$_A$=1.719 min; [M+H]$^+$=437.0 d) N-((6-amino-2,4-dimethylpyridin-3-yl)methyl)-5-benzyloxazole-2-carboxamide A mixture of (5-{[(5-Benzyl-oxazole-2-carbonyl)-amino]-methyl}-4,6-dimethyl-pyridin-2-yl)-carbamic acid tert-butyl ester (170 mg, 0.34 mmol), 2 mL TFA and 5 mL DCM was stirred of room temperature for 2 h. The mixture was evaporated in vacuo and the residue was purified by preparative HPLC (Macherey-Nagel Nucleosil 250×40 mm, 5 to 100% ACN and 0.1% TFA, flow 40 ml/min). The product containing fractions were lyophilised, then dissolved in 1 mL MeOH and the resulting mixture was filtered over a MeOH flushed PL-HCO$_3$ MP-resin column. The column was washed with MeOH, the solvent was removed and the crude product was dissolved in water/ACN and lyophilised to yield the title compound. 1H-NMR (DMSO-d6, 400 MHz) 8.80 (t, 1H), 7.27-7.37 (m, 5H), 7.10 (s, 1H), 6.11 (s, 1H), 5.72 (s, 2H), 4.31 (d, 2H), 4.12 (s, 2H), 2.30 (s, 3H), 2.17 (s, 3H); LCMS (method A) Rt$_A$=1.001 min; [M+H]$^+$=337.0.

Example 8

N-((6-amino-2,4-dimethylpyridin-3-yl)methyl)-2-(4-methoxybenzyl)oxazole-4-carboxamide

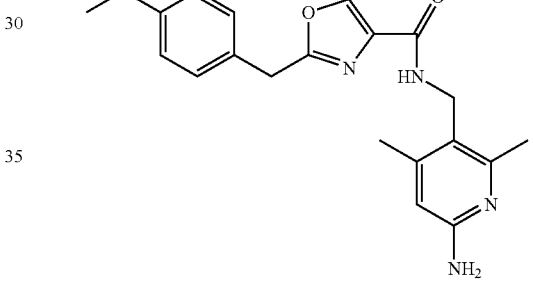

The title compound was prepared in analogy to example 13, Step b) starting from 2-(4-Methoxy-benzyl)-oxazole-4-carboxylic acid (*Journal of the American Chemical Society* 1950, 72 5401-3).

1H-NMR (DMSO-d6, 400 MHz): 8.49 (s, 1H), 7.97 (t, 1H), 7.20 (d, 2H), 6.89 (d, 2H), 6.10 (s, 1H), 5.66 (s,2 H), 4.31 (d, 2H), 4.09 (s, 2H), 3.73 (s, 3H), 2.30 (s, 3H), 2.18 (s, 3H). HPLC (Method G) Rt=1.46 min; MS [M+H]$^+$=367.3.

Example 9

1-(4-((1H-pyrazol-1-yl)methyl)-3-methoxybenzyl)-N-((6-amino-2,4-dimethylpyridin-3-yl)methyl)-1H-pyrazole-4-carboxamide

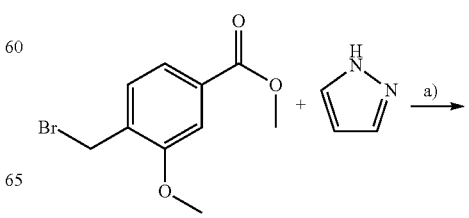

-continued

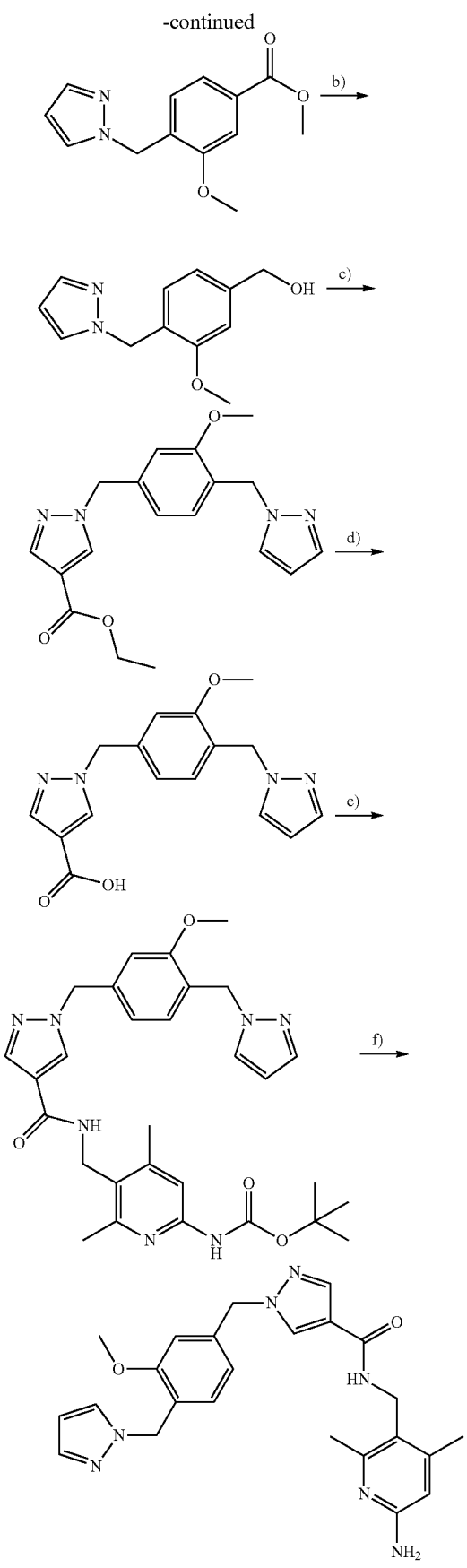

a) Methyl 4-((1H-pyrazol-1-yl)methyl)-3-methoxybenzoate

A suspension of methyl 4-(bromomethyl)-3-methoxybenzoate (400 mg, 1.544 mmol) and 1H-pyrazole (105 mg, 1.544 mmol) and K₂CO₃ (533 mg, 3.86 mmol) in DMF (5 ml) was stirred for 3.5 h at rt. A saturated solution of NaHCO₃ was added and the mixture was extracted with ethyl acetate. The combined organic extracts were dried over Na₂SO₄, filtered and concentrated under reduced pressure to afford crude Methyl 4-((1H-pyrazol-1-yl)methyl)-3-methoxybenzoate. MS [M+H]⁺=247.

b) 4-((1H-pyrazol-1-yl)methyl)-3-methoxyphenyl)methanol

To a solution of methyl 4-((1H-pyrazol-1-yl)methyl)-3-methoxybenzoate (330 mg crude) in THF (6 ml) DIBAL-H 1M in Hexane (4.02 ml, 4.02 mmol) was added dropwise at −70° C. The reaction mixture was stirred at −70° C. for 3.5 h. The reaction mixture was quenched subsequently with ethyl acetate (2 ml) and saturated aqueous NH₄Cl. The resulting mixture was extracted with ethyl acetate. The organic layer was washed with brine, dried over Na₂SO₄, filtered and concentrated under reduced pressure to afford crude (4-((1H-pyrazol-1-yl)methyl)-3-methoxyphenyl)methanol. MS [M+H]⁺=219.

c) Ethyl 1-(4-((1H-pyrazol-1-yl)methyl)-3-methoxybenzyl)-1H-pyrazole-4-carboxylate To a mixture of Ethyl 1H-pyrazole-4-carboxylate (117 mg, 0.833 mmol), crude (4-((1H-pyrazol-1-yl)methyl)-3-methoxyphenyl)methanol (256 mg, 71%, 0.833 mmol) and Triphenylphosphine (328 mg, 1.249 mmol) in THF (8 ml) DEAD 40% in Toluene (0.494 ml, 1.249 mmol) was added slowly at 0° C. The reaction mixture was stirred at 0° C. for 2 h and continued to stir for 12 h at rt. A saturated solution of NaHCO₃ was added and the mixture was extracted with ethyl acetate. The combined organic extracts were dried over Na₂SO₄, filtered and concentrated under reduced pressure to afford crude Ethyl 1-(4-((1H-pyrazol-1-yl)methyl)-3-methoxybenzyl)-1H-pyrazole-4-carboxylate. MS [M+H]⁺=341.

d) 1-(4-((1H-pyrazol-1-yl)methyl)-3-methoxybenzyl)-1H-pyrazole-4-carboxylic acid To a solution of crude ethyl 1-(4-((1H-pyrazol-1-yl)methyl)-3-methoxybenzyl)-1H-pyrazole-4-carboxylate (998 mg, 29%, 0.85 mmol) in THF:EtOH:H₂O 2:1:1 (15 ml), LiOH Monohydrate (107 mg, 2.55 mmol) was added and stirred for 12 h at 50° C. The reaction mixture was concentrated under reduced pressure. The remaining solid was taken up in ethyl acetate and extracted with water. The aqueous phase was acidified by adding aqueous HCl and extracted with ethy acetate. The organic extract was dried over Na₂SO₄, filtered and concentrated under reduced pressure to afford crude 1-(4-((1H-pyrazol-1-yl)methyl)-3-methoxybenzyl)-1H-pyrazole-4-carboxylic acid. MS [M+H]⁺=313.

e) Tert-butyl 5-((1-(4-((1H-pyrazol-1-yl)methyl)-3-methoxybenzyl)-1H-pyrazole-4-carboxamido)methyl)-4,6-dimethylpyridin-2-ylcarbamate To a mixture of 1-(4-((1H-pyrazol-1-yl)methyl)-3-methoxybenzyl)-1H-pyrazole-4-carboxylic acid (135 mg, 0.303 mmol), tert-butyl 5-(aminomethyl)-4,6-dimethylpyridin-2- ylcarbamate (76 mg, 0.303 mmol) and DIPEA (0.211 ml, 1.210 mmol) in DMF (2 ml), HATU (173 mg, 0.454 mmol) was added and stirred for 12 h at 11. The reaction mixture was purified by preparative HPLC (Waters Sun-Fire C18, 100×30 mm, 5 to 100% ACN (0.1% TFA), flow 40 ml/min) to afford tert-butyl 5-((1-(4-((1H-pyrazol-1-yl)methyl)-3-methoxybenzyl)-1H-pyrazole-4-carboxamido)methyl)-4,6-dimethyl pyridin-2-ylcarbamate. HPLC (Method H) Rt=3.19 min; MS $[M+H]^+$=546.

f) 1-(4-((1H-pyrazol-1-yl)methyl)-3-methoxybenzyl)-N-((6-amino-2,4-dimethylpyridin-3-yl)methyl)-1H-pyrazole-4-carboxamide To a solution of Tert-butyl 5-((1-(4-((1H-pyrazol-1-yl)methyl)-3-methoxybenzyl)-1H-pyrazole-4-carboxamido)methyl)-4,6-dimethylpyridin-2-ylcarbamate (100 mg, 0.147 mmol)
in DCM (3 ml), TFA (1 ml, 12.98 mmol) was added and stirred at it for 3 h. The reaction mixture was concentrated under reduced pressure and subsequently purified by preparative HPLC (Machery-Nagel Nucleosil C18, 250×40 mm, 5 to 100% ACN (0.1% TFA), flow 40 ml/min) to afford 1-(4-((1H-pyrazol-1-yl)methyl)-3-methoxybenzyl)-N-((6-amino-2,4-dimethylpyridin-3-yl)methyl)-1H-pyrazole-4-carboxamide. 1H-NMR (DMSO-d6, 400 MHz): 8.21 (s, 1H), 7.87 (m, 2 H), 7.68 (d, 1H), 7.40 (d, 1 H), 6.97 (s, 1 H), 6.79 (d, 1H), 6.72 (d, 1H), 6.22 (m, 1H), 6.09 (s, 1H), 5.62 (s, 2 H), 5.26 (s, 2 H), 5.23 (s, 2H), 4.24 (d, 2 H), 3.78 (s, 3 H), 2.26 (s, 3 H), 2.12 (s, 3 H). HPLC (Method H) Rt=2.81 min; MS $[M+H]^+$=446.

Example 10

N-((6-amino-2,4-dimethylpyridin-3-yl)methyl)-1-(biphenyl-4-ylmethyl)-1H-1,2,3-triazole-4-carboxamide

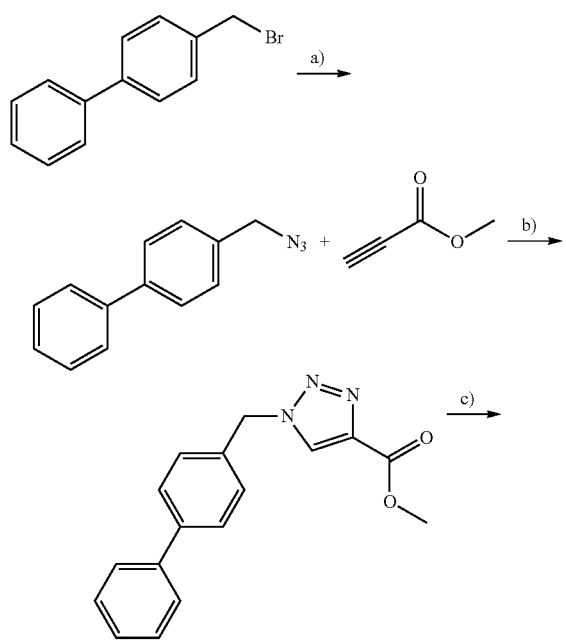

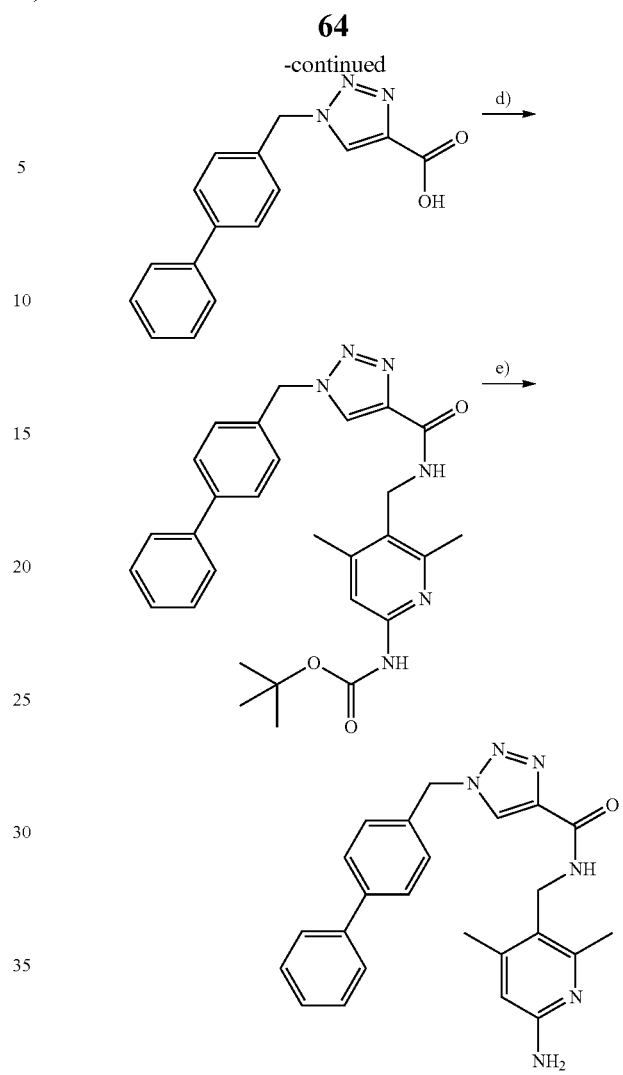

a) Azidomethyl-biphenyl

A mixture of 4-(Bromomethyl)-biphenyl (200 mg, 0.6 mmol) and sodium azide (41 mg, 0.6 mmol) in 2 mL DMF was stirred at 90° C. for 1 h. The reaction mixture was concentrated in vacuo and the residue was treated with DCM and extracted with water. The organic layer was dried over $MgSO_4$ and evaporated to give the title compound which was used in the next step without further purification. 1H-NMR ($CDCl_3$, 400 MHz) 7.62-7.66 (m, 4H), 7.39-7.50 (m, 5H), 4.42 (s, 2H).

b) 1-Biphenyl-4-ylmethyl-1H-[1,2,3]triazole-4-carboxylic acid methyl ester

A mixture of 4-Azidomethyl-biphenyl (145 mg, 0.5 mmol), methyl propiolate (44 mg, 0.5 mmol), copper(II) sulfate (17 mg, 0.1 mmol) and sodium ascorbate (103 mg, 0.5 mmol) in 3 mL tBuOH and 1 mL water was stirred at room temperature for 3 h. Ethyl acetate was added and the mixture was extracted with water. The organic layer was dried over $MgSO_4$ and evaporated in vacuo to give the title compound which was used in the next step without further purification. LCMS (method A) $Rt_A$=1.964 min; $[M+H]^+$=294.0.

c) 1-Biphenyl-4-ylmethyl-1H-[1,2,3]triazole-4-carboxylic acid

A mixture of 1-Biphenyl-4-ylmethyl-1H-[1,2,3]triazole-4-carboxylic acid methyl ester (60 mg, 0.2 mmol) and lithiumhydroxide-hydrate (35 mg, 0.8 mmol) in 4 mL MeOH and 2 mL water was stirred at 80° C. for 2 h. The mixture was evaporated in vacuo, extracted with hexane and the aq. layer was acidified with 1 N aq. HCl. After extraction with ethyl acetate, the organic layer was dried over MgSO$_4$, and evaporated to yield the crude product which was used in the next step without further purification. 1H-NMR (DMSO-d6, 400 MHz) 8.83 (s, 1H), 7.65-7.70 (m, 4H), 7.38-7.49 (m, 5H), 5.70 (s, 2H).

d) (5-{[(1-Biphenyl-4-ylmethyl-1H-[1,2,3]triazole-4-carbonyl-amino]-methyl}-4,6-dimethyl-pyridin-2-yl)-carbamic acid tert-butyl ester A mixture of 1-Biphenyl-4-ylmethyl-1H-[1,2,3]triazole-4-carboxylic acid (26 mg, 0.09 mmol), (5-Aminomethyl-4,6-dimethyl-pyridin-2-yl)-carbamic acid tert-butyl ester (23 mg, 0.09 mmol), HATU (46 mg, 0.12 mmol) and DIPEA (0.07 mL, 0.37 mmol) in 2 mL DMF was stirred at room temperature for 1 h. The crude mixture was purified by preparative HPLC (Waters Sunfire Prep C18 PBD 5 um, 30×100 mm, 5 to 100% ACN and 0.1% TFA, flow 40ml/min). LCMS (method A) $Rt_A$=1.917 min; $[M+H]^+$=513.1.

e) N-((6-amino-2,4-dimethylpyridin-3-yl)methyl)-1-(biphenyl-4-ylmethyl)-1H-1,2,3-triazole-4-carboxamide A mixture of (5-{[(1-Biphenyl-4-ylmethyl-1H-[1,2,3]triazole-4-carbonyl)-amino]-methyl}-4,6-dimethyl-pyridin-2-yl)-carbamic acid tert-butyl ester (27 mg, 0.053 mmol), 1 mL TFA and 2 mL DCM was stirred at room temperature for 2 h. The mixture was evaporated in vacuo to yield the final product (TFA salt). 1H-NMR (DMSO-d6, 400 MHz) 13.24 (bs, 1H), 8.87 (t, 1H), 8.70 (s, 1H), 7.65-7.69 (m, 4H), 7.43-7.52 (m, 6H), 7.36-7.40 (t, 1H), 6.62 (s, 1H), 5.70 (s, 2H), 4.43 (d, 2H), 2.52 (s, 3H), 2.40 (s, 3H); LCMS (method A) $Rt_A$=1.317 min; $[M+H]^+$=413.0.

Example 11

N-((6-amino-2,4-dimethylpyridin-3-yl)methyl)-1-(2-hydroxy-1-phenylethyl)-1H-pyrazole-4-carboxamide

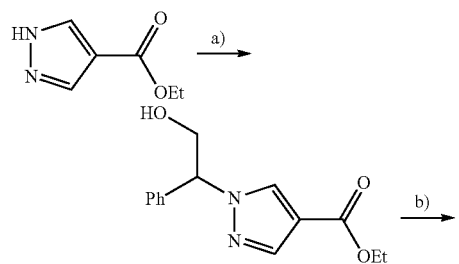

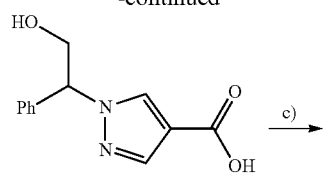

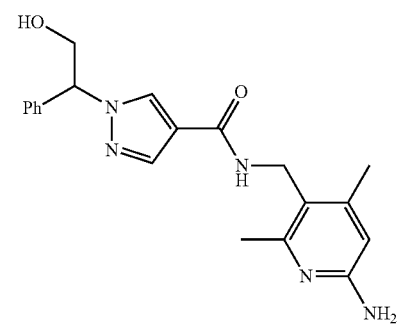

a) Ethyl 1-(2-hydroxy-1-phenylethyl)-1H-pyrazole-4-carboxylate

A mixture of ethyl 1H-pyrazole-4-carboxylate (1.5 g, 10.7 mmol), yttrium (III) nitrate hexahydrate (82.0 mg, 0.214 mmol) and styrene oxide (1.21 ml, 10.7 mmol) was stirred at rt for 17 h, before it was adsorbed on celite. Purification by column chromatography (CombiFlash Companion, 12 g SiO$_2$, heptane to EA) afforded the title compound. LCMS $Rt_M$=1.72 min, $[M+H]^+$=261.2.

b) 1-(2-Hydroxy-1-phenylethyl)-1H-pyrazole-4-carboxylic acid

A mixture of ethyl 1-(2-hydroxy-1-phenylethyl)-1H-pyrazole-4-carboxylate (110 mg, 0.423 mmol) in EtOH (2 ml) was treated with NaOH (2N, 0.634 ml, 1.268 mmol) and heated to 90° C. for 30 min. The reaction mixture was acidified with 1N HCl, and all volatiles were removed in vacuo. The remaining residue was suspended in MeOH (10 ml) and filtered. Concentration of the filtrate afforded the title compound. LCMS $Rt_M$=1.58 min, $[M+H]^+$=233.2.

c) N-((6-amino-2,4-dimethylpyridin-3-yl)methyl)-1-(2-hydroxy-1-phenylethyl)-1H-pyrazole-4-carboxamide The title compound was obtained starting from 1-(2-hydroxy-1-phenylethyl)-1H-pyrazole-4-carboxylic acid in analogy to Example 1. $^1$H-NMR (DMSO-d6, 400 MHz): 2.40 (s, 3H), 3.94 (dd, 1H), 4.18 (dd, 1H), 4.29 (d, 2H), 5.46 (dd, 1H), 6.64 (s, 1H), 7.24-7.39 (m, 5H), 7.41-7.61 (m, 2H), 7.88

(s, 1H), 8.19 (t, 1H), 8.34 (s, 1H), 13.25 (br, s, 1H). LCMS Rt$_M$=1.39 min, [M+H]$^+$=366.3.

Example 12

1-(4-Methoxy-benzenesulfonyl)-1H-pyrrole-3-carboxylic acid (6-amino-2,4-dimethyl-pyridin-3-ylmethyl)-amide

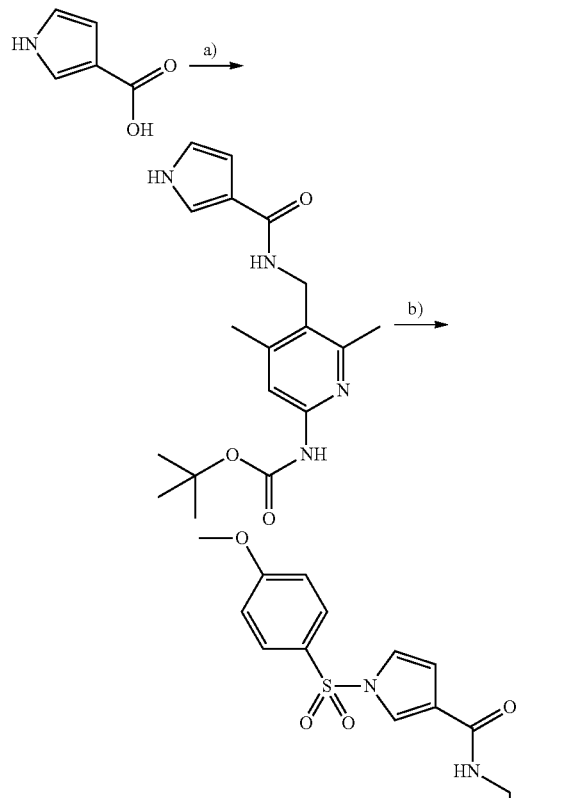

a) (4,6-Dimethyl-5-{[(1H-pyrrole-3-carbonyl)-amino]-methyl}-pyridin-2-yl)-carbamic acid tert-butyl ester To a mixture of 1H-pyrrole-3-carboxylic acid (1.40 g, 12.60 mmol), tert-butyl 5-(aminomethyl)-4,6-dimethylpyridin-2-ylcarbamate (3.48 g, 13.86 mmol) and DIPEA (6.60 ml, 37.8 mmol) in DCM (100 ml) was added HBTU (5.73 g, 15.12 mmol) at rt and was stirred at rt for 12 hours. The suspension was filtered off. The solid was washed with DCM and dried under reduced pressure to afford pure tert-butyl 5-((1H-pyrrole-3-carboxamido)methyl)-4,6-dimethylpyridin-2-ylcarbamate. HPLC (Method G) Rt=1.35 min; MS [M+H]$^+$=345.2.

b) 1-(4-Methoxy-benzenesulfonyl)-1H-pyrrole-3-carboxylic acid (6-amino-2,4-dimethyl-pyridin-3-ylmethyl)-amide To a mixture of (4,6-dimethyl-5-{[(1H-pyrrole-3-carbonyl)-amino]-methyl}-pyridin-2-yl)-carbamic acid tert-butyl ester (45 mg, 0.131 mmol) and 4-DMAP (6.38 mg, 0.052 mmol) in dry THF (0.8 ml) was added under argon atmosphere a 1.0 M solution of KOtBu in THF (0.196 ml, 0.196 mmol). The reaction mixture was stirred at it for 20 min. 4-Methoxy-benzenesulfonyl chloride (32.4 mg, 0.157 mmol) was added in one portion and the mixture was stirred for an additional 17 h at rt. The reaction mixture was diluted with MeOH (1 ml) and H$_2$O (1 ml) and the resulting solution was filtered over a PTFE membrane (0.45 um). The filtrate was purified by a preparative LC-MS system using a Waters Sunfire™ C-18 OBD column [150×30 mm, 5 um particle size] and elution at 50 ml/min using the following gradient: 0-1.5 min (90% water containing 0.1% TFA/10% acetonitrile), 1.5-11.5 min (linear gradient from 90% water containing 0.1% TFA/10 acetonitrile to 35% water containing 0.1% TFA/65% acetonitrile), 11.5-12.5 min (linear gradient from 35% water containing 0.1% TFA/65% acetonitrile to 0% water containing 0.1% TFA/100% acetonitrile), 12.5-13.5 min (0% water containing 0.1% TFA/100% acetonitrile). Product collection was triggered by the MS signal and the resulting fractions were pooled and freeze-dried to yield a colorless powder. A 50% solution of TFA in DCM (1.0 ml) was added and the reaction mixture was stirred at rt for 2 h. After evaporation to dryness, the residue was dissolved in a mixture of acetonitrile/water and freeze-dried to yield the title compound. 1H-NMR (DMSO, 400 MHz): 13.52 (br s, 1H), 8.26 (t, 1H), 7.96-7.92 (m, 2H), 7.87-7.86 (m, 1H), 7.68 (br s, 2H), 7.37 (t, 1H), 7.19-7.16 (m, 2H), 6.67-6.66 (m, 1H), 6.63 (s, 1H), 4.26 (d, 2H), 3.85 (s, 3H), 2.50 (s, 3H), 2.37 (s, 3H); LCMS (Method T) Rt$_T$=0.88 min; [M+H]$^+$=414.8.

Example 13

N-((6-amino-2,4-dimethylpyridin-3-yl)methyl)-1-(4-methoxybenzyl)-1H-pyrazole-4-carboxamide

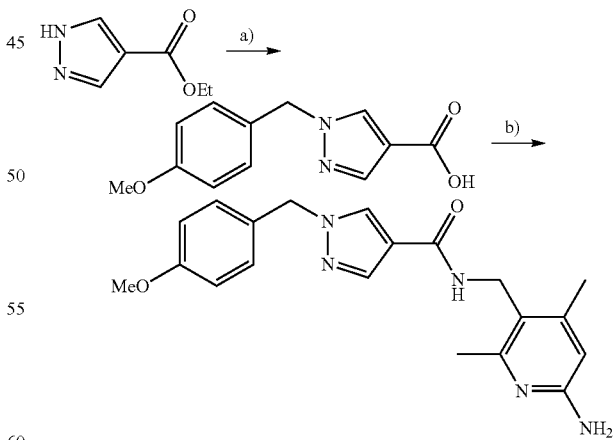

a) 1-(4-Methoxybenzyl)-1H-pyrazole-4-carboxylic acid

A mixture of ethyl 1H-pyrazole-4-carboxylate (400 mg, 2.85 mmol), K$_2$CO$_3$ (1.97 g, 14.3 mmol) and 4-methoxybenzyl bromide (0.453 ml, 3.14 mmol) in dry acetone (10 ml) was heated to 50° C. for 3 h. The reaction mixture was filtered, and the filtrate was concentrated. EtOH (10 mL) and KOH (320 mg, 5.71 mmol) were added and the mixture was heated to 65° C. for 6 h, before it was concentrated again. The crude product was dissolved in water (5 ml), washed with EA (2×10 ml) and acidified with 1N HCl. The resulting precipitate was collected by filtration, washed with water and dried in vacuo affording the title compound. LCMS $Rt_L$=0.86 min, $[M+H]^+$= 233.2.

b) N-((6-amino-2,4-dimethylpyridin-3-yl)methyl)-1-(4-methoxybenzyl)-1H-pyrazole-4-carboxamide To a mixture of tert-butyl 5-(aminomethyl)-4,6-dimethylpyridin-2-ylcarbamate (80.0 mg, 0.318 mmol) in DCM (3 ml) were added HOAt (87.0 mg, 0.637 mmol), collidine (0.127 ml, 0.955 mmol), 1-(4-methoxybenzyl)-1H-pyrazole-4-carboxylic acid (73.9 mg, 0.318 mmol) and HATU (81.0 mg, 0.212 mmol). After stirring for 2 h at rt, all volatiles were removed in vacuo. The crude intermediate was purified by column chromatography (CombiFlash Companion, 12 g $SiO_2$, TBME to TBME+10% MeOH), dissolved in DCM (3 ml) and TFA (1 ml), kept for 14 h at rt, and concentrated. Purification by column chromatography (CombiFlash Rf, 13 g RediSep Rf C18, MeCN:water 5:95+0.1% TFA to MeCN) afforded the title compound as. $^1$H-NMR (DMSO-d6, 400 MHz): 2.37 (s, 3H), 3.73 (s, 3H), 4.27 (d, 2H), 5.24 (s, 1H), 6.64 (s, 1H), 6.91 (d, 2H), 7.23 (d, 2H), 7.70 (br, s, 2H), 7.84 (s, 1H), 8.14-8.19 (m, 2H), 13.59 (s, 1H). LCMS $Rt_K$=0.71 min, $[M+H]^+$=366.4.

Example 14

N-((6-amino-4-methoxy-2-methylpyridin-3-yl)methyl)-1-benzyl-1H-pyrazole-4-carboxamide

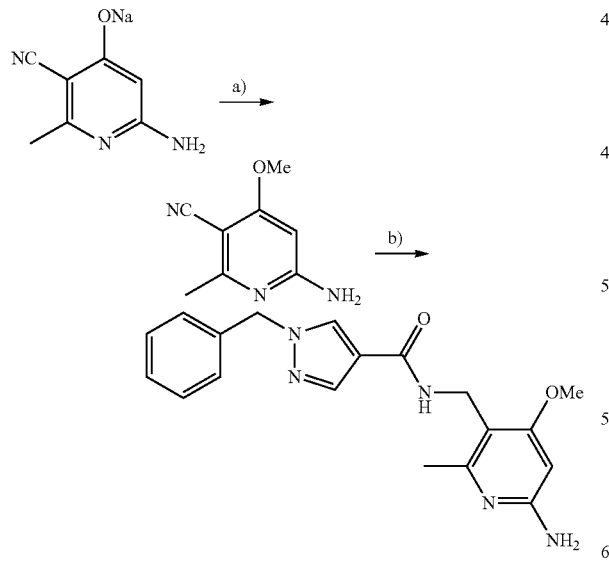

a) 6-Amino-4-methoxy-2-methylnicotinonitrile

To a mixture of sodium 6-amino-3-cyano-2-methylpyridin-4-olate (500 mg, 2.92 mmol, prepared in analogy to WO2001062233A2 and isolated as sodium salt), and $K_2CO_3$ (808 mg, 5.84 mmol) in DMF (1 ml) was added MeI (0.200 ml, 3.21 mmol), and the reaction mixture was stirred at it for 9 d. Saturated $NaHCO_3$ (50 ml) was added and the mixture was extracted with EA (4×20 ml). The combined organic extracts were diluted with additional DCM and MeOH until homogeneous, dried over $Na_2SO_4$, filtered and concentrated. The crude product was recrystallized from refluxing MeOH-DCM to afford the title compound. $^1$H-NMR (DMSO-d6, 400 MHz): 2.34 (s, 3H), 3.82 (s, 3H), 5.91 (s, 1H), 6.83 (br, s, 2H); LCMS $Rt_M$=1.11 min, $[M+H]^+$=164.2.

b) N-((6-Amino-4-methoxy-2-methylpyridin-3-yl)methyl)-1-benzyl-1H-pyrazole-4-carboxamide A mixture of 6-amino-4-methoxy-2-methylnicotinonitrile (100 mg, 0.613 mmol) in THF (4 ml) was cooled to −78° C., and treated with DIBAL-H (1M in THF, 3.68 ml, 3.68 mmol). The mixture was slowly warmed to rt. Stirring was continued for 24 h at rt, before the reaction mixture was carefully transferred to an ice-cold mixture of MeOH (50 ml) and water (0.2 ml, 11.0 mmol). The resulting suspension was adsorbed on celite (ca. 30 $cm^3$) and dried in vacuo. Elution with DCM-MeOH (9:1, 200 ml) and removal of all volatiles afforded a yellow oil. Dry THF (5 ml), 1-benzyl-1H-pyrazole-4-carboxylic acid (79.0 mg, 0.389 mmol, prepared in analogy to example 13), DIPEA (0.209 ml, 1.20 mmol), DMAP (1.8 mg, 0.015 mmol) and HATU (148 mg, 0.389 mmol) were added, and the reaction mixture was stirred at it for 14 h, before it was concentrated to dryness. The crude product was purified by column chromatography (CombiFlash Rf, 13 g RediSep Rf C18, MeCN:water 5:95+0.1% TFA to MeCN), followed by preparative HPLC (Waters Sunfire Prep C18 OBD 5 um, 100×30 mm, A: $H_2O$+0.1% TFA, B: MeCN+0.1% TFA, 5-35% B in 15 min, 30 ml/min, rt) to afford the title compound. $^1$H-NMR (DMSO-d6, 400 MHz): 2.47 (s, 3H), 3.91 (s, 3H), 4.22 (d, 2H), 5.33 (s, 2H), 6.26 (s, 1H), 7.22-7.27 (m, 2H), 7.28-7.38 (m, 3H), 7.53 (br, s, 2H), 7.86 (s, 1H), 8.09 (t, 1H), 8.23 (s, 1H), 12.95 (s, 1H); LCMS $Rt_K$=0.82 min, $[M+H]^+$=352.4.

Example 15

N-((6-amino-4-(cyclohexyloxy)-2-methylpyridin-3-yl)methyl)-1-benzyl-1H-pyrazole-4-carboxamide

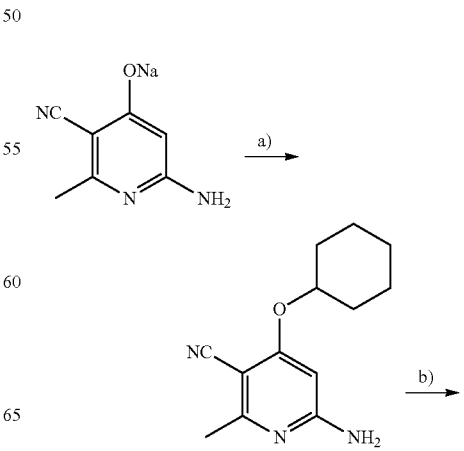

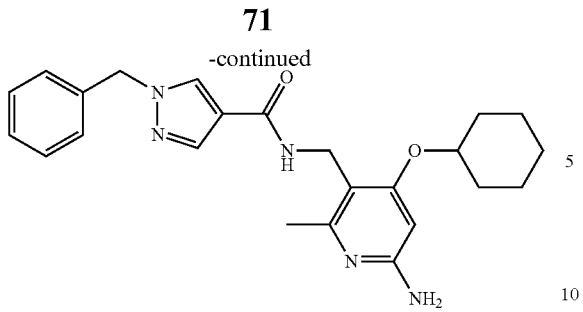

(m, 2H), 7.27-7.41 (m, 5H), 7.84 (s, 1H), 7.92 (t, 1H), 8.21 (s, 1H), 12.81 (s, 1H); LCMS $Rt_K$=1.11 min, [M+H]$^+$=420.4.

Example 16

N-((6-amino-2,4-dimethylpyridin-3-yl)methyl)-1-(4-(hydroxymethyl)benzyl)-1H-pyrazole-4-carboxamide a) 6-Amino-4-(cyclohexyloxy)-2-methylnicotinonitrile To a mixture of sodium 6-amino-3-cyano-2-methylpyridin-4-olate (300 mg, 1.75 mmol) and K$_2$CO$_3$ (485 mg, 3.51 mmol) in DMF (6 ml) was added Cyclohexenylbromide (0.213 ml, 1.84 mmol) and the reaction mixture was stirred at it for 14 h. NaHCO$_3$ (100 ml) was added and the mixture was extracted with EA (5×30 ml). The combined organic extracts were dried over Na$_2$SO$_4$, filtered and concentrated. The resulting product was dissolved in n-PrOH (10 ml), and hydrogenated (1 atm H$_2$, rt) for 1 h over Pd/C (93 mg, 0.088 mmol). The reaction mixture was filtered and the filtrate was adsorbed on celite. Purification by column chromatography (CombiFlash Companion, 10 g SiO$_2$, DCM to DCM:MeOH 9:1) afforded the desired product. LCMS $Rt_M$=1.63 min, [M+H]$^+$=232.6.

b) N-((6-Amino-4-(cyclohexyloxy)-2-methylpyridin-3-yl)methyl)-1-benzyl-1H-pyrazole-4-carboxamide To a mixture of 6-Amino-4-(cyclohexyloxy)-2-methylnicotinonitrile (30.0 mg, 0.130 mmol) in EtOH (5 ml) were added about 10 cm$^3$ of a Raney-Ni suspension in MeOH under Ar. The flask was sealed, and the suspension was vigorously stirred at it for 3 d under an atmosphere of hydrogen. The reaction mixture was filtered over a plug of cellite and eluted with DCM-MeOH (9:1, 100 ml), DCM (50 ml), MeOH (50 ml) and NH$_3$ in MeOH (7N, 50 ml). The combined filtrates were concentrated. Dry THF (5 ml), 1-benzyl-1H-pyrazole-4-carboxylic acid (26.3 mg, 0.130 mmol, prepared in analogy to example 13), DIPEA (0.091 ml, 0.520 mmol), DMAP (0.80 mg, 0.0065 mmol) and HATU (49.4 mg, 0.130 mmol) were added, and the reaction mixture was stirred at it for 10 h, before it was concentrated to dryness. The crude product was purified by column chromatography (CombiFlash Companion, 4 g SiO$_2$, DCM to DCM:MeOH 9:1), followed by preparative HPLC (Waters Sunfire Prep C18 OBD 5 um, 100×19 mm, A: H$_2$O+0.1% TFA, B: MeCN+0.1% TFA, 15-45% B in 10 min, 30 ml/min, rt) affording the title compound. $^1$H-NMR (DMSO-d6, 400 MHz): 1.15-1.27 (m, 1H), 1.27-1.38 (m, 2H), 1.40-1.50 (m, 1H), 1.51-1.62 (m, 2H), 1.62-1.72 (m, 2H), 1.77-1.88 (m, 2H), 2.44 (s, 3H), 4.24 (d, 2H), 4.47 (m$_c$, 1H), 5.34 (s, 2H), 6.29 (s, 1H), 7.19-7.25

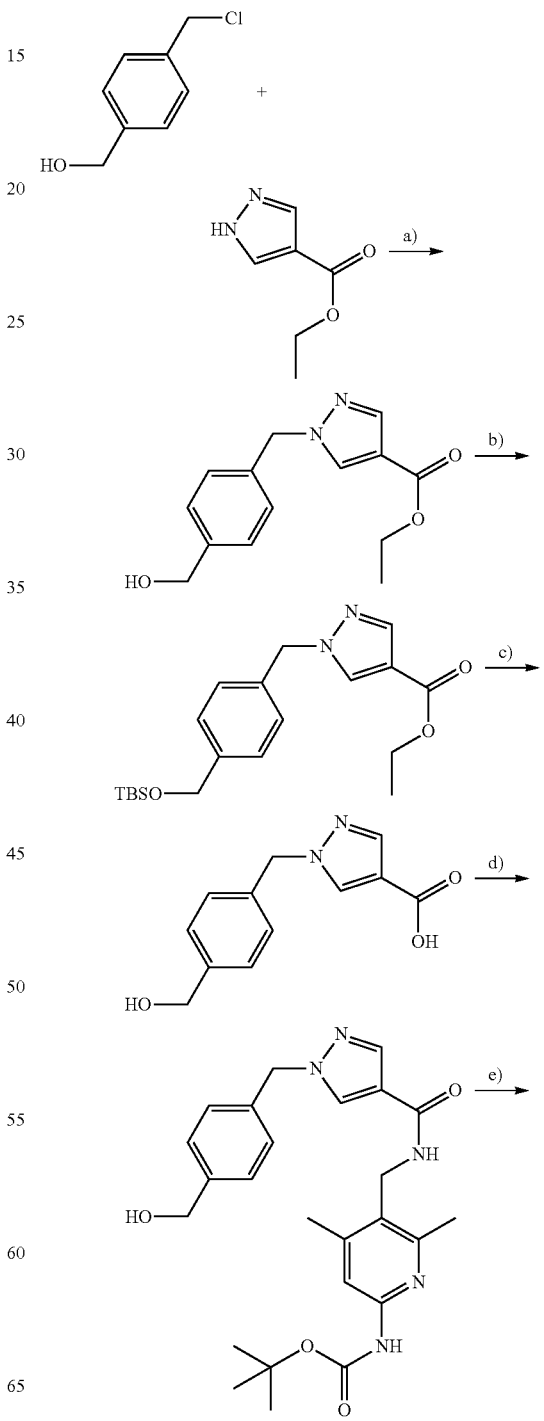

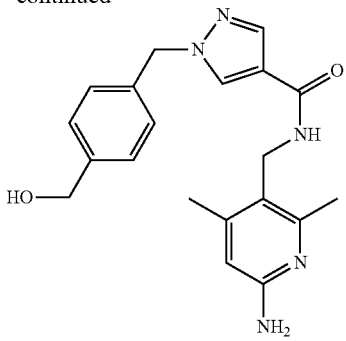

a) 1-(4-Hydroxymethyl-benzyl)-1H-pyrazole-4-carboxylic acid ethyl ester

A mixture of (4-Chloromethyl-phenyl)-methanol (600 mg, 3.8 mmol), ethyl 1H-pyrazole-4-carboxylate (537 mg, 3.8 mmol) and potassium carbonate (2.6 g, 19 mmol) in 30 mL acetone was stirred at 50° C. for 3 h. The mixture was filtrated and concentrated in vacuo. The crude was purified by preparative HPLC (Waters Sunfire Prep C18 PBD 5 um, 30×100 mm, 5 to 100% ACN and 0.1% TFA, flow 40 ml/min) to yield the title compound. LCMS (method A) $Rt_A$=1.403 min; $[M+H]^+$=261.0.

b) 1-[4-(tert-Butyl-dimethyl-silanyloxymethyl)-benzyl]-1H-pyrazole-4-carboxylic acid ethyl ester A mixture of 1-(4-Hydroxymethyl-benzyl)-1H-pyrazole-4-carboxylic acid ethyl ester (500 mg, 1.4 mmol), tert-Butyl-chloro-dimethyl-silane (261 mg, 1.7 mmol) and imidazole (245 mg, 3.6 mmol) in 5 mL DMF was stirred at RT for 6 h. The reaction mixture was evaporated in vacuo, the crude was dissolved in ethyl acetate and extracted with 1N aq. HCl-solution and aq. NaHCO₃ solution. The organic layer was dried over MgSO₄ and concentrated in vacuo to yield the title compound which was used in the next step without further purification. 1H-NMR (DMSO-d6, 400 MHz) 8.45 (s, 1H), 7.87 (s, 1H), 7.24-7.30 (m, 4H), 5.35 (s, 2H), 4.69 (s, 2H), 4.21 (q, 2H), 1.26 (t, 3H), 0.90 (s, 9H), 0.07 (s, 6H).

c) 1-(4-Hydroxymethyl-benzyl)-1H-pyrazole-4-carboxylic acid

A mixture of 1-[4-(tert-Butyl-dimethyl-silanyloxymethyl)-benzyl]-1H-pyrazole-4-carboxylic acid ethyl ester (630 mg, 1.4 mmol) and lithiumhydroxide-hydrate (119 mg, 2.8 mmol) in 20 mL MeOH and 10 mL water was stirred at RT for 32 h. The mixture was evaporated in vacuo and the aq. layer was acidified with 1 N aq. HCl. After extraction with ethyl acetate, the organic layer was dried over MgSO₄ and evaporated to yield the crude product which was used in the next step without further purification. 1H-NMR (DMSO-d6, 400 MHz) 12.3 (bs, 1H), 8.36 (s, 1H), 7.81 (s, 1H), 7.23-7.31 (s, 4H), 5.34 (s, 2H), 5.18 (t, 1H), 4.47 (s, 2H).

d) [5-({[1-(4-Hydroxymethyl-benzyl)-1H-pyrazole-4-carbonyl]-amino}-methyl)-4,6-dimethyl-pyridin-2-yl]-carbamic acid tert-butyl ester A mixture of 1-(4-Hydroxymethyl-benzyl)-1H-pyrazole-4-carboxylic acid (220 mg, 0.95 mmol), (5-Aminomethyl-4,6-dimethyl-pyridin-2-yl)-carbamic acid tert-butyl ester (238 mg, 0.95 mmol), HATU (7206 mg, 1.90 mmol) and DIPEA (0.64 mL, 2.84 mmol) in 5 mL DMF was stirred at room temperature for 16 h. The reaction mixture was concentrated in vacuo, dissolved in ethylacetate and extracted with aq. NaHCO₃-solution. The organic layer was dried over MgSO₄ and evaporated. The crude product was purified by preparative HPLC (Waters Sunfire Prep C18 PBD 5 um, 30×100 mm, 5 to 100% ACN and 0.1% TFA, flow 40ml/min). LCMS (method A) $Rt_A$=1.243 min; $[M+H]^+$=466.0.

e) N-((6-amino-2,4-dimethylpyridin-3-yl)methyl)-1-(4-(hydroxymethyl)benzyl)-1H-pyrazole-4-carboxamide A mixture of [5-({[1-(4-Hydroxymethyl-benzyl)-1H-pyrazole-4-carbonyl]-amino}-methyl)-4,6-dimethyl-pyridin-2-yl]-carbamic acid tert-butyl ester (50 mg, 0.11 mmol), 1 mL TFA and 2 mL DCM was stirred of room temperature for 2 h. The mixture was evaporated in vacuo and the residue was purified by preparative HPLC (Macherey-Nagel Nucleosil 250×40 mm, 5 to 100% ACN and 0.1% TFA, flow 40ml/min). The product containing fractions were lyophilised, then dissolved in 1 mL MeOH and the resulting mixture was filtered over a MeOH flushed PL-HCO₃ MP-resin column. The column was washed with MeOH, the solvent was removed and the product was dissolved in water/ACN and lyophilised to yield the title compound. 1H-NMR (DMSO-d6, 400 MHz) 8.24 (s, 1H), 7.93 (t, 1H), 7.88 (s, 1H), 7.28-7.30 (s, 2H), 7.21-7.23 (s, 2H), 6.15 (s, 1H), 5.78 (bs, 2H), 5.30 (s, 2H), 5.18 (t, 1H), 4.47 (d, 2H), 4.27 (d, 2H), 2.30 (s, 3H), 2.17 (s, 3H); LCMS (method A) $Rt_A$=0.128 min; $[M+H]^+$=366.1.

Example 17

N-((6-amino-2,4-dimethylpyridin-3-yl)methyl)-1-(4-((2,5-dioxopyrrolidin-1-yl)methyl)benzyl)-1H-pyrazole-4-carboxamide

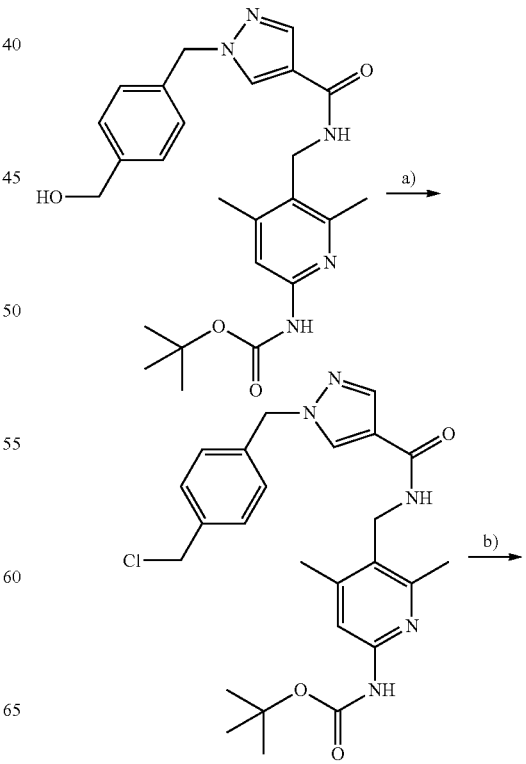

-continued

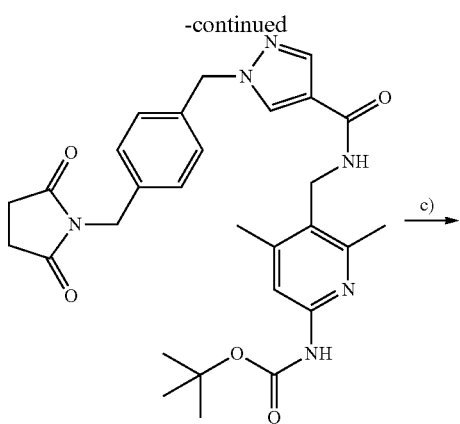

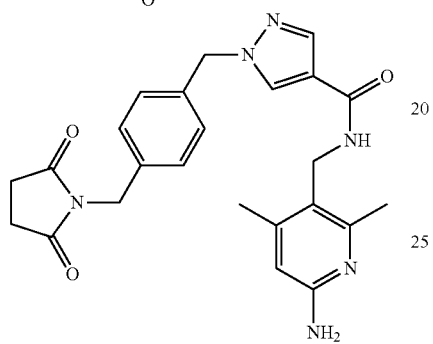

a) [5-({[1-(4-Chloromethyl-benzyl)-1H-pyrazole-4-carbonyl]-amino}-methyl)-4,6-dimethyl-pyridin-2-yl]-carbamic acid tert-butyl ester A mixture of [5-({[1-(4-Hydroxymethyl-benzyl)-1H-pyrazole-4-carbonyl]-amino}-methyl)-4,6-dimethyl-pyridin-2-yl]-carbamic acid tert-butyl ester (100 mg, 0.2 mmol, for preparation see step D, example 16), trimethylsilyl chloride (47 mg, 0.4 mmol) and DMSO (4 mg, 0.06 mmol) was stirred at RT for 10 min. Aq. NaHCO₃-solution was added and the mixture was extracted with ethyl acetate. The organic layer was dried over MgSO₄ and concentrated in vacuo to yield the title compound which was used in the next step without further purification. LCMS (method A) $Rt_A$=1.598 min; [M+H]⁺=484.0.

b) {5-[({1-[4-(2,5-Dioxo-pyrrolidin-1-ylmethyl)-benzyl]-1H-pyrazole-4-carbonyl}-amino)-methyl]-4,6-dimethyl-pyridin-2-yl}-carbamic acid tert-butyl ester A mixture of [5-({[1-(4-Chloromethyl-benzyl)-1H-pyrazole-4-carbonyl]-amino}-methyl)-4,6-dimethyl-pyridin-2-yl]-carbamic acid tert-butyl ester (67 mg, 0.1 mmol), succinimide (12 mg, 0.1 mmol) and potassium carbonate (84 mg, 0.6 mmol) in 50 mL acetone was stirred at 80° C. for 24 h. The mixture was filtrated and concentrated in vacuo. The crude was purified by preparative HPLC (Waters Sunfire Prep C18 PBD 5 um, 30×100 mm, 5 to 100% ACN and 0.1% TFA, flow 40ml/min) to yield the title compound. LCMS (method A) $Rt_A$=1.339 min; [M+H]⁺=547.2.

c) N-((6-amino-2,4-dimethylpyridin-3-yl)methyl)-1-(4-((2,5-dioxopyrrolidin-1-yl)methyl)benzyl)-1H-pyrazole-4-carboxamide A mixture of {5-[({1-[4-(2,5-Dioxo-pyrrolidin-1-ylmethyl)-benzyl]-1H-pyrazole-4-carbonyl}-amino)-methyl]-4,6-dimethyl-pyridin-2-yl]-carbamic acid tert-butyl ester (48 mg, 0.08 mmol), 1 mL TFA and 2 mL DCM was stirred of room temperature for 2 h. The mixture was evaporated in vacuo and the residue was purified by preparative HPLC (Macherey-Nagel Nucleosil 250×40 mm, 5 to 100% ACN and 0.1% TFA, flow 40ml/min). The product containing fractions were lyophilised, then dissolved in 1 mL MeOH and the resulting mixture was filtered over a MeOH flushed PL-HCO₃ MP-resin column. The column was washed with MeOH, the solvent was removed and the product was dissolved in water/ACN and lyophilised to yield the title compound. 1H-NMR (DMSO-d6, 400 MHz) 88.25 (s, 1H), 7.91 (t, 1H), 7.87 (s, 1H), 7.24 (d, 2H), 7.20 (d, 2H), 6.13 (s, 1H), 5.70 (bs, 2H), 5.28 (s, 2H), 4.52 (d, 2H), 2.67 (s, 4H), 2.29 (s, 3H), 2.15 (s, 3H); LCMS (method A) $Rt_A$=0.439 min; [M+H]⁺=447.1.

Example 18

N-((6-amino-2,4-dimethylpyridin-3-yl)methyl)-1-(pyridin-4-ylmethyl)-1H-pyrazole-4-carboxamide

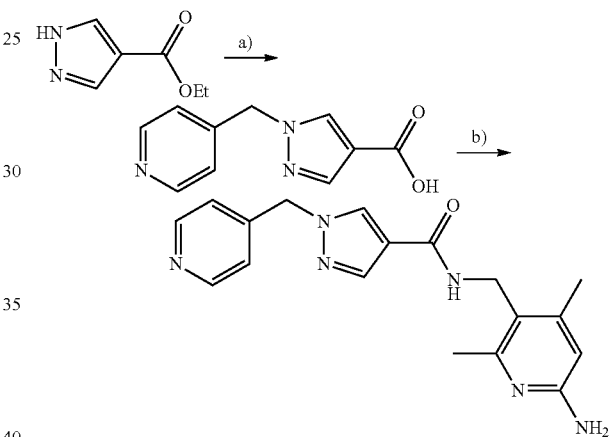

a) 1-(Pyridin-4-ylmethyl)-1H-pyrazole-4-carboxylic acid

To a mixture of ethyl 1H-pyrazole-4-carboxylate (350 mg, 2.50 mmol) in dry DMF (2 ml) were added NaH (60% in mineral oil, 400 mg, 10.0 mmol) and 4-(bromomethyl)-pyridine hydrobromide (632 mg, 2.50 mmol) at 0° C. The resulting suspension was stirred for 14 h while slowly warming to rt, before it was transferred to a sat. solution of NaHCO₃ (50 mL) and extracted with EA (4×20 ml). The combined organic extracts were dried over Na₂SO₄, filtered and concentrated. Purification by column chromatography (CombiFlash Companion, 4 g SiO₂, heptane to EA+5% NEt₃) afforded the intermediate ester, which was dissolved in EtOH (5 ml) and NaOH (1N, 5.00 ml), and heated to reflux for 20 min. The reaction mixture was neutralized with 1N HCl, and concentrated to dryness to yield the crude product which was used in the next step without any further purification. LCMS $Rt_M$=0.19 min, [M+H]⁺=204.1.

b) N-((6-amino-2,4-dimethylpyridin-3-yl)methyl)-1-(pyridin-4-ylmethyl)-1H-pyrazole-4-carboxamide The title compound was obtained as a colorless solid starting from crude 1-(pyridin-4-ylmethyl)-1H-pyrazole-4-carboxylic acid in analogy to Example 13. $^1$H-NMR (DMSO-d6, 400 MHz): 2.40 (s, 3H), 4.29 (d, 2H), 5.50 (s, 2H), 6.65 (s, 1H), 7.27 (d, 2H), 7.57 (br, s, 2H), 7.94 (s, 1H), 8.25 (t, 1H), 8.33 (s, 1H), 8.61 (d, 2H), 13.32 (br, s, 1H). LCMS $Rt_M$=1.12 min, [M+H]$^+$=337.3.

Example 19

N-((6-amino-2-methyl-4-(2-(methylamino)-2-oxoethoxy)pyridin-3-yl)methyl)-1-benzyl-1H-pyrazole-4-carboxamide

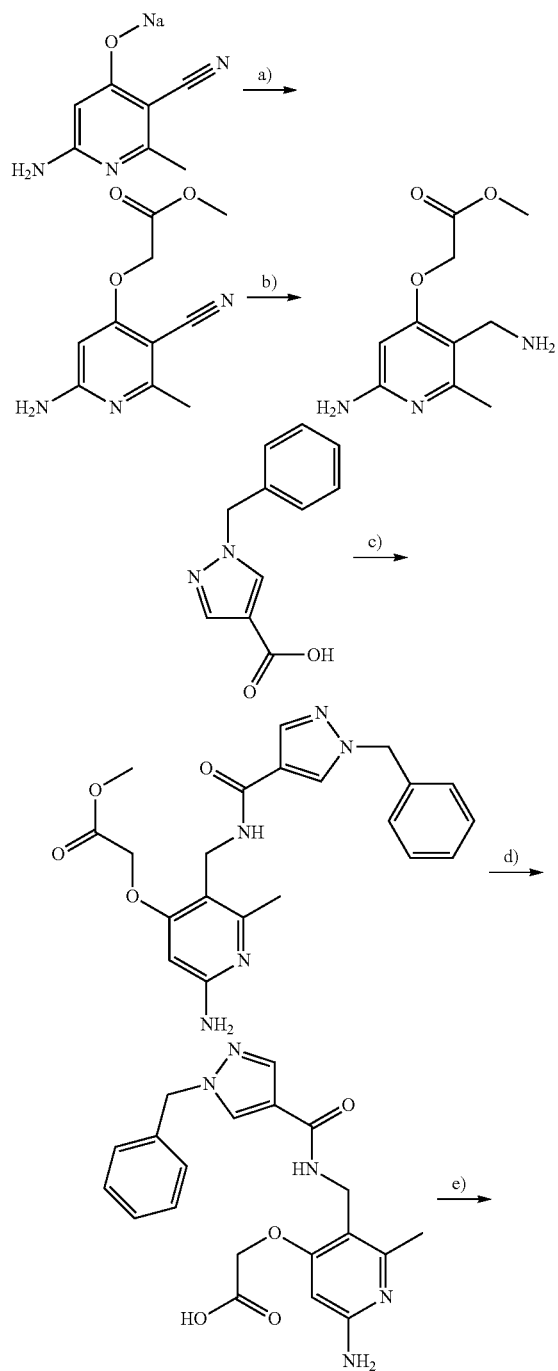

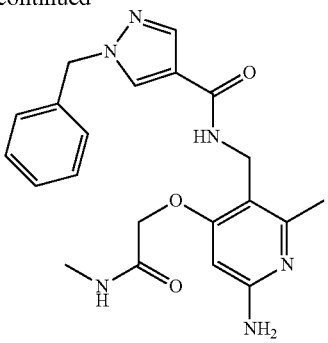

a) Methyl 2-(6-amino-3-cyano-2-methylpyridin-4-yloxy)acetate sodium 6-amino-3-cyano-2-methylpyridin-4-olate (600 mg, 3.51 mmol) and Cs$_2$CO$_3$ (1714 mg, 5.26 mmol) were suspend in DMSO (10 ml), then methyl 2-bromoacetate (1.328 ml, 14.02 mmol) was slowly added at RT. The suspension was stirring at 50° C. during 5 h. Water/brine were added and the reaction mixture was extracted with EA, dried and evaporated to afford the crude product. Purification by flash chromatography (AcOEt, then DCM:MeOH:NH$^4$OH 9:1:0.05) afforded the title compound. LCMS (method F) $Rt_F$=0.35 min; [M+H]$^+$=222.2.

b) Methyl 2-(6-amino-3-(aminomethyl)-2-methylpyridin-4-yloxy)acetate

Methyl 2-(6-amino-3-cyano-2-methylpyridin-4-yloxy)acetate (215 mg, 0.972 mmol) was dissolved in EtOH (16 ml), MeOH (8 ml) and HCl 1M (5 ml), then Palladium on carbon (310 mg, 0.292 mmol) was added and the reaction mixture was stirred at it under H$_2$ pressure during 48 h. After filtration over celite, washing with MeOH and evaporation of the solvent, the title compound was obtained. MS (Method D): [M+H]$^+$226.0/451.2.

c) Methyl 2-(6-amino-3-((1-benzyl-1H-pyrazole-4-carboxamido)methyl)-2-methylpyridin-4-yloxy)acetate Methyl 2-(6-amino-3-(aminomethyl)-2-methylpyridin-4-yloxy)acetate (271 mg, 0.909 mmol), 1-benzyl-1H-pyrazole-4-carboxylic acid (synthesis description below) (184 mg, 0.909 mmol) and DIPEA (0.794 ml, 4.54 mmol) were dissolved in DMF (2 ml), then HATU (518 mg, 1.363 mmol) was added and the reaction mixture was stirred over night at rt. Purification by prep HPLC (Sun-Fire C18, 100×30mm 5 to 100% ACN and 0.1% TFA, flow 40 mml/min.) offered the titled compound after lyophilisation. HPLC (Method C) $Rt_c$=2.789 min, MS (Method D): [M+H]$^+$=410.0.

d) 2-(6-Amino-3-((1-benzyl-1H-pyrazole-4-carboxamido)methyl)-2-methylpyridin-4-yloxy)acetic acid Methyl 2-(6-amino-3-((1-benzyl-1H-pyrazole-4-carboxamido)methyl)-2-methylpyridin-4-yloxy)acetate (28 mg, 0.051 mmol) was dissolved in THF, EtOH, H$_2$O 2:1:1 (5 ml), then LiOH (4.31 mg, 0.103 mmol) was added and the reaction mixture was stirred at rt over night. After adjusting the pH to 4, the reaction mixture was evaporated, co-evaporated with Toluene (4 times) then dried under HV to get the title com- e) N-((6-Amino-2-methyl-4-(2-(methylamino)-2-oxoethoxy)pyridin-3-yl)methyl)-1-benzyl-1H-pyrazole-4-carboxamide 2-(6-amino-3-((1-benzyl-1H-pyrazole-4-carboxamido) methyl)-2-methylpyridin-4-yloxy)acetic acid (35 mg, 0.051 mmol) was dissolved in DMF (1 ml), CDI (16.65 mg, 0.103 mmol) was added. After stirring for 15 min at rt Methylamin 2M in THF (0.257 ml, 0.513 mmol) was added and the reaction mixture was stirred 6 h at rt. Purification by prep HPLC (Nucleosil C18, 250×40 mm 5 to 100% ACN and 0.1% TFA, flow 40 mml/min.) offered the title compound. $^1$H-NMR (DMSO-d6, 400 MHz): 2.71 (d, 3H), 4.37 (d, 2H), 4.67 (s, 2H), 5.34 (s, 2H), 6.20 (s, 1H), 7.24 (m, 5H), 7.79 (s, 2H), 7.89 (s, 1H), 8.25 (d, 2H), 8.28 (s, 1H), 8.35 (t, 1H). HPLC/MS (Method B) Rtb=0.46 min, MS [M+H]$^+$=409.4.

f) 1-Benzyl-1H-pyrazole-4-carboxylic acid

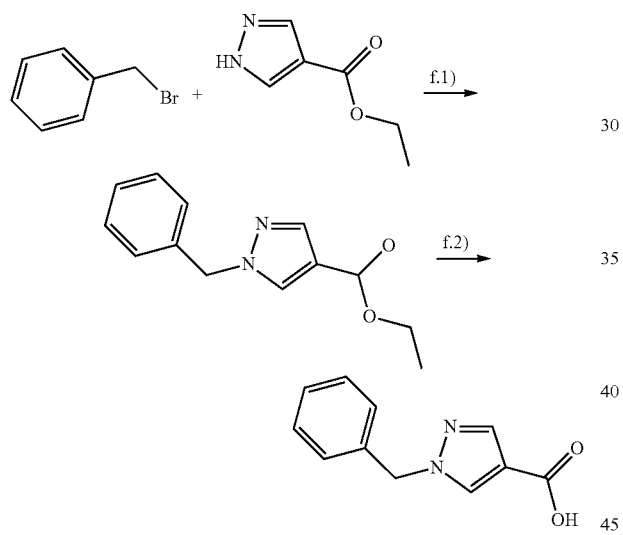

f.1) Ethyl 1-benzyl-1H-pyrazole-4-carboxylate

Bromomethyl-benzene (610 mg, 3.57 mmol) was suspended in Acetone (25 ml), ethyl 1H-pyrazole-4-carboxylate (500 mg, 3.57 mmol) and K$_2$CO$_3$ (2465 mg, 17.84 mmol) were added. The suspension was stirred 16 h at 50° C. The reaction mixture was filtrated and evaporated in vacuo to give the title compound which was used for the next step without further purification. HPLC/MS (Method A) Rt$_A$=1.82 min, MS [M+H]$^+$=230.9.

f.2) 1-Benzyl-1H-pyrazole-4-carboxylic acid

Ethyl 1-benzyl-1H-pyrazole-4-carboxylate (1.05 g, 3.56 mmol) was dissolved in MeOH (20 ml). Water (10 ml) and LiOH.H$_2$O (0.299 g, 7.11 mmol) were added and the suspension was stirred for 3 h at rt. The reaction mixture was evaporated in vacuo to remove the MeOH. The water phase was washed with AcOEt, then treated with 1N HCl until pH3, and extracted with AcOEt. The organic phase was dried over MgSO$_4$ and evaporated in vacuum to give the title compound which was used in the next step without any further purification. HPLC/MS (Method A) Rt$_A$=1.3 min, MS [M+H]$^+$=203.1.

Example 20

N-((6-amino-2,4-dimethylpyridin-3-yl)methyl)-2-(phenylamino)oxazole-4-carboxamide

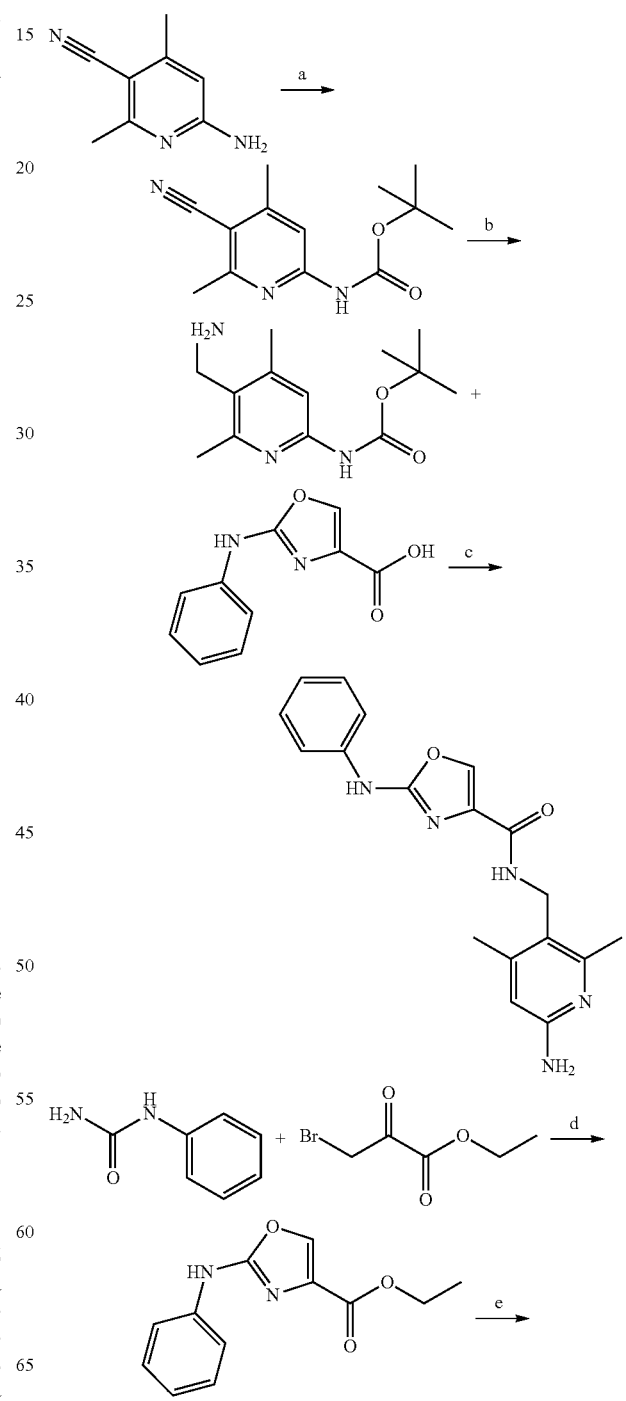

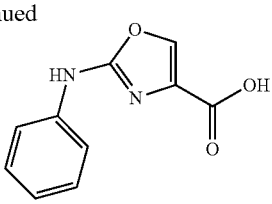

a) Tert-butyl 5-cyano-4,6-dimethylpyridin-2-ylcarbamate

To a suspension of 6-amino-2,4-dimethylnicotinonitrile (7.5 g, 48.4 mmol, prepared according to Synlett 2007, 19, 2979) and DMAP (0.591 g, 4.84 mmol) in THF (150 ml) was added $Boc_2O$ (20.23 ml, 87 mmol). The resulting mixture was stirred over night. The reaction mixture was adsorbed/concentrated onto Isolute sorbent and purified by chromatography (120 g silica, cHex/EA 100-70% cHex 30 min) to afford the desired mixture of double- and mono-protected product. The intermediate was dissolved in MeOH (175 ml) and DCM (56 ml) and cooled to 0° C. NaOH (72.6 ml, 72.6 mmol) and $H_2O_2$ (7.42 ml, 72.6 mmol) were added. Additional MeOH (ca. 15 mL) was added until the emulsion was cleared again and the reaction was stirred at that temperature for 90 min. The reaction mixture was quenched into 2N $Na_2SO_3$ (250 mL), and DCM and MeOH were slowly removed under vacuum (bath temp<50° C.). The remaining mixture was transferred into a separation funnel, diluted with additional water and extracted with DCM (6×150 mL). Drying over $Na_2SO_4$, filtration and evaporation afforded the title compound. HPLC/MS (Method F): $Rt_F$=1.59 min, $[M+H]^+$=248.3.

b) Tert-butyl 5-(aminomethyl)-4,6-dimethylpyridin-2-ylcarbamate tert-butyl 5-cyano-4,6-dimethylpyridin-2-ylcarbamate (8 g) was hydrogenated by means of raney-nickel (18.9 g) in $MeOH/NH_3$ aq. 10% (100 ml). The reaction mixture was filtered through hyflo, washed with MeOH and evaporated under reduced pressure. The crude was solved in EA (100 ml) and heptane 80 (ml) was added. The solution was partly evaporated to a volume of approx. 80 ml. The precipitated solid was filtrated to afford the title compound. HPLC/MS (Method F): $Rt_F$=0.82 min, $[M+H]^+$=252.3.

c) N-((6-amino-2,4-dimethylpyridin-3-yl)methyl)-2-(phenylamino)oxazole-4-carboxamide To a solution of 2-(phenylamino)oxazole-4-carboxylic acid (90 mg, 0.432 mmol), tert-butyl 5-(aminomethyl)-4,6-dimethylpyridin-2-ylcarbamate (130 mg, 0.518 mmol) and DIPEA (226 ul, 1.296 mmol) in DCM (4 ml) was added propylphosphonic anhydride solution (50% in EA, 390 ul, 0.662 mmol) at rt. The reaction mixture was stirred at RT. The reaction mixture was quenched with $H_2O$ and extracted twice with DCM. The combined organic phases were dried over $Na_2SO_4$, filtered and evaporated under reduced pressure to afford a suspension. The solids were filtered off and washed with DCM/MeOH to afford the Boc-protected precursor of title product. This was dissolved in HCl (4 N in dioxane, 820 ul), and the mixture was stirred at RT for 4 hours. To the resulting suspension was added diethylether (2 ml). The etheric phase was separated and the remaining crystals were dried under reduced pressure at 50° C. over night to afford the title product. $^1$H-NMR (CD3OD, 400 MHz): 7.94 (s, 1H), 7.62 (d, 2H), 7.32 (t, 2H), 7.02 (t, 1H), 6.72 (s, 1H), 4.53 (s, 2H), 2.63 (s, 3H), 2.51 (s, 3H), HPLC/MS (Method G): $Rt_G$=1.38 min, MS $[M+H]^+$=338.3.

d) Ethyl 2-(phenylamino)oxazole-4-carboxylate

A solution of 1-phenylurea (2.0 g, 14.69 mmol) and ethyl 3-bromo-2-oxopropanoate (2.16 ml, 14.69 mmol) in DMF (58 ml) was heated at 60° C. for 3 hours. The reaction mixture was allowed to cool to rt and quenched with water (300 ml)/$Na_2CO_3$-solution (50 ml). The product was extracted with EA (2×). The combined organic phases were washed with brine, dried over $Na_2SO_4$, filtered and evaporated under reduced pressure to afford crude product. Purification by flash-chromatography (Silica gel 62 g, gradient: cyclohexane/EA (80 ml/min.) from 95/5 (5 min.) to 80/20 (25 min.)) afforded the title compound. HPLC (Method U): $Rt_U$=1.91 min, MS (Method D) $[M+H]^+$=233.1.

e) 2-(Phenylamino)oxazole-4-carboxylic acid

A mixture of ethyl 2-(phenylamino)oxazole-4-carboxylate (1.64 g, 6.94 mmol) and lithiumhydroxide (332 mg, 13.88 mmol) in THF (23 ml)/water (11.5 ml) was stirred at rt for 4 hours. The reaction mixture was acidified with 2 N HCl and extracted with EA (2 x). The combined organic phases were dried over $Na_2SO^4$, filtered and evaporated under reduced pressure to afford the title product. HPLC/MS (Method G): $Rt_G$=1.41 min, MS (Method D) $[M+H]^+$=204.9.

Example 21

N-((6-amino-2,4-dimethylpyridin-3-yl)methyl)-1-benzyl-1H-1,2,3-triazole-4-carboxamide

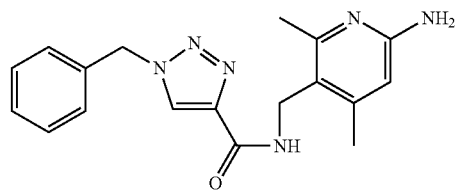 [SMILES: Cc1cc(N)nc(C)c1CNC(=O)c1cn(Cc2ccccc2)nn1]

The title compound was prepared in analogy to example 4, Step c) starting from 1-benzyl-1H-1,2,3-triazole-4-carboxylic acid (Tetrahedron Letters, 2010, 51(28), 3691). HPLC/MS (Method A) Rt=0.807 min; $[M+H]^+$=337.0.

Example 22

N-((6-amino-2,4-dimethylpyridin-3-yl)methyl)-1-benzyl-1H-imidazole-4-carboxamide

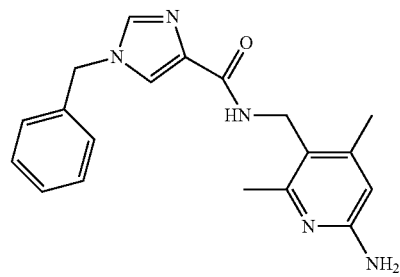 [SMILES: Cc1cc(N)nc(C)c1CNC(=O)c1cn(Cc2ccccc2)cn1]

The title compound was prepared in analogy to example 6. HPLC (Method B) Rt=0.460 min; MS [M+H]⁺=336.4.

Example 23

N-((6-amino-2,4-dimethylpyridin-3-yl)methyl)-1-(4-phenoxybenzyl)-1H-imidazole-4-carboxamide

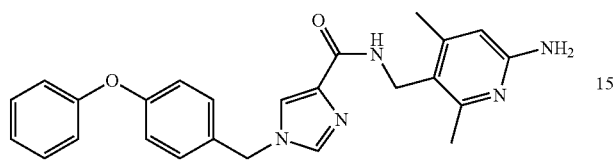

The title compound was prepared in analogy to example 6. HPLC (Method A) Rt=1.306 min; MS [M+H]⁺=428.0.

Example 24

1-(4-(1H-pyrazol-1-yl)benzyl)-N-((6-amino-2,4-dimethylpyridin-3-yl)methyl)-1H-imidazole-4-carboxamide

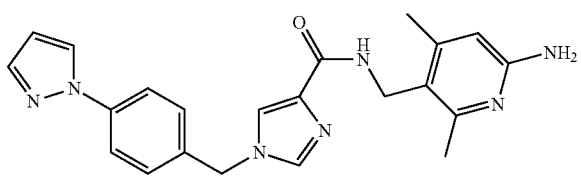 [SMILES: Cc1cc(N)nc(C)c1CNC(=O)c1cn(Cc2ccc(-n3cccn3)cc2)cn1]

The title compound was prepared in analogy to example 6. HPLC (Method A) Rt=0.933 min; MS [M+H]⁺=402.1.

Example 25

N-((6-amino-2,4-dimethylpyridin-3-yl)methyl)-1-((2-(phenylamino)thiazol-4-yl)methyl)-1H-pyrazole-4-carboxamide

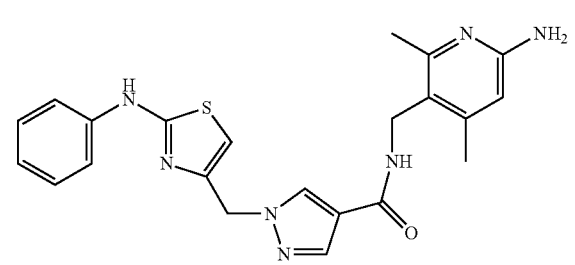 [SMILES: Cc1cc(N)nc(C)c1CNC(=O)c1cnn(Cc2csc(Nc3ccccc3)n2)c1]

The title compound was prepared in analogy to example 13. HPLC (Method A) Rt=1.099 min; MS [M+H]⁺=434.0.

Example 26

N-((6-amino-2,4-dimethylpyridin-3-yl)methyl)-1-((4-methyl-2-phenylthiazol-5-yl)methyl)-1H-pyrazole-4-carboxamide

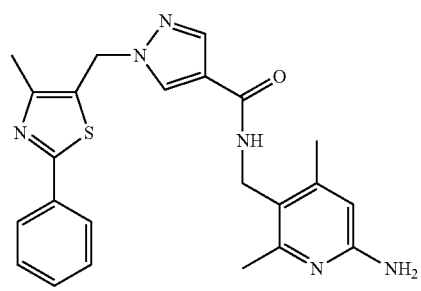 [SMILES: Cc1cc(N)nc(C)c1CNC(=O)c1cnn(Cc2sc(-c3ccccc3)nc2C)c1]

The title compound was prepared in analogy to example 13. HPLC (Method A) Rt=1.173 min; MS [M+H]⁺=433.0.

Example 27

N-((6-amino-2,4-dimethylpyridin-3-yl)methyl)-1-((2-benzylthiazol-4-yl)methyl)-1H-pyrazole-4-carboxamide

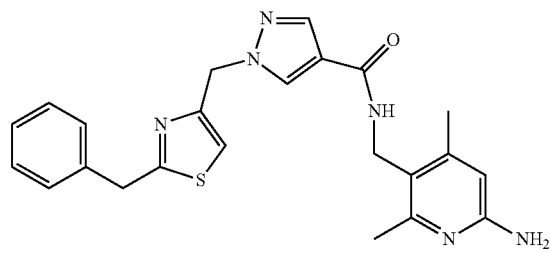 [SMILES: Cc1cc(N)nc(C)c1CNC(=O)c1cnn(Cc2csc(Cc3ccccc3)n2)c1]

The title compound was prepared in analogy to example 13. HPLC (Method A) Rt=1.137 min; MS [M+H]⁺=433.0.

Example 28

N-((6-amino-2,4-dimethylpyridin-3-yl)methyl)-1-((2-tert-butylthiazol-4-yl)methyl)-1H-pyrazole-4-carboxamide

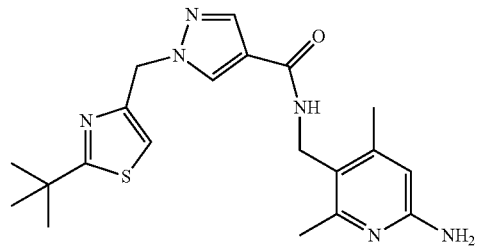 [SMILES: Cc1cc(N)nc(C)c1CNC(=O)c1cnn(Cc2csc(C(C)(C)C)n2)c1]

The title compound was prepared in analogy to example 13. HPLC (Method A) Rt=1.101 min; MS [M+H]⁺=399.1.

Example 29

N-((6-amino-2,4-dimethylpyridin-3-yl)methyl)-1-((2-(2-(dimethylamino)-2-oxoethyl)thiazol-4-yl)methyl]-1H-pyrazole-4-carboxamide

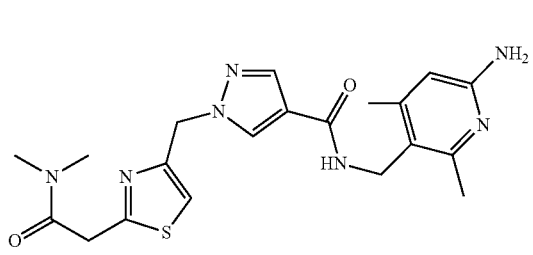 [SMILES: Cc1cc(N)nc(C)c1CNC(=O)c1cnn(Cc2csc(CC(=O)N(C)C)n2)c1]

The title compound was prepared in analogy to example 13. HPLC (Method C) Rt=2.338 min; MS (Method D) [M+H]⁺=428.3.

Example 30

N-((6-amino-2,4-dimethylpyridin-3-yl)methyl)-1-(imidazo[1,2-a]pyridin-2-ylmethyl)-1H-pyrazole-4-carboxamide

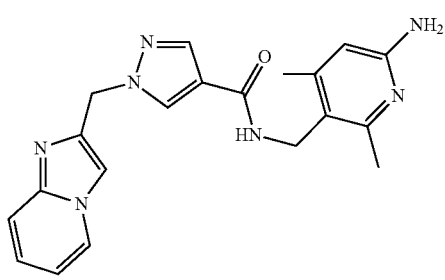 [SMILES: Cc1cc(N)nc(C)c1CNC(=O)c1cnn(Cc2cn3ccccc3n2)c1]

The title compound was prepared in analogy to example 13. HPLC (Method C) Rt=0.646 min; MS (Method D) [M+H]⁺=376.3.

Example 31

N4 (6-amino-2,4-dimethylpyridin-3-yl)methyl)-1-(benzofuran-2-ylmethyl)-1H-pyrazole-4-carboxamide

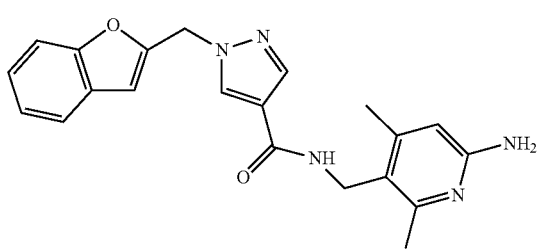 [SMILES: Cc1cc(N)nc(C)c1CNC(=O)c1cnn(Cc2cc3ccccc3o2)c1]

The title compound was prepared in analogy to example 9. HPLC (Method A) Rt=1.107 min; MS [M+H]⁺=376.0.

Example 32

N-((6-amino-2,4-dimethylpyridin-3-yl)methyl)-1-((2-phenyloxazol-4-yl)methyl)-1H-pyrazole-4-carboxamide

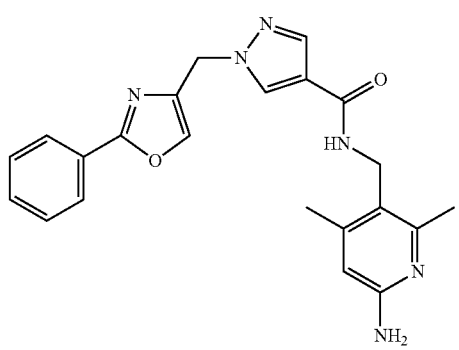 [SMILES: Cc1cc(N)nc(C)c1CNC(=O)c1cnn(Cc2coc(-c3ccccc3)n2)c1]

The title compound was prepared in analogy to example 13. HPLC (Method A) Rt=1.041 min; MS [M+H]⁺=403.0.

Example 33

1-((1H-benzo[d]imidazol-5-yl)methyl)-N-((6-amino-2,4-dimethylpyridin-3-yl)methyl)-1H-pyrazole-4-carboxamide

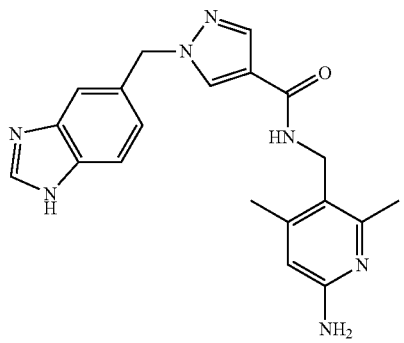 [SMILES: Cc1cc(N)nc(C)c1CNC(=O)c1cnn(Cc2ccc3[nH]cnc3c2)c1]

The title compound was prepared in analogy to example 9, Steps c)-f). HPLC (Method A) Rt=0.108 min; MS [M+H]⁺= 376.0.

Example 34

N-((6-amino-2,4-dimethylpyridin-3-yl)methyl)-1-((1-methyl-1H-indol-6-yl)methyl)-1H-pyrazole-4-carboxamide

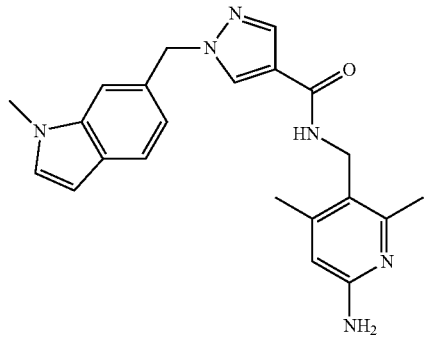

87

The title compound was prepared in analogy to example 9, Steps c)-f). HPLC (Method A) Rt=0.103 min; MS [M+H]$^+$=389.0.

Example 35

N-((6-amino-2,4-dimethylpyridin-3-yl)methyl)-1-((5-phenyloxazol-4-yl)methyl)-1H-pyrazole-4-carboxamide

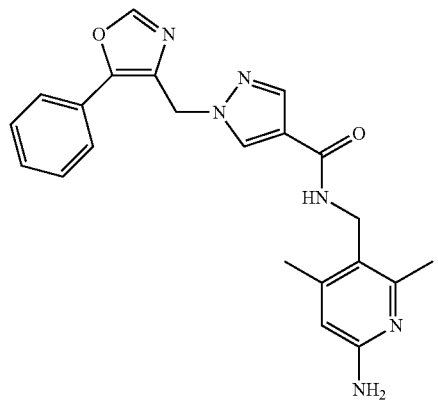 [SMILES: Cc1cc(N)nc(C)c1CNC(=O)c1cnn(Cc2ncoc2-c2ccccc2)c1]

The title compound was prepared in analogy to example 13. HPLC (Method A) Rt=1.062 min; MS [M+H]$^+$=403.0.

Example 36

N-((6-amino-2,4-dimethylpyridin-3-yl)methyl)-1-(4-((3,5-dimethyl-1H-pyrazol-1-yl)methyl)benzyl)-1H-pyrazole-4-carboxamide

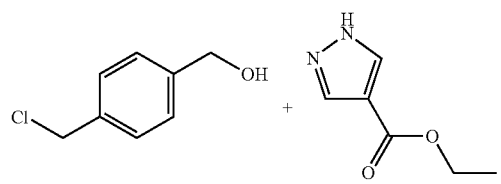

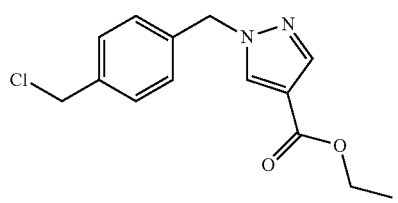

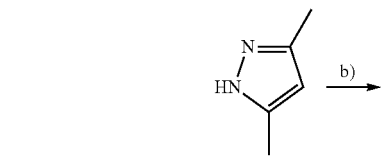

88

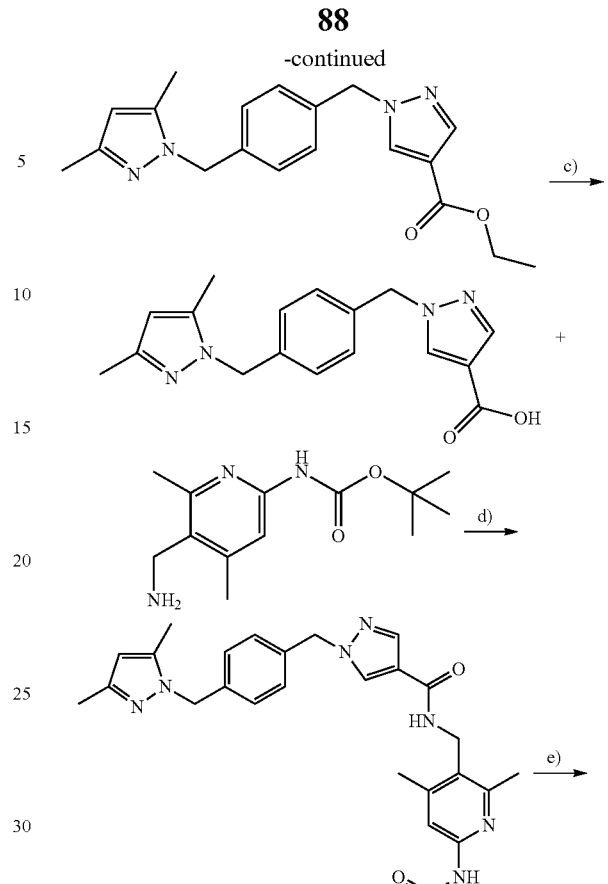

a) 1-(4-Chloromethyl-benzyl)-1H-pyrazole-4-carboxylic acid ethyl ester

The title compound was prepared in analogy to example 9, step c. (Method A) Rt=1.902 min; MS [M+H]$^+$=279.0.

b) 1-[4-(3,5-Dimethyl-pyrazol-1-ylmethyl)-benzyl]-1H-pyrazole-4-carboxylic acid ethyl ester The title compound was prepared in analogy to example 147, step f. (Method A) Rt=1.741 min; MS [M+H]$^+$=339.1.

c) 1-[4-(3,5-Dimethyl-pyrazol-1-ylmethyl)-benzyl]-1H-pyrazole-4-carboxylic acid

The title compound was prepared in analogy to example 16, step c. (Method A) Rt=1.341 min; MS [M+H]$^+$=311.0.

d) {5-[({1-[4-(3,5-Dimethyl-pyrazol-1-ylmethyl)-benzyl]-1H-pyrazole-4-carbonyl}-amino)-methyl]-4,6-dimethyl-pyridin-2-yl}-carbamic acid tert-butyl ester The title compound was prepared in analogy to example 16, step d. (Method A) Rt=1.511 min; MS [M+H]⁺=544.2.

e) N-((6-amino-2,4-dimethylpyridin-3-yl)methyl)-1-(4-((3,5-dimethyl-1H-pyrazol-1-yl)methyl)benzyl)-1H-pyrazole-4-carboxamide The title compound was prepared in analogy to example 16, step e. HPLC (Method A) Rt=1.001 min; MS [M+H]⁺=444.1.

Example 37

N-((6-amino-2,4-dimethylpyridin-3-yl)methyl)-1-(3-cyanophenylsulfonyl)-1H-pyrazole-4-carboxamide

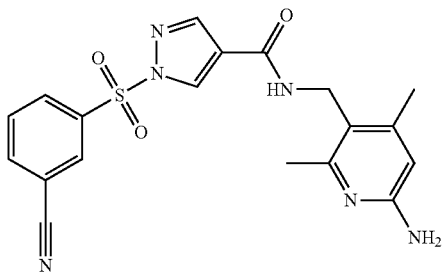 [SMILES: Cc1cc(N)nc(C)c1CNC(=O)c1cnn(S(=O)(=O)c2cccc(C#N)c2)c1]

The title compound was prepared in analogy to example 12. HPLC (Method B) Rt=0.520 min; MS [M+H]⁺=411.4.

Example 38

N-((6-amino-2,4-dimethylpyridin-3-yl)methyl)-1-(4-phenoxybenzyl)-1H-1,2,3-triazole-4-carboxamide

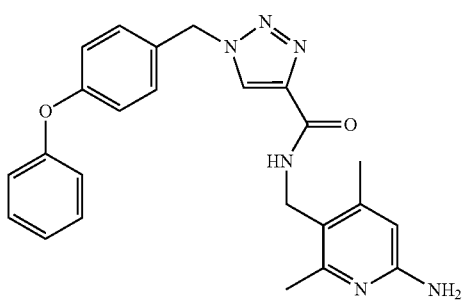 [SMILES: Cc1cc(N)nc(C)c1CNC(=O)c1cn(Cc2ccc(Oc3ccccc3)cc2)nn1]

The title compound was prepared in analogy to example 10. HPLC (Method A) Rt=1.327 min; MS [M+H]⁺=429.1.

Example 39

N-((6-amino-2,4-dimethylpyridin-3-yl)methyl)-1-(naphthalen-1-ylmethyl)-1H-1,2,3-triazole-4-carboxamide

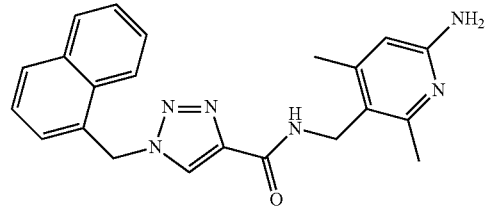 [SMILES: Cc1cc(N)nc(C)c1CNC(=O)c1cn(Cc2cccc3ccccc23)nn1]

The title compound was prepared in analogy to example 10. HPLC (Method A) Rt=1.163 min; MS [M+H]⁺=387.1.

Example 40

N-((6-amino-2,4-dimethylpyridin-3-yl)methyl)-1-(naphthalen-2-ylmethyl)-1H-1,2,3-triazole-4-carboxamide

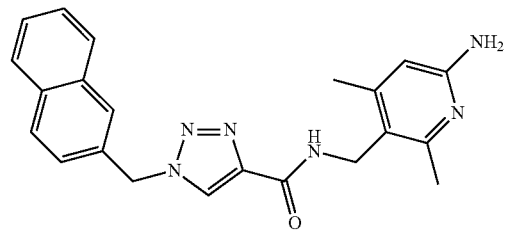 [SMILES: Cc1cc(N)nc(C)c1CNC(=O)c1cn(Cc2ccc3ccccc3c2)nn1]

The title compound was prepared in analogy to example 10. HPLC (Method A) Rt=1.190 min; MS [M+H]⁺=387.1.

Example 41

1-(4-(1H-pyrazol-1-yl)benzyl)-N-((6-amino-2,4-dimethylpyridin-3-yl)methyl]-1H-1,2,3-triazole-4-carboxamide

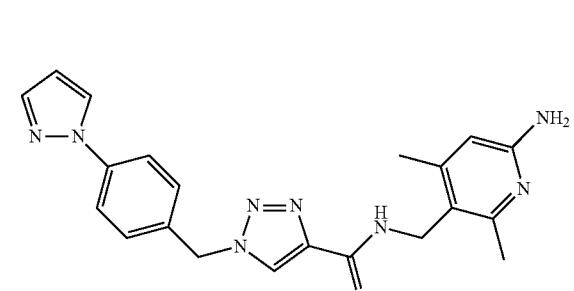

The title compound was prepared in analogy to example 10. HPLC (Method A) Rt=0.977 min; MS [M+H]+=403.0.

Example 42

1-(3-(1H-pyrazol-1-yl)benzyl)-N-((6-amino-2,4-dimethylpyridin-3-yl)methyl)-1H-1,2,3-triazole-4-carboxamide

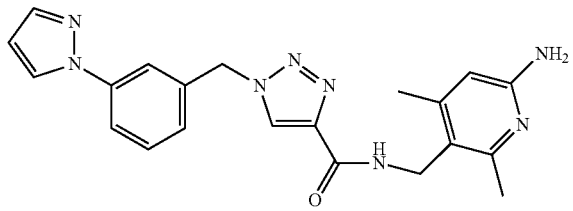 [SMILES: Cc1cc(N)nc(C)c1CNC(=O)c1cn(Cc2cccc(-n3cccn3)c2)nn1]

The title compound was prepared in analogy to example 10. HPLC (Method A) Rt=1.003 min; MS [M+H]+=403.0.

Example 43

N-((6-amino-2,4-dimethylpyridin-3-yl)methyl)-1-(3-(pyrolidin-1-yl)benzyl)-1H-1,2,3-triazole-4-carboxamide

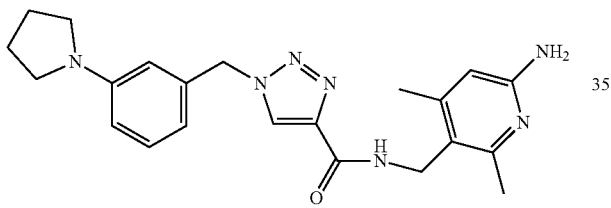

The title compound was prepared in analogy to example 10. HPLC (Method E) Rt=3.450 min; MS (Method D) [M+H]+=406.2.

Example 44

N-((6-amino-2,4-dimethylpyridin-3-yl)methyl)-2-(benzofuran-2-ylmethyl)-2H-1,2,3-triazole-4-carboxamide

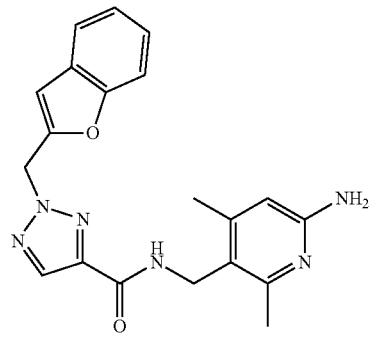 [SMILES: Cc1cc(N)nc(C)c1CNC(=O)c1cnn(Cc2cc3ccccc3o2)n1]

The title compound was prepared in analogy to example 9, Steps c)-f). HPLC (Method A) Rt=1.156min; MS [M-+H]+=377.0.

Example 45

1-(4-((1H-imidazol-1-yl)methyl)benzyl)-N-((6-amino-2,4-dimethylpyridin-3-yl)methyl)-1H-1,2,3-triazole-4-carboxamide

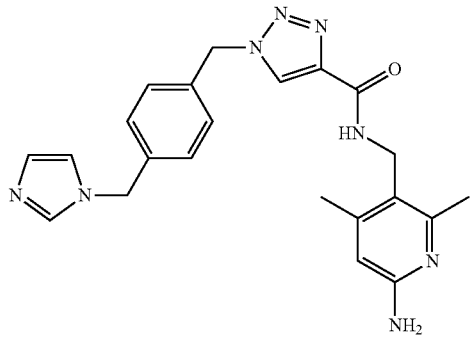 [SMILES: Cc1cc(N)nc(C)c1CNC(=O)c1cn(Cc2ccc(Cn3ccnc3)cc2)nn1]

The title compound was prepared in analogy to example 10. HPLC (Method C) Rt=2.337 min; MS (Method D) [M+H]+=417.0.

Example 46

1-(3-((1H-imidazol-1-yl)methyl)benzyl)-N-((6-amino-2,4-dimethylpyridin-3-yl)methyl)-1H-1,2,3-triazole-4-carboxamide

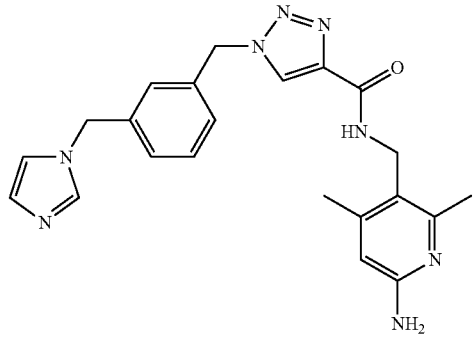 [SMILES: Cc1cc(N)nc(C)c1CNC(=O)c1cn(Cc2cccc(Cn3ccnc3)c2)nn1]

The title compound was prepared in analogy to example 10. HPLC (Method C) Rt=2.369 min; MS (Method D) [M+H]+=417.1.

Example 47

N-((6-amino-2,4-dimethylpyridin-3-yl)methyl)-2-benzylthiazole-4-carboxamide

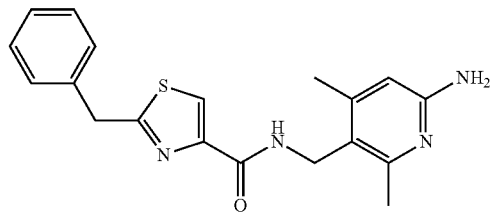 [SMILES: Cc1cc(N)nc(C)c1CNC(=O)c1csc(Cc2ccccc2)n1]

The title compound was prepared in analogy to example 1, Step d). HPLC (Method A) Rt=1.142 min; MS [M+H]+=353.0.

Example 48

N-((6-amino-2,4-dimethylpyridin-3-yl)methyl)-5-phenoxyfuran-2-carboxamide

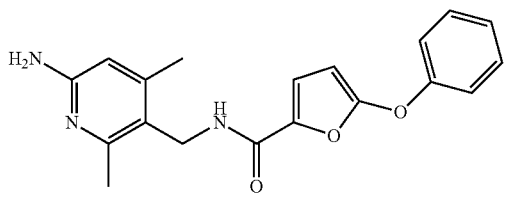 [SMILES: Cc1cc(N)nc(C)c1CNC(=O)c1ccc(Oc2ccccc2)o1]

The title compound was prepared in analogy to example 1, Step d). HPLC (Method S) Rt=1.64 min; MS [M+H]⁺=338.6.

Example 49

N-((6-amino-2,4-dimethylpyridin-3-yl)methyl)-1-benzyl-3-methyl-1H-pyrazole-4-carboxamide

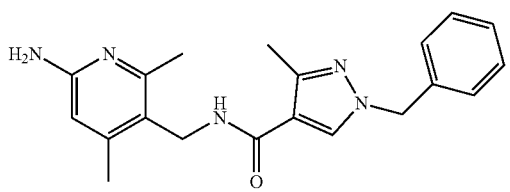 [SMILES: Cc1cc(N)nc(C)c1CNC(=O)c1cn(Cc2ccccc2)nc1C]

The title compound was prepared in analogy to example 1, Step d). HPLC (Method S) Rt=1.53 min; MS [M+H]⁺=350.6.

Example 50

N-((6-amino-2,4-dimethylpyridin-3-yl)methyl)-1-(furan-2-ylmethyl)-2,5-dimethyl-1H-pyrrole-3-carboxamide

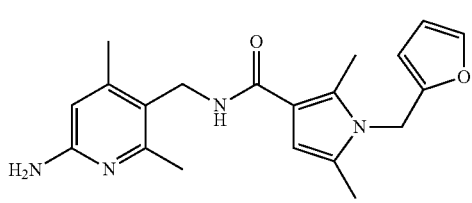 [SMILES: Cc1cc(N)nc(C)c1CNC(=O)c1cc(C)n(Cc2ccco2)c1C]

The title compound was prepared in analogy to example 1, Step d). HPLC (Method R) Rt=0.94min; MS [M+H]⁺=353.8.

Example 51

N-((6-amino-2,4-dimethylpyridin-3-yl)methyl)-2,5-dimethyl-1-(1-phenylethyl)-1H-pyrrole-3-carboxamide

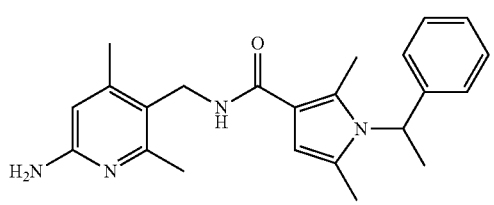 [SMILES: Cc1cc(N)nc(C)c1CNC(=O)c1cc(C)n(C(C)c2ccccc2)c1C]

The title compound was prepared in analogy to example 1, Step d). HPLC (Method S) Rt=1.74 min; MS [M+H]⁺=377.5.

Example 52

N-((6-amino-2,4-dimethylpyridin-3-yl)methyl)-4-(morpholinosulfonyl)-1H-pyrrole-2-carboxamide

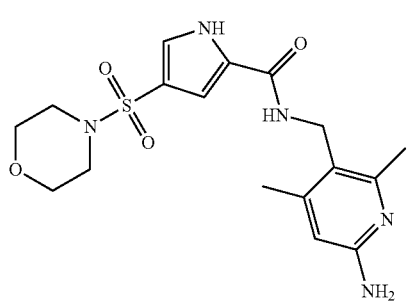 [SMILES: Cc1cc(N)nc(C)c1CNC(=O)c1cc(S(=O)(=O)N2CCOCC2)c[nH]1]

The title compound was prepared in analogy to example 1, Step d). HPLC (Method R) Rt=0.60 min; MS [M+H]⁺=394.7.

Example 53

N-((6-amino-2,4-dimethylpyridin-3-yl)methyl)-1-(2,6-difluorobenzyl)-1H-1,2,3-triazole-4-carboxamide

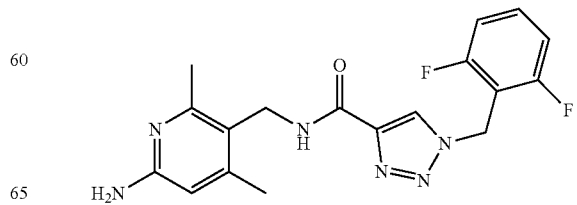

The title compound was prepared in analogy to example 1, Step d). HPLC (Method R) Rt=0.81 min; MS [M+H]⁺=373.7.

Example 54

N-((6-amino-2,4-dimethylpyridin-3-yl)methyl)-1-(3-cyanobenzyl)-1H-1,2,3-triazole-4-carboxamide

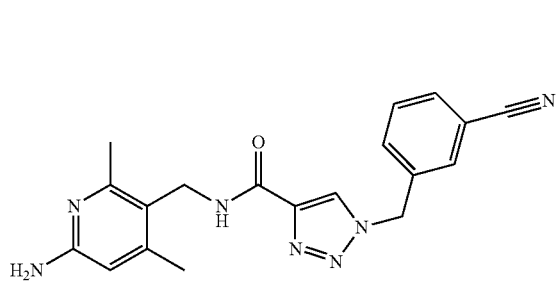 [SMILES: Cc1cc(N)nc(C)c1CNC(=O)c1cn(Cc2cccc(C#N)c2)nn1]

The title compound was prepared in analogy to example 1, Step d). HPLC (Method R) Rt=0.75 min; MS [M+H]⁺=362.7.

Example 55

N-((6-amino-2,4-dimethylpyridin-3-yl)methyl)-2-benzyl-4-methylthiazole-5-carboxamide

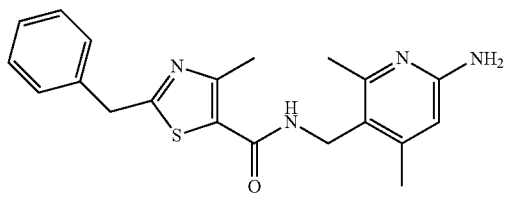 [SMILES: Cc1cc(N)nc(C)c1CNC(=O)c1sc(Cc2ccccc2)nc1C]

The title compound was prepared in analogy to example 1, Step d). HPLC (Method S) Rt=1.61 min; MS [M+H]⁺=367.7.

Example 56

N-((6-amino-2,4-dimethylpyridin-3-yl)methyl)-1-benzyl-1H-1,2,4-triazole-3-carboxamide

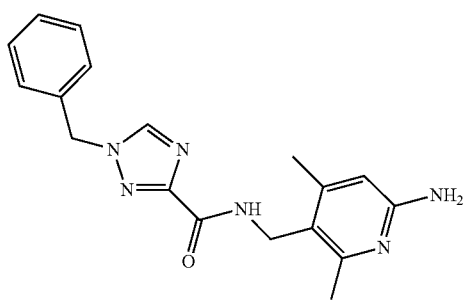 [SMILES: Cc1cc(N)nc(C)c1CNC(=O)c1ncn(Cc2ccccc2)n1]

The title compound was prepared in analogy to example 13. HPLC (Method G) Rt=1.19 min; MS [M+H]⁺=337.2.

Example 57

N-((6-amino-2,4-dimethylpyridin-3-yl)methyl)-1-(4-(6-methylpyrazin-2-yloxy)benzyl)-1H-pyrazole-4-carboxamide

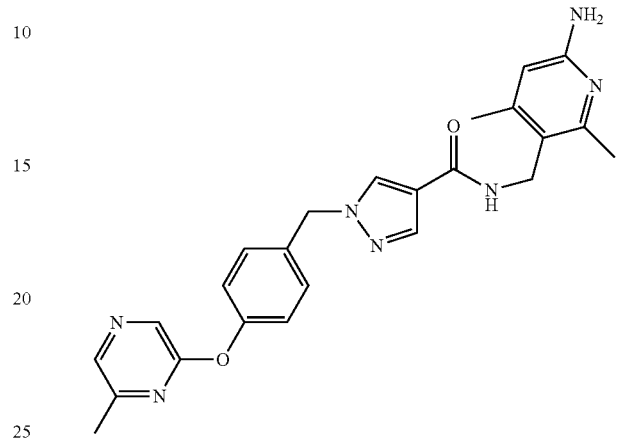

The title compound was prepared in analogy to example 13. HPLC (Method G) Rt=1.409min; MS [M+H]⁺=444.5.

Example 58

N-((6-amino-2,4-dimethylpyridin-3-yl)methyl)-2-benzyloxazole-4-carboxamide

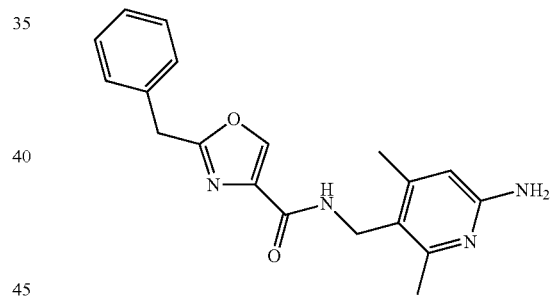

The title compound was prepared in analogy to example 8. HPLC (Method G) Rt=1.40 min; MS [M+H]⁺=337.3.

Example 59

1-(4-((1H-1,2,4-triazol-1-yl)methyl)benzyl-N-((6-amino-2,4-dimethylpyridin-3-yl)methyl)-1H-1,2,4-triazole-3-carboxamide

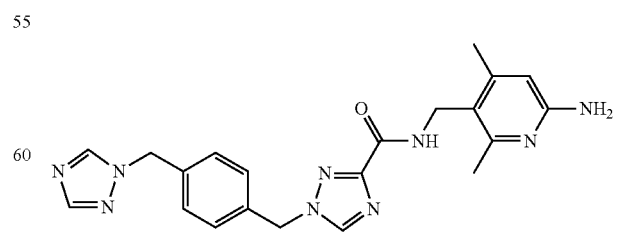

The title compound was prepared in analogy to example 9, Steps c)-f). HPLC (Method J) Rt=2.61 min; MS [M+H]⁺=418.5.

Example 60

N-((6-amino-4-(2-methoxyethoxy)-2-methylpyridin-3-yl)methyl)-1-benzyl-1H-pyrazole-4-carboxamide

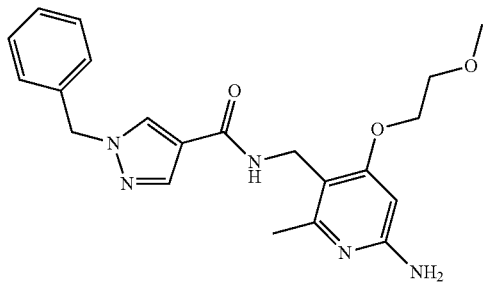 [SMILES: COCCOc1cc(N)nc(C)c1CNC(=O)c1cnn(Cc2ccccc2)c1]

The title compound was prepared in analogy to example 15. HPLC (Method G) Rt=1.37 min; MS [M+H]⁺=396.3.

Example 61

N-((6-amino-2,4-dimethylpyridin-3-yl)methyl)-1-(biphenyl-4-ylmethyl)-1H-1,2,4-triazole-3-carboxamide

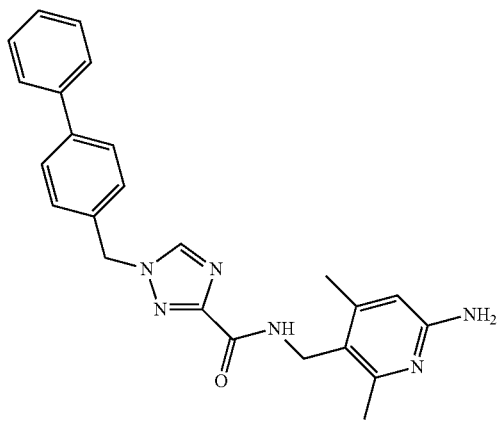 [SMILES: Cc1cc(N)nc(C)c1CNC(=O)c1ncn(Cc2ccc(-c3ccccc3)cc2)n1]

The title compound was prepared in analogy to example 13. HPLC (Method G) Rt=1.62 min; MS [M+H]⁺=413.5.

Example 62

N-((6-amino-2,4-dimethylpyridin-3-yl)methyl)-1-(naphthalen-1-ylmethyl)-1H-1,2,4-triazole-3-carboxamide

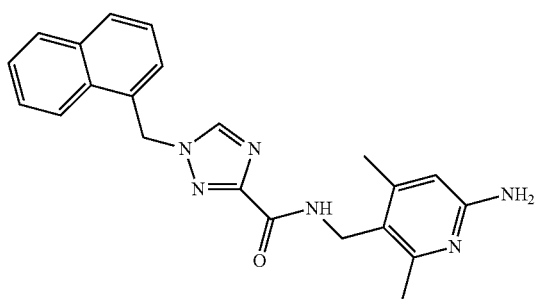 [SMILES: Cc1cc(N)nc(C)c1CNC(=O)c1ncn(Cc2cccc3ccccc23)n1]

The title compound was prepared in analogy to example 13. HPLC (Method G) Rt=1.47 min; MS [M+H]⁺=387.4.

Example 63

N-((6-amino-2,4-dimethylpyridin-3-yl)methyl)-1-(4-phenoxybenzyl)-1H-1,2,4-triazole-3-carboxamide

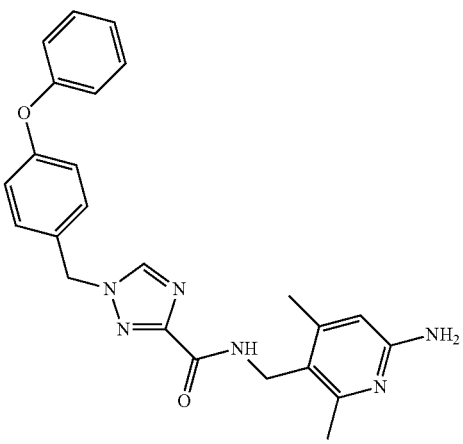 [SMILES: Cc1cc(N)nc(C)c1CNC(=O)c1ncn(Cc2ccc(Oc3ccccc3)cc2)n1]

The title compound was prepared in analogy to example 13. HPLC (Method G) Rt=1.63 min; MS [M+H]⁺=429.4.

Example 64

N-((6-amino-2,4-dimethylpyridin-3-yl)methyl)-1-(naphthalen-2-ylmethyl)-1H-1,2,4-triazole-3-carboxamide

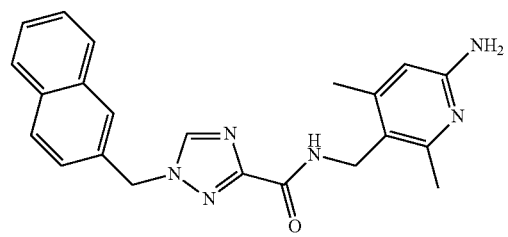 [SMILES: Cc1cc(N)nc(C)c1CNC(=O)c1ncn(Cc2ccc3ccccc3c2)n1]

The title compound was prepared in analogy to example 13. HPLC (Method G) Rt=1.50 min; MS [M+H]⁺=387.4.

Example 65

N-((6-amino-2,4-dimethylpyridin-3-yl)methyl)-1-(4-(2-oxopyrrolidin-1-yl)benzyl)-1H-pyrazole-4-carboxamide

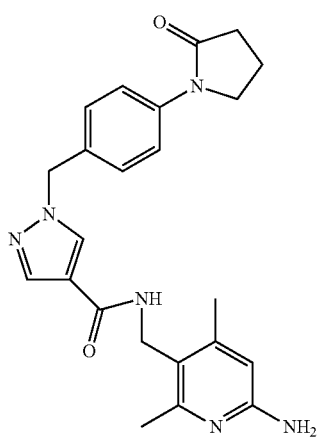 [SMILES: Cc1cc(N)nc(C)c1CNC(=O)c1cnn(Cc2ccc(N3CCCC3=O)cc2)c1]

The title compound was prepared in analogy to example 13. HPLC (Method H) Rt=2.53 min; MS [M+H]$^+$=419.

Example 66

1-(4-(1H-pyrazol-1-yl)benzyl)-N-((6-amino-2,4-dimethylpyridin-3-yl)methyl)-1H-1,2,4-triazole-3-carboxamide

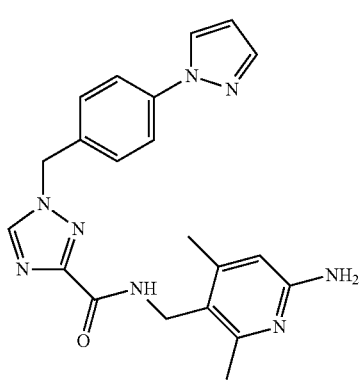 [SMILES: Cc1cc(N)nc(C)c1CNC(=O)c1ncn(Cc2ccc(-n3cccn3)cc2)n1]

The title compound was prepared in analogy to example 13. HPLC (Method G) Rt=1.31 min; MS [M+H]$^+$=403.4.

Example 67

1-(3-(1H-pyrazol-1-yl)benzyl)-N-((6-amino-2,4-dimethylpyridin-3-yl)methyl)-1H-1,2,4-triazole-3-carboxamide

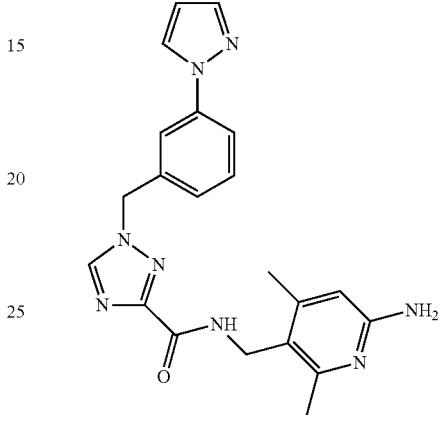

The title compound was prepared in analogy to example 13. HPLC (Method G) Rt=1.31 min; MS [M+H]$^+$=403.4.

Example 68

N-((6-amino-2,4-dimethylpyridin-3-yl)methyl)-1-(3-(pyrrolidin-1-yl)benzyl)-1H-1,2,4-triazole-3-carboxamide

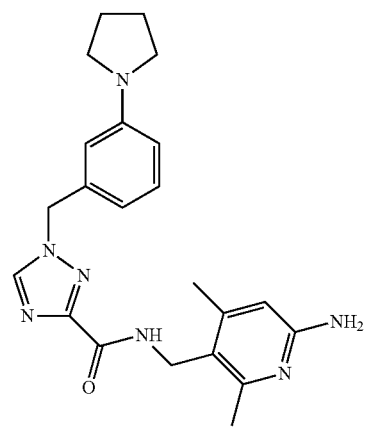 [SMILES: Cc1cc(N)nc(C)c1CNC(=O)c1ncn(Cc2cccc(N3CCCC3)c2)n1]

The title compound was prepared in analogy to example 9, Steps c)-f). HPLC (Method G) Rt=1.22 min; MS [M+H]⁺= 406.5.

Example 69

N-((6-amino-2,4-dimethylpyridin-3-yl)methyl)-1-((2-morpholinopyridin-4-yl)methyl)-1H-pyrazole-4-carboxamide

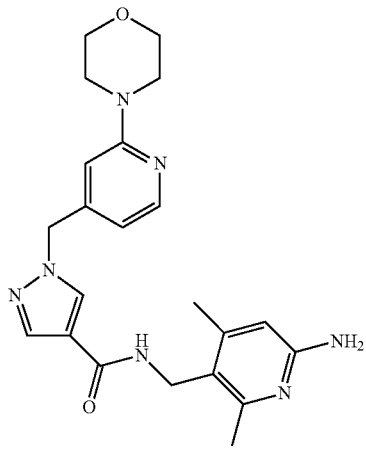 [SMILES: Cc1cc(N)nc(C)c1CNC(=O)c1cnn(Cc2ccnc(N3CCOCC3)c2)c1]

The title compound was prepared in analogy to example 9, Steps c)-f). HPLC (Method H) Rt=2.26 min; MS [M+H]⁺= 422.

Example 70

N-((6-amino-2,4-dimethylpyridin-3-yl)methyl)-1-benzyl-1H-pyrrole-3-carboxamide

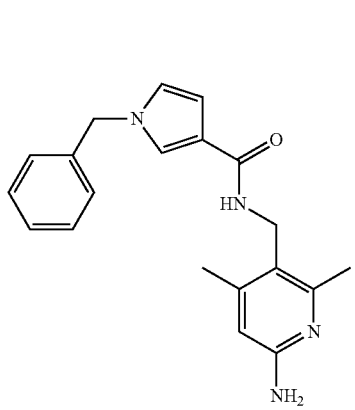 [SMILES: Cc1cc(N)nc(C)c1CNC(=O)c1ccn(Cc2ccccc2)c1]

The title compound was prepared in analogy to example 13. HPLC (Method G) Rt=1.44 min; MS [M+H]⁺=335.3.

Example 71

N-((6-amino-2,4-dimethylpyridin-3-yl)methyl)-1-(3-(2-methoxyethyl)benzyl)-1H-pyrazole-4-carboxamide

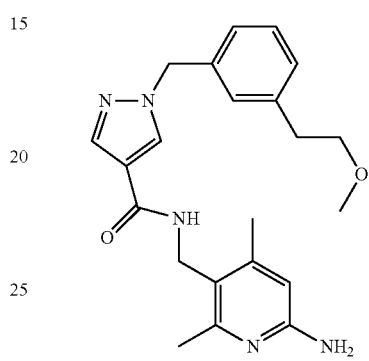

The title compound was prepared in analogy to example 9, Steps c)-f). HPLC (Method H) Rt=2.75 min; MS [M+H]⁺= 394.

Example 72

N-((6-amino-2,4-dimethylpyridin-3-yl)methyl)-2,5-dimethyl-1-(Phenylsulfonyl)-1H-pyrrole-3-carboxamide

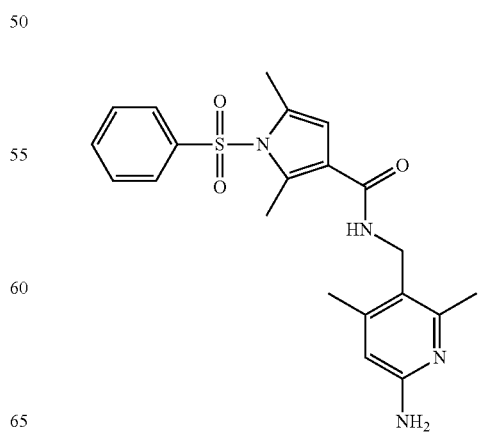

The title compound was prepared in analogy to example 12. HPLC (Method G) Rt=1.61 min; MS [M+H]⁺=413.0.

Example 73

N-((6-amino-2,4-dimethylpyridin-3-yl)methyl)-1-(3,5-dimethoxybenzyl)-1H-pyrazole-4-carboxamide

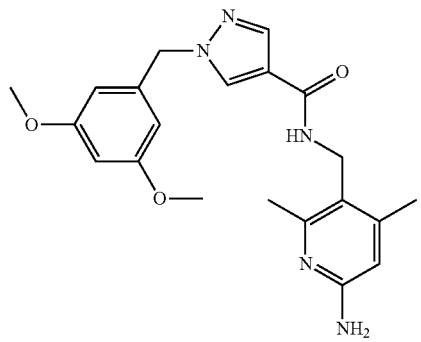

The title compound was prepared in analogy to example 13. HPLC (Method H) Rt=2.78 min; MS [M+H]⁺=396.

Example 74

N-((6-amino-2,4-dimethylpyridin-3-yl)methyl)-4-methyl-1-(phenylsulfonyl)-1H-pyrrole-3-carboxamide

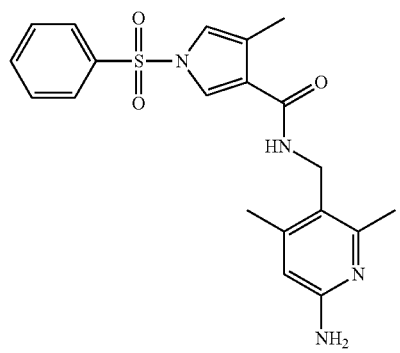 [SMILES: Cc1cn(S(=O)(=O)c2ccccc2)cc1C(=O)NCc1c(C)cc(N)nc1C]

The title compound was prepared in analogy to example 12. HPLC (Method G) Rt=1.62 min; MS [M+H]⁺=399.0.

Example 75

N-((6-amino-2,4-dimethylpyridin-3-yl)methyl)-1-((2,3-dimethyl-1H-indol-5-yl)methyl)-1H-pyrazole-4-carboxamide

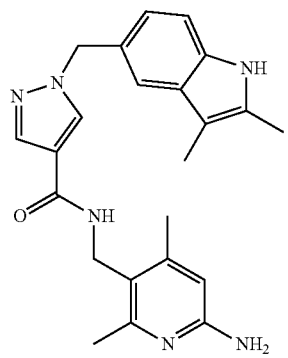 [SMILES: Cc1cc(N)nc(C)c1CNC(=O)c1cnn(Cc2ccc3[nH]c(C)c(C)c3c2)c1]

The title compound was prepared in analogy to example 9, Steps c)-f). HPLC (Method B) Rt=0.57 min; MS [M+H]⁺=403.

Example 76

N-((6-amino-2,4-dimethylpyridin-3-yl)methyl)-1-benzyl-4-methyl-1H-pa role-3-carboxamide

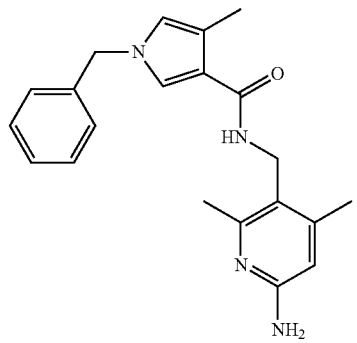 [SMILES: Cc1cn(Cc2ccccc2)cc1C(=O)NCc1c(C)cc(N)nc1C]

The title compound was prepared in analogy to example 13. HPLC (Method H) Rt=3.03 min; MS [M+H]⁺=349.

Example 77

N-((6-amino-4-(2-amino-2-oxoethoxy)-2-methylpyridin-3-yl)methyl)-1-benzyl-1H-pyrazole-4-carboxamide

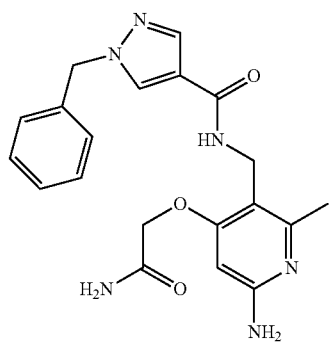 [SMILES: Cc1nc(N)cc(OCC(N)=O)c1CNC(=O)c1cnn(Cc2ccccc2)c1]

The title compound was prepared in analogy to example 19. HPLC (Method H) Rt=2.60 min; MS [M+H]⁺=395.2.

Example 78

N-((6-amino-2,4-dimethylpyridin-3-yl)methyl)-2-phenoxyoxazole-4-carboxamide

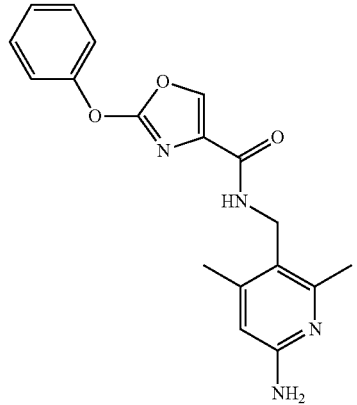 [SMILES: Cc1cc(N)nc(C)c1CNC(=O)c1coc(Oc2ccccc2)n1]

The title compound was prepared in analogy to example 20. HPLC (Method B) $Rt_B$=0.49 min; MS [M+H]$^+$=339.3.

Example 79

N-((6-amino-2,4-dimethylpyridin-3-yl)methyl)-2-methyl-5-((1-oxoisoquinolin-2(1H)-yl)methyl)furan-3-carboxamide

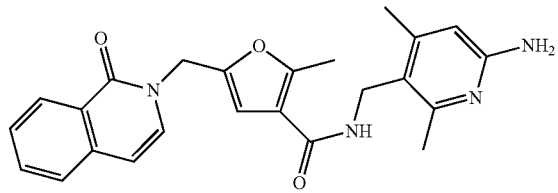 [SMILES: Cc1cc(N)nc(C)c1CNC(=O)c1cc(Cn2ccc3ccccc3c2=O)oc1C]

The title compound was prepared in analogy to example 1. HPLC (Method L) Rt=1.56 min; MS [M+H]$^+$=417.4.

Example 80

N-((6-amino-2,4-dimethylpyridin-3-yl)methyl)-1-(4-(trifluoromethoxy)benzyl)-1H-pyrazole-4-carboxamide

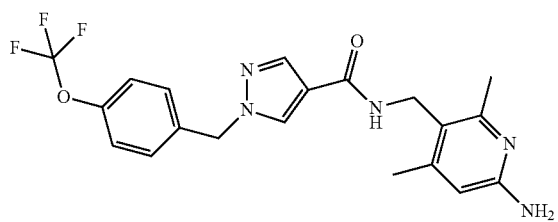 [SMILES: Cc1cc(N)nc(C)c1CNC(=O)c1cnn(Cc2ccc(OC(F)(F)F)cc2)c1]

The title compound was prepared in analogy to example 13. HPLC (Method K) Rt=0.96 min; MS [M+H]$^+$=420.3.

Example 81

N-((6-amino-2,4-dimethylpyridin-3-yl)methyl)-1-(3-cyanobenzyl)-1H-pyrazole-4-carboxamide

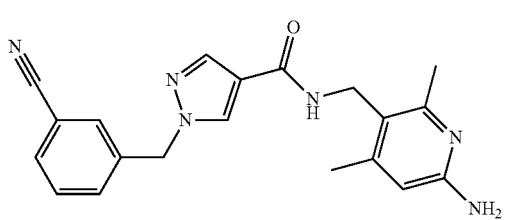 [SMILES: Cc1cc(N)nc(C)c1CNC(=O)c1cnn(Cc2cccc(C#N)c2)c1]

The title compound was prepared in analogy to example 13. HPLC (Method K) Rt=0.62 min; MS [M+H]$^+$=361.2.

Example 82

N-((6-amino-2,4-dimethylpyridin-3-yl)methyl)-1-(4-cyanobenzyl)-1H-pyrazole-4-carboxamide

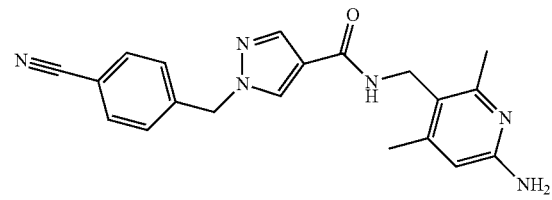 [SMILES: Cc1cc(N)nc(C)c1CNC(=O)c1cnn(Cc2ccc(C#N)cc2)c1]

The title compound was prepared in analogy to example 13. HPLC (Method K) Rt=0.62 min; MS [M+H]$^+$=361.2.

Example 83

N-((6-amino-2,4-dimethylpyridin-3-yl)methyl)-1-(naphthalen-2-ylmethyl)-1H-pyrazole-4-carboxamide

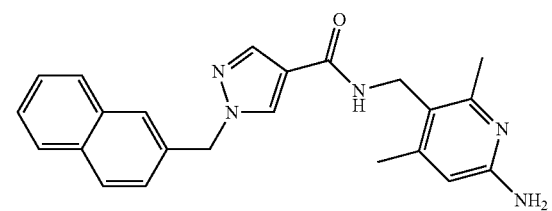 [SMILES: Cc1cc(N)nc(C)c1CNC(=O)c1cnn(Cc2ccc3ccccc3c2)c1]

The title compound was prepared in analogy to example 13. HPLC (Method K) Rt=0.90 min; MS [M+H]$^+$=386.4.

Example 84

N-((6-amino-2,4-dimethylpyridin-3-yl)methyl)-1-(3-fluorobenzyl)-1H-pyrazole-4-carboxamide

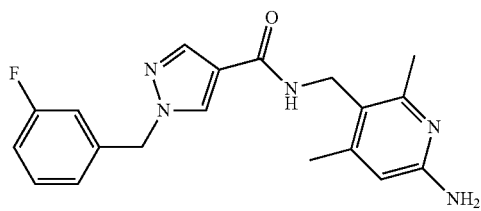 [SMILES: Cc1cc(N)nc(C)c1CNC(=O)c1cnn(Cc2cccc(F)c2)c1]

The title compound was prepared in analogy to example 13. HPLC (Method K) Rt=0.73 min; MS [M+H]⁺=354.4.

Example 85

N-((6-amino-2-methylpyridin-3-yl)methyl)-1-benzyl-1H-pyrazole-4-carboxamide

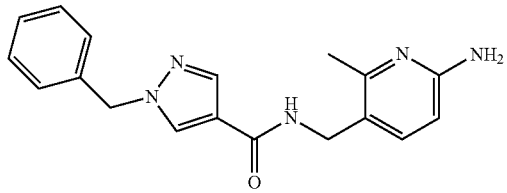 [SMILES: Cc1nc(N)ccc1CNC(=O)c1cnn(Cc2ccccc2)c1]

The title compound was prepared in analogy to example 13. HPLC (Method M) Rt=1.36 min; MS [M+H]⁺=322.3.

Example 86

N-((6-amino-2,4-dimethylpyridin-3-yl)methyl)-1-((6-methylpyridin-2-yl)methyl)-1H-pyrazole-4-carboxamide

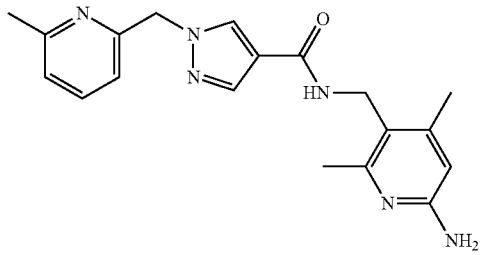

The title compound was prepared in analogy to example 18. HPLC (Method M) Rt=1.19 min; MS [M+H]⁺=351.3.

Example 87

N-((6-amino-2,4-dimethylpyridin-3-yl)methyl)-1-(2-chlorobenzyl)-1H-pyrazole-4-carboxamide

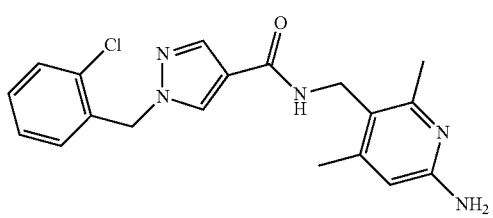 [SMILES: Cc1cc(N)nc(C)c1CNC(=O)c1cnn(Cc2ccccc2Cl)c1]

The title compound was prepared in analogy to example 13. HPLC (Method Q) Rt=4.89 min; MS [M+H]⁺=370.5.

Example 88

N-((6-amino-2,4-dimethylpyridin-3-yl)methyl)-1-(cyclohexylmethyl)-1H-pyrazole-4-carboxamide

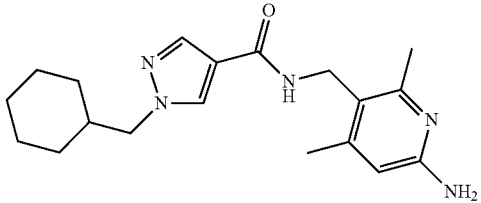 [SMILES: Cc1cc(N)nc(C)c1CNC(=O)c1cnn(CC2CCCCC2)c1]

The title compound was prepared in analogy to example 13. HPLC (Method Q) Rt=4.89 min; MS [M+H]⁺=342.6.

Example 89

N-((6-amino-2,4-dimethylpyridin-3-yl)methyl)-1-(4-(Phenoxymethyl)benzyl)-1H-pyrazole-4-carboxamide

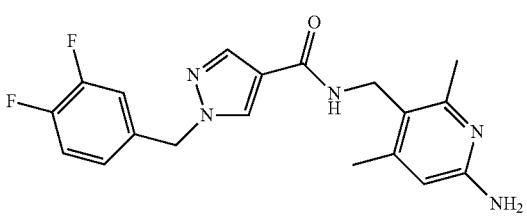 [SMILES: Cc1cc(N)nc(C)c1CNC(=O)c1cnn(Cc2ccc(F)c(F)c2)c1]

The title compound was prepared in analogy to example 13. HPLC (Method Q) Rt=5.63 min; MS [M+H]⁺=442.6.

Example 90

N-((6-amino-2,4-dimethylpyridin-3-yl)methyl)-1-(3,4-difluorobenzyl)-1H-pyrazole-4-carboxamide The title compound was prepared in analogy to example 13. HPLC (Method Q) Rt=4.71 min; MS [M+H]⁺=372.5.

Example 91

N-((6-amino-2,4-dimethylpyridin-3-yl)methyl)-1-(4-(3-methyl-1,2,4-oxadiazol-5-yl)benzyl)-1H-pyrazole-4-carboxamide

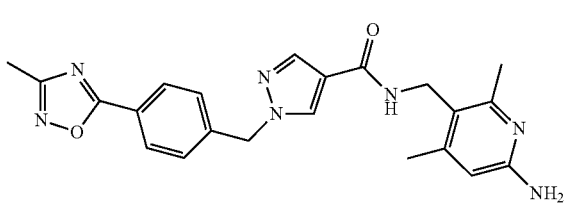 [SMILES: Cc1noc(-c2ccc(Cn3cc(C(=O)NCc4c(C)cc(N)nc4C)cn3)cc2)n1]

The title compound was prepared in analogy to example 13. HPLC (Method Q) Rt=4.58 min; MS [M+H]⁺=418.5.

Example 92

N-((6-amino-2,4-dimethylpyridin-3-yl)methyl)-1-(3-chlorobenzyl)-1H-pyrazole-4-carboxamide

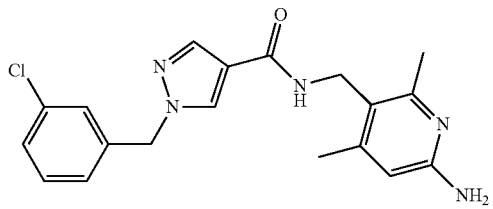 [SMILES: Cc1cc(N)nc(C)c1CNC(=O)c1cnn(Cc2cccc(Cl)c2)c1]

The title compound was prepared in analogy to example 13. HPLC (Method Q) Rt=4.89 min; MS [M+H]⁺=370.5.

Example 93

N-((6-amino-2,4-dimethylpyridin-3-yl)methyl)-1-(2,4-difluorobenzyl)-1H-pyrazole-4-carboxamide

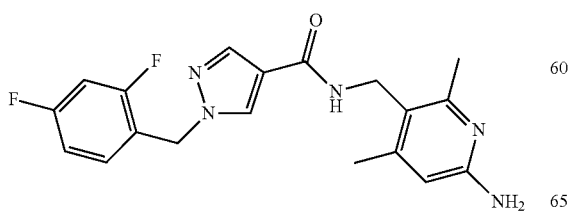

The title compound was prepared in analogy to example 13. HPLC (Method Q) Rt=4.66 min; MS [M+H]⁺=372.5.

Example 94

N-((6-amino-2,4-dimethylpyridin-3-yl)methyl)-1-(4-(benzyloxy)benzyl)-1H-pyrazole-4-carboxamide

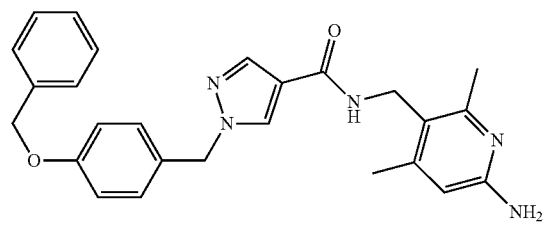 [SMILES: Cc1cc(N)nc(C)c1CNC(=O)c1cnn(Cc2ccc(OCc3ccccc3)cc2)c1]

The title compound was prepared in analogy to example 13. HPLC (Method Q) Rt=5.64 min; MS [M+H]⁺=442.6.

Example 95

N-((6-amino-2,4-dimethylpyridin-3-yl)methyl)-1-((3,4-dihydro-2H-benzo[b][1,4]dioxepin-6-yl)methyl)-1H-pyrazole-4-carboxamide

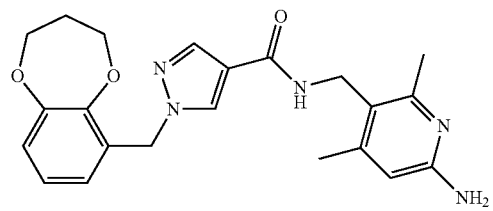 [SMILES: Cc1cc(N)nc(C)c1CNC(=O)c1cnn(Cc2cccc3c2OCCCO3)c1]

The title compound was prepared in analogy to example 13. HPLC (Method Q) Rt=4.49 min; MS [M+H]⁺=408.6.

Example 96

N-((6-amino-2,4-dimethylpyridin-3-yl)methyl)-1-(4-chlorobenzyl)-1H-pyrazole-4-carboxamide

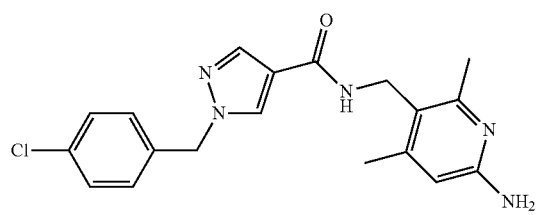 [SMILES: Cc1cc(N)nc(C)c1CNC(=O)c1cnn(Cc2ccc(Cl)cc2)c1]

111

The title compound was prepared in analogy to example 13. HPLC (Method Q) Rt=4.89 min; MS [M+H]⁺=370.5.

Example 97

N-((6-amino-2,4-dimethylpyridin-3-yl)methyl)-1-((2-methylthiazol-4-yl)methyl)-1H-pyrazole-4-carboxamide

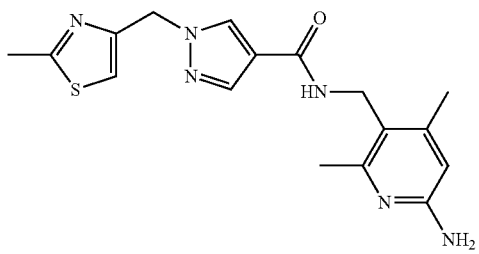 [SMILES: Cc1nc(Cn2cc(C(=O)NCc3c(C)cc(N)nc3C)cn2)cs1]

The title compound was prepared in analogy to example 13. HPLC (Method K) Rt=0.60 min; MS [M+H]⁺=357.3.

Example 98

N-((6-amino-2,4-dimethylpyridin-3-yl)methyl)-1-(pyridin-3-ylmethyl)-1H-pyrazole-4-carboxamide

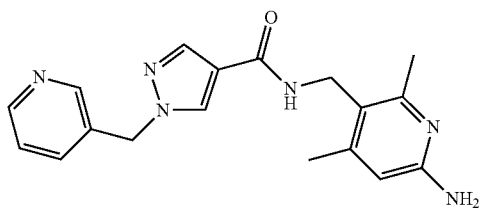 [SMILES: Cc1cc(N)nc(C)c1CNC(=O)c1cnn(Cc2cccnc2)c1]

The title compound was prepared in analogy to example 18. HPLC (Method Q) Rt=2.85 min; MS [M+H]⁺=337.5.

Example 99

N-((6-amino-2,4-dimethylpyridin-3-yl)methyl)-1-((6-(hydroxymethyl)pyridin-2-yl)methyl)-1H-pyrazole-4-carboxamide

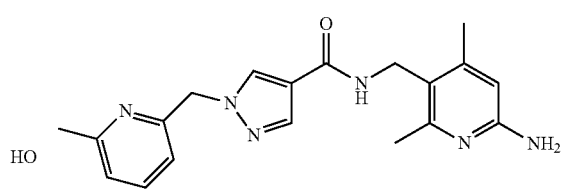

112

The title compound was prepared in analogy to example 13. HPLC (Method N) Rt=1.25 min; MS [M+H]⁺=367.6.

Example 100

N-((6-amino-2,4-dimethylpyridin-3-yl)methyl)-1-(1-phenylethyl)-1H-pyrazole-4-carboxamide

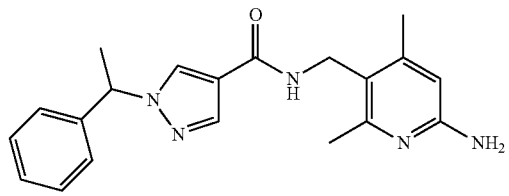 [SMILES: Cc1cc(N)nc(C)c1CNC(=O)c1cnn(C(C)c2ccccc2)c1]

The title compound was prepared in analogy to example 13. HPLC (Method N) Rt=0.91 min; MS [M+H]⁺=350.3.

Example 101

N-((6-amino-2,4-dimethylpyridin-3-yl)methyl)-1-((1-methyl-1H-benzo[d][1,2,3]triazol-5-yl)methyl)-1H-pyrazole-4-carboxamide

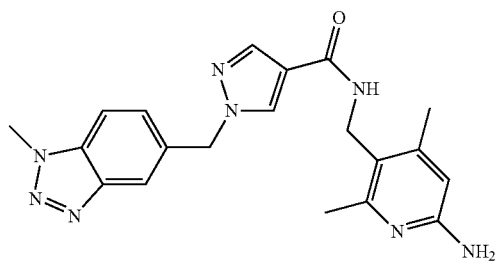 [SMILES: Cc1cc(N)nc(C)c1CNC(=O)c1cnn(Cc2ccc3c(c2)nnn3C)c1]

The title compound was prepared in analogy to example 13. HPLC (Method P) Rt=1.95 min; MS [M+H]⁺=391.4.

Example 102

N-((6-amino-2,4-dimethylpyridin-3-yl)methyl)-1-(3-carbamoylbenzyl)-1H-pyrazole-4-carboxamide

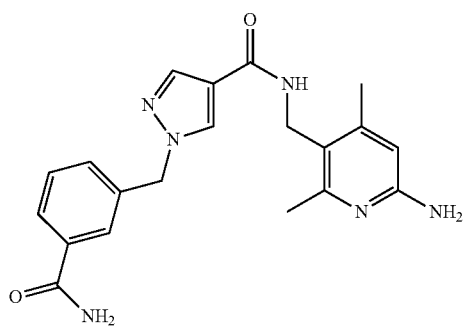 [SMILES: Cc1cc(N)nc(C)c1CNC(=O)c1cnn(Cc2cccc(C(N)=O)c2)c1]

Example 103

N-((6-amino-2,4-dimethylpyridin-3-yl)methyl)-1-(benzo[d][1,3]dioxol-5-ylmethyl)-1H-pyrazole-4-carboxamide

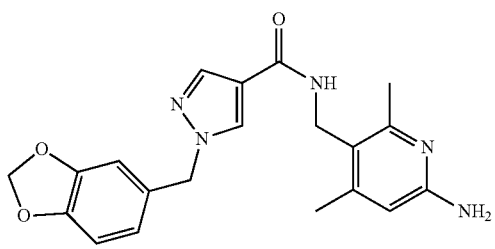 [SMILES: Cc1cc(N)nc(C)c1CNC(=O)c1cnn(Cc2ccc3c(c2)OCO3)c1]

The title compound was prepared in analogy to example 13. HPLC (Method O) Rt=0.85 min; MS [M+H]⁺=380.7.

Example 104

N-((6-amino-2,4-dimethylpyridin-3-yl)methyl)-1-((3-methylquinoxalin-2-yl)methyl)-1H-pyrazole-4-carboxamide

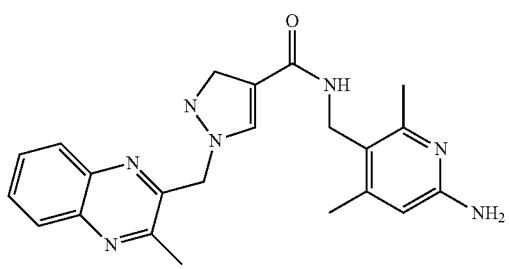 [SMILES: Cc1cc(N)nc(C)c1CNC(=O)C1=CN(Cc2nc3ccccc3nc2C)NC1]

The title compound was prepared in analogy to example 13. HPLC (Method O) Rt=0.82 min; MS [M+H]⁺=402.7.

Example 105

N-((6-amino-2,4-dimethylpyridin-3-yl)methyl)-1-(benzo[d]thiazol-2-ylmethyl)-1H-pyrazole-4-carboxamide

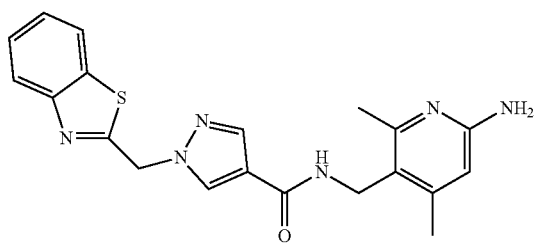 [SMILES: Cc1cc(N)nc(C)c1CNC(=O)c1cnn(Cc2nc3ccccc3s2)c1]

The title compound was prepared in analogy to example 13. HPLC (Method M) Rt=1.45 min; MS [M+H]⁺=393.2.

Example 106

N-((6-amino-2,4-dimethylpyridin-3-yl)methyl)-1-(benzo[d]isoxazol-3-ylmethyl)-1H-pyrazole-4-carboxamide

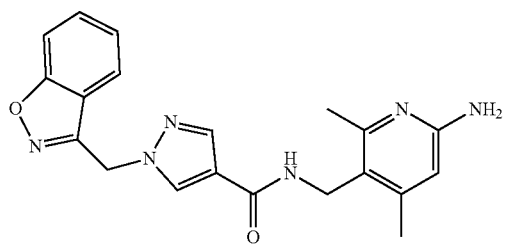 [SMILES: Cc1cc(N)nc(C)c1CNC(=O)c1cnn(Cc2noc3ccccc23)c1]

The title compound was prepared in analogy to example 13. HPLC (Method M) Rt=1.45 min; MS [M+H]⁺=377.2.

Example 107

N-((6-amino-2,4-dimethylpyridin-3-yl)methyl)-1-(2-cyanobenzyl)-1H-indole-3-carboxamide

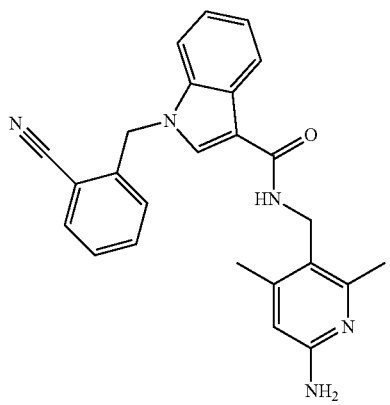 [SMILES: Cc1cc(N)nc(C)c1CNC(=O)c1cn(Cc2ccccc2C#N)c2ccccc12]

The title compound was prepared in analogy to example 1, Step d). HPLC (Method R) Rt=1.00 min; MS [M+H]⁺=410.5.

Example 108

N-((6-amino-2,4-dimethylpyridin-3-yl)methyl)-1-benzyl-1H-indole-3-carboxamide

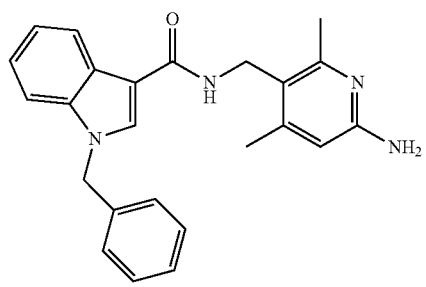 [SMILES: Cc1cc(N)nc(C)c1CNC(=O)c1cn(Cc2ccccc2)c2ccccc12]

The title compound was prepared in analogy to example 1, Step d). HPLC (Method R) Rt=1.05 min; MS [M+H]⁺=385.5.

Example 109

N-((6-amino-2,4-dimethylpyridin-3-yl)methyl)-1-benzyl-2,5-dimethyl-1H-pyrrole-3-carboxamide

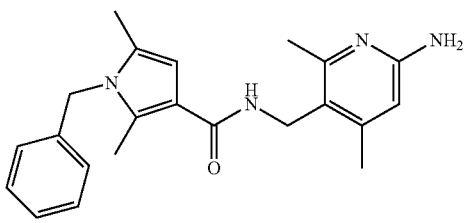 [SMILES: Cc1cc(N)nc(C)c1CNC(=O)c1cc(C)n(Cc2ccccc2)c1C]

The title compound was prepared in analogy to example 1, Step d). HPLC (Method R) Rt=1.00 min; MS [M+H]$^+$=363.6.

Example 110

N-((6-amino-2,4-dimethylpyridin-3-yl)methyl)-1-(4-(morpholinomethyl)benzyl)-1H-pyrazole-4-carboxamide

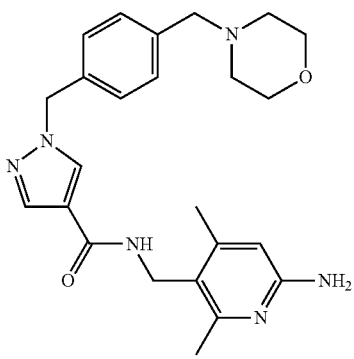 [SMILES: Cc1cc(N)nc(C)c1CNC(=O)c1cnn(Cc2ccc(CN3CCOCC3)cc2)c1]

The title compound was prepared in analogy to example 9. HPLC (Method J) Rt=0.796 min; MS [M+H]$^+$=435.5.

Example 111

1-[4-(1,1-Dioxo-tetrahydro-1lambda*6*-thiophen-3-ylcarbamoyl)-benzyl]-1H-pyrazole-4-carboxylic acid (6-amino-2,4-dimethyl-pyridin-3-ylmethyl)-amide

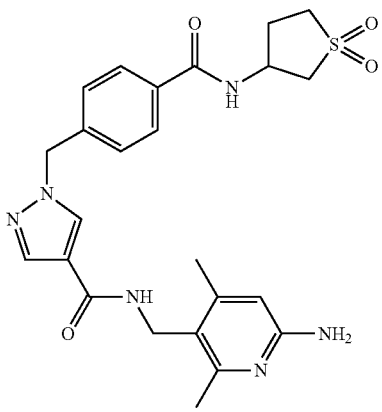 [SMILES: Cc1cc(N)nc(C)c1CNC(=O)c1cnn(Cc2ccc(C(=O)NC3CCS(=O)(=O)C3)cc2)c1]

The title compound was prepared in analogy to example 13. HPLC (Method J) Rt=2.655 min; MS (Method F) [M+H]$^+$= 497.4.

Example 112

N-((6-amino-2,4-dimethylpyridin-3-yl)methyl)-1-(4-(3-cyclopropylureido)benzyl)-1H-pyrazole-4-carboxamide

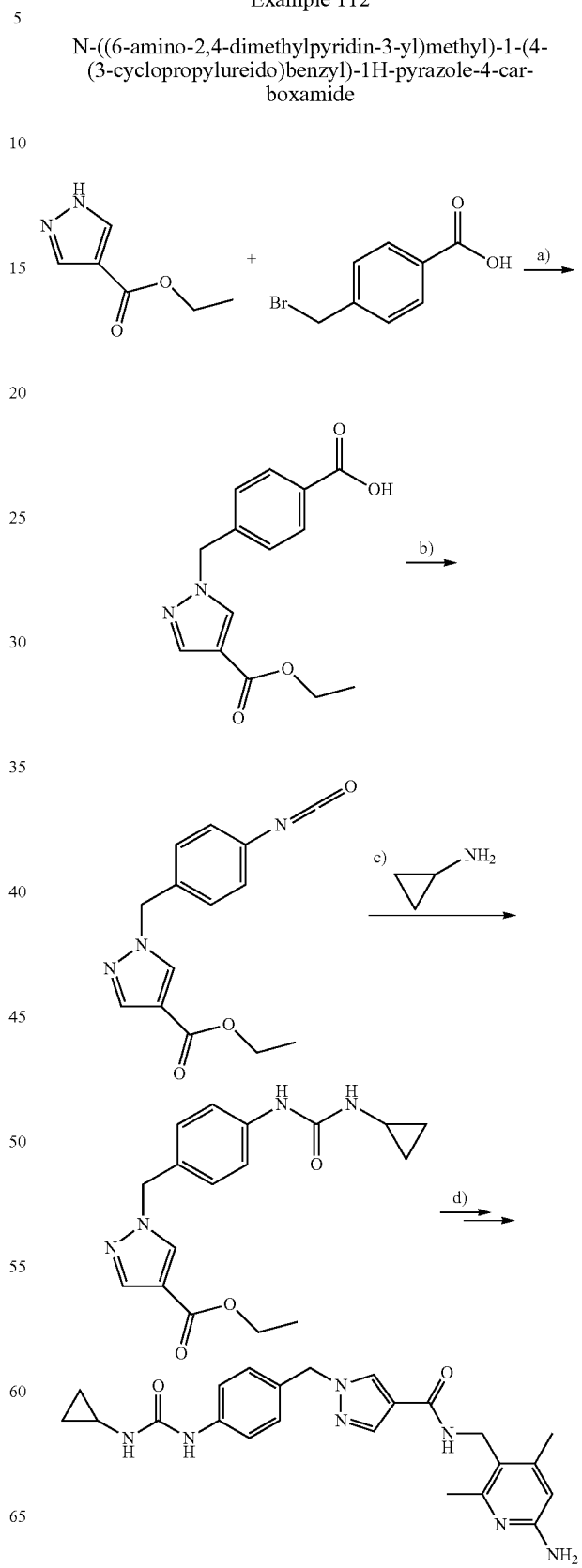

acid ethyl ester

To a solution of ethyl pyrazole-4-carboxylate (500 mg, 3.57 mmol) and bromo-para-toluic acid (767 mg, 3.57 mmol) in acetone (10 ml) was added potassium carbonate (2.465 g, 17.84 mmol). The suspension was stirred at 50° C. overnight. Water was added to the reaction, and the aqueous phase was washed with ethyl acetate. The pH of the aqueous phase was acidified with 1M hydrochloric acid, and the product was extracted with ethyl acetate. Organic layer was dried over sodium sulfate, filtered and evaporated to afford the title compound. HPLC (method G) Rt=1.642 min; UPLC (method F) Rt=0.69 min, [M+H]$^+$275.3 [M−H]$^−$ 273.3.

b) 1-(4-Isocyanato-benzyl)-1H-pyrazole-4-carboxylic acid ethyl ester

To a solution of 1-(4-carboxy-benzyl)-1H-pyrazole-4-carboxylic acid ethyl ester (200 mg, 0.729 mmol) in THF (3 ml) was added triethylamine (0.132 ml, 0.948 mmol). The mixture was stirred at 23° C. under N$_2$ atmosphere. Then, DPPA (0.228 ml, 0.948 mmol) was added and reaction mixture was stirred 2 h at 23° C. under N$_2$ atmosphere. The solvent was evaporated, and the residual oil was purified by silica gel chromatography (cyclohexane/ethyl acetate from 100/0 to 50/50). Fractions were combined and evaporated to afford pure acyl azide intermediate. HPLC (method G) Rt=2.092 min; UPLC (method F) Rt=0.99 min, MS [M+H]$^+$300.3.

Acyl azide was dissolved in toluene (9.00 ml) and heated for 1 h at reflux (oil bath 120° C.) under N$_2$ atmosphere. Toluene was evaporated to afford the title compound as a pale yellow solid.

UPLC (method F) Rt=0.53 min, MS [M+H]$^+$246.3 (corresponding amine, isocyanate unstable under HPLC analysis conditions)

c) 1-[4-(3-Cyclopropyl-ureido)-benzyl]-1H-pyrazole-4-carboxylic acid ethyl ester To a solution of 1-(4-isocyanato-benzyl)-1H-pyrazole-4-carboxylic acid ethyl ester (99 mg, 0.365 mmol) in THF (2 ml) was added cyclopropylamine (41.7 mg, 0.730 mmol). The resulting solution was stirred for 30 min at 23° C. The solvent was evaporated, and the residual white solid was triturated in diethyl ether, filtered, washed with diethyl ether and ethanol, and dried under vacuum to afford the title compound.

HPLC (method G) Rt=1.683 min; UPLC (method BF Rt=0.73 min, MS [M+H]$^+$329.4.

d) N-((6-amino-2,4-dimethylpyridin-3-yl)methyl)-1-(4-(3-cyclopropylureido)benzyl)-1H-pyrazole-4-carboxamide The title compound was prepared from 1-[4-(3-cyclopropyl-ureido)-benzyl]-1H-pyrazole-4-carboxylic acid ethyl ester in an analogous way according to the synthesis of Example 13. $^1$H-NMR (DMSO-d6, 400 MHz): 0.38 (dt, 2H), 0.61 (dt, 2H), 1.14 (d, 1H), 2.14 (s, 3H), 2.27 (s, 3H), 4.25 (d, 2H), 5.19 (s, 2H), 5.63 (s, 2H), 6.10 (s, 1H), 6.39 (s, 1H), 7.14 (d, 2H), 7.36 (d, 2H), 7.85 (s, 1H), 7.88 (t, 1H), 8.19 (s, 1H), 8.35 (s, 1H). HPLC (method G) Rt=1.202 min; UPLC (method F) Rt=0.42 min, MS [M+H]$^+$ 434.5.

Example 113

N-((6-amino-2,4-dimethylpyridin-3-yl)methyl)-5-benzyl-1H-1,2,4-triazole-3-carboxamide

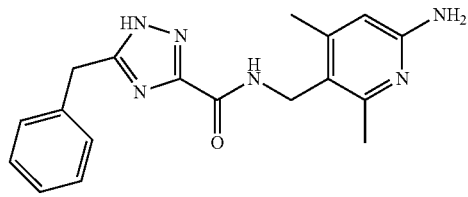 [SMILES: Cc1cc(N)nc(C)c1CNC(=O)c1n[nH]c(Cc2ccccc2)n1]

The title compound was prepared in analogy to example 2. HPLC (Method G) Rt=1.186 min; MS (Method F) [M+H]$^+$= 337.4.

Example 114

N-((6-amino-2,4-dimethylpyridin-3-yl)methyl)-1-(4-(pyridin-4-yl)benzyl)-1H-pyrazole-4-carboxamide

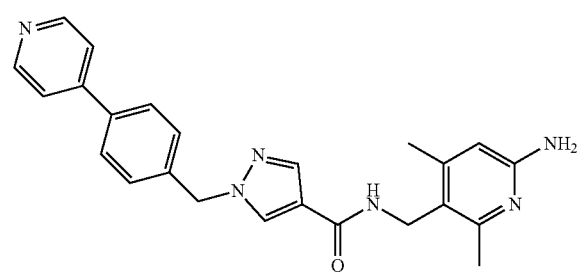 [SMILES: Cc1cc(N)nc(C)c1CNC(=O)c1cnn(Cc2ccc(-c3ccncc3)cc2)c1]

The title compound was prepared in analogy to example 9. HPLC (Method I) Rt=0.28 min; MS [M+H]$^+$=413.4.

Example 115

N-((6-amino-2,4-dimethylpyridin-3-yl)methyl)-1-(biphenyl-3-ylmethyl)-1H-pyrazole-4-carboxamide

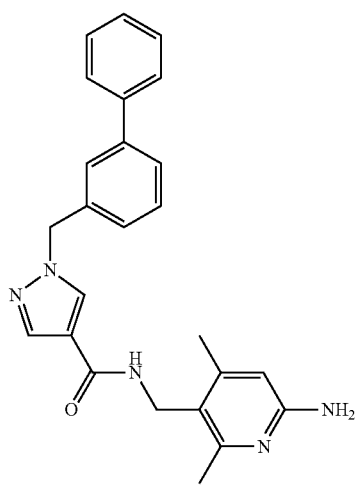 [SMILES: Cc1cc(N)nc(C)c1CNC(=O)c1cnn(Cc2cccc(-c3ccccc3)c2)c1]

The title compound was prepared in analogy to example 13. HPLC (Method J) Rt=3.408 min; MS (Method F) [M+H]$^+$= 412.4.

Example 116

N-((6-amino-2,4-dimethylpyridin-3-yl)methyl)-1-(3-(morpholinosulfonyl)benzyl)-1H-pyrazole-4-carboxamide

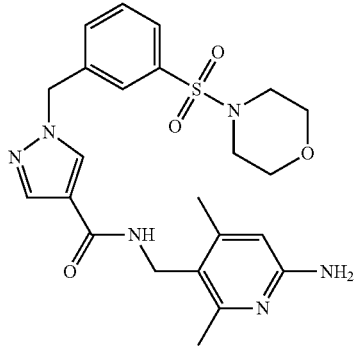 [SMILES: Cc1cc(N)nc(C)c1CNC(=O)c1cnn(Cc2cccc(S(=O)(=O)N3CCOCC3)c2)c1]

The title compound was prepared in analogy to example 13. HPLC (Method J) Rt=3.040 min; MS (Method F) [M+H]⁺= 485.4.

Example 117

N-((6-amino-2,4-dimethylpyridin-3-yl)methyl)-1-(3-(phenylcarbamoyl)benzyl)-1H-pyrazole-4-carboxamide

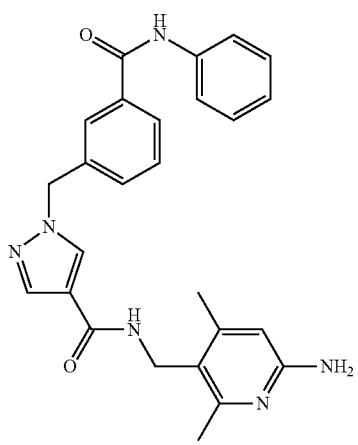 [SMILES: Cc1cc(N)nc(C)c1CNC(=O)c1cnn(Cc2cccc(C(=O)Nc3ccccc3)c2)c1]

The title compound was prepared in analogy to example 13. HPLC (Method J) Rt=3.189 min; MS (Method F) [M+H]⁺= 455.5.

Example 118

N-((6-amino-2,4-dimethylpyridin-3-yl)methyl)-1-(4-(pyrrolidin-1-ylmethyl)benzyl)-1H-pyrazole-4-carboxamide

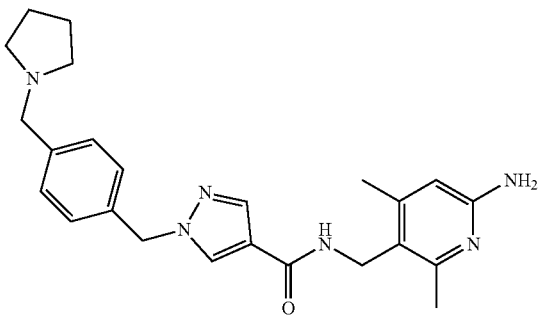 [SMILES: Cc1cc(N)nc(C)c1CNC(=O)c1cnn(Cc2ccc(CN3CCCC3)cc2)c1]

The title compound was prepared in analogy to example 9, Steps c)-f). HPLC (Method J) Rt=2.509 min; MS (Method F) [M+H]⁺=419.5.

Example 119

N-((6-amino-2,4-dimethylpyridin-3-yl)methyl)-1-(3-(piperidine-1-carbonyl)benzyl)-1H-pyrazole-4-carboxamide

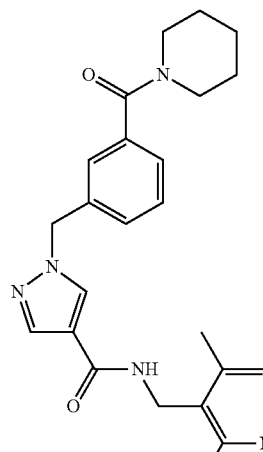

The title compound was prepared in analogy to example 13. HPLC (Method J) Rt=3.007 min; MS (Method F) [M+H]⁺= 447.5.

Example 120

N-((6-amino-2,4-dimethylpyridin-3-yl)methyl)-1-(4-(isopropylcarbamoyl)benzyl)-1H-pyrazole-4-carboxamide

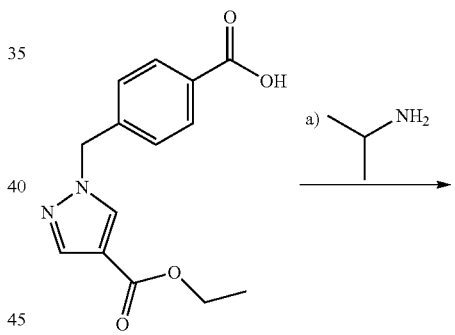

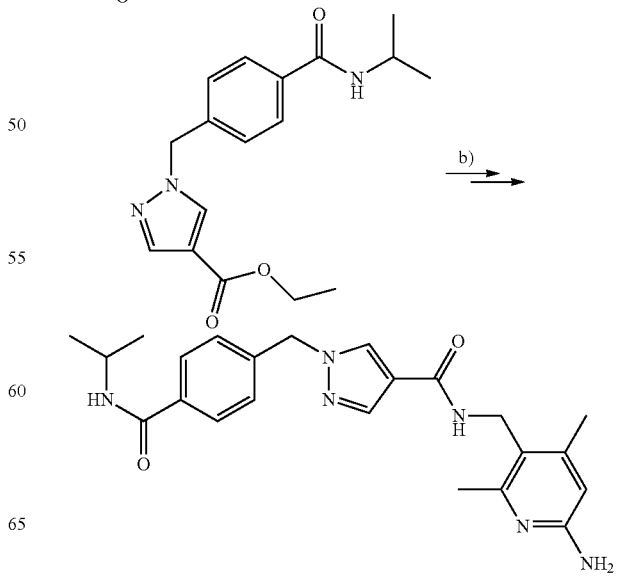

1-(4-Carboxy-benzyl)-1H-pyrazole-4-carboxylic acid ethyl ester was prepared as described in Example 112.

a) 1-(4-Isopropylcarbamoyl-benzyl)-1H-pyrazole-4-carboxylic acid ethyl ester

To a solution of 1-(4-carboxy-benzyl)-1H-pyrazole-4-carboxylic acid ethyl ester (50 mg, 0.153 mmol) in DCM (1 ml) were added DIPEA (40.1 μl, 0.230 mmol), HBTU (63.9 mg, 0.168 mmol) and isopropylamine (13 μl, 0.153 mmol). Reaction mixture was stirred over a weekend at 23° C. The solvent was evaporated, and the residual oil was dissolved in ethyl acetate and washed with 1M hydrochloric acid, saturated sodium bicarbonate solution and brine. Organic layer was dried (sodium sulfate), filtered and evaporated to afford the title compound. HPLC (method G) Rt=1.761 min; UPLC (method F) Rt=0.79 min, MS [M+H]⁺316.3.

b) N-((6-amino-2,4-dimethylpyridin-3-yl)methyl)-1-(4-(isopropylcarbamoyl)benzyl)-1H-pyrazole-4-carboxamide The title compound was prepared from 1-(4-isopropylcarbamoyl-benzyl)-1H-pyrazole-4-carboxylic acid ethyl ester in an analogous way according to the synthesis of Example 13. ¹H-NMR (DMSO-d6, 400 MHz): 1.15 (d, 6H), 2.15 (s, 3H), 2.28 (s, 3H), 4.07 (m, 1H), 4.27 (d, 2H), 5.37 (s, 2H), 5.63 (s, 2H), 6.11 (s, 1H), 7.30 (d, 2H), 7.80 (d, 2H), 7.90 (br s, 2H), 8.17 (d, 1H), 8.27 (s, 1H). HPLC (method G) Rt=1.283 min; UPLC (method F) Rt=0.44 min, MS [M+H]⁺421.5.

Example 121

N-((6-amino-2,4-dimethylpyridin-3-yl)methyl)-1-(4-(morpholine-4-carbonyl)benzyl)-1H-pyrazole-4-carboxamide

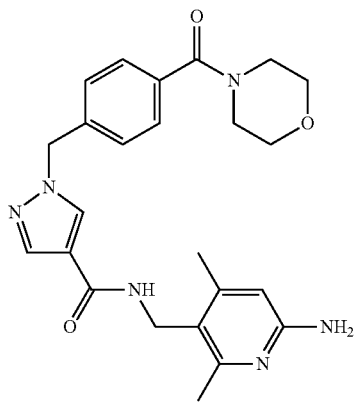 [SMILES: Cc1cc(N)nc(C)c1CNC(=O)c1cnn(Cc2ccc(C(=O)N3CCOCC3)cc2)c1]

The title compound was prepared in analogy to example 13. HPLC (Method J) Rt=2.809 min; MS (Method F) [M+H]⁺= 449.5.

Example 122

N-((6-amino-2,4-dimethylpyridin-3-yl)methyl)-1-(4-(1-methyl-1H-pyrazol-3-ylcarbamoyl)benzyl)-1H-pyrazole-4-carboxamide

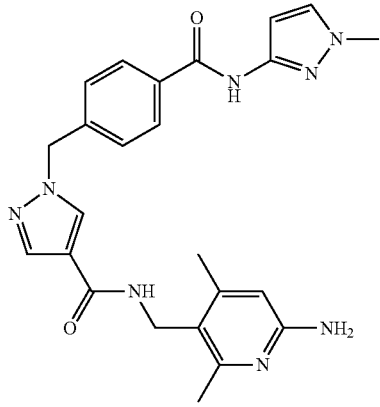 [SMILES: Cc1cc(N)nc(C)c1CNC(=O)c1cnn(Cc2ccc(C(=O)Nc3ccn(C)n3)cc2)c1]

The title compound was prepared in analogy to example 13. HPLC (Method J) Rt=2.818 min; MS (Method F) [M+H]⁺= 459.5.

Example 123

(S)-5-(amino(phenyl)methyl)-N-((6-amino-2,4-dimethylpyridin-3-yl)methyl)-1H-1,2,4-triazole-3-carboxamide

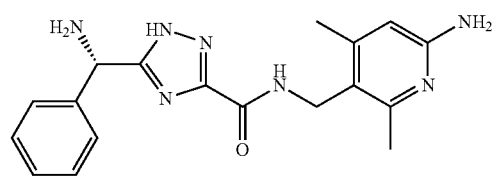 [SMILES: Cc1cc(N)nc(C)c1CNC(=O)c1n[nH]c([C@@H](N)c2ccccc2)n1]

The title compound was prepared in analogy to example 2. HPLC (Method J) Rt=2.412 min; MS (Method D) [M+H]⁺= 352.1.

Example 124

N-((6-amino-2,4-dimethylpyridin-3-yl)methyl)-3-(biphenyl-4-ylmethyl)-1H-1,2,4-triazole-5-carboxamide

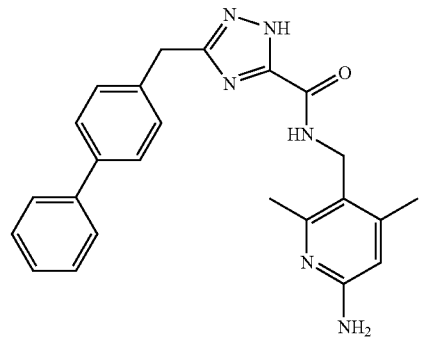 [SMILES: Cc1cc(N)nc(C)c1CNC(=O)c1nc(Cc2ccc(-c3ccccc3)cc2)n[nH]1]

The title compound was prepared in analogy to example 2. HPLC (Method J) Rt=3.277 min; MS (Method F) [M+H]⁺= 413.4.

Example 125

N-((6-amino-2,4-dimethylpyridin-3-yl)methyl)-3-(4-phenoxybenzyl)-1H-1,2,4-triazole-5-carboxamide

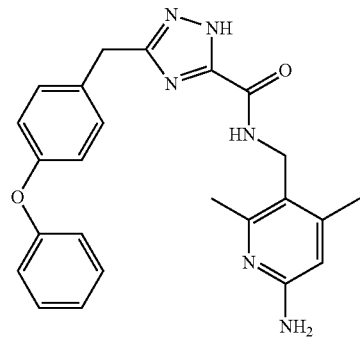 [SMILES: Cc1cc(N)nc(C)c1CNC(=O)c1nc(Cc2ccc(Oc3ccccc3)cc2)n[nH]1]

The title compound was prepared in analogy to example 2. HPLC (Method J) Rt=3.262 min; MS (Method F) [M+H]$^+$= 429.4.

Example 126

N-((6-amino-2,4-dimethylpyridin-3-yl)methyl)-1-(4-(N,N-dimethylsulfamoyl)benzyl)-1H-pyrazole-4-carboxamide

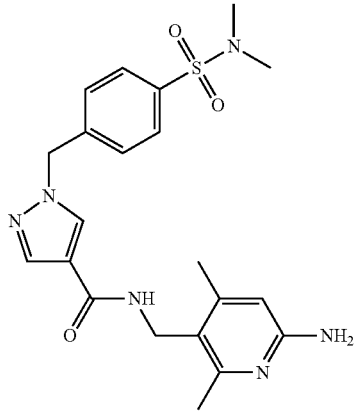 [SMILES: Cc1cc(N)nc(C)c1CNC(=O)c1cnn(Cc2ccc(S(=O)(=O)N(C)C)cc2)c1]

The title compound was prepared in analogy to example 13. HPLC (Method J) Rt=2.941 min; MS (Method F) [M+H]$^+$= 443.4

Example 127

N-((6-amino-2,4-dimethylpyridin-3-yl)methyl)-1-(biphenyl-4-ylsulfonyl)-1H-pyrrole-3-carboxamide

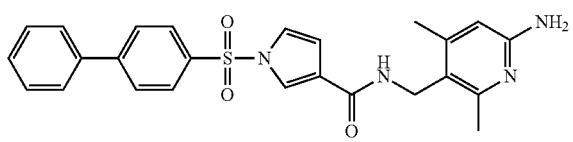 [SMILES: Cc1cc(N)nc(C)c1CNC(=O)c1ccn(S(=O)(=O)c2ccc(-c3ccccc3)cc2)c1]

The title compound was prepared in analogy to example 12. HPLC (Method T) Rt=0.96 min; MS [M+H]$^+$=460.7

Example 128

N-((6-amino-2,4-dimethylpyridin-3-yl)methyl)-1-(5-chlorothiophen-2-ylsulfonyl)-1H-pyrrole-3-carboxamide

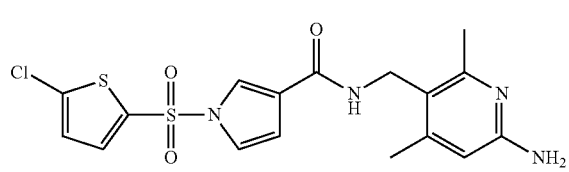 [SMILES: Cc1cc(N)nc(C)c1CNC(=O)c1ccn(S(=O)(=O)c2ccc(Cl)s2)c1]

The title compound was prepared in analogy to example 12. HPLC (Method T) Rt=0.87 min; MS [M+H]$^+$=424.7.

Example 129

N-((6-amino-2,4-dimethylpyridin-3-yl)methyl)-1-(3-methoxyphenylsulfonyl)-1H-pyrrole-3-carboxamide

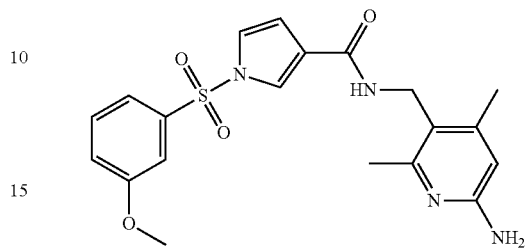

The title compound was prepared in analogy to example 12. HPLC (Method T) Rt=0.84 min; MS [M+H]$^+$=414.8.

Example 130

N-((6-amino-2,4-dimethylpyridin-3-yl)methyl)-1-(4-methyl-3,4-dihydro-2H-benzo[b][1,4]oxazin-6-ylsulfonyl)-1H-pyrrole-3-carboxamide

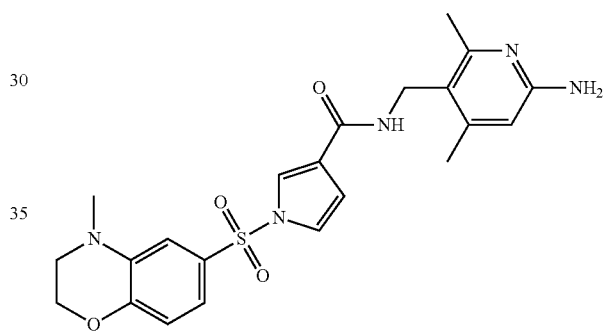

The title compound was prepared in analogy to example 12. HPLC (Method T) Rt=0.86 min; MS [M+H]$^+$=455.9.

Example 131

N-((6-amino-2,4-dimethylpyridin-3-yl)methyl)-1-(1-methyl-1H-indol-5-ylsulfonyl)-1H-pyrrole-3-carboxamide

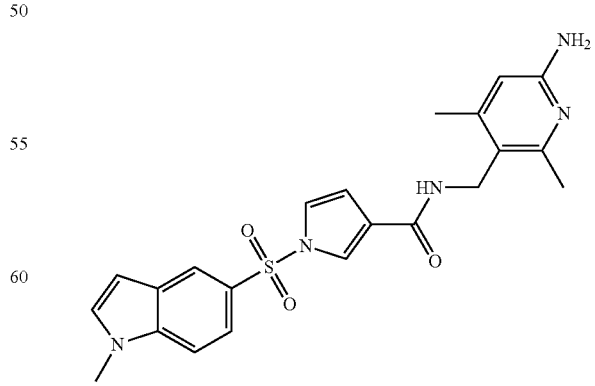

The title compound was prepared in analogy to example 12. HPLC (Method T) Rt=0.86 min; MS [M+H]$^+$=437.8.

Example 132

N-((6-amino-2,4-dimethylpyridin-3-yl)methyl)-1-(3-(pyrimidin-2-yl)phenylsulfonyl)-1H-pyrrole-3-carboxamide

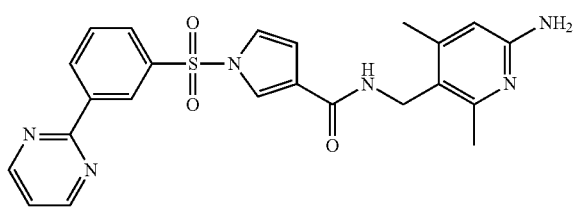 [SMILES: Cc1cc(N)nc(C)c1CNC(=O)c1ccn(S(=O)(=O)c2cccc(-c3ncccn3)c2)c1]

The title compound was prepared in analogy to example 12. HPLC (Method T) Rt=0.85 min; MS [M+H]$^+$=462.8.

Example 133

N-((6-amino-2,4-dimethylpyridin-3-yl)methyl)-1-(4-(3,5-dimethyl-1H-pyrazol-1-yl)phenylsulfonyl)-1H-pyrrole-3-carboxamide

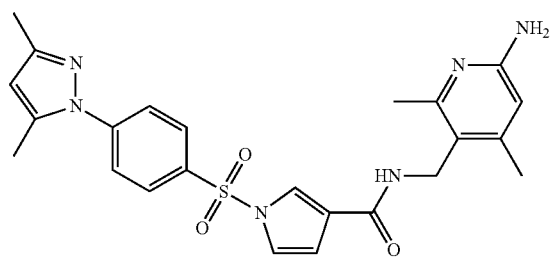 [SMILES: Cc1cc(C)n(-c2ccc(S(=O)(=O)n3ccc(C(=O)NCc4c(C)cc(N)nc4C)c3)cc2)n1]

The title compound was prepared in analogy to example 12. HPLC (Method T) Rt=0.87 min; MS [M+H]$^+$=478.8.

Example 134

2-(4-((4-((6-amino-2,4-dimethylpyridin-3-yl)methylcarbamoyl)-1H-pyrazol-1-yl)methyl)phenoxy)acetic acid

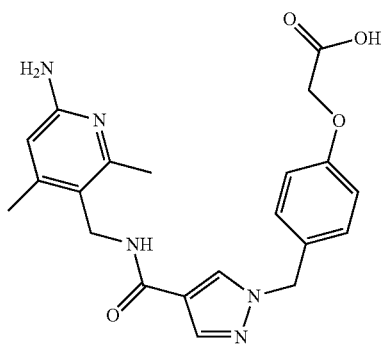 [SMILES: Cc1cc(N)nc(C)c1CNC(=O)c1cnn(Cc2ccc(OCC(=O)O)cc2)c1]

Hydrolysis of example 135: To N-((6-amino-2,4-dimethylpyridin-3-yl)methyl)-1-(4-(cyanomethoxy)benzyl)-1H-pyrazole-4-carboxamide (15 mg, 0.038 mmol) was added K$_2$CO$_3$ (15.93 mg, 0.115 mmol) in THF/H$_2$O (0.3 ml). The reaction mixture was stirred at 50° C. for 17 min, then at 90° C. for 1 h. The reaction mixture was diluted with water (2 mL) containing few drops of HCl (4M). Purification by preparative LC-MS (Flow 50 mL/min Waters Sunfire C18-ODB 30×150 mm, 5 um, 8% to 100% acetonitrile/water+0.1% of trifluoroacetic acid, in 14 min.) offered the title product after lyophilization. HPLC (Method I) Rt=0.70 min; MS [M+H]$^+$=410.5.

Example 135

N-((6-amino-2,4-dimethylpyridin-3-yl)methyl)-1-(4-(cyanomethoxy)benzyl)-1H-pyrazole-4-carboxamide

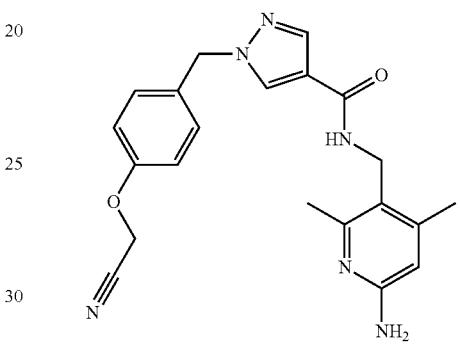

The title compound was prepared in analogy to example 1, Step d). HPLC (Method R) Rt=0.82 min; MS [M+H]$^+$=391.6.

Example 136

N-((6-amino-2-methyl-4-(oxazol-2-ylmethoxy)pyridin-3-yl)methyl)-1-benzyl-1H-1,2,3-triazole-4-carboxamide

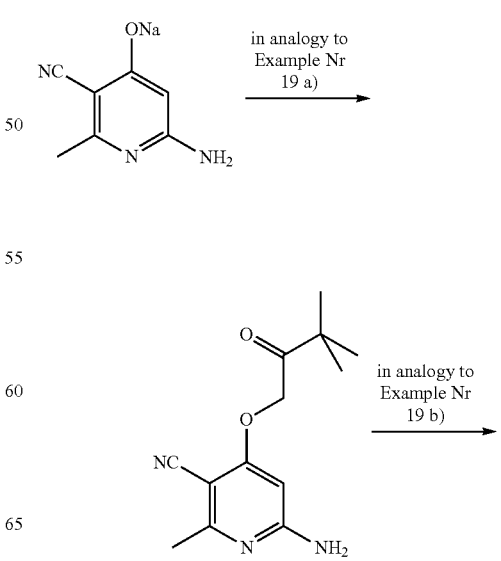

-continued

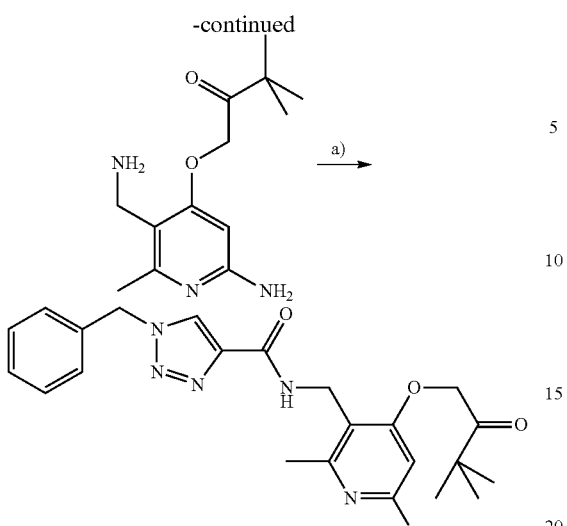

Step a): A suspension of 1-benzyl-1H-1,2,3-triazole-4-carboxylic acid (259 mg, 1.147 mmol) in SOCl$_2$ (1.522 ml, 20.85 mmol) was stirred at 40° C. for 1 h, and subsequently evaporated under reduced pressure. The remaining residue was dissolved in DMF (2 ml). After addition of 1-(6-amino-3-(aminomethyl)-2-methylpyridin-4-yloxy)-3,3-dimethylbutan-2-one (300 mg, 1.042 mmol, HCl-Salt: obtained in analogy to example 19 steps a) and b))
and DIPEA (1.092 ml, 6.25 mmol) the reaction mixture was stirred for 12 h at rt. Purification by prep HPLC (Nucleosil C18, 250×40 mm 5 to 100% ACN and 0.1% TFA, flow 40 mml/min) offered the titled compound after lyophilisation. HPLC (Method H) Rt=3.12 min; MS [M+H]$^+$=437.3.

Example 137

N-((6-amino-2-methyl-4-(oxazol-2-ylmethoxy)pyridin-3-yl)methyl)-1-benzyl-1H-1,2,3-triazole-4-carboxamide

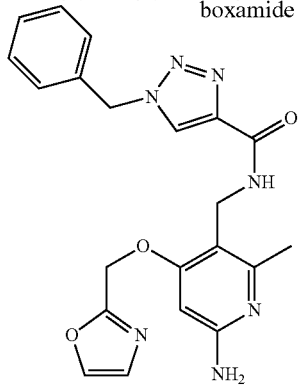

The title compound was prepared in analogy to example 136. HPLC (Method H) Rt=2.64 min; MS [M+H]$^+$=420.0.

Example 138

N-((6-amino-4-methylpyridin-3-yl)methyl)-1-benzyl-1H-pyrazole-4-carboxamide

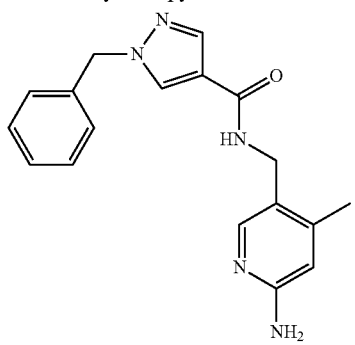

The title compound was prepared from known 5-(aminomethyl)-4-methylpyridin-2-amine in analogy to the final synthetic step of example 14. LCMS Rt$_L$=1.22 min, MS [M+H]$^+$=322.4.

Example 139

N-((6-amino-2,4-dimethylpyridin-3-yl)methyl)-1-(4-((3-oxo-2,3-dihydro-1H-pyrazol-1-yl)methyl)benzyl)-1H-pyrazole-4-carboxamide

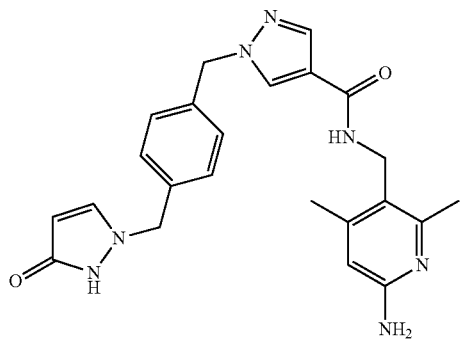 [SMILES: Cc1cc(N)nc(C)c1CNC(=O)c1cnn(Cc2ccc(Cn3ccc(=O)[nH]3)cc2)c1]

The title compound was prepared in analogy to example 17. LCMS (Method A) Rt$_A$=0.933; [M+H]$^+$=432.1.

Example 140

1-(4-((1H-1,2,3-triazol-1-yl)methyl)benzyl)-N-((6-amino-2,4-dimethylpyridin-3-yl)methyl)-1H-pyrazole-4-carboxamide

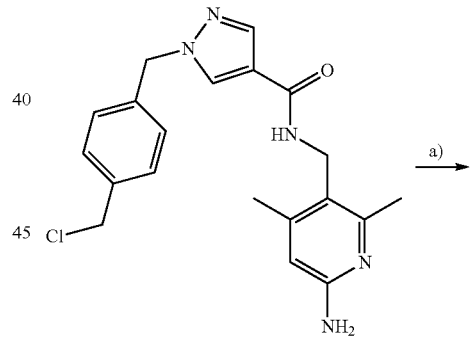

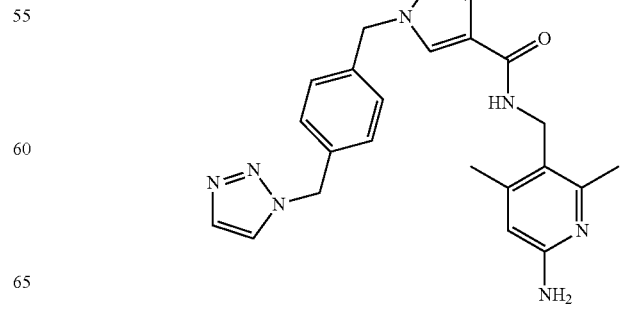

A suspension of [5-({[1-(4-Chloromethyl-benzyl)-1H-pyrazole-4-carbonyl]-amino}-methyl)-4,6-dimethyl-pyridin-2-yl]-carbamic acid tert-butyl ester (100 mg, 0.207 mmol, prepared according to step a) of example 17), sodium azide (13.43 mg, 0.207 mmol), ethynyltrimethylsilane (20.29 mg, 0.207 mmol), DIPEA (3.61 µL, 0.021 mmol), copper sulfate (3.30 mg, 0.021 mmol) and sodium ascorbate (4.09 mg, 0.021 mmol) in 2.5 mL of DMSO and 0.5 mL of water was stirred for 3 hours at 60° C. The mixture was allowed to cool to room temperature, was diluted with ethyl acetate and washed with water. The organic solution was concentrated under reduced pressure. The residue was dissolved in mL of methanol and 2 mL of concentrated aqueous HCl was added. This solution was stirred for 2 hours at 60° C. The volatiles were evaporated under reduced pressure. The residue was adjusted to basic pH with 1N NaOH. The resulting aqueous solution was extracted with ethyl acetate. The organic solution was dried of MgSO$_4$, filtered and concentrated under reduced pressure. The residue was purified by preparative HPLC (Macherey Nagel C18 100×10 mm, Flow 40 mL/min, ACN/water (0.1% TFA) 5/95 over 2 min, then ACN/water (0.1% TFA) 5/95-100/0 over 15 min). The fractions containing product were pooled, freeze-dried and redissolved in methanol. This solution was filtered over a methanol-flushed PL-HCO$_3$-MP resin column, which was subsequently washed twice with 5 mL methanol. The methanolic solution was concentrated under reduced pressure. The residue was taken up in ACN—water and freeze dried to afford the title compound. LCMS (Method A) Rt$_A$=0.316; [M+H]$^+$=417.1.

Example 141

N-((6-amino-2,4-dimethylpyridin-3-yl)methyl)-1-(4-((2,5-dimethyl-3-oxo-2,3-dihydro-1H-pyrazol-1-yl)methyl)benzyl)-1H-pyrazole-4-carboxamide

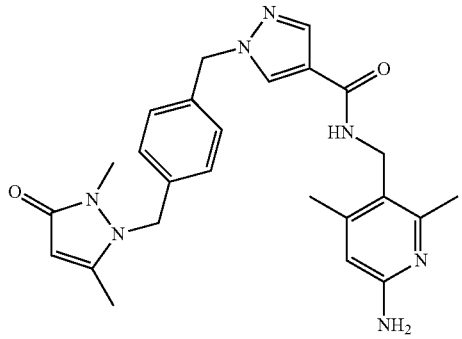 [SMILES: Cc1cc(N)nc(C)c1CNC(=O)c1cnn(Cc2ccc(Cn3c(C)cc(=O)n3C)cc2)c1]

The title compound was prepared in analogy to example 17. LCMS (Method A) Rt$_A$=0.493; [M+H]$^+$=460.1.

Example 142

N-((6-amino-2,4-dimethylpyridin-3-yl)methyl)-1-(4-((2-oxopyridin-1(2H)-yl)methyl)benzyl)-1H-pyrazole-4-carboxamide

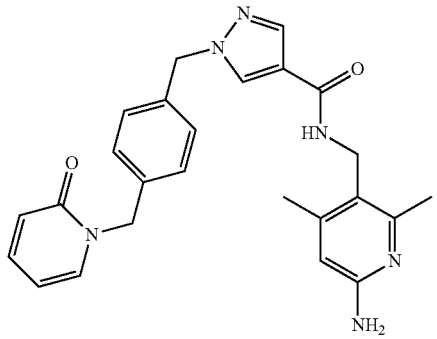 [SMILES: Cc1cc(N)nc(C)c1CNC(=O)c1cnn(Cc2ccc(Cn3ccccc3=O)cc2)c1]

The title compound was prepared in analogy to example 17. $^1$H NMR (DMSO-d6, 400 MHz) 8.24 (d, 1H, 0.5 Hz), 7.88-7.90 (t, 1H, 4.7 Hz), 7.87 (d, 1H, 0.5H), 7.75-7.77 (dd, 1H, 6.6 Hz, 2.2 Hz), 7.39-7.44 (m, 1H), 7.25-7.27 (d, 2H, 8.3 Hz), 7.21-7.23 (d, 2H, 8.3 Hz), 6.39-6.41 (d, 1H, 9.1 Hz), 6.21-6.25 (dt, 1H, 9.1 Hz, 2.2 Hz), 6.11 (s, 1H), 5.64 (s, 2H), 5.29 (s, 2H), 5.07 (s, 2H), 4.25-4.27 (d, 2H, 4.7 Hz), 2.28 (s, 3H), 2.15 (s, 3H), HPLC (Method H) Rt=2.53 min; MS [M+H]$^+$=443.0.

Example 143

N-((6-amino-2,4-dimethylpyridin-3-yl)methyl)-1-(4-((2-oxopyrrolidin-1-yl)methyl)benzyl)-1H-pyrazole-4-carboxamide

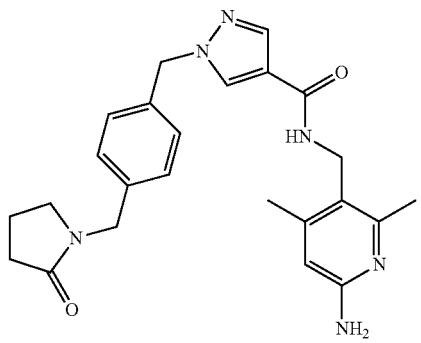 [SMILES: Cc1cc(N)nc(C)c1CNC(=O)c1cnn(Cc2ccc(CN3CCCC3=O)cc2)c1]

The title compound was prepared in analogy to example 17. LCMS (Method A) Rt$_A$=0.822; [M+H]$^+$=433.1.

Example 144

N-((6-amino-4-chloro-2-methylpyridin-3-yl)methyl]-1-benzyl-1H-pyrazole-4-carboxamide

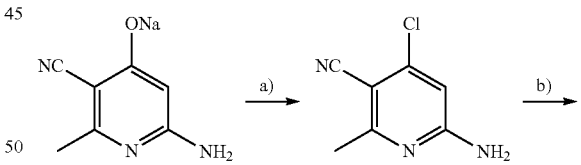

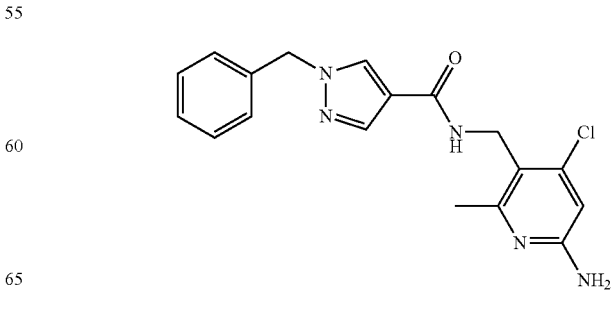

131 a) 6-amino-4-chloro-2-methylnicotinonitrile

A suspension of sodium 6-amino-3-cyano-2-methylpyridin-4-olate (690 mg, 4.03 mmol, prepared in analogy to WO2001062233A2 and isolated as sodium salt) in $PCl_3$ (3.50 ml, 40.3 mmol) and $POCl_3$ (0.94 ml, 10.1 mmol) was heated to reflux for 12 h. After cooling to room temperature, the reaction mixture was carefully given onto 2N NaOH (200 ml) and 50 g ice. The mixture was extracted with DCM (7×50 ml), and the combined organic extracts were dried over $Na_2SO_4$, filtered and concentrated. The crude product was used without additional purification. LCMS $Rt_M$=1.45 min, $[M+H]^+$=168.1.

b) N-((6-amino-4-chloro-2-methylpyridin-3-yl)methyl)-1-benzyl-1H-pyrazole-4-carboxamide The title compound was prepared in analogy to example 14b. LCMS (method K) $Rt_K$=0.83 min, $[M+H]^+$=356.4.

Example 145

1-(4-((1H-pyrazol-1-yl)methyl)benzyl)-N-((6-amino-2,4-dimethylpyridin-3-yl)methyl)-1H-pyrazole-4-carboxamide

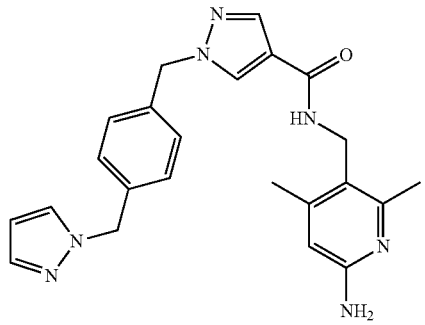 [SMILES: Cc1cc(N)nc(C)c1CNC(=O)c1cnn(Cc2ccc(Cn3cccn3)cc2)c1]

The title compound was prepared in analogy to example 9. HPLC (Method H) Rt=2.64 min; MS $[M+H]^+$=416.0.

Example 146

N-((6-amino-2,4-dimethylpyridin-3-yl)methyl)-1-(4-((4-methyl-1H-pyrazol-1-yl)methyl)benzyl)-1H-pyrazole-4-carboxamide

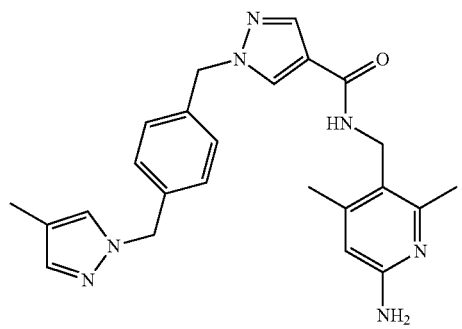

The title compound was prepared in analogy to example 9. HPLC (Method H) Rt=2.79 min; MS $[M+H]^+$=430.0.

Example 147

N-((6-amino-2,4-dimethylpyridin-3-yl)methyl)-1-(4-((5-methyl-1H-pyrazol-1-yl)methyl)benzyl)-1H-1,2,3-triazole-4-carboxamide

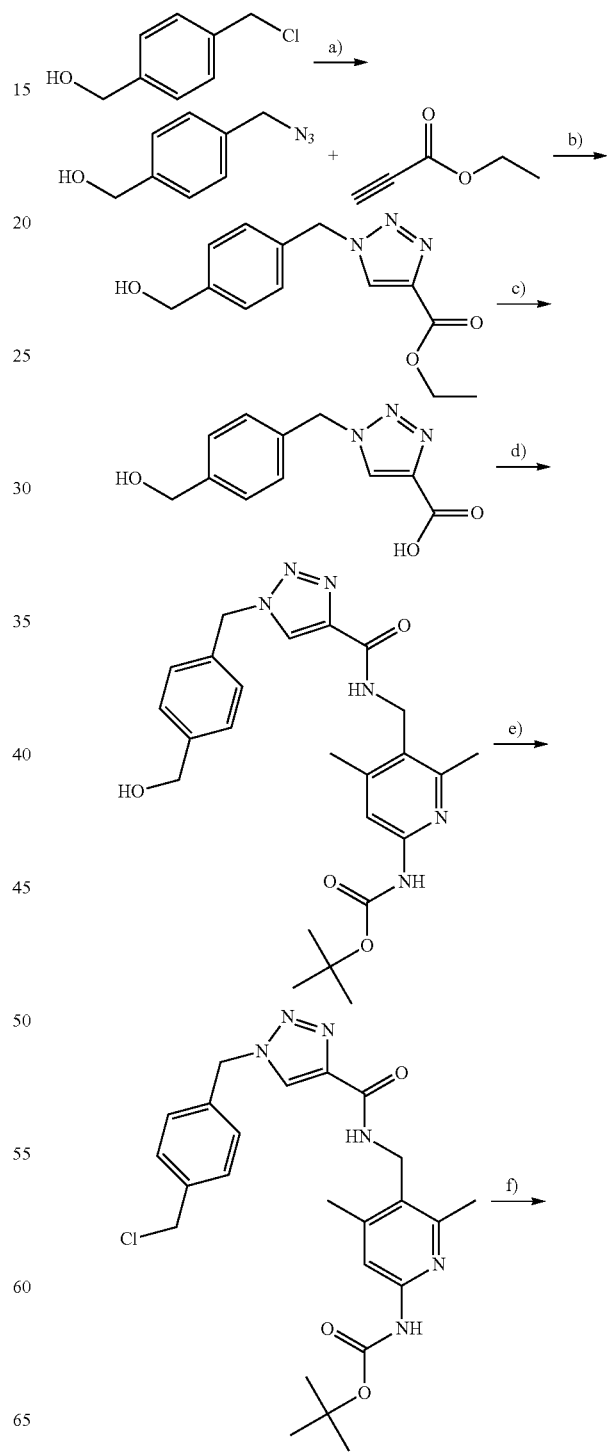

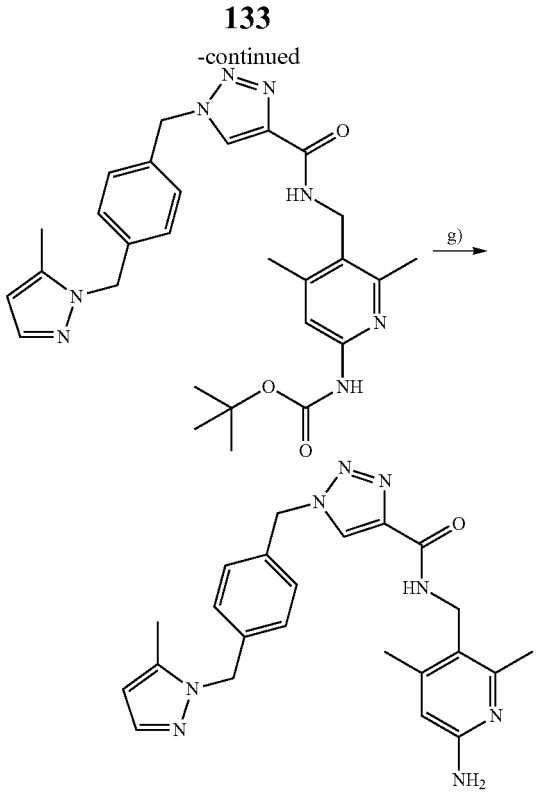

-continued g)

a) (4-Azidomethyl-phenyl)-methanol

A mixture of (4-Chloromethyl-phenyl)-methanol (5 g, 31.9 mmol) and sodium azide (2.283 g, 35.1 mmol) in 50 mL DMF was stirred at 90° C. for 16 h. The reaction mixture was concentrated in vacuo and the residue was treated with DCM and extracted with water. The organic layer was dried over $MgSO_4$ and evaporated to give the title compound which was used in the next step without further purification. 1H-NMR ($CDCl_3$, 400 MHz) 7.38-7.31 (m, 4H), 4.52 (d, 2H, 5.6 Hz), 4.42 (s, 2H).

b) 1-(4-Hydroxymethyl-benzyl)-1H-[1,2,3]triazole-4-carboxylic acid ethyl ester A mixture of (4-Azidomethyl-phenyl)-methanol (4.12 g, 25 mmol), ethyl propiolate (2.54 mL, 25 mmol), copper(II) sulfate (798 mg, 5 mmol) and sodium ascorbate (4.95 g, 25 mmol) in 30 mL n-BuOH and 30 mL water was stirred at room temperature for 16 h. Ethyl acetate was added and the mixture was extracted with water. The organic layer was dried over $MgSO_4$ and evaporated in vacuo to give the title compound which was used in the next step without further purification. LCMS (Method A) $Rt_A$=1.157; $[M+H]^+$=467.0MS $[M+H]^+$=262.0.

c) 1-(4-Hydroxymethyl-benzyl)-1H-[1,2,3]triazole-4-carboxylic acid

A mixture of 1-(4-Hydroxymethyl-benzyl)-1H-[1,2,3]triazole-4-carboxylic acid ethyl ester (4.35 g, 9.42 mmol) and lithiumhydroxide-hydrate (1.976 g, 47.1 mmol) in 80 mL MeOH and 80 mL water was stirred at 30° C. for 3 h. The methanol was evaporated in vacuo. The residual aqueous layer was washed with ethyl acetate, acidified with 1 N aq. HCl and extracted with ethyl acetate. The organic layer was dried over $MgSO_4$, filtered and evaporated to yield the crude product which was used in the next step without further purification. 1H-NMR (DMSO-d6, 400 MHz) 13.1 (broad s, 1H), 8.76 (s, 1H), 7.27-7.39 (m, 4H), 5.63 (s, 2H), 5.20 (t, 1H), 4.48 (d, 2H).

d) [5-({[1-(4-Hydroxymethyl-benzyl)-1H-[1,2,3]triazole-4-carbonyl]-amino}-methyl)-4,6-dimethyl-pyridin-2-yl]carbamic acid tert-butyl ester A mixture of 1-(4-hydroxymethyl-benzyl)-1H-[1,2,3]triazole-4-carboxylic acid (0.95 g, 4.07 mmol), (5-Aminomethyl-4,6-dimethyl-pyridin-2-yl)-carbamic acid tert-butyl ester (1.024 g, 4.07 mmol), HATU (2.013 g, 5.30 mmol) and DIPEA (2.85 mL, 16.29 mmol) in 50 mL DMF was stirred at room temperature for 3 h. The reaction mixture was concentrated under reduced pressure. The residue was taken up in ethyl acetate and washed with 1 n HCl solution and saturated sodium bicarbonate solution. The organic solution was dried over $MgSO_4$, filtered and concentrated to yield the crude product which was used in the next step without further purification. LCMS (Method A) $Rt_A$=1.279; $[M+H]^+$=467.0.

e) [5-({[1-(4-Chloromethyl-benzyl)-1H-[1,2,3]triazole-4-carbonyl]-amino}-methyl)-4,6-dimethyl-pyridin-2-yl]carbamic acid tert-butyl ester To a solution of [5-({[1-(4-Hydroxymethyl-benzyl)-1H-[1,2,3]triazole-4-carbonyl]-amino}-methyl)-4,6-dimethyl-pyridin-2-yl]-carbamic acid tert-butyl ester (690 mg, 1.331 mmol) in 10 mL of DCM was added dropwise a solution of thionyl chloride (0.107 mL, 1.464 mmol) and pyridine (1.615 µL, 0.02 mmol) in 10 mL of DCM. The reaction mixture was stirred for 3 h at 40° C. and saturated aqueous bicarbonate solution was added. The layers were separated and the aqueous layer was extracted with DCM. The combined organic solution was dried over $MgSO_4$, filtered and concentrated under vacuum to yield the crude product which was used in the next step without further purification. LCMS (Method A) $Rt_A$=1.681; $[M+H]^+$=485.0.

f) {4,6-Dimethyl-5-[({1-[4-(5-methyl-pyrazol-1-ylmethyl)-benzyl]-1H-[1,2,3]triazole-4-carbonyl}-amino)-methyl]-pyridin-2-yl}-carbamic acid tert-butyl ester A mixture of [5-({[1-(4-Chloromethyl-benzyl)-1H-[1,2,3]triazole-4-carbonyl]-amino}-methyl)-4,6-dimethyl-pyridin-2-yl]-carbamic acid tert-butyl ester (200 mg, 0.412 mmol), 3-methylpyrazole (33.9 mg, 0.412 mmol) and cesium carbonate (269 mg, 0.825 mmol) in 2 mL of DMF was stirred at 80° C. for 2 h. The reaction mixture was filtered and concentrated under reduced pressure. The residue was purified by preparative HPLC (Waters SunFire Prep C18 OBD 5 µm 30×100 mm, Flow 40 mL/min, ACN/water (0.1% TFA) 5/95 over 2 min, then ACN/water (0.1% TFA) 5195-100/0 over 15 min). LCMS (Method A) $Rt_A$=1.527; $[M+H]^+$=531.1.

g) 1-[4-(5-Methyl-pyrazol-1-ylmethyl)-benzyl]-1H-[1,2,3]triazole-4-carboxylic acid (6-amino-2,4-dimethyl-pyridin-3-ylmethyl)-amide A mixture of {4,6-Dimethyl-5-[({1-[4-(5-methyl-pyrazol-1-ylmethyl)-benzyl]-1H-[1,2,3]triazole-4-carbonyl}-amino)-methyl]-pyridin-2-yl}-carbamic acid tert-butyl ester (132 mg, 0.249 mmol) and 5 mL of TFA in 10 mL of DCM was stirred at room temperature for 2 h. The reaction mixture was concentrated under reduced pressure. The residue was purified by preparative HPLC (Waters SunFire Prep C18 OBD 5 μm 30×100 mm, Flow 40 mL/min, ACN/water (0.1% TFA) 5/95 over 2 min, then ACN/water (0.1% TFA) 5/95-100/0 over 15 min) to yield the title compound. 1H-NMR (DMSO-d6, 600 MHz) 8.59 (s, 1H), 8.29 (t, 1H), 7.33 (s, 1H), 7.28 (d, 2H), 7.09 (d, 2H), 6.09 (s, 1H), 6.05 (s, 1H), 5.63 (s, 2H), 5.59 (s, 2H), 5.26 (s, 2H), 4.32 (d, 2H), 2.29 (s, 3H), 2.17 (s, 3H), 2.16 (s, 3H); [M+H]⁺=431.0.

Example 148

N-((6-amino-2,4-dimethylpyridin-3-yl)methyl)-1-(4-((3,5-dimethyl-1H-pyrazol-1-yl)methyl)benzyl)-1H-1,2,3-triazole-4-carboxamide

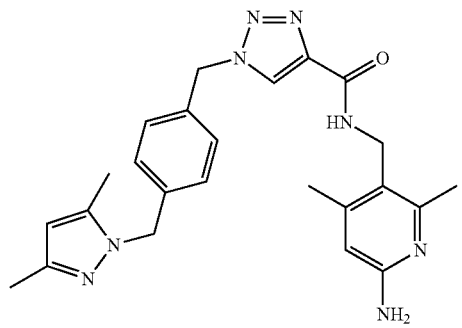

The title compound was prepared in analogy to example 147. 1H-NMR (DMSO-d6, 600 MHz) 8.60 (s, 1H), 8.30 (t, 1H), 7.29 (d, 2H), 7.09 (d, 2H), 6.10 (s, 1H), 5.84 (s, 1H), 5.64 (s, 2H), 5.60 (s, 2H), 5.16 (s, 2H), 4.33 (d, 2H), 2.30 (s, 3H), 2.18 (s, 3H), 2.14 (s, 3H), 2.08 (s, 3H); [M+H]⁺=445.1.

Example 149

N-((6-amino-4-(3,3-dimethyl-2-oxobutoxy)-2-methylpyridin-3yl)methyl)-1-(naphthalen-2-ylmethyl)-1H-pyrazole-4-carboxamide

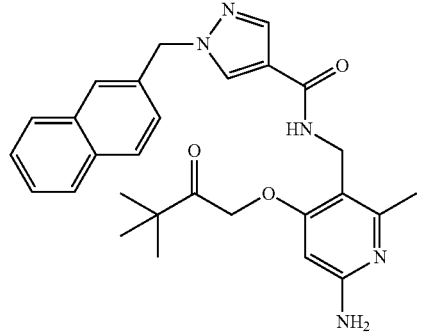 [SMILES: Cc1nc(N)cc(OCC(=O)C(C)(C)C)c1CNC(=O)c1cnn(Cc2ccc3ccccc3c2)c1]

The title compound was prepared in analogy to example 1 step d) using 1-(6-amino-3-(aminomethyl)-2-methylpyridin-4-yloxy)-3,3-dimethylbutan-2-one (from example 136) and 1-Naphthalen-2-ylmethyl-1H-pyrazole-4-carboxylic acid (from example 83). HPLC (Method H) Rt=3.33 min; MS [M+H]⁺=486.2.

Example 150

N-((6-Amino-2,4-dimethylpyridin-3-yl)methyl)-1-((1-(2-methoxyethyl)-1,2,3,4-tetrahydroquinolin-7-yl)methyl)-1H-pyrazole-4-carboxamide

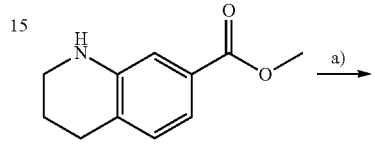

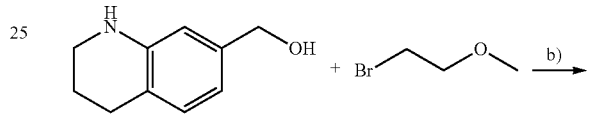

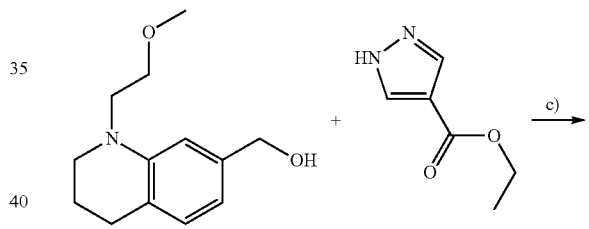

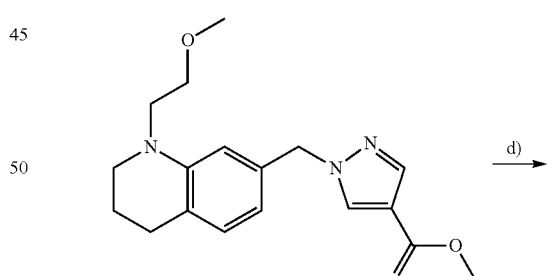

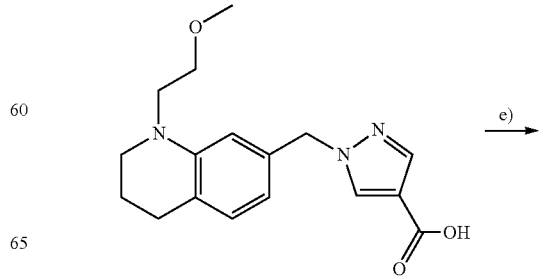

-continued

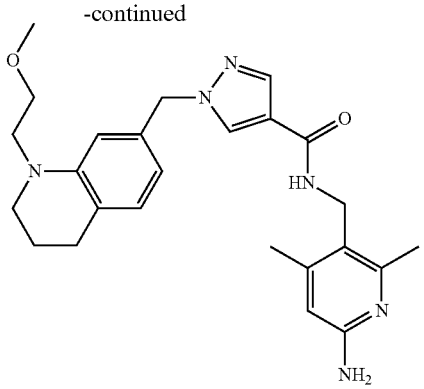

a) (1,2,3,4-Tetrahydroquinolin-7-yl)methanol

To a cooled (0° C.) solution 1 g (5.23 mmol) of methyl 1,2,3,4-tetrahydroquinoline-7-carboxylate in THF (10 ml) was added 20.92 ml, (20.92 mmol) of a solution of DIBAL-H in THF. The reaction mixture was stirred for 2 hr at 0° C. Additional DIBAL-H in THF (15.69 ml, 15.69 mmol) was added. The reaction mixture was allowed to warm to 20° C. and stirring was continued for 16 hr. The reaction mixture was treated with 30 mL of 10% aqueous sodium potassium tartrate and stirred for 1 h. Water was added and the mixture was extracted with AcOEt. The organic layer was dried over MgSO4 and concentrated under reduced pressure to give (1,2,3,4-tetrahydroquinolin-7-yl)methanol. HPLC (Method H) Rt=2.74 min; MS (Method A) [M+H]$^+$=164.1 b) (1-(2-Methoxyethyl)-1,2,3,4-tetrahydroquinolin-7-yl)methanol

A mixture of (1,2,3,4-tetrahydroquinolin-7-yl)methanol (370 mg, 1.496 mmol), 1-bromo-2-methoxyethane (0.141 ml, 1.496 mmol) and Cs$_2$CO$_3$ (731 mg, 2.244 mmol) in DMF (10 ml). was stirred for 16 hr at 80° C. Additional 1-bromo-2-methoxyethane (0.070 ml, 0.748 mmol) was added and stirring was continued for 16 hr at 80° C. A third batch of 1-bromo-2-methoxyethane (0.070 ml, 0.748 mmol) was added and stirring was continued for 1 additional hour at 80° C. The reaction mixture was cooled to room temperature and water was added. The mixture was extracted with AcOEt. The organic layer was dried over MgSO4 and concentrated under reduced pressure to give the title compound. HPLC (Method A) Rt=1.173 min; MS (Method A) [M+H]$^+$=221.9 c) Ethyl 1-((1-(2-methoxyethyl)-1,2,3,4-tetrahydroquinolin-7-yl)methyl)-1H-pyrazole-4-carboxylate (1-(2-Methoxyethyl)-1,2,3,4-tetrahydroquinolin-7-yl)methanol (357 mg, 0.807 mmol) and ethyl 1H-pyrazole-4-carboxylate (113 mg, 0.807 mmol) were dissolved in THF (5 ml). Triphenylphosphine (317 mg, 1.210 mmol) was added, and, after cooling to 0° C., a 40% solution of DEAD in Toluene (0.479 ml, 1.210 mmol) was added dropwise. The reaction mixture was stirred for 2 hr at 0° C., then overnight at 20° C. The reaction mixture was diluted with AcOEt and washed with 1N HCl, and saturated aqueous NaHCO$_3$. The organic layer was dried over MgSO4 and concentrated under reduced pressure. The crude product was purified by preparative-HPLC (Waters SunFire Prep C18 OBD 5 μm 19*50, Flow 20 mL/min, ACN: 2 min at 5%, then to 100% within 17.5 min, RT 11.80 min) to give the title compound. HPLC (Method A) Rt=2.001 min; MS (Method A) [M]$^+$=343.9 d) 1-((1-(2-Methoxyethyl)-1,2,3,4-tetrahydroquinolin-7-yl)methyl)-1H-pyrazole-4-carboxylic acid Ethyl 1-((1-(2-methoxyethyl)-1,2,3,4-tetrahydroquinolin-7-yl)methyl)-1H-pyrazole-4-carboxylate (484 mg, 0.874 mmol) was dissolved in a mixture of MeOH (5 ml) and 1N NaOH (5.00 ml). The reaction mixture was stirred for 2 hr at 20° C. and the MeOH was removed by evaporation under reduced pressure. The aqeuous phase was washed with AcOEt, then acidified with HCl and extracted with AcOEt. The organic layer was concentrated under reduced pressure to afford the title compound. HPLC (Method H) Rt=2.74 min e) N-((6-amino-2,4-dimethylpyridin-3-yl)methyl)-1-((1-(2-methoxyethyl)-1,2,3,4-tetrahydroquinolin-7-yl)methyl)-1H-pyrazole-4-carboxamide The title compound was obtained by an analogous procedure as in example 13b). HPLC (Method H) Rt=2.70 min; MS (Method A) [M+H]$^+$=449.0

Example 151

N-((6-Amino-2,4-dimethylpyridin-3-yl)methyl)-1-((4-methyl-3-oxo-3,4-dihydro-2H-benzo[b][1,4]oxazin-6-yl)methyl)-1H-pyrazole-4-carboxamide

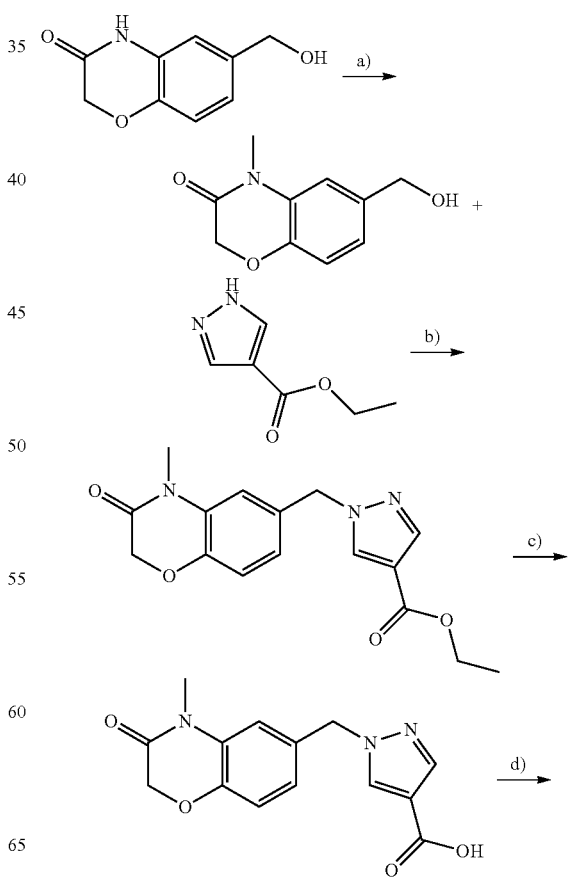

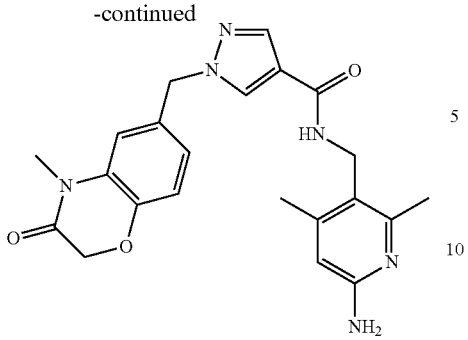

a) 6-(Hydroxymethyl)-4-methyl-2H-benzo[b][1,4]] oxazin-3(4H)-one

A suspension of 6-(hydroxymethyl)-2H-benzo[b][1,4]oxazin-3(4H)-one (180 mg, 1.005 mmol), $Cs_2CO_3$ (655 mg, 2.009 mmol) and iodomethane (0.060 ml, 0.954 mmol) was stirred for 45 min at 20° C. The reaction mixture was filtered and concentrated under reduced pressure. The crude product was purified by preparative HPLC (Macherey-Nagel Nucleosil 100-10 C18, Flow 40 mL/min, ACN: 2 min at 5%, then to 100% within 17.5 min, RT 14.14 min) to yield the title compound. HPLC (Method A) Rt=0.93 min; MS (Method A) [M+H]$^+$=193.9 b) Ethyl 1-((4-methyl-3-oxo-3,4-dihydro-2H-benzo[b][1,4]oxazin-6-yl)methyl)-1H-pyrazole-4-carboxylate To a stirred, cooled (0° C.) solution of 6-(hydroxymethyl)-4-methyl-2H-benzo[b][1,4]oxazin-3(4H)-one (122 mg, 0.631 mmol), ethylpyrazol-4-carboxylate (88 mg, 0.631 mmol) and triphenylphosphine (248 mg, 0.947 mmol) in THF (5 ml) was added dropwise a 40% solution of DEAD in toluene (0.375 ml, 0.947 mmol). The reaction mixture was stirred for 2 h at 0° C., then over night at 20° C. Saturated aqueous NaHCO3 was added and the mixture was extracted with AcOEt. The organic layer was dried over MgSO4, filtered and concentrated under reduced pressure to give the title compound. MS (Method A) [M+H]$^+$=316.9 c) 1-((4-Methyl-3-oxo-3,4-dihydro-2H-benzo[b][1,4] oxazin-6-yl)methyl)-1H-pyrazole-4-carboxylic acid Ethyl 1-((4-methyl-3-oxo-3,4-dihydro-2H-benzo[b][1,4] oxazin-6-yl)methyl)-1H-pyrazole-4-carboxylate (780 mg, 0.618 mmol) was dissolved in a mixture of MeOH (5 ml) and 1N NaOH (5.00 ml). The reaction mixture was stirred for 2 hr at 20° C. and the MeOH was removed by evaporation under reduced pressure. The aqeuous phase was washed with AcOEt, then acidified with HCl and extracted with AcOEt. The organic layer was concentrated under reduced pressure to afford the title compound. HPLC (Method H) Rt=2.636 min; MS (Method A) [M−H]$^-$=286.1 d) N-((6-Amino-2,4-dimethylpyridin-3-yl)methyl)-1-((4-methyl-3-oxo-3,4-dihydro-2H-benzo[b][1,4]oxazin-6-yl)methyl)-1H-pyrazole-4-carboxamide The title compound was obtained by an analogous procedure as in example 13b). 1H-NMR (DMSO-d6, 400 MHz) δ 8.24 (s, 1H), 7.97 (broad s, 1H), 7.88 (s, 1H), 7.18 (s, 1H), 6.98 (d, 1H), 6.92 (d, 1H), 6.26 (s, 1H), 6.11 (broad, 2H), 5.29 (s, 2H), 4.64 (s, 2H), 4.27 (d, 2H), 3.26 (s, 3H), 2.35 (s, 3H), 2.22 (s, 3H); HPLC (Method H) Rt=2.529 min; MS (Method A) [M+H]$^+$=421.0

Example 152

N-((6-Amino-2,4-dimethylpyridin-3-yl)methyl)-1-((1-methyl-1,2,3,4-tetrahydroquinolin-7-yl)methyl)-1H-pyrazole-4-carboxamide

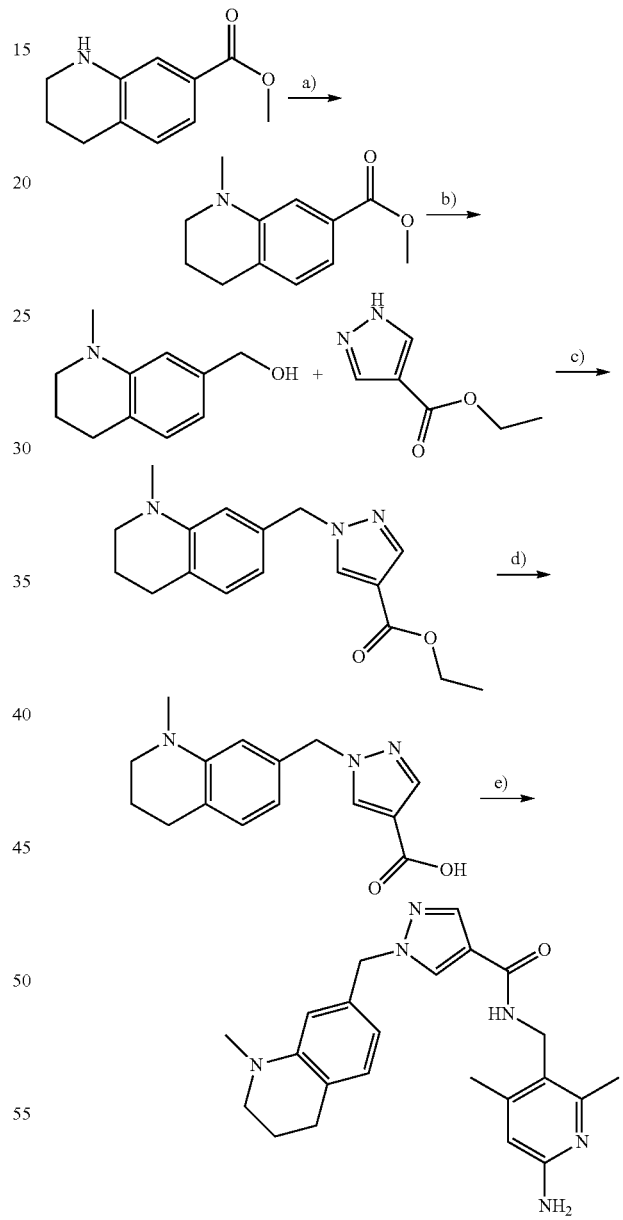

a) Methyl 1-methyl-1,2,3,4-tetrahydroquinoline-7-carboxylate

A suspension of methyl 1,2,3,4-tetrahydroquinoline-7-carboxylate (380 mg, 1.987 mmol), $Cs_2CO_3$ (1295 mg, 3.97 mmol) and iodomethane (0.118 ml, 1.888 mmol) was stirred for 16 hours at 20° C. After that time, more iodomethane (0.118 ml, 1.888 mmol) was added and stirring was continued for 8 hours at 60° C. The reaction mixture was allowed to cool to room temperature, filtered and concentrated under reduced pressure. The crude product was purified by preparative HPLC (Macherey-Nagel Nucleosil 100-10 C18, Flow 40 mL/min, ACN: 2 min at 5%, then to 100% within 17.5 min, RT 15.52 min) to yield the title compound. HPLC (Method H) Rt=3.005 min; MS (Method A) [M+H]$^+$=206.1 b) (1-Methyl-1,2,3,4-tetrahydroquinolin-7-yl)methanol

To a cooled (0° C.) solution of methyl 1-methyl-1,2,3,4-tetrahydroquinoline-7-carboxylate (320 mg, 1.559 mmol) in THF (25 mL) was added a solution of DIBAL-H in THF (6.24 ml, 6.24 mmol). The reaction mixture was stirred for 3 hr at 0° C. The reaction mixture was treated with 30 mL of 10% aqueous sodium potassium tartrate and stirred for 2 h at 20° C. The mixture was extracted with AcOEt. The organic layer was dried over MgSO4, filtered and concentrated under reduced pressure to give the title compound. MS (Method A) [M+H]$^+$=178.0 c) Ethyl 1-((1-methyl-1,2,3,4-tetrahydroquinolin-7-yl)methyl)-1H-pyrazole-4-carboxylate To a stirred, cooled (0° C.) solution of (1-methyl-1,2,3,4-tetrahydroquinolin-7-yl)methanol (200 mg, 0.733 mmol), ethyl 1H-pyrazole-4-carboxylate (103 mg, 0.733 mmol) and triphenylphosphine (289 mg, 1.100 mmol) in THF (10 ml) was added dropwise a 40% solution of DEAD in toluene (0.435 ml, 1.1 mmol). The reaction mixture was stirred for 2 h at 0° C., then over night at 20° C. Saturated aqueous NaHCO3 was added and the mixture was extracted with AcOEt. The organic layer was dried over MgSO4, filtered and concentrated under reduced pressure to give the title compound. The crude product was purified by preparative HPLC (Waters SunFire Prep C18 OBD 5 μm 30*100, Flow 40 mL/min, ACN: 2 min at 5%, then to 100% within 17.5 min, RT 10.00 min) to give the title compound. HPLC (Method H) Rt=2.919 min; MS (Method A) [M+H]$^+$=300.0 d) 1-((1-Methyl-1,2,3,4-tetrahydroquinolin-7-yl)methyl)-1H-pyrazole-4-carboxylic acid Ethyl 1-((1-methyl-1,2,3,4-tetrahydroquinolin-7-yl)methyl)-1H-pyrazole-4-carboxylate (233 mg, 0.607 mmol) was dissolved in a mixture of MeOH (6 ml) and 1N NaOH (3.00 ml). The reaction mixture was stirred for 8 hr at 20° C. and the solvents were removed by evaporation under reduced pressure to afford the title compound. HPLC (Method A) Rt=1.348 min; MS (Method A) [M+H]$^+$=271.9 e) N-((6-Amino-2,4-dimethylpyridin-3-yl)methyl)-1-((1-methyl-1,2,3,4-tetrahydroquinolin-7-yl)methyl)-1H-pyrazole-4-carboxamide The title compound was obtained by an analogous procedure as in example 13b). 1H-NMR (DMSO-d6, 400 MHz) δ 8.18 (s, 1H), 7.87 (broad s, 1H), 7.86 (s, 1H), 6.84 (d, 1H), 6.51 (s, 1H), 6.40 (d, 1H), 6.12 (s, 1H), 5.62 (s, 2H), 5.16 (s, 2H), 4.27 (d, 2H), 3.17 (7, 3H), 2.80 (s, 3H), 2.65 (t, 2H), 2.28 (s, 3H), 2.15 (s, 3H), 1.85 (m, 2H); HPLC (Method H), Rt=2.443 min; MS (Method A) [M+H]$^+$=405.1

Example 153

N-((6-amino-2,4-dimethylpyridin-3-yl)methyl)-1-((2-methylquinolin-6-yl)methyl)-1H-1,2,3-triazole-4-carboxamide

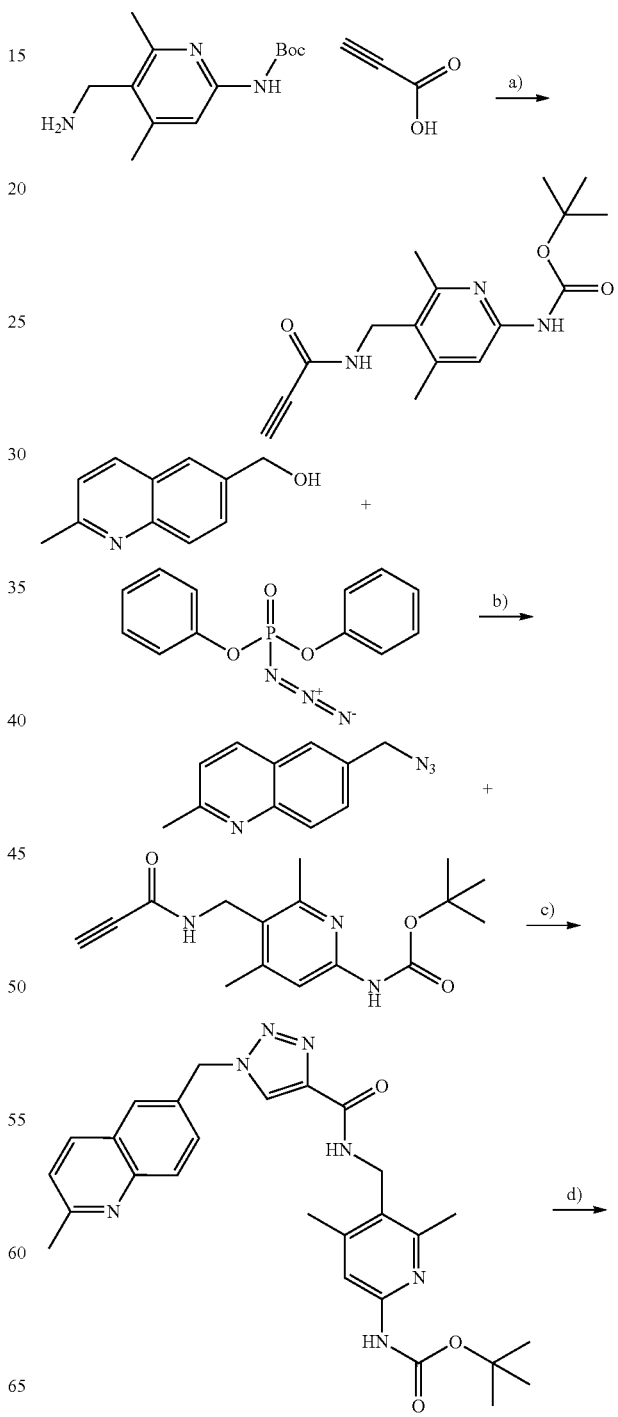

-continued

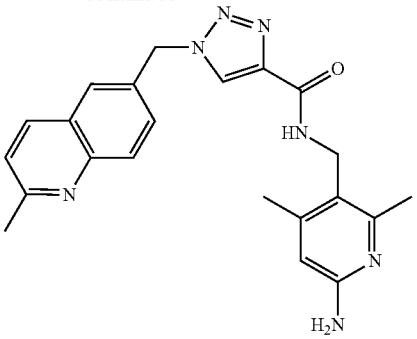

a) tert-butyl (4,6-dimethyl-5-(propiolamidomethyl) pyridin-2-yl)carbamate

To a solution of (5-aminomethyl-4,6-dimethyl-pyridin-2-yl)-carbamic acid tert-butyl ester (4.50 g, 17.90 mmol), propiolic acid (0.918 ml, 14.92 mmol), DIPEA (7.82 ml, 44.8 mmol) in DCM (140 ml) at 23° C. was added dropwise over 5 min 50% propylphosphonic anhydride in DMF (12.5 ml, 21.41 mmol). The reaction was stirred at 23° C. for 1 day. The reaction was quenched by addition of brine, and the phases were separated. The aqueous phase was further extracted with DCM, and the combined organic phase was dried over $Na_2SO_4$, filtered, and evaporated to provide the crude product, which was purified by flash column chromatography (silica gel 0.040-0.063 mm, 160 g, flow rate 60 ml/min, detection at 220 nm, MeOH in DCM 0->1% over 10 min, then 1->5% over 20 min) to yield the title compound. HPLC (Method G) Rt=1.333 min; MS (Method F) [M+H]$^+$=304.31.

b) 6-(azidomethyl)-2-methylquinoline

To a solution of (2-methyl-6-quinolinyl)methanol (100 mg, 0.560 mmol) and DBU (0.152 ml, 1.008 mmol) in DMF (4 ml) was added DPPA (0.205 ml, 0.952 mmol). The reaction mixture was stirred overnight at 23° C. Reaction mixture was poured into water and extracted twice with ethyl acetate. Organic layer was washed with brine, dried over sodium sulfate, filtered and evaporated to afford a crude material, which was purified by silicagel chromatography (cyclohexane:ethyl acetate from 100:0 to 0:100) to afford the title compound. HPLC (Method G) Rt=1.048 min; MS (Method F) [M+H]$^+$=199.2 c) tert-butyl (4,6-dimethyl-5-((1-((2-methylquinolin-6-yl)methyl)-1H-1,2,3-triazole-4-carboxamido)methyl)pyridin-2-yl)carbamate To a solution of 6-(azidomethyl)-2-methylquinoline (58.9 mg, 0.297 mmol) and tert-butyl (4,6-dimethyl-5-(propiolamidomethyl)pyridin-2-yl)carbamate (90 mg, 0.297 mmol) in t-BuOH (2 ml)/water (2 ml) were added copper(II) sulfate pentahydrate (14.84 mg, 0.059 mmol) and sodium ascorbate (58.9 mg, 0.297 mmol). Reaction mixture was stirred for 1.5 h at 23° C. Reaction mixture was poured into water and extracted twice with ethyl acetate. Combined organic layers were washed with brine, dried over sodium sulfate and evaporated to afford the crude material, which was purified by silicagel chromatography (DCM/methanol from 10/0 to 9/1) to afford the title compound. HPLC (Method G) Rt=1.308 min; MS (Method F) [M+H]$^+$=502.5 d) N-((6-amino-2,4-dimethylpyridin-3-yl)methyl)-1-((2-methylquinolin-6-yl)methyl)-1H-1,2,3-triazole-4-carboxamide To a solution of tert-butyl (4,6-dimethyl-5-((1-((2-methylquinolin-6-yl)methyl)-1H-1,2,3-triazole-4-carboxamido)methyl)pyridin-2-yl)carbamate (131.9 mg, 0.263 mmol) in DCM (1.2 ml) was added TFA (0.405 ml, 5.26 mmol). Reaction mixture was stirred overnight at 23° C. Reaction mixture was evaporated to afford the crude material, which was purified by preparative HPLC (Sunfire C18-ODB, 5 μm, 100×30 mm, elution with A=water+0.1% TFA and B=ACN+0.1% TFA, gradient from 5% to 100% B in 25 min, flow: 40 mL/min). Fractions were combined and acetonitrile was evaporated. Residual aqueous layer was frozen and lyophilized to afford the product as a TFA salt, which was dissolved in acetonitrile/methanol and eluted through a PL-HCO$_3$ MP-resin column (Stratosphere SPE). The eluted solution was evaporated, and the residue was triturated in Et$_2$O and filtered to afford the title compound as a free base. 1H-NMR (DMSO-d6, 400 MHz) δ 8.70 (s, 1H), 8.62 (broad s, 1H), 8.24 (d, 1H), 7.91 (d, 1H), 7.86 (s, 1H), 7.66 (d, 1H), 7.43 (d, 1H), 6.37 (broad s, 1H), 5.82 (s, 2H), 4.33 (d, 2H), 2.64 (s, 3H), 2.42 (s, 3H), 2.29 (s, 3H); HPLC (Method G) Rt=0.932 min; MS (Method F) [M+H]$^+$=402.5.

Example 154

N-((6-amino-2,4-dimethylpyridin-3-yl)methyl)-1-((2-methylquinolin-6-yl)methyl)-1H-pyrazole-4-carboxamide

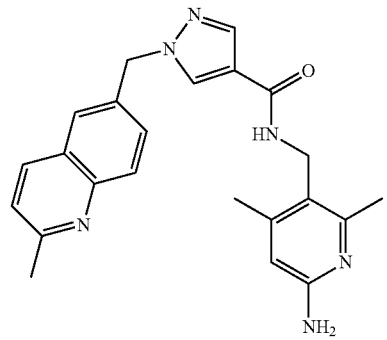 [SMILES: Cc1ccc2cc(Cn3cc(C(=O)NCc4c(C)cc(N)nc4C)cn3)ccc2n1]

The title compound was prepared in analogy to example 13. HPLC (Method G) Rt=0.909 min, MS (Method F) [M+H]$^+$=401.5.

Example 155

N-((6-amino-2,4-dimethylpyridin-3-yl)methyl)-1-(quinolin-3-ylmethyl)-1H-pyrazole-4-carboxamide

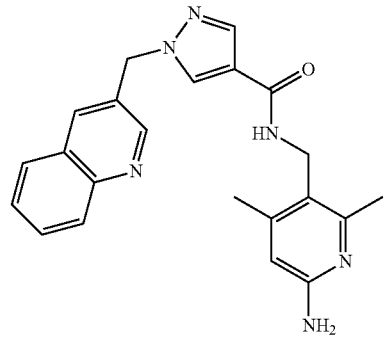 [SMILES: Cc1cc(N)nc(C)c1CNC(=O)c1cnn(Cc2cnc3ccccc3c2)c1]

The title compound was prepared in analogy to example 13. HPLC (Method G) Rt=1.020 min, MS (Method F) [M+H]$^+$=387.2.

Example 156

N-((6-amino-2,4-dimethylpyridin-3-yl)methyl)-1-((7-methylquinolin-3-yl)methyl)-1H-1,2,3-triazole-4-carboxamide

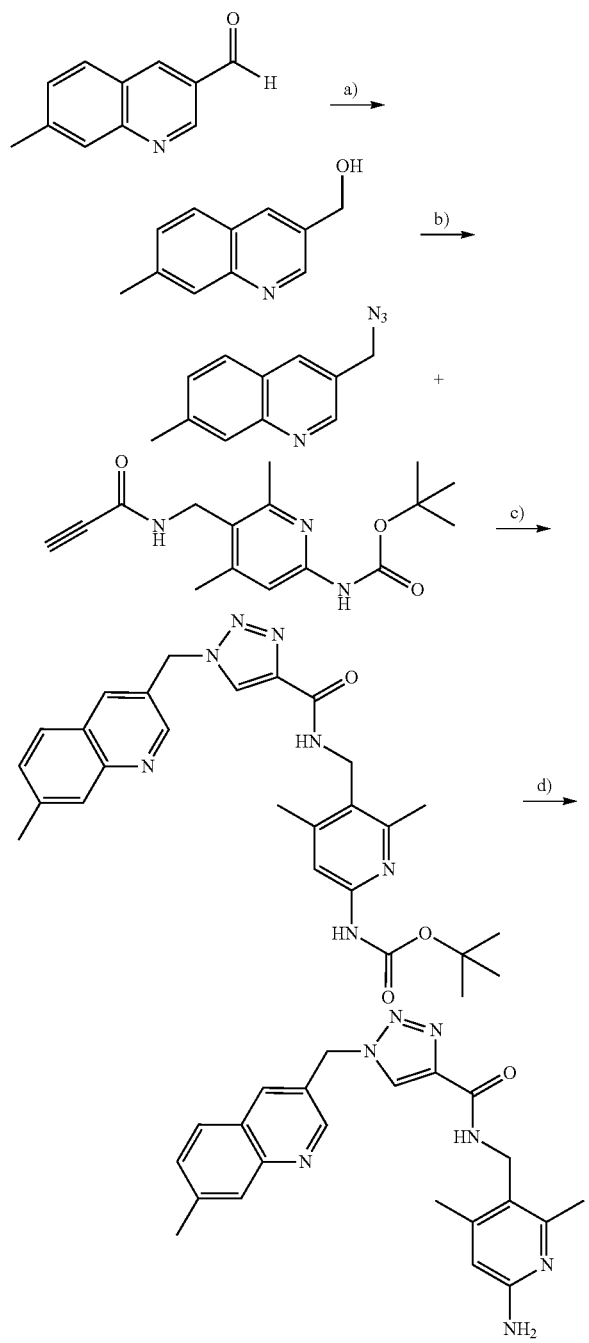

a) (7-methylquinolin-3-yl)methanol

To a solution of 7-methyl-3-quinoline carboxaldehyde (200 mg, 1.168 mmol) in THF (4.5 ml) was added 2M LiBH$_4$ solution in THF (2.337 ml, 4.67 mmol) at 0° C. Reaction mixture was stirred at 0° C. for 2 h, then slowly poured into NaHCO$_3$ sat. solution and extracted twice with ethyl acetate. Organic layer was dried over sodium sulfate, filtered and evaporated to afford the crude material, which was purified by silica gel chromatography (cyclohexane/ethyl acetate form 100/0 to 0/100) to afford the title compound. HPLC (Method G) Rt=0.68 min, MS (Method V) [M+H]$^+$=174.2.

b) 3-(azidomethyl)-7-methylquinoline

To a solution of (7-methylquinolin-3-yl)methanol 41.5 mg, 0.232 mmol) and DBU (0.063 ml, 0.418 mmol) in DMF (0.8 ml) was added DPPA (0.085 ml, 0.395 mmol). The reaction mixture was stirred for 1.5 h at 23° C. Reaction mixture was poured in brine and extracted twice with ethyl acetate. Organic layer was dried over sodium sulfate, filtered and evaporated to afford the title compound. HPLC (Method G) Rt=1.174 min, MS (Method V) [M+H]$^+$=199.2.

c) tert-butyl (4,6-dimethyl-5-((1-((7-methylquinolin-3-yl)methyl)-1H-1,2,3-triazole-4-carboxamido)methyl)pyridin-2-yl)carbamate To a solution of 3-(azidomethyl)-7-methylquinoline (46.0 mg, 0.232 mmol) and tert-butyl (4,6-dimethyl-5-(propionamidomethyl)pyridin-2-yl)carbamate (70 mg, 0.231 mmol) in t-BuOH (1.8 ml)/water (1.8 ml) were added copper(II) sulfate pentahydrate (11.52 mg, 0.046 mmol) and sodium ascorbate (45.7 mg, 0.231 mmol). Reaction mixture was stirred overnight at 23° C. Reaction mixture was poured into water and extracted twice with ethyl acetate. Combined organic layers were washed with brine, dried over sodium sulfate and evaporated to afford a crude product, which was purified by silica gel chromatography (cyclohexane/ethyl acetate from 100/0 to 0/100) to afford the title compound. HPLC (Method G) Rt=1.408 min, MS (Method V) [M+H]$^+$=502.4.

d) N-((6-amino-2,4-dimethylpyridin-3-yl)methyl)-1-((7-methylquinolin-3-yl)methyl)-1H-1,2,3-triazole-4-carboxamide To a solution of tert-butyl (4,6-dimethyl-5-((1-((7-methylquinolin-3-yl)methyl)-1H-1,2,3-triazole-4-carboxamido)methyl)pyridin-2-yl)carbamate (70 mg, 0.140 mmol) in DCM (1 ml) was added TFA (0.215 ml, 2.79 mmol). Reaction mixture was stirred over a weekend at 23° C. Reaction mixture was evaporated to afford a crude product, which was purified by preparative HPLC (Sunfire C18-ODB, 5 μm, 100× 30 mm, elution with A=water+0.1% HCOOH and B=ACN+ 0.1% HCOOH, gradient from 10% to 100% B in 25 min, flow: 40 mL/min). Fractions were combined and solvents were evaporated to afford athe product as a formic acid salt, which was dissolved in methanol and eluted through a PL-HCO$_3$ MP-resin column (Stratosphere SPE) in order to remove salt. The eluted solution was evaporated and dried overnight under high vacuum (dessicator, 50° C.) to afford the title compound as a free base. 1H-NMR (DMSO-d6, 400 MHz) δ 8.90 (s, 1H), 8.72 (s, 1H), 8.30 (broad s, 1H), 8.26 (s, 1H), 7.89 (d, 1H), 7.83 (s, 1H), 7.49 (d, 1H), 6.10 (s, 1H), 5.87 (s, 2H), 5.61

(broad s, 2H), 4.33 (d, 2H), 2.54 (s, 3H), 2.31 (s, 3H), 2.18 (s, 3H); HPLC (Method G) Rt=1.079 min; MS (Method V) [M+H]⁺=402.4.

Example 157

N-((6-amino-2,4-dimethylpyridin-3-yl)methyl)-1-((7-chloroquinolin-2-yl)methyl)-1H-pyrazole-4-carboxamide

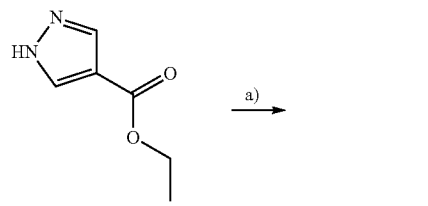

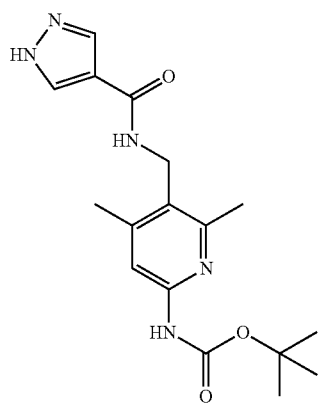

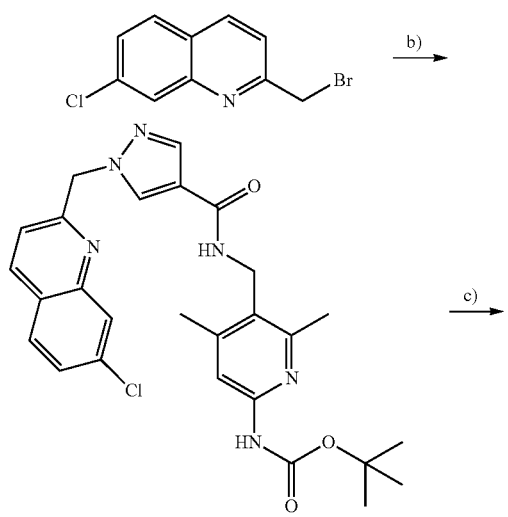

-continued

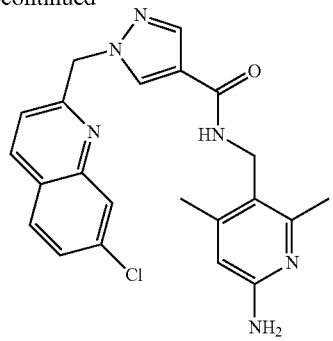

a) tert-butyl (5-((1H-pyrazole-4-carboxamido)methyl)-4,6-dimethylpyridin-2-yl)carbamate To a solution of ethyl pyrazole-4-carboxylate (1 g, 7.14 mmol) in EtOH/THF/water 2/1/1 (8 ml) was added LiOH monohydrate (329 mg, 7.84 mmol). Reaction mixture was stirred for 1 day at 80° C. 4M HCl in dioxane (1.962 ml, 7.85 mmol) was added to reaction mixture which was evaporated to dryness to afford the free carboxylic acid. This material (1.218 g, 7.14 mmol) was dissolved in DMF (30 ml), to which were added HBTU (4.06 g, 10.71 mmol), DIPEA (3.74 ml, 21.43 mmol) then tert-butyl (5-(aminomethyl)-4,6-dimethylpyridin-2-yl)carbamate (2.69 g, 10.71 mmol). Reaction mixture was stirred overnight at 23° C. Reaction mixture was diluted with ethyl acetate and water. Phases were separated and organic layer was washed with NaHCO₃ sat. solution and brine. Organic layer was dried over sodium sulfate, filtered and evaporated to afford the crude material, which was purified by normal phase chromatography (silica gel, 100% ethyl acetate) followed by reverse phase chromatography (C18, acetonitrile/water) to afford the title compound. HPLC (Method G) Rt=1.245 min, MS (Method V) [M+H]⁺=346.2.

b) tert-butyl (5-((1-((7-chloroquinolin-2-yl)methyl)-1H-pyrazole-4-carboxamido)methyl)-4,6-dimethylpyridin-2-yl)carbamate To a solution of tert-butyl (5-((1H-pyrazole-4-carboxamido)methyl)-4,6-dimethylpyridin-2-yl)carbamate (100 mg, 0.290 mmol) in acetone (2.5 ml) were added 2-(bromomethyl)-7-chloroquinoline (74.3 mg, 0.290 mmol) and K₂CO₃ (200 mg, 1.448 mmol). Reaction mixture was stirred for 5 h at 50° C. Reaction mixture was diluted with ethyl acetate and water. Phases were separated and organic layer was washed with brine, dried over sodium sulfate, filtered and evaporated to afford the title compound. HPLC (Method G) Rt=1.736 min, MS (Method V) [M+H]⁺=521.3.

c) N-((6-amino-2,4-dimethylpyridin-3-yl)methyl)-1-((7-chloroquinolin-2-yl)methyl)-1H-pyrazole-4-carboxamide To a solution of tert-butyl (5-((1-((7-chloroquinolin-2-yl)methyl)-1H-pyrazole-4-carboxamido)methyl)-4,6-dimethylpyridin-2-yl)carbamate (151 mg, 0.29 mmol) in DCM (2 ml) was added TFA (0.447 ml, 5.80 mmol). Reaction mixture was stirred for 7.5 h at 23° C. After evaporation of solvents, the crude material was purified by preparative HPLC (SunFire C18-ODB, 5 µm, 100×30 mm, elution with A=water+ 0.1% TFA and B=ACN+0.1% TFA, gradient from 5% to 100% B in 25 min, flow: 40 mL/min). Fractions were combined, and the solvents were evaporated to afford the title cpd as a TFA salt, which was dissolved in hot methanol/ACN and eluted through a PL-HCO$_3$ MP-resin column (Stratosphere SPE) in order to remove salt. The eluted solution was evaporated, and the residue was dried over a weekend under high vacuum (dessicator, 50° C.) to afford the title compound as a free base. 1H-NMR (DMSO-d6, 400 MHz) δ 8.40 (d, 1H), 8.38 (s, 1H), 8.03 (s, 1H), 8.02 (d, 1H), 7.94 (broad s, 2H), 7.65 (d, 1H), 7.24 (d, 1H), 6.11 (s, 1H), 5.63 (s, 2H), 5.61 (broad s, 2H), 4.28 (d, 2H), 2.29 (s, 3H), 2.16 (s, 3H); HPLC (Method G) Rt=1.476 min, MS (Method V) [M+H]$^+$=422.3.

Example 158

N-((6-amino-2,4-dimethylpyridin-3-yl)methyl)-1-((7-chloroquinolin-2-yl)methyl)-1H-1,2,3-triazole-4-carboxamide

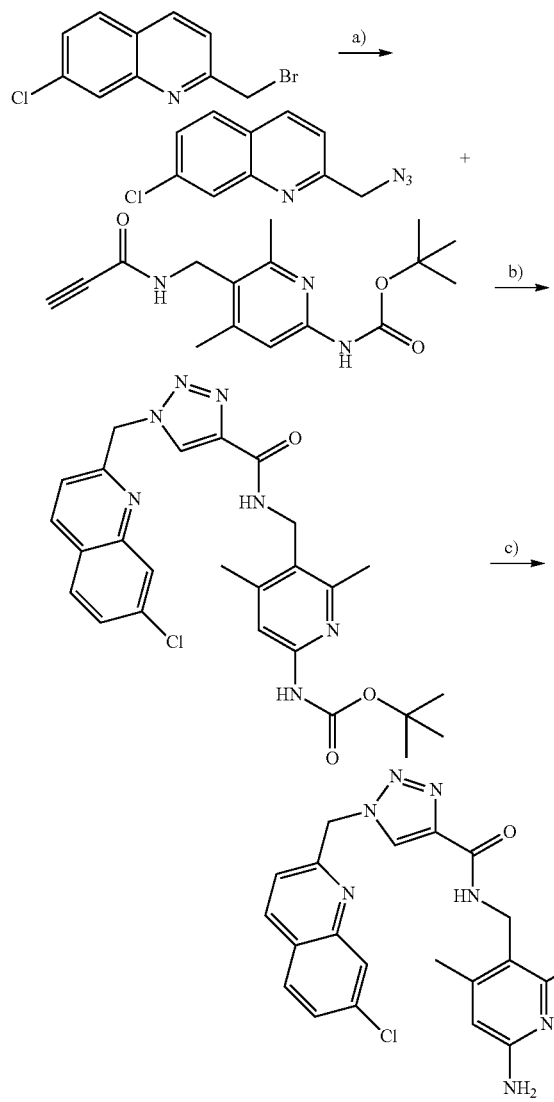

a) 2-(azidomethyl)-7-chloroquinoline

To a solution of 2-(bromomethyl)-7-chloroquinoline (50 mg, 0.195 mmol) in DMF (0.5 ml) was added sodium azide (19.01 mg, 0.292 mmol). Reaction mixture was stirred for 2 h at 90° C. Reaction mixture was diluted with ethyl acetate/water. Layers were separated and organic layer was washed twice with water and with brine, dried over sodium sulfate, filtered and evaporated to afford the title compound. HPLC (Method G) Rt=1.990 min, MS (Method V) [M+H]$^+$=219.1.

b) tert-butyl (5-((1-((7-chloroquinolin-2-yl)methyl)-1H-1,2,3-triazole-4-carboxamido)methyl)-4,6-dimethylpyridin-2-yl)carbamate To a solution of 2-(azidomethyl)-7-chloroquinoline (37.1 mg, 0.134 mmol) and tert-butyl (4,6-dimethyl-5-(propiolamidomethyl)pyridin-2-yl)carbamate (40.7 mg, 0.134 mmol) in t-BuOH (1 ml)/water (1 ml) were added copper(II) sulfate pentahydrate (33.5 mg, 0.134 mmol) and sodium ascorbate (26.6 mg, 0.134 mmol). Reaction mixture was stirred for 3 days at 23° C.

Reaction mixture was poured into water and extracted twice with ethyl acetate. Combined organic layers were washed with brine, dried over sodium sulfate and evaporated to afford a crude product, which was purified by silica gel chromatography (cyclohexane/ethyl acetate from 100/0 to 0/100) to afford the title compound. HPLC (Method G) Rt=1.778 min, MS (Method V) [M+H]$^+$=522.2.

c) N-((6-amino-2,4-dimethylpyridin-3-yl)methyl)-1-((7-chloroquinolin-2-yl)methyl)-1H-1,2,3-triazole-4-carboxamide To a solution of tert-butyl (5-((1-((7-chloroquinolin-2-yl)methyl)-1H-1,2,3-triazole-4-carboxamido)methyl)-4,6-dimethylpyridin-2-yl)carbamate (46.7 mg, 0.089 mmol) in DCM (0.6 ml) was added TFA (0.138 ml, 1.789 mmol). Reaction mixture was stirred overnight at 23° C.

Reaction mixture was evaporated to afford a crude product, which was purified by preparative HPLC (Sunfire C18-ODB, 5 μm, 100×30 mm, elution with A=water+0.1% TFA and B=ACN+0.1% TFA, gradient from 5% to 100% B in 25 min, flow: 40 mL/min). Fractions were combined and solvents were evaporated to afford the product as a TFA salt, which was dissolved in hot methanol/ACN and eluted through a PL-HCO$_3$ MP-resin column (Stratosphere SPE) in order to remove salt. The eluted solution was evaporated and dried overnight under high vacuum (dessicator, 50° C.) to afford the title compound as a free base. 1H-NMR (DMSO-d6, 400 MHz) δ 8.70 (s, 1H), 8.46 (d, 1H), 8.34 (broad s, 1H), 8.05 (d, 1H), 8.00 (s, 1H), 7.66 (d, 1H), 7.45 (d, 1H), 6.10 (s, 1H), 5.98 (s, 2H), 5.62 (broad s, 2H), 4.34 (d, 2H), 2.32 (s, 3H), 2.19 (s, 3H); HPLC (Method G) Rt=1.519 min, MS (Method V) [M+H]$^+$=422.2.

Example 159

N-((6-amino-2-methylpyridin-3-yl)methyl)-1-((2-methylquinolin-6-yl)methyl)-1H-pyrazole-4-carboxamide

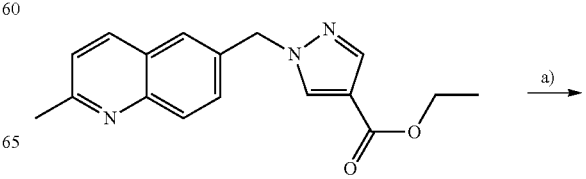

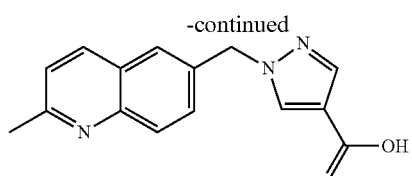

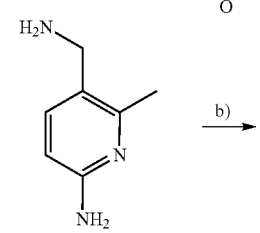

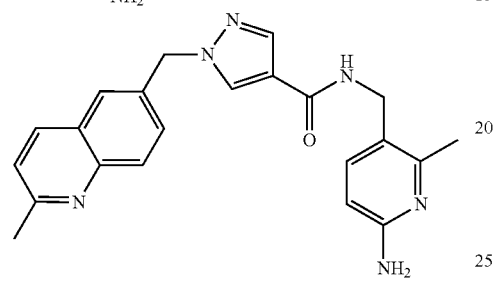

a) 1-((2-methylquinolin-6-yl)methyl)-1H-pyrazole-4-carboxylic acid

The starting material ethyl 1-((2-methylquinolin-6-yl)methyl)-1H-pyrazole-4-carboxylate was prepared in analogy to Example 9, Step c). To a solution of ethyl 1-((2-methylquinolin-6-yl)methyl)-1H-pyrazole-4-carboxylate (2.067 g, 3.5 mmol) in ethanol (10 ml) was added 6M NaOH aqueous solution (0.700 ml, 4.20 mmol). The yellow solution was shaken at 23° C. for 4 days, after which additional 6M NaOH aqueous solution (0.700 ml, 4.20 mmol) was added, and stirring continued at gentle reflux (80° C.) for 24 h. After evaporation of ethanol, water was added, and the mixture was washed with EA to remove impurities. Aqueous phase was neutralized by addition of 1M HCl aq. then concentrated in vacuo to give the crude material, which was suspended in methanol, treated in ultrasonic bath, then filtered, washed with methanol. The filtrate was evaporated to give the title compound, containing some NaCl. UPLC (Method V) Rt=0.36 min, MS (Method V) [M+H]$^+$=268.2.

b) N-((6-amino-2-methylpyridin-3-yl)methyl)-1-((2-methylquinolin-6-yl)methyl)-1H-pyrazole-4-carboxamide To a suspension of 1-((2-methylquinolin-6-yl)methyl)-1H-pyrazole-4-carboxylic acid (incl. NaCl) (100 mg, 0.337 mmol), EDC.HCl (84 mg, 0.438 mmol) and HOAt (59.6 mg, 0.438 mmol) in DMF (1 ml) was added N-methylmorpholine (0.185 ml, 1.684 mmol). The reaction mixture was stirred for 1 h at 50° C., then 5-(aminomethyl)-6-methylpyridin-2-amine (70.7 mg, 0.337 mmol) was added. Stirring continued at 50° C. for 18 h. Reaction mixture was diluted with methanol, then applied onto a PL-SO$_3$H cartridge (500 mg/6 ml by VARIAN) to catch the desired amine product, washed the cartridge with DMF, DCM and MeOH to remove all impurities, then the product was released from the cartridge by washing with 2M NH$_3$ in MeOH. The basic filtrate was evaporated to give the crude material, which was treated with 0.2 ml of MeOH and 1 ml of ACN in ultrasonic bath. The precipitate formed was filtered, washed with 1 ml of ACN and dried under high vacuum for 4 days to yield the title compound. HPLC (Method J) Rt=2.373 min, MS (Method V) [M+H]$^+$=387.1.

Example 160

N-((6-amino-2-methylpyridin-3-yl)methyl)-1-((6-fluoro-4-(trifluoromethyl)quinolin-2-yl)methyl)-1H-pyrazole-4-carboxamide

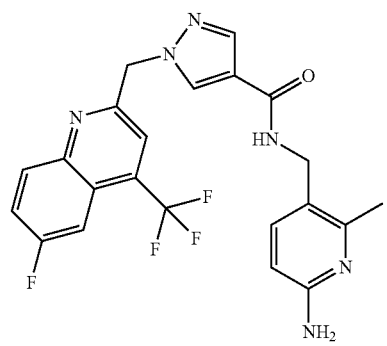 [SMILES: Cc1nc(N)ccc1CNC(=O)c1cnn(Cc2cc(C(F)(F)F)c3cc(F)ccc3n2)c1]

The Boc protected precursor of the title compound was prepared in analogy to Example 159 Step b) from the corresponding carboxylic acid and a known amine tert-butyl (5-(aminomethyl)-6-methylpyridin-2-yl)carbamate (prepared according to P. E. J. Sanderson et. al, *Journal of Medicinal Chemistry* 1998, 41, 4466). The Boc group of the coupling product fell off spontaneously after purification by reverse-phase preparative HPLC to afford the title compound. HPLC (Method J) Rt=3.302 min, MS (Method V) [M+H]$^+$=459.2.

Example 161

N-((6-amino-2-methylpyridin-3-yl)methyl)-1-((2,5,7-trimethylquinolin-3-yl)methyl)-1H-pyrazole-4-carboxamide

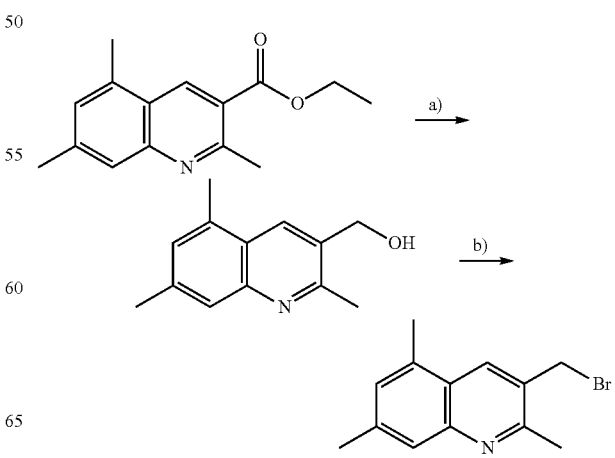

-continued

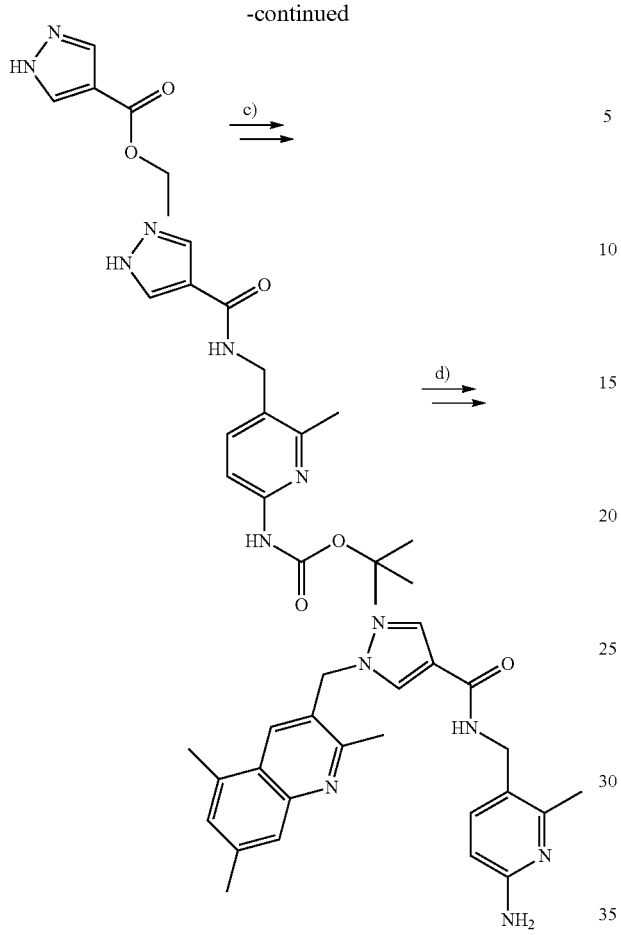

a) (2,5,7-trimethylquinolin-3-yl)methanol

To a solution of 2,5,7-trimethylquinoline-3-carboxylic acid ethyl ester (50 mg, 0.206 mmol) in DCM (1.7 ml) at −78° C. was added DIBAl-H 1M in Toluene (29.2 mg, 0.206 mmol). Reaction mixture was stirred 1 h at −78° C. Methanol (1 ml) was added to quench the reaction at −78° C. Mixture was then warmed up to 23° C. Sat. potassium/sodium tartrate solution (Rochelle's salt, 2 ml) was added and mixture was stirred 30 min at RT. Solid was filtered off and filtrate was extracted twice with DCM. Combined organic layer was washed with sat. NaHCO₃ solution, brine, dried over sodium sulfate, filtered and evaporated to afford the title compound. HPLC (Method G) Rt=1.113 min, MS (Method V) [M+H]⁺=202.1 b) 3-(bromomethyl)-2,5,7-trimethylquinoline

To a solution of (2,5,7-trimethylquinolin-3-yl)methanol (42.1 mg, 0.205 mmol) in DCM (1.5 ml) was added PBr₃ (0.039 ml, 0.410 mmol). Reaction mixture was stirred overnight at 23° C. Reaction mixture was diluted with ethyl acetate/NaHCO₃ sat. aq solution. Layers were separated and aqueous layer was extracted once more with ethyl acetate. Organic layer was dried over sodium sulfate, filtered and evaporated to afford the title compound. HPLC (Method G) Rt=1.409 min, MS (Method V) [M+H]⁺=264.2, 266.2.

c) tert-butyl (5-((1H-pyrazole-4-carboxamido)methyl)-4,6-dimethylpyridin-2-yl)carbamate The starting material ethyl pyrazole-4-carboxylate was saponified in analogy to Example 157, Step a), To a solution of the free acid (1 g, 5.86 mmol) in DMF (40 ml) were added DIPEA (4.10 ml, 23.46 mmol) and tert-butyl (5-(aminomethyl)-6-methylpyridin-2-yl)carbamate (1.531 g, 6.45 mmol). At 0° C., propylphosphonic anhydride (50% in DMF, 3.42 ml, 5.86 mmol) was added dropwise. Reaction mixture was stirred for 30 min at 0° C., then diluted with ethyl acetate and water. Phases were separated and organic layer was washed with NaHCO₃ sat. solution and brine. Organic layer was dried over sodium sulfate, filtered and evaporated to afford the crude material, which was purified by silicagel chromatography (DCM/MeOH from 100/0 to 9/1 in 30 min) to afford the title compound. HPLC (Method G) Rt=1.209 min, MS (Method V) [M+H]⁺=332.3.

d) N-((6-amino-2-methylpyridin-3-yl)methyl)-1-((2,5,7-trimethylquinolin-3-yl)methyl)-1H-pyrazole-4-carboxamide The subsequent steps of synthesis were done in analogy to Example 157, Steps b) and c) to afford the title compound. HPLC (Method G) Rt=1.128 min, MS (Method V) [M+H]⁺=415.4.

Example 162

N-((6-amino-2,4-dimethylpyridin-3-yl)methyl)-1-((6-fluoro-4-(trifluoromethyl)quinolin-2-yl)methyl)-1H-pyrazole-4-carboxamide

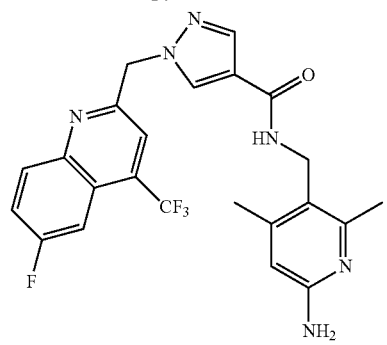 [SMILES: Cc1cc(N)nc(C)c1CNC(=O)c1cnn(Cc2cc(C(F)(F)F)c3cc(F)ccc3n2)c1]

The title compound was prepared in analogy to Example 13. HPLC (Method G) Rt=1.680 min, MS (Method V) [M+H]⁺=473.1.

Example 163

N-((6-amino-2,4-dimethylpyridin-3-yl)methyl)-1-((6-methoxynaphthalen-2-yl)methyl)-1H-pyrazole-4-carboxamide

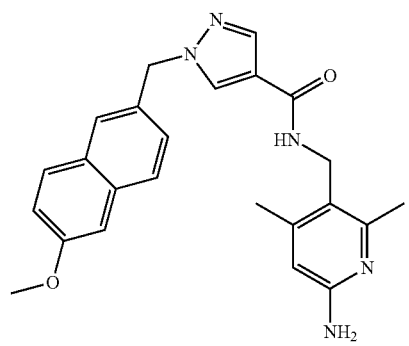

The title compound was prepared in analogy to Example 13. HPLC (Method G) Rt=1.561 min, MS (Method V) [M+H]⁺=461.2.

Example 164

N-((6-Amino-2,4-dimethylpyridin-3-yl)cyclopropyl)-1-((2-methylquinolin-6-yl)methyl)-1H-1,2,3-triazole-4-carboxamide

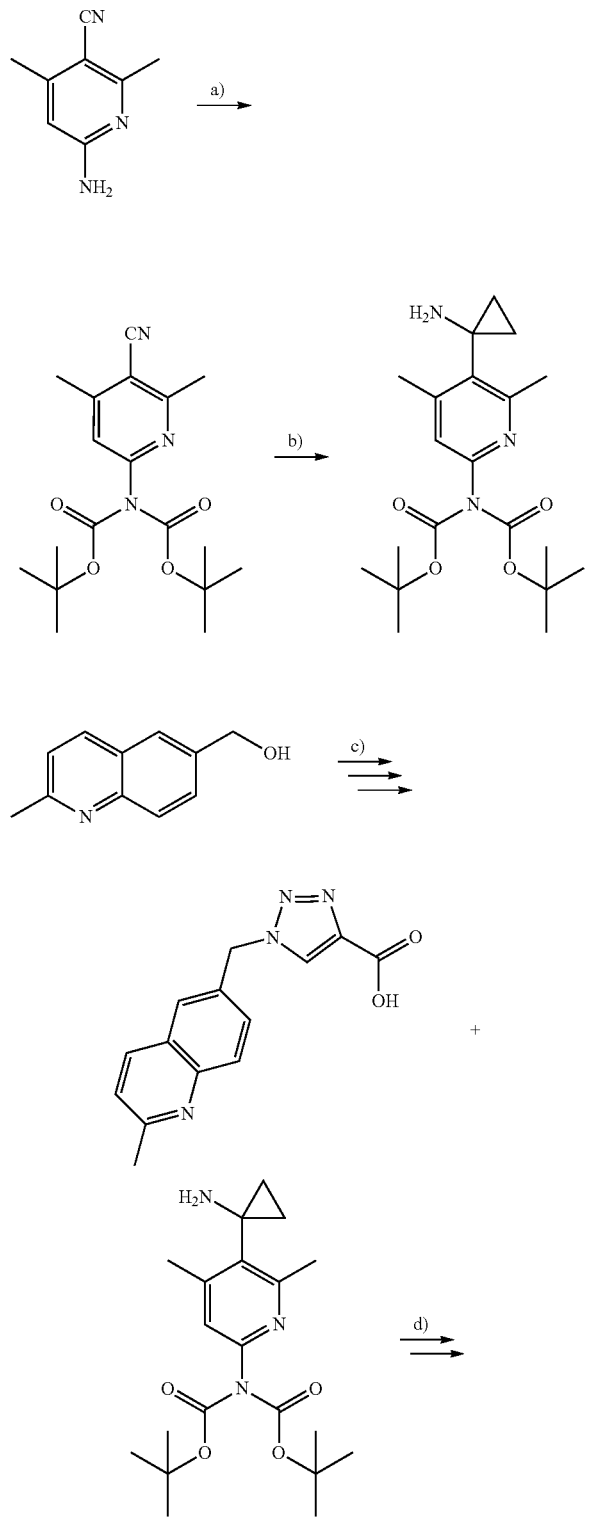

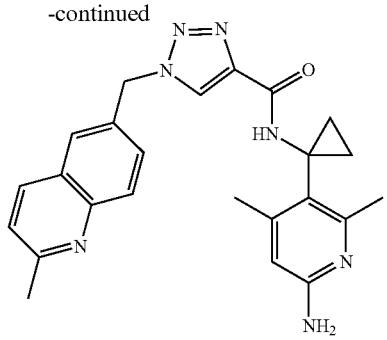

a) Bis-BOC-protected 6-amino-2,4-dimethylnicotinonitrile

To a brown suspension of 6-amino-2,4-dimethylnicotinonitrile (10 g, 67.9 mmol) and DMAP (0.830 g, 6.79 mmol) in THF (200 ml) was added (BOC)2O (31.6 ml, 136 mmol) and the mixture was stirred at 23° C. for 6 hr. The dark-brown solution was concentrated under reduced pressure, Purification by flash-chromatography (Silica gel, cyclohexane/EA=9:1) afforded the title compound. HPLC-MS (method F) Rt 1.36 min. $[M+H]^+=348.2$ b) Bis-tert-butyl 5-(1-aminocyclopropyl)-4,6-dimethylpyridin-2-ylcarbamate

To a solution of Bis-BOC-protected 6-amino-2,4-dimethylnicotinonitrile (3 g, 8.64 mmol) and Ti(Oi-Pr)4 (2.78 ml, 9.50 mmol) in diethylether (100 ml) EtMgBr (1M in diethylether, 19.86 ml, 19.86 mmol) was added slowly at −70° C. After 10 min at −70° C. the solution was warmed to 23° C., followed by adding of BF3.OEt2 (2.19 ml, 17.27 mmol). The mixture was stirred for 1 h, 1N HCl and diethylether were added. 4 N NaOH was added and the mixture was extracted with Et OAc. The organic layer was dried over MgSO4, filtered and concentrated under vacuum. The crude product was splitted off into 6 parts and purified by prep. HPLC. The fractions were collected, made alkaline with NaHCO3 and extracted with EA to afford a mixture of the title compound and tert-butyl 5-(1-aminocyclopropyl)-4,6-dimethylpyridin-2-ylcarbamate.

c) 1-((2-Methylquinolin-6-yl)methyl)-1H-1,2,3-triazole-4-carboxylic acid

The title compound was prepared in analogy to Example 153, Step b) and Example 10, Steps b) and c). MS (Method V) $[M+H]^+=269.0$ d) N-((6-Amino-2,4-dimethylpyridin-3-yl)cyclopropyl)-1-((2-methylquinolin-6-yl)methyl)-1H-1,2,3-triazole-4-carboxamide The title compound was prepared in analogy to Example 9, Steps e) and f). HPLC (Method H) Rt=2.42 min, MS (Method V) $[M+H]^+=428.2$.

Example 165

N-((6-Amino-2,4-dimethylpyridin-3-yl)methyl)-1-((1,2-dimethyl-1H-benzo[d]imidazol-5-yl)methyl)-1H-pyrazole-4-carboxamide

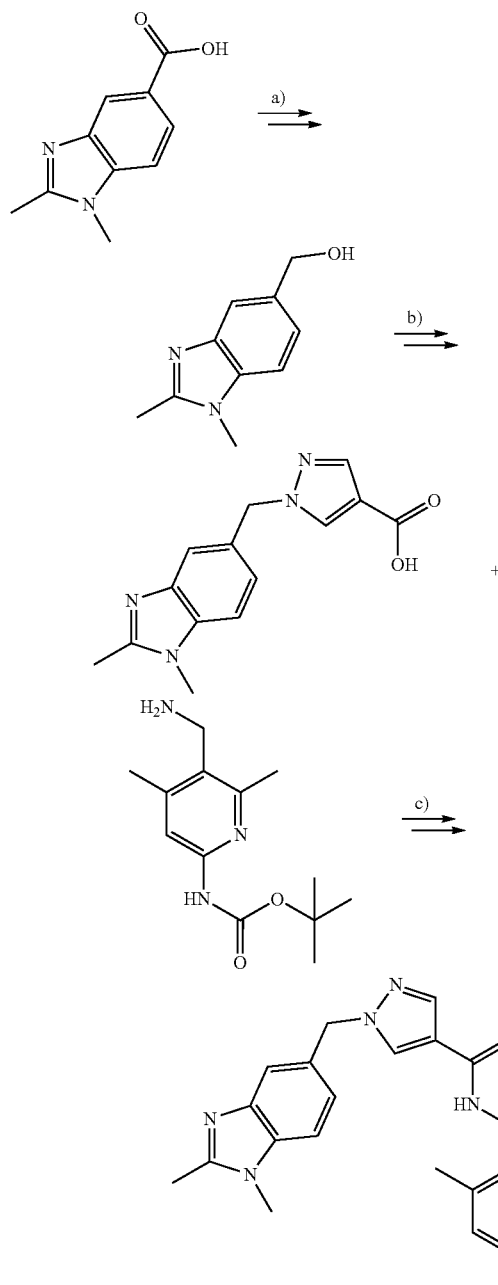

a) (1,2-Dimethyl-1H-benzo[d]imidazol-5-yl)methanol

To a suspension of 1,2-Dimethyl-1H-benzo[d]imidazole-5-carboxylic acid (crude, 2.54 g, approx. 9.35 mmol) in MeOH (15.5 ml)/toluene (78 ml) Trimethylsilyldiazomethane (2 M solution in hexane, 7.0 ml, 14 mmol) was added at 0-10° C. The reaction mixture was stirred at it for 1 hour. The reaction mixture was evaporated under reduced pressure. The residue was taken up in DCM, Remaining insoluble solid was filtered off. The filtrate was evaporated again to dryness to afford crude Methyl 1,2-dimethyl-1H-benzo[d]imidazole-5-carboxylate To a solution of Methyl 1,2-dimethyl-1H-benzo[d]imidazole-5-carboxylate (500 mg, 2.448 mmol) in THF (24.5 ml) Lithiumaluminium hydride (1 M in THF, 2.44 ml) was added at 0° C. After 2 hours sodium sulfate decahydrate and citric acid was added to the reaction to destroy the excess of lithiumaluminiumhydride. After 1 hour, methanol (25 ml) was added and the fine suspension was filtered off. The filtrate was evaporated under reduced pressure to afford a brown solid. EA (50 ml) was added and the suspension was treated in an ultra sonic bath. The solid was filtered off and this procedure was repeated twice. The yellow filtrate was evaporated under reduced pressure to afford crude (1,2-Dimethyl-1H-benzo[d]imidazol-5-yl)methanol.

b). 1-((1,2-Dimethyl-1H-benzo[d]imidazol-5-yl)methyl)-1H-pyrazole-4-carboxylic acid The title compound was prepared in analogy to Example 9, Steps c) and d). MS (Method V) [M+H]$^+$=271.0.

c) N-((6-amino-2,4-dimethylpyridin-3-yl)methyl)-1-((1,2-dimethyl-1H-benzo[d]imidazol-5-yl)-methyl)-1H-pyrazole-4-carboxamide The title compound was prepared in analogy to Example 20, Step c), and Example 9, Step f). HPLC (Method H) Rt=3.329 min, MS (Method V) [M+H]$^+$=404.1.

Example 166

N-((6-amino-2,4-dimethylpyridin-3-yl)methyl)-1-((1,2,3-trimethyl-1H-indol-5-yl)methyl)-1H-1,2,3-triazole-4-carboxamide

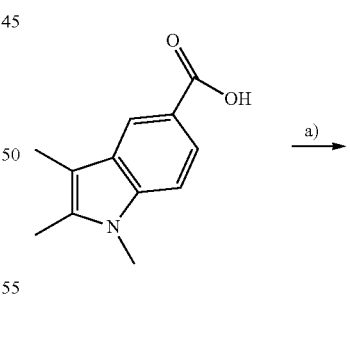

a)

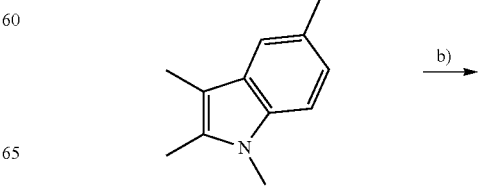

b)

-continued

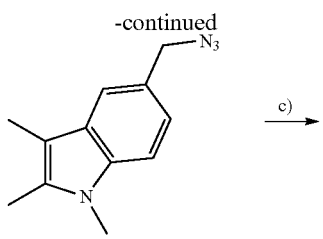

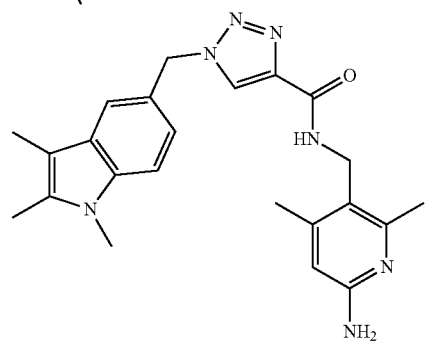

a) (1,2,3-Trimethyl-1H-indol-5-yl)methanol

The title compound was prepared in analogy to Example 165a). HPLC (Method G) Rt=1.795 min, MS (Method V) [M+H]⁺=190.2.

b) 5-(Azidomethyl)-1,2,3-trimethyl-1H-indole

The title compound was prepared in analogy to Example 153b). HPLC (Method G) Rt=2.43 min, MS (Method V) [M+H]⁺=213.0.

c) N-((6-Amino-2,4-dimethylpyridin-3-yl)methyl)-1-((1,2,3-trimethyl-1H-indol-5-yl)methyl)-1H-1,2,3-triazole-4-carboxamide The title compound was prepared in analogy to Example 153c) and 153d). HPLC (Method G) Rt=1.736 min, MS (Method V) [M+H]⁺=418.3.

Example 167

N-((6-Amino-4-chloro-2-methylpyridin-3-yl)methyl)-1-(4-((2-oxopyridin-1(2H)-yl)methyl)benzyl)-1H-pyrazole-4-carboxamide The title compound was prepared in analogy to example 17. HPLC (Method G) Rt=1.244 min, MS (Method V) [M+H]⁺=463.2.

Example 168

N-((6-Amino-2,4-dimethylpyridin-3-yl)methyl)-1-((1,2-dimethyl-1H-indol-5-yl)methyl)-1H-pyrazole-4-carboxamide

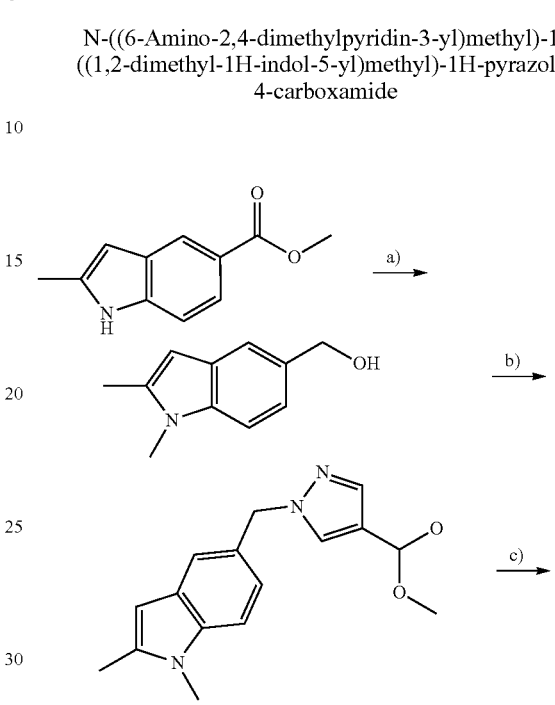

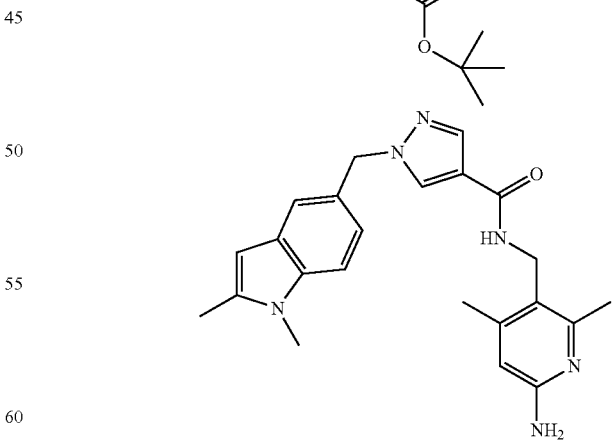

a) Methyl 1,2-dimethyl-1H-indole-5-carboxylate

To a solution of Methyl 2-methyl-1H-indole-5-carboxylate (1000 mg, 5.29 mmol) in THF (53 ml) KOtBu (723 mg, 6.44 mmol) was added and subsequently Iodomethane (1.05 ml, 16.81 mmol) was added at rt. The reaction mixture was stirred at it for 40 hours. The orange reaction mixture was quenched with water/brine and extracted twice with EA. The combined organic layers were washed with brine, dried over Na$_2$SO$_4$, filtered and concentrated under vacuum to afford crude methyl 1,2-Dimethyl-1H-indole-5-carboxylate.

To a solution of methyl 1,2-Dimethyl-1H-indole-5-carboxylate (crude, 1.14 mg, 5.31 mmol) in THF (54 ml) Lithiumaluminium hydride (1 M in THF, 5.31 ml) was added at 0° C. The reaction mixture was stirred at rt for 2 hours. Sodium sulfate decahydrate was added to the reaction mixture to destroy the excess of Lithiumaluminium hydride. After 1 hour, methanol was added and the fine suspension was filtered off. The filtrate was concentrated under vacuum to afford crude (1,2-Dimethyl-1H-indol-5-yl)methanol. MS (Method V) [M+H]$^+$=176.3.

b) Ethyl 1-((1,2-dimethyl-1H-indol-5-yl)methyl)-1H-pyrazole-4-carboxylate

To a solution of (1,2-Dimethyl-1H-indol-5-yl)methanol (crude, 250 mg, 76%, 1.084 mmol), Ethyl 1H-pyrazole-4-carboxylate (266 mg, 1.898 mmol) and Triphenylphosphine (341 mg, 1.3 mmol) in toluene (10.5 ml) Diethyl azodicarboxylate (206 ul, 1.3 mmol) was added at rt. The reaction mixture was stirred at rt for 16 hours. The reaction mixture was quenched with brine and extracted twice with DCM. The combined organic layers were dried over Na$_2$SO$_4$, filtered and concentrated under vacuum. The crude product was purified by flash-chromatography on silica gel (60 g), gradient of cyclohexane/EA (50 ml/min.) from 100/0 (3 min.) to 70/30 (20 min.) to afford pure ethyl 1-((1,2-dimethyl-1H-indol-5-yl)methyl)-1H-pyrazole-4-carboxylate. MS (Method V) [M+H]$^+$=298.4.

c) tert-Butyl 5-((1-((1,2-dimethyl-1H-indol-5-yl)methyl)-1H-pyrazole-4-carboxamido)methyl)-4,6-dimethylpyridin-2-ylcarbamate A mixture of Ethyl 1-((1,2-dimethyl-1H-indol-5-yl)methyl)-1H-pyrazole-4-carboxylate (88%, 122 mg, 0.361 mmol) and 2 N NaOH (0.9 ml, 1.8 mmol) in dioxane (1 ml) was stirred at rt for 16 hours. The reaction mixture was acidified with 1 N HCl to pH 2 and extracted with EtOAc (2×). The combined organic layers were dried over Na$_2$SO$_4$, filtered and concentrated under vacuum to afford crude 1-((1,2-dimethyl-1H-indol-5-yl)methyl)-1H-pyrazole-4-carboxylic acid.

To a solution of 1-((1-Methyl-1H-pyrrolo[2,3-b]pyridin-5-yl)methyl)-1H-pyrazole-4-carboxylic acid (130 mg, 0.330 mmol, 65%), tert-Butyl 5-(aminomethyl)-4,6-dimethylpyridin-2-ylcarbamate (99 mg, 0.396 mmol) and DIPEA (0.308 ml, 1.764 mmol) in DCM (4 ml) Propanephosphonic anhydride (50% in EA (0.156 ml, 0.529 mmol) was added at rt. The reaction mixture was stirred at it for 1 h. The reaction mixture was quenched with 1 N NaOH and extracted twice with DCM. The combined organic layers were dried over Na$_2$SO$_4$, filtered and concentrated under vacuum. The crude product was purified by flash-chromatography on silica gel (26 g), gradient of DCM/DCM:MeOH 8:2 (40 ml/min.) from 100/0 (5 min.) to 80/20 (20 min) to 80/20 5 min. to afford tert-Butyl 5-((1-((1,2-dimethyl-1H-indol-5-yl)methyl)-1H-pyrazole-4-carboxamido)methyl)-4,6-dimethylpyridin-2-ylcarbamate. MS (Method V) [M+H]$^+$=503.4.

d) N-((6-Amino-2,4-dimethylpyridin-3-yl)methyl)-1-((1,2-dimethyl-1H-indol-5-yl)methyl)-1H-pyrazole-4-carboxamide To a solution of tert-Butyl 5-((1-((1,2-dimethyl-1H-indol-5-yl)methyl)-1H-pyrazole-4-carboxamido)methyl)-4,6-dimethylpyridin-2-ylcarbamate (160 mg, 0.318 mmol) in DCM (5 ml) Silica gel (2000 mg) was added. The resulting suspension was concentrated under vacuum to dryness and kept at 75° C. for 6 days under high vacuum. The mixture was taken up in suspended in DCM/NH3 (in MeOH 7N) 9:1, the solution was filtered of and concentrated under reduced pressure to afford the title compound. The crude product was purified by preparative HPLC (Waters Sunfire Prep C18 ODB 5 um, 30×100 mm, 1 to 99% ACN and 0.1% TFA, flow 45 ml/min) to yield pure title compound.

$^1$H-NMR (CH3-OD, 400 MHz): ppm 2.26 (s, 3 H) 2.38 (s, 3 H) 2.41-2.44 (m, 3 H) 3.68 (s, 3 H) 4.44 (s, 2 H) 5.37 (s, 2 H) 6.20 (s, 1 H) 6.31 (s, 1H) 7.05 (dd, J=8.56, 1.71 Hz, 1 H) 7.29 (d, J=8.31 Hz, 1 H) 7.39-7.41 (m, 1 H) 7.93 (s, 1 H) 8.04 (s, 1 H). HPLC (Method F) Rt=0.70 min, MS (Method V) [M+H]$^+$=403.2.

Example 169

N-((6-amino-2,4-dimethylpyridin-3-yl)methyl)-1-((2-methylimidazo[1,2-a]pyridin-6-yl)methyl)-1H-pyrazole-4-carboxamide

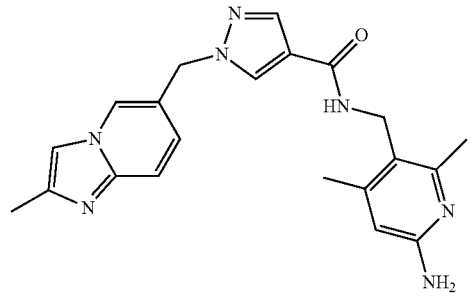

The title compound was prepared in analogy to Example 165. HPLC (Method F) Rt=0.33 min, MS (Method V) [M+H]$^+$=390.4.

Example 170

N-((6-amino-2,4-dimethylpyridin-3-yl)methyl)-2-((2-methylquinolin-6-yl)methyl)oxazole-4-carboxamide

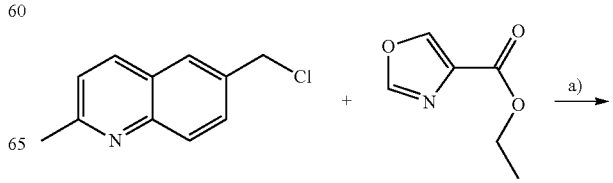

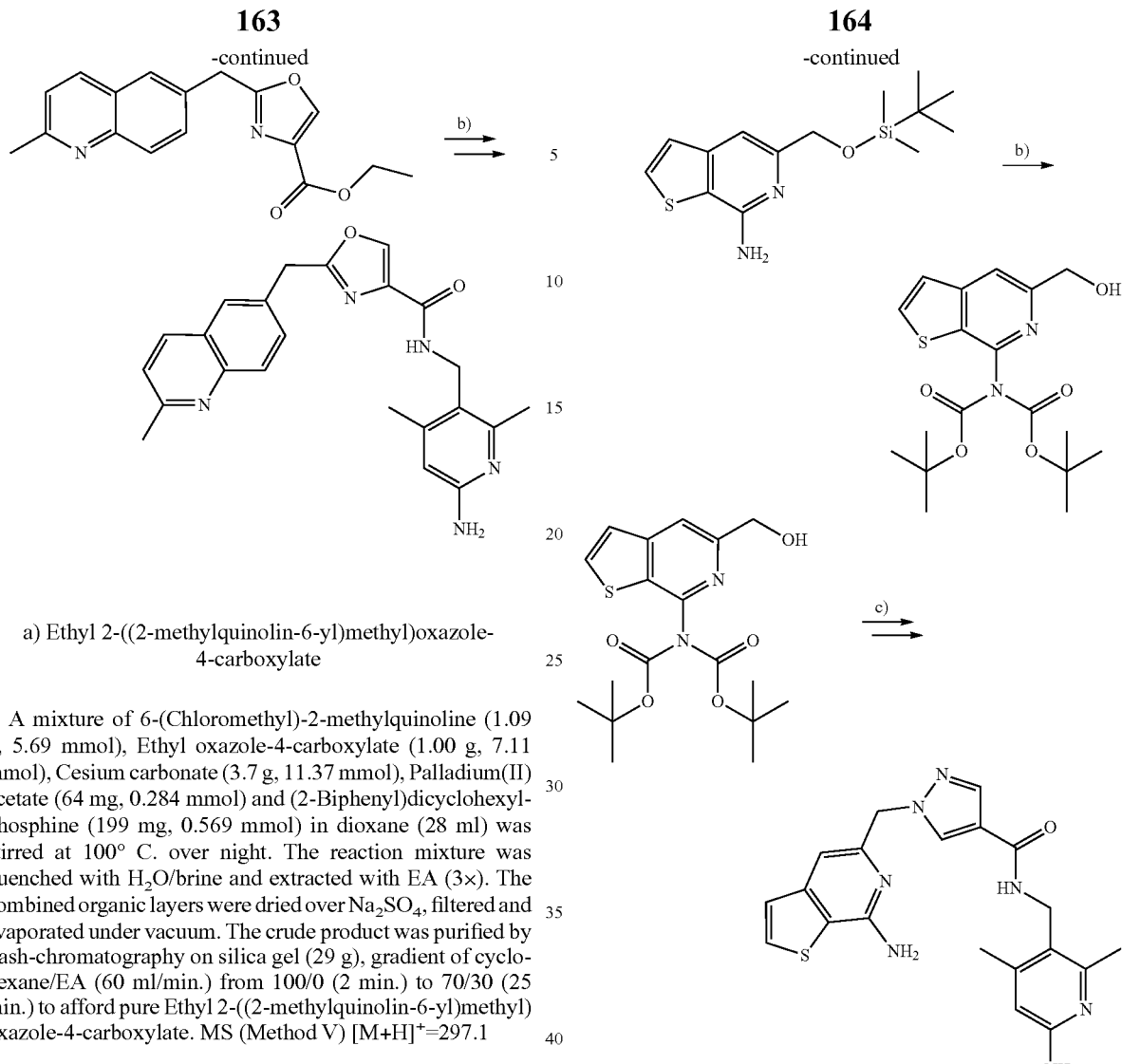

a) Ethyl 2-((2-methylquinolin-6-yl)methyl)oxazole-4-carboxylate

A mixture of 6-(Chloromethyl)-2-methylquinoline (1.09 g, 5.69 mmol), Ethyl oxazole-4-carboxylate (1.00 g, 7.11 mmol), Cesium carbonate (3.7 g, 11.37 mmol), Palladium(II) acetate (64 mg, 0.284 mmol) and (2-Biphenyl)dicyclohexylphosphine (199 mg, 0.569 mmol) in dioxane (28 ml) was stirred at 100° C. over night. The reaction mixture was quenched with $H_2O$/brine and extracted with EA (3×). The combined organic layers were dried over $Na_2SO_4$, filtered and evaporated under vacuum. The crude product was purified by flash-chromatography on silica gel (29 g), gradient of cyclohexane/EA (60 ml/min.) from 100/0 (2 min.) to 70/30 (25 min.) to afford pure Ethyl 2-((2-methylquinolin-6-yl)methyl)oxazole-4-carboxylate. MS (Method V) $[M+H]^+=297.1$ b) N-((6-Amino-2,4-dimethylpyridin-3-yl)methyl)-2-((2-methylquinolin-6-yl)methyl)oxazole-4-carboxamide The title compound was prepared in analogy to Example 165. HPLC (Method G) Rt=0.436 min, MS (Method V) $[[M/2+H]^+=201.7$.

Example 171

N-((6-Amino-2,4-dimethylpyridin-3-yl)methyl)-1-((7-aminothieno[2,3-c]pyridin-5-yl)methyl)-1H-pyrazole-4-carboxamide a) 5-((Tert-butyldimethylsilyloxy)methyl)thieno[2,3-c]pyridin-7-amine To a solution of (7-Aminothieno[2,3-c]pyridin-5-yl)methanol (67 mg, 0.394 mmol) and Imidazole (71.2 mg, 0.985 mmol) in DMF (2.6 ml) tert-Butylchlorodimethylsilane (71.2 mg, 0.473 mmol) was added at rt. The reaction mixture was stirred at rt over night (16 hours). The orange reaction mixture was quenched with water/brine and extracted twice with EA. The organic layers were dried over $Na_2SO_4$, filtered and concentrated under vacuum to afford crude title compound.

b) Bis-BOC-(7-Amino-thieno[2,3-c]pyridin-5-yl)-methanol

To a solution of 5-((tert-Butyldimethylsilyloxy)methyl)thieno[2,3-c]pyridin-7-amine (crude, 125 mg, 0.393 mmol) and DMAP (2.4 mg, 0.02 mmol) in acetonitrile (4 ml) $(BOC)_2O$ (107 mg, 0.49 mmol) was added $(BOC)_2O$ (107 mg, 0.49 mmol) at rt. to afford crude bis-BOC-protected 5-((tert-butyldimethylsilyloxy)methyl)thieno[2,3-c]pyridin-7-amine To a solution of this crude product (138 mg, 0.279 mmol) in THF (4 ml) tetrabutylammonium fluoride trihydrate (88 mg, 0.279 mmol) was added at rt. The reaction mixture was purified by flash-chromatography on silica gel (10 g), gradient of cyclohexane/EA (40 ml/min.) from 100/0 (5 min.) to 80/20 (20 min). MS (Method V) [M+H]$^+$=381.1 c) N-((6-Amino-2,4-dimethylpyridin-3-yl)methyl)-1-((7-aminothieno[2,3-c]pyridin-5-yl)methyl)-1H-pyrazole-4-carboxamide The title compound was prepared in analogy to Example 165. HPLC (Method G) Rt=0.965 min, MS (Method V) [M+H]$^+$=408.2.

Example 172

N-((6-amino-4-chloro-2-methylpyridin-3-yl)methyl)-1-(naphthalen-2-ylmethyl)-1H-pyrazole-4-carboxamide

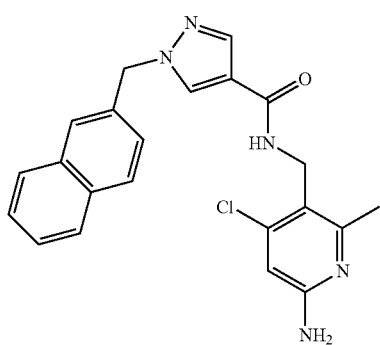 [SMILES: Cc1nc(N)cc(Cl)c1CNC(=O)c1cnn(Cc2ccc3ccccc3c2)c1]

The title compound was prepared in analogy to Example 13. HPLC (Method H) Rt=2.96 min, MS (Method V) [M+H]$^+$= 406.3.

Example 173

N-((6-Amino-2,4-dimethylpyridin-3-yl)methyl)-1-((3-chloroquinolin-6-yl)methyl)-1H-pyrazole-4-carboxamide

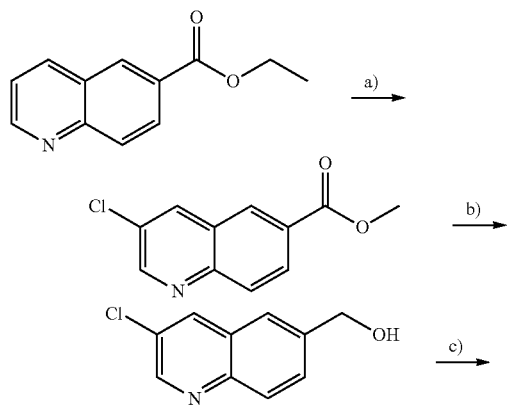

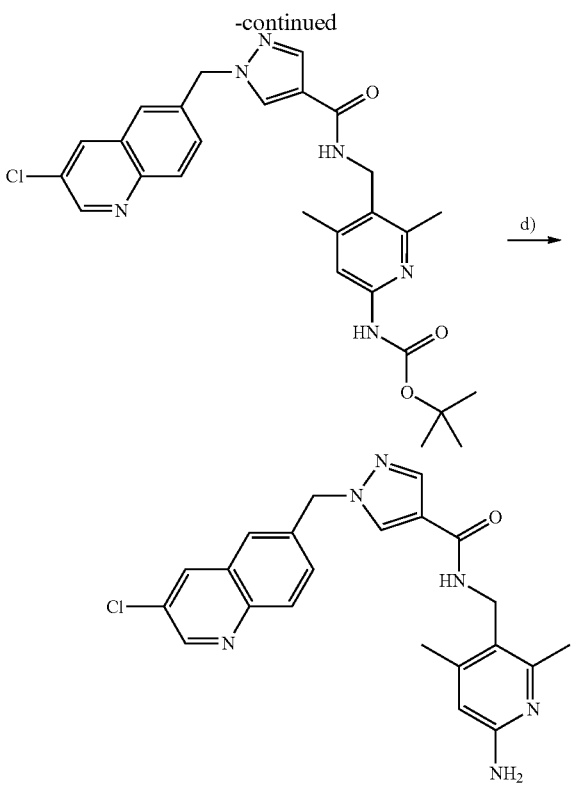

a) Methyl 3-chloroquinoline-6-carboxylate

To a solution of Methyl quinoline-6-carboxylate (1000 mg, 5.34 mmol) in DMF (20 ml) was added N-Chlorosuccinimide (2141 mg, 16.0 mmol) and the reaction mixture was stirred at 120° C. for 20 hr.

The reaction mixture was allowed to cool to ambient temperature, treated with water, neutralized with solid NaHCO$_3$ and further stirred at 23° C. for 30 minutes. Finally, powdered sodium thiosulfate was carefully added to remove excess of N-chlorosuccinimide. The mixture was stirred at 23° C. for 1 h and extracted with EA. The organic layer was dried over Na$_2$SO$_4$, filtered and concentrated under vacuum. The crude product was purified by flash-chromatography on silica gel (120 g), gradient of cyclohexane/EA (85 ml/min.) from 100/0 (5 min.) to 70/30 (30 min.) to afford pure Methyl 3-chloroquinoline-6-carboxylate. HPLC (Method G) Rt=2.01 min, HPLC-MS (Method F) [M+H]$^+$=222.2.

b) (3-Chloroquinolin-6-yl)methanol

To a solution of Methyl 3-chloroquinoline-6-carboxylate (145 mg, 0.654 mmol) in THF (6 ml) Lithiumaluminium hydride 1M in THF (0.654 ml, 0.654 mmol) was added slowly at rt. The reaction was stirred for 2 h at rt. Sodium sulfate decahydrate was added to the reaction mixture to destroy the excess of Lithiumaluminium hydride. After 1 h, methanol was added and the fine suspension was filtered off. The filtrate was concentrated under vacuum, to afford crude (3-chloroquinolin-6-yl)methanol. MS (Method V) [M+H]$^+$=194.2.

c) tert-Butyl 5-((1-((3-chloroquinolin-6-yl)methyl)-1H-pyrazole-4-carboxamido)methyl)-4,6-dimethylpyridin-2-ylcarbamate To a solution of (3-Chloroquinolin-6-yl)methanol (142 mg, 0.660 mmol, 90%) and Triethyl amine (0.092 ml, 0.660 mmol) in DCM (4 ml) Methane sulfonyl chloride (0.051 ml, 0.660 mmol) was added slowly at rt. The reaction was stirred for 1 h at rt and subsequently quenched with H₂O and extracted twice with DCM. The organic layer was dried with Na₂SO₄, filtered and evaporated to dryness to afford crude (3-Chloroquinolin-6-yl)methyl methanesulfonate, which was immediately used in the following step.

A solution of tert-Butyl 5-((1H-pyrazole-4-carboxamido)methyl)-4,6-dimethylpyridin-2-ylcarbamate (145 mg, 0.421 mmol), (3-Chloroquinolin-6-yl)methyl methanesulfonate (143 mg, 0.421 mmol 80%) and K2CO3 (291 mg, 2.105 mmol) in Acetone (3 ml) was stirred for 20 h at 50° C. The reaction was quenched with H₂O and extracted twice with DCM. The organic layer was dried with Na₂SO₄, filtered and evaporated to dryness to afford crude title compound. The crude product was purified by preparative HPLC (Macherey-Nagel Nucleosil 250×40 mm, 5 to 100% ACN and 0.1% TFA, flow 40 ml/min) to afford pure title compound. MS (Method V) [M+H]+=521.4.

d) N-((6-Amino-2,4-dimethylpyridin-3-yl)methyl)-1-((3-chloroquinolin-6-yl)methyl)-1H-pyrazole-4-carboxamide To a solution of tent-Butyl 5-((1-((3-chloroquinolin-6-yl)methyl)-1H-pyrazole-4-carboxamido)methyl)-4,6-dimethylpyridin-2-ylcarbamate (125 mg, 0.240 mmol) in DCM (1 ml) Tri fluoro acetic acid (0.092 ml, 1.200 mmol) was added at rt. The reaction was stirred for 2 h at II. The reaction mixture was concentrated under vacuum to afford crude title compound. The crude product was dissolved in MeOH and filtered over a PL-HCO3-cartridge (MP-resin, VARIAN) to afford pure title compound.

¹H-NMR (DMSO-d6, 400 MHz): ppm 2.17 (s, 3 H) 2.30 (s, 3 H) 4.28 (d, J=4.65 Hz, 2 H) 5.56 (s, 2 H) 6.13 (s, 1 H) 7.67 (dd, J=8.68, 2.08 Hz, 1 H) 7.82 (s, 1 H) 7.94 (s, 1 H) 8.04 (d, J=8.56 Hz, 1 H) 8.35 (s, 1 H) 8.59 (d, J=2.45 Hz, 1 H) 8.89 (d, J=2.45 Hz, 1 H). HPLC (Method G) Rt=1.407 min, MS (Method V) [M+H]⁺=421.3.

Example 174

N-((6-amino-2,4-dimethylpyridin-3-yl)methyl)-1-((1,1-dioxido-2,3-dihydrobenzo[b]thiophen-5-yl)methyl)-1H-pyrazole-4-carboxamide

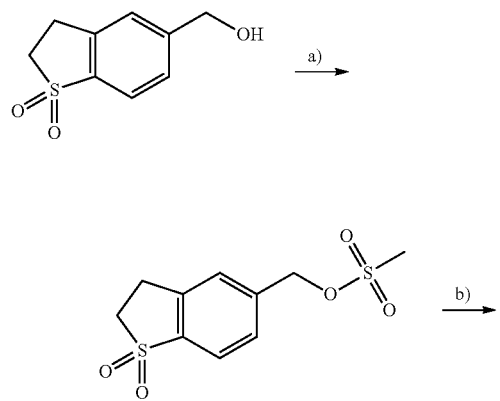

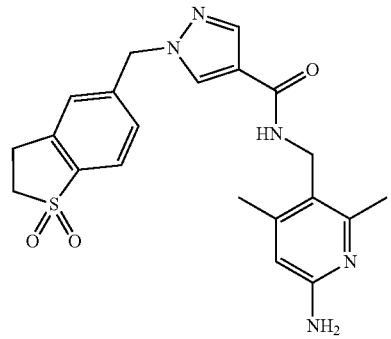

a) Methanesulfonic acid 1,1-dioxo-2,3-dihydro-1H-1lambda*6*-benzo[b]thiophen-5-ylmethyl ester To a solution of (1,1-Dioxo-2,3-dihydro-1H-1lambda*6*-benzo[b]thiophen-5-yl)-methanol (crude, 160 mg, 0.64 mmol) and triethylamne (180 ul, 1.29 mmol) in DCM (7 ml) Methanesulfonylchloride (60 ul, 0.77 mmol) was added at rt. The reaction mixture was stirred at it for 3 hours.

The reaction mixture was quenched with brine and extracted twice with DCM. The combined organic layers were dried over Na₂SO₄, filtered and concentrated under vacuum to afford crude title compound.

b) N-((6-amino-2,4-dimethylpyridin-3-yl)methyl)-1-((1,1-dioxido-2,3-dihydrobenzo[b]thiophen-5-yl)methyl)-1H-pyrazole-4-carboxamide The title compound was prepared in analogy to Example 157b) and 157c). HPLC (Method G) Rt=1.164 min, MS (Method V) [M+H]⁺=426.3.

Example 175

N-((6-Amino-4-chloro-2-methylpyridin-3-yl)methyl)-1-((2-methylquinolin-6-yl)methyl)-1H-1,2,3-triazole-4-carboxamide

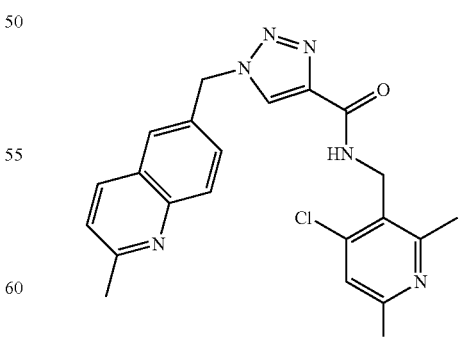

The title compound was prepared from 1-((2-Methylquinolin-6-yl)methyl)-1H-1,2,3-triazole-4-carboxylic acid and 5-(aminomethyl)-4-chloro-6-methylpyridin-2-amine in analogy to Example 20c). HPLC-MS (Method F) Rt=0.44 min. [M+H]⁺=422.1.

Example 176

N-((6-Amino-2,4-dimethylpyridin-3-yl)methyl)-2-methyl-1-(phenylsulfonyl)-1H-pyrrole-3-carboxamide

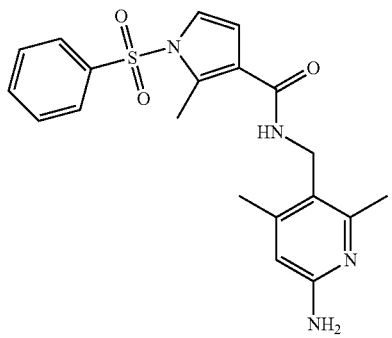 [SMILES: Cc1cc(N)nc(C)c1CNC(=O)c1ccn(S(=O)(=O)c2ccccc2)c1C]

The title compound was prepared in analogy to Example 74. HPLC-MS (Method G) Rt=1.61 min. [M+H]⁺=399.0.

Example 177

N-((6-Amino-2,4-dimethylpyridin-3-yl)methyl)-1-benzyl-5-methyl-1H-1,2,3-triazole-4-carboxamide

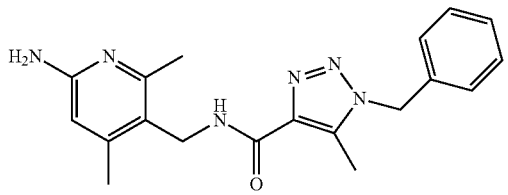 [SMILES: Cc1cc(N)nc(C)c1CNC(=O)c1nnn(Cc2ccccc2)c1C]

The title compound was prepared in analogy to Example 1d). HPLC-MS (Method R) Rt=0.87 min. [M+H]⁺=350.4.

Example 178

N-((6-Amino-2,4-dimethylpyridin-3-yl)methyl)-1-(pyrimidin-2-ylmethyl)-1H-1,2,3-triazole-4-carboxamide

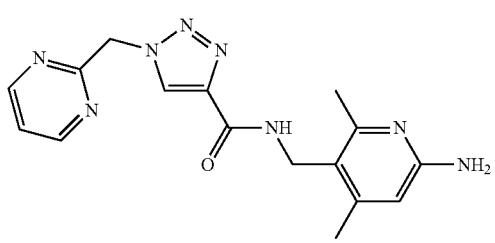 [SMILES: Cc1cc(N)nc(C)c1CNC(=O)c1cn(Cc2ncccn2)nn1]

The title compound was prepared in analogy to Example 153. HPLC-MS (Method G) Rt=1.198 min. [M+H]⁺=339.4.

Example 179

N-((6-Amino-2,4-dimethylpyridin-3-yl)methyl)-1-benzyl-2-methyl-1H-pyrrole-3-carboxamide

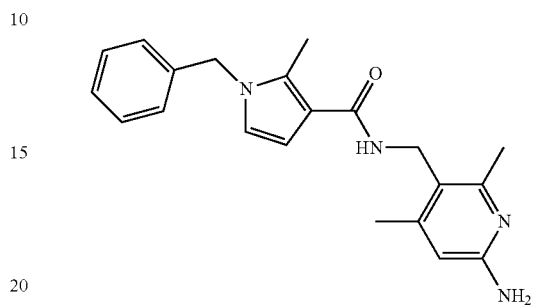

The title compound was prepared from 1 Ethyl 1-benzyl-2-methyl-1H-pyrrole-3-carboxylate in analogy to Example 19a and b). HPLC-MS (Method G) Rt=1.534 min. [M+H]⁺=349.1.

Example 180

N-((6-Amino-4-(difluoromethoxy)-2-methylpyridin-3-yl)methyl)-1-benzyl-1H-pyrazole-4-carboxamide

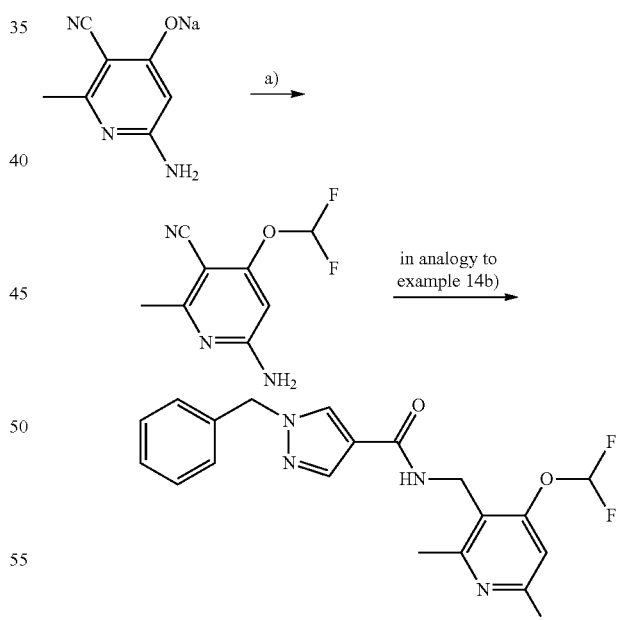

a) 4-(Difluoromethoxy)-5-isocyano-6-methylpyridin-2-amine

To a suspension sodium 6-amino-3-cyano-2-methylpyridin-4-olate (500 mg, 2.92 mmol) in DMF (5 ml) was added NaH (117 mg, 2.92 mmol) at it and the reaction mixture was stirred for 15 min. Methyl chlorodifluoroacetate (1.3 g, 9.4 mmol) was added dropwise with vigorous stirring over the course of 20 min. After 15 min, the suspension was warmed to 70° C. for 14 h. The reaction mixture was quenched into brine:Na2CO3 (70+70 mL) and extracted with EA (3×60 mL). The combined organic phases were dried over Na2SO4, filtered and concentrated under reduced pressure.

Column chromatography (Combiflash Companion, 4 g SiO2, DCM:(DCM/MeOH 9:1)) afforded the tithe compound. $[M+H]^+=200.4$.

b) N-((6-Amino-4-(difluoromethoxy)-2-methylpyridin-3-yl)methyl)-1-benzyl-1H-pyrazole-4-carboxamide The title compound was prepared in analogy to Example 14b). HPLC-MS (Method F) Rt=0.94 min. $[M+H]^+=388.2$.

Example 181

N-((6-Amino-4-bromo-2-methylpyridin-3-yl)methyl)-1-benzyl-1H-pyrazole-4-carboxamide

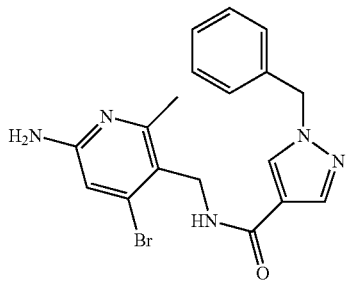 [SMILES: Cc1nc(N)cc(Br)c1CNC(=O)c1cnn(Cc2ccccc2)c1]

The title compound was prepared in analogy to Example 144. HPLC-MS (Method F) Rt=0.83 min. $[M+H]^+=400.2$.

Example 182

N-((6-Aminopyridin-3-yl)methyl)-1-benzyl-1H-pyrazole-4-carboxamide

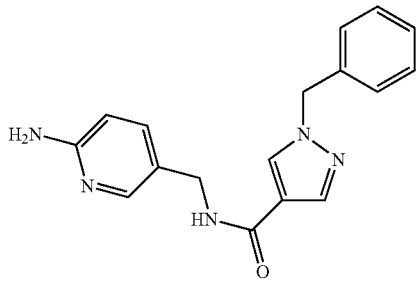 [SMILES: Nc1ccc(CNC(=O)c2cnn(Cc3ccccc3)c2)cn1]

The title compound was prepared in analogy to Example 13b). $[M+H]^+=308.5$.

Example 183

N-((6-Amino-2,4-dimethylpyridin-3-yl)methyl)-2,4,5-trimethyl-1-(Phenylsulfonyl)-1H-pyrrole-3-carboxamide

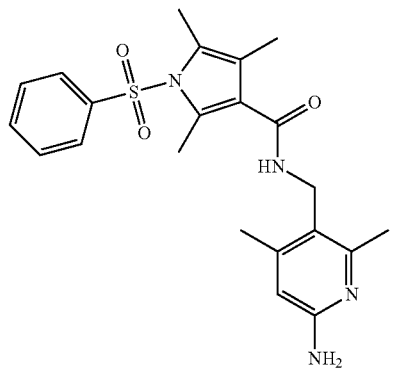 [SMILES: Cc1cc(N)nc(C)c1CNC(=O)c1c(C)c(C)n(S(=O)(=O)c2ccccc2)c1C]

The title compound was prepared in analogy to Example 74. HPLC-MS (Method G) Rt=1.67 min. $[M+H]^+=427.0$.

Table 1: In-vitro Plasma Kallikrein Inhibition

Materials

The fluorogenic substrate $_D$Pro-Phe-Arg-(Rh110)-γGlu-OH (where $_D$Pro is the amino acid d-proline, Rh110 is the fluorophore rhodamine 110 and γGlu is a glutamine linked to Rh110 via the gamma-carbonyl function; from Biosyntan, Berlin, Germany), being based on the chromogenic substrate described in Gallimore et al (Thromb Res 25, 293-298, 1982), was dissolved in DMSO at 5 mM and stored at −80° C. All other chemicals were of analytical grade.

Human plasma kallikrein was purchased from Kordia (Leiden, Netherlands, batch HPKA 1303). A stock solution of 0.17 mg/ml deinonized water was stored at −80° C. Enzymatic reactions were conducted in 'assay buffer', comprising 50 mM Hepes/NaOH at pH 7.8, 150 mM NaCl, 1 mM EDTA and 0.05% (w/v) CHAPS.

Both, enzyme and substrate were diluted in assay buffer.

All protein and peptide containing solutions were handled in siliconized tubes (Life Systems Design, Merenschwand, Switzerland). The compound solutions as well as the enzyme and the substrate solutions were transferred to 384-well plates (black Cliniplate; cat. no. 95040020 Labsystems Oy, Finland) by means of a CyBi-Well 96-channel pipettor (CyBio AG, Jena, Germany). Plate measurements were conducted by the means of a Safire2 reader (TECAN, Maennedorf, Switzerland). The Safire2 is a monochomator-based instrument and wavelengths of 485 nm and 535 nm were taken for fluorescence excitation and emission acquisition, respectively. The bandwidths were set to 10 nm in both the excitation and the emission path. The fluorescence in each well was excited by three flashes per measurement.

Determination of $IC_{50}$ Values

For the determination of $IC_{50}$ values, the assays were performed at room temperature in 384-well plates with a total assay volume of 25.25 μl per well.

The test compound was dissolved in 90% (v/v) DMSO/water. For the assays, 250 nL of the 90% (v/v) DMSO/water solution or compound solution were added per well, followed by the addition of 12.5 μl protease solution (protease in assay buffer). The final assay concentration of the human plasma kallikrein was nominally 25 pM, the 11 compound concentrations in the dilution series were in the range form 1 nM to 100 uM. After 1 hour of pre-incubation at room temperature, the reactions were started by the addition of 12.5 μl substrate solution (in assay buffer, final assay concentration was 0.5 uM). After the addition of the substrate solution, the final DMSO concentration in the assay was 0.9% (v/v). The effect of the compound on the enzymatic activity was obtained from the linear part of the progress curves and determined after 1 hour (t=60 min). The $IC_{50}$ value was calculated from the plot of percentage of inhibition vs. inhibitor concentration by a logistics fit according to the following equation:

$$y=A2+(A1-A2)/(1+(x/IC50)^p)$$

where y is the %-inhibition at the inhibitor concentration, x. A1 is the lowest inhibition value, i.e. 0%, and A2 the maximum inhibition value, i.e. 100%. The exponent, p, is the Hill coefficient. The curve fitting was conducted with the non-linear regression routine of the analysis software Origin 7.55R6 (OriginLab Corporation).

TABLE 1

| Example | $IC_{50}$ (μM) |
| --- | --- |
| 1 | 0.81 |
| 2 | 7.67 |
| 3 | 2.26 |
| 4 | 7.6 |
| 5 | 4.5 |
| 6 | 0.0002 |
| 7 | 2.03 |
| 8 | 2.64 |
| 9 | 9.12E−05 |
| 10 | 0.03 |
| 11 | 12.2 |
| 12 | 1.37 |
| 13 | 0.15 |
| 14 | 0.32 |
| 15 | 0.23 |
| 16 | 0.15 |
| 17 | 0.098 |
| 18 | 1.1 |
| 19 | 0.07 |
| 20 | 7.4 |
| 21 | 2.54 |
| 22 | 1.7 |
| 23 | 0.009 |
| 24 | 0.238 |
| 25 | 0.109 |
| 26 | 0.019 |
| 27 | 0.021 |
| 28 | 0.343 |
| 29 | 0.248 |
| 30 | 0.204 |
| 31 | 0.143 |
| 32 | 0.041 |
| 33 | 0.262 |
| 34 | 0.046 |
| 35 | 3.9 |
| 36 | 0.000134 |
| 37 | 5.3 |
| 38 | 0.019 |
| 39 | 0.634 |
| 40 | 0.009 |
| 41 | 0.108 |
| 42 | 0.145 |
| 43 | 0.113 |
| 44 | 0.215 |
| 45 | 0.045 |
| 46 | 1.1 |
| 47 | 3.2 |
| 48 | 35.5 |
| 49 | 0.679 |

TABLE 1-continued

| Example | $IC_{50}$ (μM) |
| --- | --- |
| 50 | 0.739 |
| 51 | 7 |
| 52 | 5.7 |
| 53 | 3.6 |
| 54 | 1.8 |
| 55 | 6.3 |
| 56 | 4.4 |
| 57 | 0.144 |
| 58 | 3.8 |
| 59 | 0.209 |
| 60 | 0.379 |
| 61 | 0.046 |
| 62 | 0.681 |
| 63 | 0.011 |
| 64 | 0.014 |
| 65 | 0.029 |
| 66 | 0.325 |
| 67 | 0.06 |
| 68 | 0.034 |
| 69 | 1.6 |
| 70 | 4.1 |
| 71 | 0.19 |
| 72 | 0.937 |
| 73 | 0.114 |
| 74 | 0.595 |
| 75 | 0.0031 |
| 76 | 0.949 |
| 77 | 0.072 |
| 78 | 10.1 |
| 79 | 0.166 |
| 80 | 0.117 |
| 81 | 0.411 |
| 82 | 0.678 |
| 83 | 0.018 |
| 84 | 0.498 |
| 85 | 4.1 |
| 86 | 7.5 |
| 87 | 1.3 |
| 88 | 1.8 |
| 89 | 0.006 |
| 90 | 2.0 |
| 91 | 0.133 |
| 92 | 0.867 |
| 93 | 0.674 |
| 94 | 0.0021 |
| 95 | 0.485 |
| 96 | 0.291 |
| 97 | 1.9 |
| 98 | 3.8 |
| 99 | 7.0 |
| 100 | 0.642 |
| 101 | 0.07 |
| 102 | 4.0 |
| 103 | 0.299 |
| 104 | 0.113 |
| 105 | 0.168 |
| 106 | 0.415 |
| 107 | 1.8 |
| 108 | 0.798 |
| 109 | 1.3 |
| 110 | 0.249 |
| 111 | 2.1 |
| 112 | 0.229 |
| 113 | 5.8 |
| 114 | 0.03 |
| 115 | 0.0033 |
| 116 | 0.197 |
| 117 | 0.152 |
| 118 | 0.183 |
| 119 | 0.289 |
| 120 | 0.223 |
| 121 | 0.369 |
| 122 | 0.752 |
| 123 | 15.8 |
| 124 | 0.071 |
| 125 | 0.036 |
| 126 | 0.67 |
| 127 | 0.016 |

TABLE 1-continued

| Example | IC$_{50}$ (μM) |
|---|---|
| 128 | 0.301 |
| 129 | 0.244 |
| 130 | 0.067 |
| 131 | 0.009 |
| 132 | 0.071 |
| 133 | 0.196 |
| 134 | 1.1 |
| 135 | 0.089 |
| 136 | 0.024 |
| 137 | 0.127 |
| 138 | 62.7 |
| 139 | 0.0049 |
| 140 | 0.0046 |
| 141 | 0.0012 |
| 142 | 2.24E−05 |
| 143 | 0.0026 |
| 144 | 42.4 |
| 145 | 0.0002 |
| 146 | 0.00004 |
| 147 | 0.0001 |
| 148 | 0.00003 |
| 149 | 0.0078 |
| 150 | 0.01 |
| 151 | 0.013 |
| 152 | 0.004 |
| 153 | 0.016 |
| 154 | 0.002 |
| 155 | 0.003 |
| 156 | 0.00092 |
| 157 | 0.002 |
| 158 | 0.004 |
| 159 | 0.007 |
| 160 | 0.02 |
| 161 | 0.004 |
| 162 | 0.005 |
| 163 | 0.005 |
| 164 | 1.2 |
| 165 | 0.006 |
| 166 | 0.0002 |
| 167 | 0.0002 |
| 168 | 0.0001 |
| 169 | 0.003 |
| 170 | 0.0097 |
| 171 | 0.026 |
| 172 | 0.06 |
| 173 | 0.0004 |
| 174 | 0.075 |
| 175 | 0.061 |
| 176 | 45.0 |
| 177 | 52.1 |
| 178 | 67.3 |
| 179 | 85.8 |
| 180 | >100 |
| 181 | 37.0 |
| 182 | >100 (38% inhibition at 100 μM) |
| 183 | >100 (39% inhibition at 100 μM) |

In-Vivo Inhibition of Leakage

Description of Assay

For imaging of vascular leakiness a CRi Maestro 2 system was used (CRi, Woburn, Mass. 01801 USA). The temperature of the animal was maintained at 37° during the imaging procedure using warming pad. Female mice (C57BL/6JRj Mouse, MA512) were used for the assay. The compound to be tested was dissolved in 0.5% methylcellulose and applied orally at a volume of 10ml/kg (timepoint 0). Forty minutes later, animals were anaesthetized using a mixture of oxygen (100%) and isofluran (2%). Anaesthesia was delivered by a face mask. Then, the contrast agent (in house developed near-infrared tracer based on the Kodak Xsight 670LSS near-infrared dye bound to albumin, 2.5 mg/kg/5 ml) was injected intravenously. At timepoint 50 min, the back of the animal was shaved and a reference image was recorded. At timepoint 60 min, dextran sulfate (8%, 0.05 ml/injection site) was injected intradermally using a 30 G needle at 4 sites arranged in a rectangular pattern with about 10 mm distance between the spots. 5 mins after dextran sulfate injection time lapse imaging was started. The recording interval was 5 mins for a total recording time of 15mins.

For data analysis regions-of-interest were defined for each of the injection sites (ROI2-5) and the area surrounding the injection sites (ROI1). For these and the time course of the fluorescence signal was plotted and statistically evaluated for each experimental group as mean+/−standard-error-of-mean.

FIG. 1 shows the leakage vs min after dextran sulfate (DX) injection for Example 153 at doses of 3, 30 and 100 mg/kg po.

The following are further embodiments of the invention:

Embodiment 1: A compound of the formula I

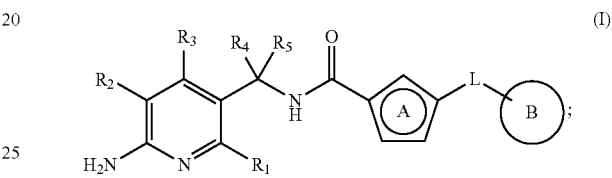

wherein

R$_1$ is hydrogen; halogen; cyano; nitro; hydroxy; amino; —C(O)H; —C(O)OH; —C(O)NH$_2$;

C$_{1-6}$alkyl; C$_{1-6}$halogenalkyl; C$_{1-6}$hydroxyalkyl; C$_{1-4}$alkoxy-C$_{1-6}$alkyl; C$_{1-6}$aminoalkyl;

C$_{2-6}$alkenyl; C$_{2-6}$halogenalkenyl; C$_{2-6}$alkinyl; C$_{2-6}$halogenalkinyl;

C$_{1-6}$alkoxy; C$_{1-6}$halogenalkoxy; C$_{9-4}$alkoxy-C$_{1-6}$alkoxy; C$_{9-6}$alkylamino; di(C$_{1-6}$alkyl)amino;

or C$_{3-7}$cycloalkyl, wherein one carbon atom may be replaced by an oxygen atom, wherein the C$_{3-7}$cycloalkyl may be attached directly to the pyridine ring or via a C$_{1-2}$alkylene or an oxygen, and wherein the C$_{3-7}$cycloalkyl may be substituted once or more than once by halogen, C$_{1-4}$alkyl or C$_{1-4}$alkoxy;

R$_2$ is hydrogen or fluoro;

R$_3$ is hydrogen; halogen; cyano; nitro; hydroxy; amino; —C(O)H; —C(O)OH; —C(O)NH$_2$; or —X$_1$—R$_6$;

X$_1$ is selected from bond; carbonyl; oxygen; sulfur; —S(O)—; —S(O)$_2$—; amino, which may be substituted by C$_{1-4}$alkyl; —NH—C(O)—; —C(O)—NH—; —NH—S(O)$_2$—; and —S(O)$_2$—NH—;

R$_6$ is C$_{1-6}$alkyl; C$_{1-6}$halogenalkyl; C$_{1-6}$cyanoalkyl; C$_{1-6}$carboxyalkyl; C$_{1-6}$hydroxyalkyl; C$_{1-4}$alkoxy-C$_{1-6}$alkyl; C$_{1-4}$alkoxy-C$_{1-4}$alkoxy-C$_{1-6}$alkyl; C$_{1-4}$alkylcarbonyl-C$_{1-6}$alkyl; C$_{1-4}$alkoxycarbonyl-C$_{1-6}$alkyl; C$_{1-4}$alkylcarbonyloxy-C$_{1-6}$alkyl; C$_{1-6}$aminoalkyl; C$_{1-4}$alkylamino-C$_{1-6}$alkyl; di(C$_{1-4}$alkyl)amino-C$_{1-6}$alkyl; aminocarbonyl-C$_{1-6}$alkyl; C$_{1-4}$alkylaminocarbonyl-6alkyl; di(C$_{1-4}$alkyl)aminocarbonyl-C$_{1-6}$alkyl; C$_{1-4}$alkylcarbonylamino-C$_{1-6}$alkyl; C$_{1-4}$alkylaminosulfonyl-C$_{1-6}$alkyl; di(C$_{1-4}$alkyl)aminosulfonyl-C$_{1-6}$alkyl;

C$_{2-6}$alkenyl; C$_{2-6}$halogenalkenyl; C$_{2-6}$alkinyl; C$_{2-6}$halogenalkinyl;

or R$_6$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may be attached directly to group $X_1$ or via a $C_{1-2}$alkylene, wherein the ring system may in turn be substituted once or more than once by $R_7$, and wherein a substituent on a nitrogen in a heterocyclic ring system may not be halogen;

each $R_7$ independently is halogen, cyano, $C_{1-4}$alkyl, $C_{1-4}$halogenalkyl, $C_{1-4}$alkoxy, or $C_{1-4}$halogenalkoxy; or two $R_7$ at the same ring atom together are oxo;

$R_4$ and $R_5$ are each independently hydrogen; cyano;

$C_{1-6}$alkyl; $C_{1-6}$halogenalkyl; $C_{1-6}$hydroxyalkyl; $C_{1-4}$alkoxy-$C_{1-6}$alkyl; $C_{2-6}$alkenyl; $C_{2-6}$halogenalkenyl; $C_{2-6}$alkinyl; $C_{2-6}$halogenalkinyl;

$C_{1-6}$alkylamino; di($C_{1-6}$alkyl)amino;

or $C_{3-7}$cycloalkyl, wherein one carbon atom may be replaced by an oxygen atom, wherein the $C_{3-7}$cycloalkyl may be attached directly to the methylene or via a $C_{1-2}$alkylene, and wherein the $C_{3-7}$cycloalkyl may be substituted once or more than once by halogen, $C_{1-4}$alkyl or $C_{1-4}$alkoxy;

or $R_4$ and $R_5$ together with the carbon atom to which they are bound form a $C_{3-7}$cycloalkyl;

or $R_4$ and $R_5$ together are oxo;

or $R_4$ and $R_5$ together are imino, which may be substituted by $C_{1-4}$alkyl;

A is a five-membered monocyclic aromatic ring system which contains from 1 to 4 hetero atoms selected from nitrogen, oxygen and sulfur, wherein the ring system may contain not more than 1 hetero atom selected from oxygen and sulfur, and wherein the group L is attached to a ring atom being separated by one further ring atom from the ring atom to which the carboxamide group is attached, wherein the ring system may be substituted once, twice or three times by $R_8$, and wherein a substituent on a ring nitrogen atom may not be halogen;

each $R_8$ independently is halogen; cyano; nitro; hydroxy; amino; —C(O)H; —C(O)OH; —C(O)NH$_2$;

$C_{1-6}$alkyl; $C_{1-6}$halogenalkyl; $C_{1-6}$hydroxyalkyl; $C_{1-4}$alkoxy-$C_{1-6}$alkyl; $C_{1-6}$aminoalkyl;

$C_{2-6}$alkenyl; $C_{2-6}$halogenalkenyl; $C_{2-6}$alkinyl; $C_{2-6}$halogenalkinyl;

$C_{1-6}$alkoxy; $C_{1-6}$halogenalkoxy; $C_{1-4}$alkoxy-$C_{1-6}$alkoxy; $C_{1-6}$alkylamino; di($C_{1-6}$alkyl)amino;

or $C_{3-7}$cycloalkyl, wherein one carbon atom may be replaced by an oxygen atom, wherein the $C_{3-7}$cycloalkyl may be attached directly to group A or via a $C_{1-2}$alkylene or an oxygen, and wherein the $C_{3-7}$cycloalkyl may be substituted once or more than once by halogen, $C_{1-4}$alkyl or $C_{1-4}$alkoxy;

or two $R_8$ at adjacent ring atoms atoms form together with said ring atoms a fused five- to seven-membered monocyclic aromatic or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_9$, and wherein a substituent on a nitrogen in a heterocyclic ring system may not be halogen; and wherein each $R_9$ independently is halogen, $C_{1-4}$alkyl or $C_{1-4}$alkoxy, or two $R_9$ at the same ring atom together are oxo;

L is —C($R_{10}$)$_2$—; —O—; —S—; —S(O)—; or —S(O)$_2$—;

each $R_{10}$ independently is hydrogen;

halogen; cyano; hydroxy; nitro; amino;

$C_{1-6}$alkyl; $C_{1-6}$halogenalkyl; $C_{1-6}$hydroxyalkyl; $C_{1-4}$alkoxy-$C_{1-6}$alkyl; amino-$C_{1-6}$alkyl; $C_{1-4}$alkylamino-$C_{1-6}$alkyl; di($C_{1-4}$alkyl)amino-$C_{1-6}$alkyl;

$C_{2-6}$alkenyl; $C_{2-6}$halogenalkenyl; $C_{2-6}$alkinyl; $C_{2-6}$halogenalkinyl;

$C_{1-6}$alkoxy; $C_{1-6}$halogenalkoxy; $C_{1-4}$alkoxy-$C_{1-6}$alkoxy; $C_{1-6}$alkylamino; di($C_{1-6}$alkyl)amino; or $C_{3-7}$cycloalkyl, wherein one carbon atom may be replaced by an oxygen atom, wherein the $C_{3-7}$cycloalkyl may be attached directly to the methylene or via a $C_{1-2}$alkylene or an oxygen, and wherein the $C_{3-7}$cycloalkyl may be substituted once or more than once by halogen, $C_{1-4}$alkyl or $C_{1-4}$alkoxy;

or two $R_{10}$ together with the carbon atom to which they are bound form a $C_{3-7}$cycloalkyl;

or two $R_{10}$ together are oxo;

or two $R_{10}$ together are imino, which may be substituted by $C_{1-4}$alkyl;

$R_{11}$ is hydrogen;

$C_{1-6}$alkyl;

or $C_{3-7}$cycloalkyl, wherein one carbon atom may be replaced by an oxygen atom, wherein the $C_{3-7}$cycloalkyl may be attached directly to the nitrogen atom or via a $C_{1-2}$alkylene;

B is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_{12}$, and wherein a substituent on a nitrogen in a heterocyclic ring system may not be halogen;

each $R_{12}$ independently is halogen; cyano; nitro; hydroxy; amino; —C(O)H; —C(O)OH; —C(O)NH$_2$; —X$_2$—R$_{13}$; or —X$_3$—B$_1$;

$X_2$ is selected from bond; carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$R_{13}$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-6}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; $C_{2-6}$halogenalkinyl;

$X_3$ is bond or $C_{1-3}$alkylene, wherein one carbon atom of the $C_{1-3}$alkylene may be replaced by a group selected from carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$B_1$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may in turn be substituted once or more than once by $R_{14}$, and wherein a substituent on a nitrogen in a heterocyclic ring system may not be halogen;

each $R_{14}$ independently is halogen, cyano, $C_{1-4}$alkyl, $C_{1-4}$halogenalkyl, $C_{1-4}$alkoxy, or $C_{1-4}$halogenalkoxy; or two $R_{14}$ at the same ring atom together are oxo;

or two $R_{12}$ at adjacent ring atoms atoms form together with said ring atoms a fused five- to seven-membered monocyclic unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{15}$, and wherein a substituent on a nitrogen in a heterocyclic ring system may not be halogen; and wherein each $R_{15}$ independently is halogen, $C_{1-4}$alkyl, $C_{1-4}$alkoxy, or $C_{1-4}$alkoxy$C_{1-4}$alkyl, or two $R_{15}$ at the same ring atom together are oxo;

or B is a three- to ten-membered monocyclic or fused polycyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_{16}$, and wherein a substituent on a nitrogen in a heterocyclic ring system may not be halogen;

each $R_{16}$ independently is halogen; cyano; nitro; hydroxy; amino; —C(O)H; —C(O)OH; —C(O)NH$_2$; —X$_4$—R$_{17}$; or —X$_5$—B$_2$;

X$_4$ is selected from bond; carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$R_{17}$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; $C_{2-6}$halogenalkinyl;

X$_5$ is bond or $C_{1-3}$alkylene, wherein one carbon atom of the $C_{1-3}$alkylene may be replaced by a group selected from carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

B$_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may in turn be substituted once or more than once by $R_{18}$, and wherein a substituent on a nitrogen in a heterocyclic ring system may not be halogen;

each $R_{18}$ independently is halogen, cyano, $C_{1-4}$alkyl, $C_{1-4}$halogenalkyl, $C_{1-4}$alkoxy, or $C_{1-4}$halogenalkoxy; or two $R_{18}$ at the same ring atom together are oxo;

or two $R_{16}$ at adjacent ring atoms atoms form together with said ring atoms a fused five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{19}$, and wherein a substituent on a nitrogen in a heterocyclic ring system may not be halogen; and wherein each $R_{19}$ independently is halogen, $C_{1-4}$alkyl or $C_{1-4}$alkoxy;

or two $R_{16}$ at the same ring atom together are oxo;

or two $R_{16}$ at the same ring atom together with the ring atom to which they are bound form a $C_{3-7}$cycloalkyl;

or two $R_{16}$ at the same ring atom together are imino, which may be substituted by $C_{1-4}$alkyl;

in free form or in salt form.

Embodiment 2: A compound of formula I according to embodiment 1, wherein $R_1$ is $C_{1-4}$alkyl or $C_{1-4}$halogenalkyl; $R_2$ is hydrogen; $R_3$ is —X$_1$—R$_6$, X$_1$ is bond; and $R_6$ is $C_{1-4}$alkyl or $C_{1-4}$halogenalkyl.

Embodiment 3: A compound of formula I according to embodiment 1, wherein $R_1$ is $C_{1-4}$alkyl or $C_{1-4}$halogenalkyl; $R_2$ is hydrogen; $R_3$ is —X$_1$—R$_6$, X$_1$ is oxygen; and $R_6$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkyl-carbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; $C_{2-6}$halogenalkinyl;

or $R_6$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may be attached directly to group $X_1$ or via a $C_{1-2}$alkylene, wherein the ring system may in turn be substituted once or more than once by $R_7$, and wherein a substituent on a nitrogen in a heterocyclic ring system may not be halogen;

each $R_7$ independently is halogen, cyano, $C_{1-4}$alkyl, $C_{1-4}$halogenalkyl, $C_{1-4}$alkoxy, or $C_{1-4}$halogenalkoxy; or two $R_7$ at the same ring atom together are oxo.

Embodiment 4: A compound of formula I according to any of embodiments 1 to 3, wherein $R_4$ and $R_5$ are each hydrogen; L is —C($R_{10}$)$_2$—; and each $R_{10}$ is hydrogen.

Embodiment 5: A compound of formula I according to any of embodiments 1 to 4, wherein A is a ring system selected from

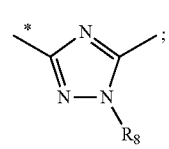

A$_1$

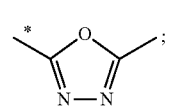

A$_2$

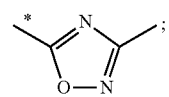

A$_3$

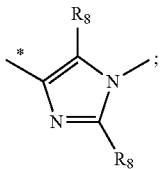
A4

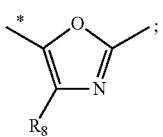
A5

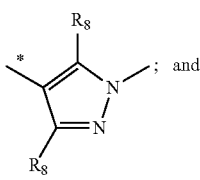
A6; and

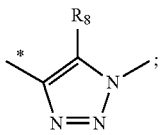
A7 wherein the bond marked with the asterisk is attached to the carboxamide group and wherein each $R_8$ independently is hydrogen; halogen; $C_{1-4}$alkyl; $C_{1-4}$halogenalkyl; $C_{1-4}$alkoxy; or $C_{1-4}$halogenalkoxy.

Embodiment 6: A compound of formula I according to any of embodiments 1 to 5, wherein B is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted once by —$X_3$—$B_1$; and wherein the ring system may be further substituted once or more than once by halogen; cyano; hydroxy; amino; or —$X_2$—$R_{13}$; and wherein a substituent on a nitrogen in a heterocyclic ring system may not be halogen;

$X_2$ is selected from bond; oxygen; $R_{13}$ is $C_{1-6}$alkyl; $C_{1-6}$halogenalkyl;

$X_3$ is bond or $C_{1-3}$alkylene, wherein one carbon atom of the $C_{1-3}$alkylene may be replaced by a group selected from oxygen; sulfur; amino, which may be substituted by $C_{1-4}$alkyl;

$B_1$ is a three- to seven-membered monocyclic ring system which may be aromatic, saturated or unsaturated non-aromatic and which may contain from 1 to 4 hetero atoms selected from nitrogen, oxygen and sulfur, wherein the ring system may contain not more than 2 oxygen atoms and not more than 2 sulfur atoms, wherein the ring system may in turn be substituted once or more than once by $R_{14}$, and wherein a substituent on a nitrogen in a heterocyclic ring system may not be halogen;

each $R_{14}$ independently is halogen, cyano, $C_{1-4}$alkyl, $C_{1-4}$halogenalkyl, $C_{1-4}$alkoxy, or $C_{1-4}$halogenalkoxy; or two $R_{14}$ at the same ring atom together are oxo.

Embodiment 7: A compound of formula I according to any of embodiments 1 to 5, wherein B is a nine- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_{12}$; and wherein a substituent on a nitrogen in a heterocyclic ring system may not be halogen;

each $R_{12}$ independently is halogen; cyano; hydroxy; amino; —$X_2$—$R_{13}$;

$X_2$ is selected from bond; oxygen; and amino, which may be substituted by $C_{1-4}$alkyl;

$R_{13}$ is $C_{1-6}$alkyl; $C_{1-6}$halogenalkyl.

Embodiment 8: A compound of formula I according to any of embodiments 1 to 7 which is selected from N-((6-amino-2,4-dimethylpyridin-3-yl)methyl)-5-benzyl-1-methyl-1H-1,2,4-triazole-3-carboxamide;
N-((6-amino-2,4-dimethylpyridin-3-yl)methyl)-3-benzyl-isoxazole-5-carboxamide;
N-((6-amino-2,4-dimethylpyridin-3-yl)methyl)-5-benzyl-1,3,4-oxadiazole-2-carboxamide;
N-((6-amino-2,4-dimethylpyridin-3-yl)methyl)-3-benzyl-1,2,4-oxadiazole-5-carboxamide;
1-(4-((1H-pyrazol-1-yl)methyl)benzyl)-N-((6-amino-2,4-dimethylpyridin-3-yl)methyl)-1H-imidazole-4-carboxamide;
N-((6-amino-2,4-dimethylpyridin-3-yl)methyl)-5-benzyloxazole-2-carboxamide;
N-((6-amino-2,4-dimethylpyridin-3-yl)methyl)-2-(4-methoxybenzyl)oxazole-4-carboxamide
1-(4-((1H-pyrazol-1-yl)methyl)-3-methoxybenzyl)-N-((6-amino-2,4-dimethylpyridin-3-yl)methyl)-1H-pyrazole-4-carboxamide;
N-((6-amino-2,4-dimethylpyridin-3-yl)methyl)-1-(biphenyl-4-ylmethyl)-1H-1,2,3-triazole-4-carboxamide;
N-((6-amino-2,4-dimethylpyridin-3-yl)methyl)-1-(2-hydroxy-1-phenylethyl)-1H-pyrazole-4-carboxamide;
N-((6-amino-2,4-dimethylpyridin-3-yl)methyl)-1-(phenylsulfonyl)-1H-pyrrole-3-carboxamide;
N-((6-amino-2,4-dimethylpyridin-3-yl)methyl)-1-(4-methoxybenzyl)-1H-pyrazole-4-carboxamide;
N-((6-amino-4-methoxy-2-methylpyridin-3-yl)methyl)-1-benzyl-1H-pyrazole-4-carboxamide;
N-((6-amino-4-(cyclohexyloxy)-2-methylpyridin-3-yl)methyl)-1-benzyl-1H-pyrazole-4-carboxamide;
N-((6-amino-2,4-dimethylpyridin-3-yl)methyl)-1-(4-(hydroxymethyl)benzyl)-1H-pyrazole-4-carboxamide;
N-((6-amino-2,4-dimethylpyridin-3-yl)methyl)-1-(4-((2,5-dioxopyrrolidin-1-yl)methyl)benzyl)-1H-pyrazole-4-carboxamide;
N-((6-amino-2,4-dimethylpyridin-3-yl)methyl)-1-(pyridin-4-ylmethyl)-1H-pyrazole-4-carboxamide;
N-((6-amino-2,4-dimethylpyridin-3-yl)methyl)-1-benzyl-1H-1,2,3-triazole-4-carboxamide;
N-((6-amino-2,4-dimethylpyridin-3-yl)methyl)-1-benzyl-1H-imidazole-4-carboxamide;
N-((6-amino-2,4-dimethylpyridin-3-yl)methyl)-1-(4-phenoxybenzyl)-1H-imidazole-4-carboxamide;
1-(4-(1H-pyrazol-1-yl)benzyl)-N-((6-amino-2,4-dimethylpyridin-3-yl)methyl)-1H-imidazole-4-carboxamide;
N-((6-amino-2,4-dimethylpyridin-3-yl)methyl)-1-((2-(phenylamino)thiazol-4-yl)methyl)-1H-pyrazole-4-carboxamide;
N-((6-amino-2,4-dimethylpyridin-3-yl)methyl)-1-((4-methyl-2-phenylthiazol-5-yl)methyl)-1H-pyrazole-4-carboxamide;
N-((6-amino-2,4-dimethylpyridin-3-yl)methyl)-1-((2-benzylthiazol-4-yl)methyl)-1H-pyrazole-4-carboxamide;
N-((6-amino-2,4-dimethylpyridin-3-yl)methyl)-1-((2-tert-butylthiazol-4-yl)methyl)-1H-pyrazole-4-carboxamide;

N-((6-amino-2,4-dimethylpyridin-3-yl)methyl)-1-((2-(2-(dimethylamino)-2-oxoethyl)thiazol -4-yl)methyl)-1H-pyrazole-4-carboxamide;

N-((6-amino-2,4-dimethylpyridin-3-yl)methyl)-1-(imidazo[1,2-a]pyridin-2-ylmethyl)-1H-pyrazole -4-carboxamide;

N-((6-amino-2,4-dimethylpyridin-3-yl)methyl)-1-(benzofuran-2-ylmethyl)-1H-pyrazole-4-carboxamide;

N-((6-amino-2,4-dimethylpyridin-3-yl)methyl)-1-((2-phenyloxazol-4-yl)methyl)-1H-pyrazole -4-carboxamide;

1-((1H-benzo[d]imidazol-5-yl)methyl)-N-((6-amino-2,4-dimethylpyridin-3-yl)methyl)-1H-pyrazole -4-carboxamide;

N-((6-amino-2,4-dimethylpyridin-3-yl)methyl)-1-((1-methyl-1H-indol-6-yl)methyl)-1H-pyrazole -4-carboxamide;

N-((6-amino-2,4-dimethylpyridin-3-yl)methyl)-1-((5-phenyloxazol-4-yl)methyl)-1H-pyrazole -4-carboxamide;

N-((6-amino-2,4-dimethylpyridin-3-yl)methyl)-1-(4-((3,5-dimethyl-1H-pyrazol-1-yl)methyl)benzyl)-1H-pyrazole-4-carboxamide;

N-((6-amino-2,4-dimethylpyridin-3-yl)methyl)-1-(3-cyanophenylsulfonyl)-1H-pyrazole-4-carboxamide;

N-((6-amino-2,4-dimethylpyridin-3-yl)methyl)-1-(4-phenoxybenzyl)-1H-1,2,3-triazole-4-carboxamide;

N-((6-amino-2,4-dimethylpyridin-3-yl)methyl)-1-(naphthalen-1-ylmethyl)-1H-1,2,3-triazole -4-carboxamide;

N-((6-amino-2,4-dimethylpyridin-3-yl)methyl)-1-(naphthalen-2-ylmethyl)-1H-1,2,3-triazole -4-carboxamide;

1-(4-(1H-pyrazol-1-yl)benzyl)-N-((6-amino-2,4-dimethylpyridin-3-yl)methyl)-1H-1,2,3-triazole-4-carboxamide;

1-(3-(1H-pyrazol-1-yl)benzyl)-N-((6-amino-2,4-dimethylpyridin-3-yl)methyl)-1H-1,2,3-triazole-4-carboxamide;

N-((6-amino-2,4-dimethylpyridin-3-yl)methyl)-1-(3-(pyrrolidin-1-yl)benzyl)-1H-1,2,3-triazole-4-carboxamide;

N-((6-amino-2,4-dimethylpyridin-3-yl)methyl)-2-(benzofuran-2-ylmethyl)-2H-1,2,3-triazole -4-carboxamide;

1-(4-((1H-imidazol-1-yl)methyl)benzyl)-N-((6-amino-2,4-dimethylpyridin-3-yl)methyl)-1H -1,2,3-triazole-4-carboxamide;

1-(3-((1H-imidazol-1-yl)methyl)benzyl)-N-((6-amino-2,4-dimethylpyridin-3-yl)methyl)-1H -1,2,3-triazole-4-carboxamide;

N-((6-amino-2,4-dimethylpyridin-3-yl)methyl)-2-benzylthiazole-4-carboxamide;

N-((6-amino-2,4-dimethylpyridin-3-yl)methyl)-5-phenoxyfuran-2-carboxamide;

N-((6-amino-2,4-dimethylpyridin-3-yl)methyl)-1-benzyl-3-methyl-1H-pyrazole-4-carboxamide;

N-((6-amino-2,4-dimethylpyridin-3-yl)methyl)-1-(furan-2-ylmethyl)-2,5-dimethyl-1H-pyrrole -3-carboxamide;

N-((6-amino-2,4-dimethylpyridin-3-yl)methyl)-2,5-dimethyl-1-(1-phenylethyl)-1H-pyrrole-3-carboxamide;

N-((6-amino-2,4-dimethylpyridin-3-yl)methyl)-4-(morpholinosulfonyl)-1H-pyrrole-2-carboxamide;

N-((6-amino-2,4-dimethylpyridin-3-yl)methyl)-1-(2,6-difluorobenzyl)-1H-1,2,3-triazole-4-carboxamide;

N-((6-amino-2,4-dimethylpyridin-3-yl)methyl)-1-(3-cyanobenzyl)-1H-1,2,3-triazole-4-carboxamide;

N-((6-amino-2,4-dimethylpyridin-3-yl)methyl)-2-benzyl-4-methylthiazole-5-carboxamide;

N-((6-amino-2,4-dimethylpyridin-3-yl)methyl)-1-benzyl-1H-1,2,4-triazole-3-carboxamide;

N-((6-amino-2,4-dimethylpyridin-3-yl)methyl)-1-(4-(6-methylpyrazin-2-yloxy)benzyl)-1H-pyrazole -4-carboxamide;

N-((6-amino-2,4-dimethylpyridin-3-yl)methyl)-2-benzyloxazole-4-carboxamide;

1-(4-((1H-1,2,4-triazol-1-yl)methyl)benzyl)-N-((6-amino-2,4-dimethylpyridin-3-yl)methyl) -1H-1,2,4-triazole-3-carboxamide;

N-((6-amino-4-(2-methoxyethoxy)-2-methylpyridin-3-yl)methyl)-1-benzyl-1H-pyrazole-4-carboxamide;

N-((6-amino-2,4-dimethylpyridin-3-yl)methyl)-1-(biphenyl-4-ylmethyl)-1H-1,2,4-triazole-3-carboxamide;

N-((6-amino-2,4-dimethylpyridin-3-yl)methyl)-1-(naphthalen-1-ylmethyl)-1H-1,2,4-triazole -3-carboxamide;

N-((6-amino-2,4-dimethylpyridin-3-yl)methyl)-1-(4-phenoxybenzyl)-1H-1,2,4-triazole-3-carboxamide;

N-((6-amino-2,4-dimethylpyridin-3-yl)methyl)-1-(naphthalen-2-ylmethyl)-1H-1,2,4-triazole -3-carboxamide;

N-((6-amino-2,4-dimethylpyridin-3-yl)methyl)-1-(4-(2-oxopyrrolidin-1-yl)benzyl)-1H-pyrazole -4-carboxamide;

1-(4-(1H-pyrazol-1-yl)benzyl)-N-((6-amino-2,4-dimethylpyridin-3-yl)methyl)-1H-1,2,4-triazole-3-carboxamide;

1-(3-(1H-pyrazol-1-yl)benzyl)-N-((6-amino-2,4-dimethylpyridin-3-yl)methyl)-1H-1,2,4-triazole-3-carboxamide;

N-((6-amino-2,4-dimethylpyridin-3-ylmethyl)-1-(3-(pyrrolidin-1-yl)benzyl)-1H-1,2,4-triazole-3-carboxamide;

N-((6-amino-2,4-dimethylpyridin-3-yl)methyl)-1-((2-morpholinopyridin-4-yl)methyl)-1H-pyrazole -4-carboxamide;

N-((6-amino-2,4-dimethylpyridin-3-yl)methyl)-1-benzyl-1H-pyrrole-3-carboxamide;

N-((6-amino-2,4-dimethylpyridin-3-yl)methyl)-1-(3-(2-methoxyethyl)benzyl)-1H-pyrazole-4-carboxamide;

N-((6-amino-2,4-dimethylpyridin-3-yl)methyl)-2,5-dimethyl-1-(phenylsulfonyl)-1H-pyrrole -3-carboxamide;

N-((6-amino-2,4-dimethylpyridin-3-ylmethyl)-1-(3,5-dimethoxybenzyl)-1H-pyrazole-4-carboxamide;

N-((6-amino-2,4-dimethylpyridin-3-yl)methyl)-4-methyl-1-(phenylsulfonyl)-1H-pyrrole-3-carboxamide;

N-((6-amino-2,4-dimethylpyridin-3-ylmethyl)-1-((2,3-dimethyl-1H-indol-5-yl)methyl)-1H-pyrazole -4-carboxamide;

N-((6-amino-2,4-dimethylpyridin-3-yl)methyl)-1-benzyl-4-methyl-1H-pyrrole-3-carboxamide;

N-((6-amino-2,4-dimethylpyridin-3-ylmethyl)-2-methyl-5-((1-oxoisoquinolin-2(1H)-yl)methyl)furan -3-carboxamide;

N-((6-amino-2,4-dimethylpyridin-3-yl)methyl)-1-(4-(trifluoromethoxy)benzyl)-1H-pyrazole -4-carboxamide;

N-((6-amino-2,4-dimethylpyridin-3-ylmethyl)-1-(3-cyanobenzyl)-1H-pyrazole-4-carboxamide;

N-((6-amino-2,4-dimethylpyridin-3-ylmethyl)-1-(4-cyanobenzyl)-1H-pyrazole-4-carboxamide;

N-((6-amino-2,4-dimethylpyridin-3-ylmethyl)-1-(naphthalen-2-ylmethyl)-1H-pyrazole-4-carboxamide;

N-((6-amino-2,4-dimethylpyridin-3-ylmethyl)-1-(3-fluorobenzyl)-1H-pyrazole-4-carboxamide;

N-((6-amino-2-methyl pyridin-3-yl)methyl)-1-benzyl-1H-pyrazole-4-carboxamide;

N-((6-amino-2,4-dimethylpyridin-3-ylmethyl)-1-((6-methylpyridin-2-yl)methyl)-1H-pyrazole -4-carboxamide;

N-((6-amino-2,4-dimethylpyridin-3-ylmethyl)-1-(2-chlorobenzyl)-1H-pyrazole-4-carboxamide;

N-((6-amino-2,4-dimethylpyridin-3-ylmethyl)-1-(cyclohexylmethyl)-1H-pyrazole-4-carboxamide;

N-((6-amino-2,4-dimethylpyridin-3-ylmethyl)-1-(4-(phenoxymethyl)benzyl)-1H-pyrazole-4-carboxamide;

N-((6-amino-2,4-dimethylpyridin-3-ylmethyl)-1-(3,4-difluorobenzyl)-1H-pyrazole-4-carboxamide;

N-((6-amino-2,4-dimethylpyridin-3-ylmethyl)-1-(4-(3-methyl-1,2,4-oxadiazol-5-yl)benzyl) -1H-pyrazole-4-carboxamide;

N-((6-amino-2,4-dimethylpyridin-3-yl)methyl)-1-(3-chlorobenzyl)-1H-pyrazole-4-carboxamide;
N-((6-amino-2,4-dimethylpyridin-3-yl)methyl)-1-(2,4-difluorobenzyl)-1H-pyrazole-4-carboxamide;
N-((6-amino-2,4-dimethylpyridin-3-yl)methyl)-1-(4-(benzyloxy)benzyl)-1H-pyrazole-4-carboxamide;
N-((6-amino-2,4-dimethylpyridin-3-yl)methyl)-1-((3,4-dihydro-2H-benzo[b][1,4]dioxepin-6-yl)methyl)-1H-pyrazole-4-carboxamide;
N-((6-amino-2,4-dimethylpyridin-3-yl)methyl)-1-(4-chlorobenzyl)-1H-pyrazole-4-carboxamide;
N-((6-amino-2,4-dimethylpyridin-3-yl)methyl)-1-((2-methylthiazol-4-yl)methyl)-1H-pyrazole-4-carboxamide;
N-((6-amino-2,4-dimethylpyridin-3-yl)methyl)-1-(pyridin-3-ylmethyl)-1H-pyrazole-4-carboxamide;
N-((6-amino-2,4-dimethylpyridin-3-yl)methyl)-1-((6-(hydroxymethyl)pyridin-2-yl)methyl) -1H-pyrazole-4-carboxamide;
N-((6-amino-2,4-dimethylpyridin-3-yl)methyl)-1-(1-phenylethyl)-1H-pyrazole-4-carboxamide;
N-((6-amino-2,4-dimethylpyridin-3-yl)methyl)-1-((1-methyl-1H-benzo[d][1,2,3]triazol-5-yl)methyl)-1H-pyrazole-4-carboxamide;
N-((6-amino-2,4-dimethylpyridin-3-yl)methyl)-1-(3-carbamoylbenzyl)-1H-pyrazole-4-carboxamide;
N-((6-amino-2,4-dimethylpyridin-3-yl)methyl)-1-(benzo[d][1,3]dioxol-5-ylmethyl)-1H-pyrazole-4-carboxamide;
N-((6-amino-2,4-dimethylpyridin-3-yl)methyl)-1-((3-methylquinoxalin-2-yl)methyl)-1H-pyrazole-4-carboxamide;
N-((6-amino-2,4-dimethylpyridin-3-yl)methyl)-1-(benzo[d]thiazol-2-ylmethyl)-1H-pyrazole-4-carboxamide;
N-((6-amino-2,4-dimethylpyridin-3-yl)methyl)-1-(benzo[d]isoxazol-3-ylmethyl)-1H-pyrazole-4-carboxamide;
N-((6-amino-2,4-dimethylpyridin-3-yl)methyl)-1-(2-cyanobenzyl)-1H-indole-3-carboxamide;
N-((6-amino-2,4-dimethylpyridin-3-yl)methyl)-1-benzyl-1H-indole-3-carboxamide;
N-((6-amino-2,4-dimethylpyridin-3-yl)methyl)-1-benzyl-2,5-dimethyl-1H-pyrrole-3-carboxamide;
N-((6-amino-2,4-dimethylpyridin-3-yl)methyl)-1-(4-(morpholinomethyl)benzyl)-1H-pyrazole-4-carboxamide;
N-((6-amino-2,4-dimethylpyridin-3-yl)methyl)-1-(4-(3-cyclopropylureido)benzyl)-1H-pyrazole-4-carboxamide;
N-((6-amino-2,4-dimethylpyridin-3-yl)methyl)-5-benzyl-1H-1,2,4-triazole-3-carboxamide;
N-((6-amino-2,4-dimethylpyridin-3-yl)methyl)-1-(4-(pyridin-4-yl)benzyl)-1H-pyrazole-4-carboxamide;
N-((6-amino-2,4-dimethylpyridin-3-yl)methyl)-1-(biphenyl-3-ylmethyl)-1H-pyrazole-4-carboxamide;
N-((6-amino-2,4-dimethylpyridin-3-yl)methyl)-1-(3-(morpholinosulfonyl)benzyl)-1H-pyrazole-4-carboxamide;
N-((6-amino-2,4-dimethylpyridin-3-yl)methyl)-1-(3-(phenylcarbamoyl)benzyl)-1H-pyrazole-4-carboxamide;
N-((6-amino-2,4-dimethylpyridin-3-yl)methyl)-1-(4-(pyrrolidin-1-ylmethyl)benzyl)-1H-pyrazole-4-carboxamide;
N-((6-amino-2,4-dimethylpyridin-3-yl)methyl)-1-(3-(piperidine-1-carbonyl)benzyl)-1H-pyrazole-4-carboxamide;
N-((6-amino-2,4-dimethylpyridin-3-yl)methyl)-1-(4-(isopropylcarbamoyl)benzyl)-1H-pyrazole-4-carboxamide;
N-((6-amino-2,4-dimethylpyridin-3-yl)methyl)-1-(4-(morpholine-4-carbonyl)benzyl)-1H-pyrazole -4-carboxamide;
N-((6-amino-2,4-dimethylpyridin-3-yl)methyl)-1-(4-(1-methyl-1H-pyrazol-3-ylcarbamoyl)benzyl)-1H-pyrazole-4-carboxamide;
5-(amino(phenyl)methyl)-N-((6-amino-2,4-dimethylpyridin-3-yl)methyl)-1H-1,2,4-triazole-3-carboxamide;
N-((6-amino-2,4-dimethylpyridin-3-yl)methyl)-3-(biphenyl-4-ylmethyl)-1H-1,2,4-triazole-5-carboxamide;
N-((6-amino-2,4-dimethylpyridin-3-yl)methyl)-3-(4-phenoxybenzyl)-1H-1,2,4-triazole-5-carboxamide;
N-((6-amino-2,4-dimethylpyridin-3-yl)methyl)-1-(4-(N,N-dimethylsulfamoyl)benzyl)-1H-pyrazole -4-carboxamide;
N-((6-amino-2,4-dimethylpyridin-3-yl)methyl)-1-(biphenyl-4-ylsulfonyl)-1H-pyrrole-3-carboxamide;
N-((6-amino-2,4-dimethylpyridin-3-yl)methyl)-1-(5-chlorothiophen-2-ylsulfonyl)-1H-pyrrole -3-carboxamide;
N-((6-amino-2,4-dimethylpyridin-3-yl)methyl)-1-(3-methoxyphenylsulfonyl)-1H-pyrrole-3-carboxamide;
N-((6-amino-2,4-dimethylpyridin-3-yl)methyl)-1-(4-methyl-3,4-dihydro-2H-benzo[b][1,4]oxazin-6-ylsulfonyl)-1H-pyrrole-3-carboxamide;
N-((6-amino-2,4-dimethylpyridin-3-yl)methyl)-1-(1-methyl-1H-indol-5-ylsulfonyl)-1H-pyrrole -3-carboxamide;
N-((6-amino-2,4-dimethylpyridin-3-yl)methyl)-1-(3-(pyrimidin-2-yl)phenylsulfonyl)-1H-pyrrole -3-carboxamide;
N-((6-amino-2,4-dimethylpyridin-3-yl)methyl)-1-(4-(3,5-dimethyl-1H-pyrazol-1-yl)phenylsulfonyl)-1H-pyrrole-3-carboxamide;
2-(4-((4-((6-amino-2,4-dimethylpyridin-3-yl)methylcarbamoyl)-1H-pyrazol-1-yl)methyl)phenoxy)acetic acid;
N-((6-amino-2,4-dimethylpyridin-3-yl)methyl)-1-(4-(cyanomethoxy)benzyl)-1H-pyrazole-4-carboxamide;
N-((6-amino-2-methyl-4-(oxazol-2-ylmethoxy)pyridin-3-yl)methyl)-1-benzyl-1H-1,2,3-triazole-4-carboxamide;
N-((6-amino-2-methyl-4-(oxazol-2-ylmethoxy)pyridin-3-yl)methyl)-1-benzyl-1H-1,2,3-triazole-4-carboxamide;
N-((6-amino-4-methylpyridin-3-yl)methyl)-1-benzyl-1H-pyrazole-4-carboxamide;
N-((6-amino-2,4-dimethylpyridin-3-yl)methyl)-1-(4-((3-oxo-2,3-dihydro-1H-pyrazol-1-yl)methyl)benzyl)-1H-pyrazole-4-carboxamide;
1-(4-((1H-1,2,3-triazol-1-yl)methyl)benzyl)-N-((6-amino-2,4-dimethylpyridin-3-yl)methyl)-1H-pyrazole-4-carboxamide;
N-((6-amino-2,4-dimethylpyridin-3-yl)methyl)-1-(4-((2,5-dimethyl-3-oxo-2,3-dihydro-1H-pyrazol-1-yl)methyl)benzyl)-1H-pyrazole-4-carboxamide;
N-((6-amino-2,4-dimethylpyridin-3-yl)methyl)-1-(4-((2-oxopyridin-1(2H)-yl)methyl)benzyl)-1H-pyrazole-4-carboxamide;
N-((6-amino-2,4-dimethylpyridin-3-yl)methyl)-1-(4-((2-oxopyrrolidin-1-yl)methyl)benzyl)-1H-pyrazole-4-carboxamide;
N-((6-amino-4-chloro-2-methylpyridin-3-yl)methyl)-1-benzyl-1H-pyrazole-4-carboxamide;
1-(4-((1H-pyrazol-1-yl)methyl)benzyl)-N-((6-amino-2,4-dimethylpyridin-3-yl)methyl)-1H-pyrazole-4-carboxamide;
N-((6-amino-2,4-dimethylpyridin-3-yl)methyl)-1-(4-((4-methyl-1H-pyrazol-1-yl)methyl)benzyl)-1H-pyrazole-4-carboxamide;
N-((6-amino-2,4-dimethylpyridin-3-yl)methyl)-1-(4-((5-methyl-1H-pyrazol-1-yl)methyl)benzyl)-1H-1,2,3-triazole-4-carboxamide;
N-((6-amino-2,4-dimethylpyridin-3-yl)methyl)-1-(4-((3,5-dimethyl-1H-pyrazol-1-yl)methyl)benzyl)-1H-1,2,3-triazole-4-carboxamide;
N-((6-amino-4-(3,3-dimethyl-2-oxobutoxy)-2-methylpyridin-3-yl)methyl)-1-(naphthalen-2-ylmethyl)-1H-pyrazole-4-carboxamide;

N-((6-Amino-2,4-dimethylpyridin-3-yl)methyl)-1-((1-(2-methoxyethyl)-1,2,3,4-tetrahydroquinolin-7-yl)methyl)-1H-pyrazole-4-carboxamide;
N-((6-Amino-2,4-dimethylpyridin-3-yl)methyl)-1-((4-methyl-3-oxo-3,4-dihydro-2H-benzo[b][1,4]oxazin-6-yl)methyl)-1H-pyrazole-4-carboxamide;
N-((6-Amino-2,4-dimethylpyridin-3-yl)methyl)-1-((1-methyl-1,2,3,4-tetrahydroquinolin-7-yl)methyl)-1H-pyrazole-4-carboxamide;
N-((6-amino-2,4-dimethylpyridin-3-yl)methyl)-1-((2-methylquinolin-6-yl)methyl)-1H-1,2,3-triazole-4-carboxamide;
N-((6-amino-2,4-dimethylpyridin-3-yl)methyl)-1-((2-methylquinolin-6-yl)methyl)-1H-pyrazole-4-carboxamide;
N-((6-amino-2,4-dimethylpyridin-3-yl)methyl)-1-(quinolin-3-ylmethyl)-1H-pyrazole-4-carboxamide;
N-((6-amino-2,4-dimethylpyridin-3-yl)methyl)-1-((7-methylquinolin-3-yl)methyl)-1H-1,2,3-triazole-4-carboxamide;
N-((6-amino-2,4-dimethylpyridin-3-yl)methyl)-1-((7-chloroquinolin-2-yl)methyl)-1H-pyrazole-4-carboxamide;
N-((6-amino-2,4-dimethylpyridin-3-yl)methyl)-1-((7-chloroquinolin-2-yl)methyl)-1H-1,2,3-triazole-4-carboxamide;
N-((6-amino-2-methylpyridin-3-yl)methyl)-1-((2-methylquinolin-6-yl)methyl)-1H-pyrazole-4-carboxamide;
N-((6-amino-2-methylpyridin-3-yl)methyl)-1-((6-fluoro-4-(trifluoromethyl)quinolin-2-yl)methyl)-1H-pyrazole-4-carboxamide;
N-((6-amino-2-methylpyridin-3-yl)methyl)-1-((2,5,7-trimethylquinolin-3-yl)methyl)-1H-pyrazole-4-carboxamide;
N-((6-amino-2,4-dimethylpyridin-3-yl)methyl)-1-((6-fluoro-4-(trifluoromethyl)quinolin-2-yl)methyl)-1H-pyrazole-4-carboxamide;
N-((6-amino-2,4-dimethylpyridin-3-yl)methyl)-1-((6-methoxynaphthalen-2-yl)methyl)-1H-pyrazole-4-carboxamide;
N-((6-Amino-2,4-dimethylpyridin-3-yl)cyclopropyl)-1-((2-methylquinolin-6-yl)methyl)-1H-1,2,3-triazole-4-carboxamide;
N-((6-Amino-2,4-dimethylpyridin-3-yl)methyl)-1-((1,2-dimethyl-1H-benzo[d]imidazol-5-yl)methyl)-1H-pyrazole-4-carboxamide;
N-((6-amino-2,4-dimethylpyridin-3-yl)methyl)-1-((1,2,3-trimethyl-1H-indol-5-yl)methyl)-1H-1,2,3-triazole-4-carboxamide;
N-((6-Amino-4-chloro-2-methylpyridin-3-yl)methyl)-1-(4-((2-oxopyridin-1(2H)-yl)methyl)benzyl)-1H-pyrazole-4-carboxamide;
N-((6-Amino-2,4-dimethylpyridin-3-yl)methyl)-1-((1,2-dimethyl-1H-indol-5-yl)methyl)-1H-pyrazole-4-carboxamide;
N-((6-amino-2,4-dimethylpyridin-3-yl)methyl)-1-((2-methylimidazo[1,2-a]pyridin-6-yl)methyl)-1H-pyrazole-4-carboxamide;
N-((6-amino-2,4-dimethylpyridin-3-yl)methyl)-2-((2-methylquinolin-6-yl)methyl)oxazole-4-carboxamide;
N-((6-Amino-2,4-dimethylpyridin-3-yl)methyl)-1-((7-aminothieno[2,3-c]pyridin-5-yl)methyl)-1H-pyrazole-4-carboxamide;
N-((6-amino-4-chloro-2-methylpyridin-3-yl)methyl)-1-(naphthalen-2-ylmethyl)-1H-pyrazole-4-carboxamide;
N-((6-Amino-2,4-dimethylpyridin-3-yl)methyl)-1-((3-chloroquinolin-6-yl)methyl)-1H-pyrazole-4-carboxamide;
N-((6-amino-2,4-dimethylpyridin-3-yl)methyl)-1-((1,1-dioxido-2,3-dihydrobenzo[b]thiophen-5-yl)methyl)-1H-pyrazole-4-carboxamide and N-((6-Amino-4-chloro-2-methylpyridin-3-yl)methyl)-1-((2-methylquinolin-6-yl)methyl)-1H-1,2,3-triazole-4-carboxamide.

Embodiment 9: A pharmaceutical composition comprising a therapeutically effective amount of a compound according to any one of embodiments 1 to 8 and one or more pharmaceutically acceptable carriers.

Embodiment 10: A combination comprising a therapeutically effective amount of the compound according to any one of embodiments 1 to 8 and one or more therapeutically active agents.

Embodiment 11: A method of inhibiting plasmakallikrein activity in a subject, wherein the method comprises administering to the subject a therapeutically effective amount of the compound according to any one of embodiments 1 to 8.

Embodiment 12: A method of treating a disorder or a disease in a subject mediated by plasmakallikrein, wherein the method comprises administering to the subject a therapeutically effective amount of the compound according to any one of embodiments 1 to 8.

Embodiment 13: A compound according to any one of embodiments 1 to 8, for use as a medicament.

Embodiment 14: Use of a compound according to any one of embodiments 1 to 8, for the treatment of a disorder or disease in a subject mediated by plasmakallikrein.

Embodiment 15: Use of a compound according to any one of embodiments 1 to 8, for the treatment of a disorder or disease in a subject characterized by an abnormal activity of plasmakallikrein.

Embodiment 16: A compound of formula IIa

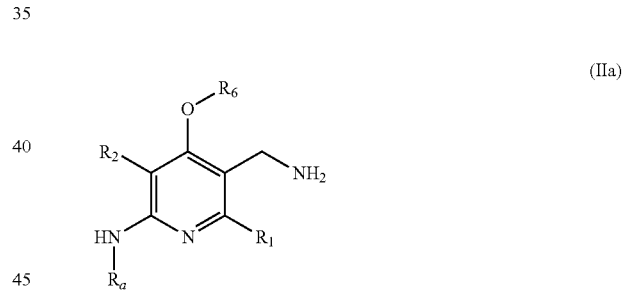

(IIa)

wherein $R_1$, $R_2$ and $R_6$ are as defined according to embodiment 1; and $R_a$ is hydrogen or an amine protecting group.

The invention claimed is:

1. A compound, or salt thereof, of Formula 1A:

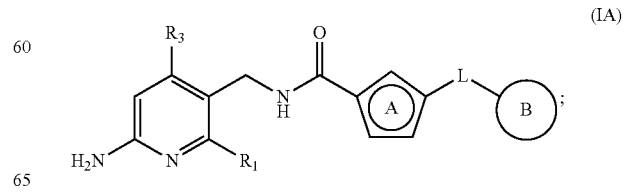

(IA)

wherein
$R_1$ and $R_3$ are $C_{1-4}$alkyl;
A is a ring system selected from

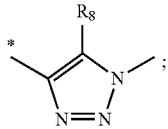

wherein the bond marked with the asterisk is attached to the carboxamide group and wherein each $R_8$ is hydrogen;
L is —$C(R_{10})_2$—; and each $R_{10}$ is hydrogen;
B is a quinolinyl, wherein the quinolinyl may be substituted once or more than once by $R_{12}$;
and wherein a substituent on a nitrogen in a heterocyclic ring system may not be halogen;
each $R_{12}$ independently is halogen; —$X_2$—$R_{13}$;
$X_2$ is selected from bond; and
$R_{13}$ is $C_{1-6}$alkyl; $C_{1-6}$halogenalkyl.

2. A compound, or salt thereof, of claim 1
wherein
$R_1$ and $R_3$ are $C_{1-4}$alkyl;
A is a ring system selected from $A_7$

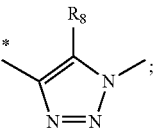

wherein the bond marked with the asterisk is attached to the carboxamide group and wherein each $R_8$ is hydrogen;
L is —$C(R_{10})_2$—; and each $R_{10}$ is hydrogen;
B is a quinolin-2-yl, quinol-3-yl, quinol-6-yl, wherein the quinolinyl may be substituted once or more than once by $R_{12}$; and wherein a substituent on a nitrogen in a heterocyclic ring system may not be halogen;
each $R_{12}$ independently is halogen; —$X_2$—$R_{13}$;
$X_2$ is selected from bond; and
$R_{13}$ is $C_{1-6}$alkyl; $C_{1-6}$halogenalkyl.

3. A compound, or salt thereof, of claim 1 selected from:
N-((6-amino-2,4-dimethylpyridin-3-yl)methyl)-1-((2-methylquinolin-6-yl)methyl)-1H-1,2,3-triazole-4-carboxamide;
N-((6-amino-2,4-dimethylpyridin-3-yl)methyl)-1-((7-methylquinolin-3-yl)methyl)-1H-1,2,3-triazole-4-carboxamide; and
N-((6-amino-2,4-dimethylpyridin-3-yl)methyl)-1-((7-chloroquinolin-2-yl)methyl)-1H-1,2,3-triazole-4-carboxamide.

4. A compound, or salt thereof, of claim 1 wherein the compound is

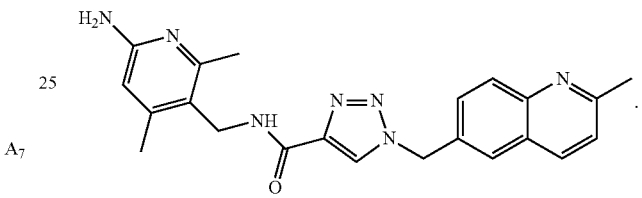

5. A pharmaceutical composition comprising a therapeutically effective amount of a compound according to claim 1 in free form or in pharmaceutically acceptable salt form and one or more pharmaceutically acceptable carriers.

* * * * *